United States Patent [19]
Andreiko et al.

[11] Patent Number: 5,431,562
[45] Date of Patent: Jul. 11, 1995

[54] METHOD AND APPARATUS FOR DESIGNING AND FORMING A CUSTOM ORTHODONTIC APPLIANCE AND FOR THE STRAIGHTENING OF TEETH THEREWITH

[75] Inventors: Craig A. Andreiko, Alta Loma; Mark A. Payne, Whittier, both of Calif.

[73] Assignee: Ormco Corporation, Glendora, Calif.

[21] Appl. No.: 973,973

[22] Filed: Nov. 9, 1992

Related U.S. Application Data

[63] Continuation-in-part of Ser. No. 875,663, Apr. 29, 1992, abandoned, Ser. No. 775,589, Oct. 15, 1991, abandoned, and Ser. No. 467,162, Jan. 19, 1990, Pat. No. 5,139,419, said Ser. No. 875,663, is a continuation of Ser. No. 467,162, Jan. 19, 1990, said Ser. No. 775,589, is a continuation-in-part of Ser. No. 467,162, Jan. 19, 1990.

[51] Int. Cl.⁶ .............................................. A61G 3/00
[52] U.S. Cl. .................................................. 433/24
[58] Field of Search ........................ 433/24; 364/413.28

[56] References Cited

U.S. PATENT DOCUMENTS

| | | | |
|---|---|---|---|
| 3,477,128 | 11/1969 | Andrews | 433/24 |
| 3,660,900 | 5/1972 | Andrews | 433/24 |
| 3,738,005 | 6/1973 | Cohen et al. | 433/24 |
| 3,906,634 | 9/1975 | Aspel | 433/24 |
| 3,949,478 | 4/1976 | Schinhammer | 433/24 |
| 4,014,096 | 3/1977 | Dellinger | 433/24 |
| 4,160,322 | 7/1979 | Frazier | 433/24 |
| 4,324,546 | 4/1982 | Heitlinger et al. | 433/25 |
| 4,415,330 | 11/1983 | Daisley et al. | 433/16 |
| 4,611,288 | 9/1986 | Duret et al. | 433/25 |
| 4,663,720 | 5/1987 | Duret et al. | 433/214 |
| 4,742,464 | 5/1988 | Duret et al. | 433/214 |
| 4,837,732 | 6/1989 | Brandestini et al. | 433/223 |
| 4,850,864 | 7/1989 | Diamond | 433/24 |
| 4,983,120 | 1/1991 | Coleman et al. | 433/24 |
| 5,011,405 | 4/1991 | Lemchen | 433/24 |
| 5,027,281 | 6/1991 | Rekow et al. | 364/474.24 |
| 5,131,843 | 7/1992 | Hilgers et al. | 433/20 |

FOREIGN PATENT DOCUMENTS

| | | |
|---|---|---|
| 8911257 | 11/1989 | WIPO . |
| 9008512 | 8/1990 | WIPO . |

OTHER PUBLICATIONS

Rekow, D., "Computer-aided design and manufacturing in dentistry; A review of the state of the art", Journal of Prosthetic Dentistry, vol. 58, Oct. 1987, pp. 513–516.

Leinfelder, K. F. et al., "A new method for generating ceramic restorations: a CAD-CAM system", Journal American Dental Association, vol. 118, Jun. 1989, pp. 703–707.

*Primary Examiner*—Cary E. O'Connor
*Attorney, Agent, or Firm*—Wood, Herron & Evans

[57] ABSTRACT

A system and method by which an orthodontic appliance is automatically designed and manufactured from digital lower jaw and tooth shape data of a patient provides for preferably scanning a model of the patient's mouth to produce two or three dimensional images and digitizing contours and selected points. A computer is programmed to construct archforms and calculate finish positions of the teeth, then to design an appliance, preferably including archwires and brackets, to move the teeth to the calculated positions. The lower teeth are positioned at their roots on an arch defined by the lower jaw bone, and the arch is modified to best fit the tooth tips on a smooth curve. Then upper archforms are constructed for the upper teeth. Crown long axes of the teeth are derived and preserved in the treatment which places all lower teeth but the cuspids in a plane and fits the occluding teeth to them. Overlaps for the upper incisors and for cuspid rise are calculated.

69 Claims, 54 Drawing Sheets

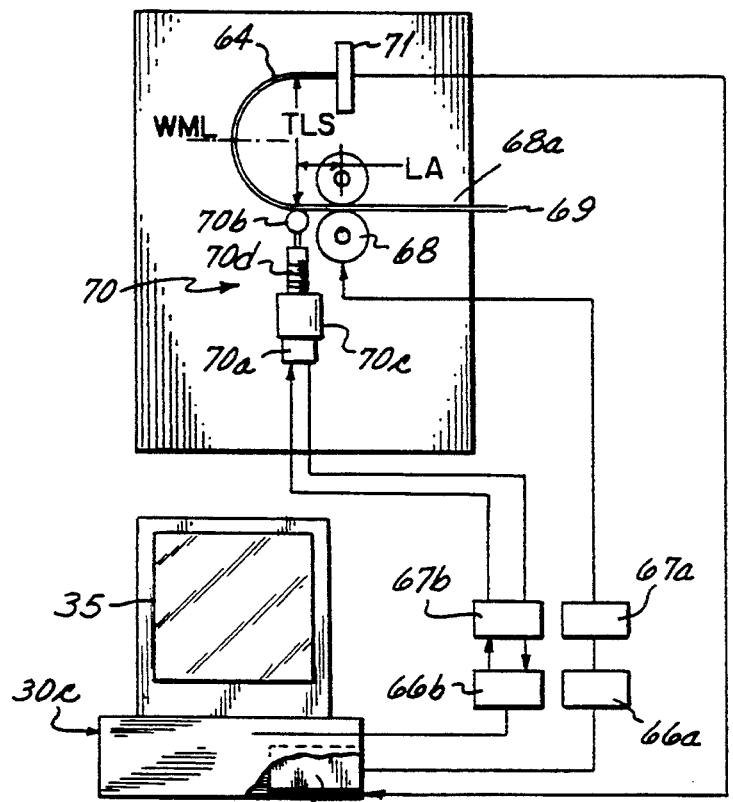
FIG. IE
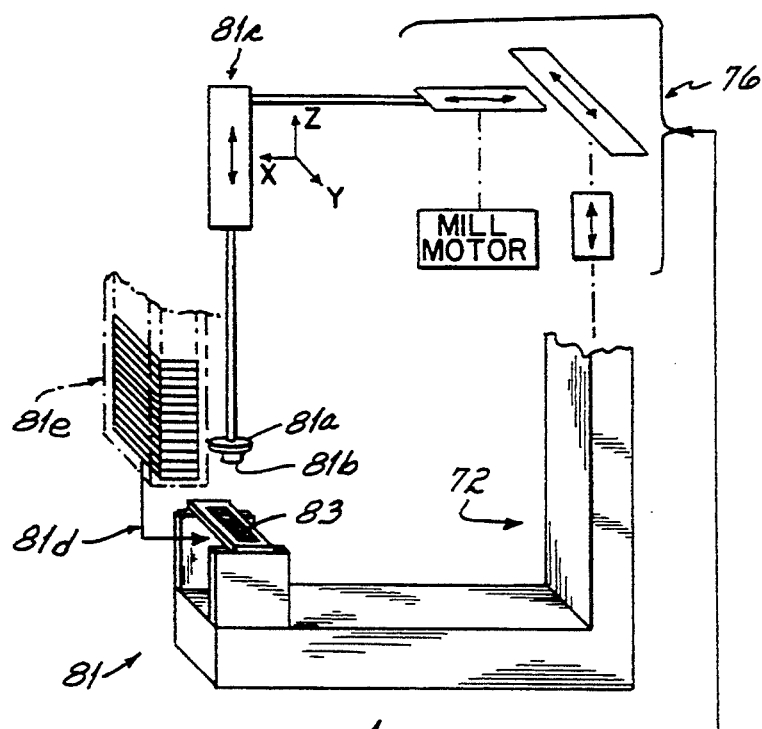
FIG. IF

3060 COMBINE NC CODE WITH CALCULATED VALUES AND GENERATE INDIVIDUAL TOOTH SUBROUTINES:

IF TOOTH IS A BICUSPID:
one$ = "G91 C" + "TtaStrt"
two$ = "G90 G00 X" + "xs" + "Z" + "z"
three$ = "Y" +"ys"
IF TOOTH IS LOWER 2ND BICUSPID
THEN {FOUR$="G01 x" + "XE" +
"f6.0"}
ELSE {FOUR$ = "G01 X +"xe"
five$ = "g00 Y1.7"
six$ = "Z0.0"
seven$ = "G91 C +"TtaEnd"

ELSE:
one$="G91 C" + "ThaStrt"
two$ = "G90 g00 X" + xs + "Z" + "z"
three$ = "Y" + "ys"
four$ = G02 I" + "NCi" + "J-" + "NCj" + X" + "xe"
five = "g00 U1.7"
six$ = Z0.0"
seven$ = "g91 C" + "ThaEnd"

---

3065 WRITE P-CODE SUBROUTINES:
  3066 FOR BICUSPIDS:

P01
    G91 C-12.52
    G90 G00 X3.8000 Z0.1294
    Y-0.0551
    G01 X-3.2000
    G00 Y0.300
    Z0.0
    G91 C12.52
    M12

---

3067 FOR OTHER TEETH:

P03
    G91 C-9.82
    G90 G00 X-3.0229 Z0.1049
    Y-0.1411
    G02 I0.5229 J-1.4368 X-1.9771
    G00 Y0.300
    Z0.0
    G91 C9.82
    M12

( 3099 EXIT )

FIG. 2X-4

(3605) CREATE AN ARCHWIRE SLOT TOOL PATH (ASTP):
(a) DETERMINE THE DISTANCE FROM THE SURFACE OF THE TOOTH IN THE x DIRECTION THAT WILL ALLOW A PLASTIC SHIM TO FIT INTO THE TORQUE SLOT: THE DIMENSIONS OF THE SHIM ARE:
(torque slot width) x 0.085 x 0.100;
LnEnd=TSx+Elan-0.012+0.085-ToolRad
WHERE: LnEnd=x LOCATION
Elan = BRACKET In-out (IO)
(b) CONSTRUCT A LINE ABOVE AND PARALLEL TO THE ARCHWIRE PLANE SUCH THAT THE ENDMILL WILL GENERATE A LINE CONGRUENT WITH THE BRACKET TORQUE SLOT WALL; THE HEIGHT ABOVE THE ARCHWIRE PLANE IS:
(torque slot width)/2 - ToolRad;
(c) DETERMINE THE LINE SEGMENT ON THE BRACKET BASE COMPENSATION TOOL PATH THAT INTERSECTS (a);
(d) DELETE (b);
(e) CONSTRUCT A LINE BELOW AND PARALLEL TO THE ARCHWIRE PLANE SUCH THAT THE ENDMILL WILL GENERATE A LINE CONGRUENT WITH THE BRACKET TORQUE SLOT WALL:
THE HEIGHT ABOVE THE ARCHWIRE PLANE IS:
(torque slot width)/2 - ToolRad.
(f) DETERMINE THE LINE SEGMENT ON THE BRACKET BASE COMPENSATION PATH THAT INTERSECTS (a):
THIS IS POINT 8: P8x,P8y;
(g) DELETE (e);
(h) CONSTRUCT A LINE FROM POINT 1 (P1x,P1y) TO POINT 2 (P1X, LnEnd - 0.001);
(i) CONSTRCUT A LINE FROM POINT 2 (P1x, LnEnd - 0.001) TO POINT 3 (P1x + 2.5ToolRad, LnEnd - 0.001);
(j) CONSTRUCT A LINE FROM POINT 3 (P1x + 2.5ToolRad, LnEnd - 0.001) TO POINT 4 (P1x + 2.5ToolRad, LnEnd);
(k) CONSTRUCT A LINE FROM POINT 3 (P1x + 2.5ToolRad, LnEnd- 0.001) TO POINT 4 (P1x + 2.5ToolRad, LnEnd);
(l) CONSTRUCT A LINE FROM POINT 5 (P2x - 2.5ToolRad, LnEnd) TO POINT 6 (P2x - 2.5ToolRad, LnEnd - 0.001);
(m) CONSTRUCT A LINE FROM POINT 6 (P2x - 2.5ToolRad, LnEnd - 0.001) TO POINT 7 (P2x, LnEnd - 0.001);
(n) CONSTRUCT A LINE FROM POINT 7 (P2x, LnEnd - 0.001) TO POINT 8 (Plx,P8y)

3625 CREATE A CNC MACHINE CODE AND WRITE IT TO FILE:
(a) WRITE PCount GENERATED P-CODE ROUTINE NOMENCLATURE TO FILE:
   IF PCount<=9, THEN:   { PCount$=str(pcOUNT);
                           strext(count$,PCount$,0,1);
                           strcat(one$,"P0",count$);   }
   ELSE:                 { d$=str(PCount);
                           strext(count$,d$,0,2);
                           strcat(one$,"P",count$);   }
   WRITE(h1,one$);
(b) WRITE RAPID TO 0.020 ABOVE WORKPIECE TO FILE: "G00 G90 Z.020";
(c) DETERMINE END OF INITIAL LINE AND NAME AS P1x AND P1y;
(d) DETERMINE STARTING POSITION RELATIVE TO JIG BLANK CENTER:
       GStrtx=P1x-Toolx;
       GStrty=P1Y-Tooly;
       strcat(two$,"G00 G91 X",str(GStrtx),"Y",str(GStrty));
       WRITE(h1,two$);
(e) CREATING PECKING MOTION TO CLEAR WORKPIECE ENTRANCE:
       WRITE(h1,"G01 G90 Z-.055 F1.0");
       WRITE(h!,"G00 A.020");
       WRITE(h!,"G01 Z-.055 P1.0");
(f) CREATE EACH INCREMENTAL MOVE
       AND WRITE TO FILE:                    IF i==CutStrt + 1 THEN
   i=CutStrt + 1;                              { five$="";
   WHILE i<= CutEnd do                           strcat(five$,"G01 G91
       { inqobj(i,10,Begx,Begy,Endx,Endy);       X",str(x),"Y",str(y),"F1.5")'
         P2x=Endx;                               WRITE(h1,five$);   }
         P2y=Endy;                           ELSE
         addobj(40,P2x,P2y,ToolRad);           { five$=""
         x=P2x-P1x;                              strcat(five$,"X",str(x),"Y",str(y));
         y=P2y-P1y;                              write(h1,five$);   }
                                                 P1x=P2x;
                                                 P1y=P2y;
                                                 i=i+1;   }
(g) DETERMINE AND CREATE LAST MOVE TO CLOSE LOOP:
       inqobj(CutStrt,10,Begx,Begy,Endx,Endy);
       addobj(10,Endx-.01,Endy,Endx+.01,Endy);
       addobj(10,ENdx,Endy-.01,Endx,Endy+.01);
       P2x=Endx;
       P2y=Endy;
       x=P2x-P1x;
       y=P2y-P1y;
       six$="";
       strcat(six$,"X",str(x),"Y",str(y));
       WRITE(h1,six$);
(h) TURN ON ABSOLUTE TO MOVE .500 ABOVE WORKPIECE AND P-CODE:
       WRITE(h1,"G00 G90 Z.5");
       WRITE(h1,"M12");

3629 EXIT

FIG. 2Z-6

LOWER FRONT TEETH

LOWER RIGHT TEETH

LOWER RIGHT TEETH

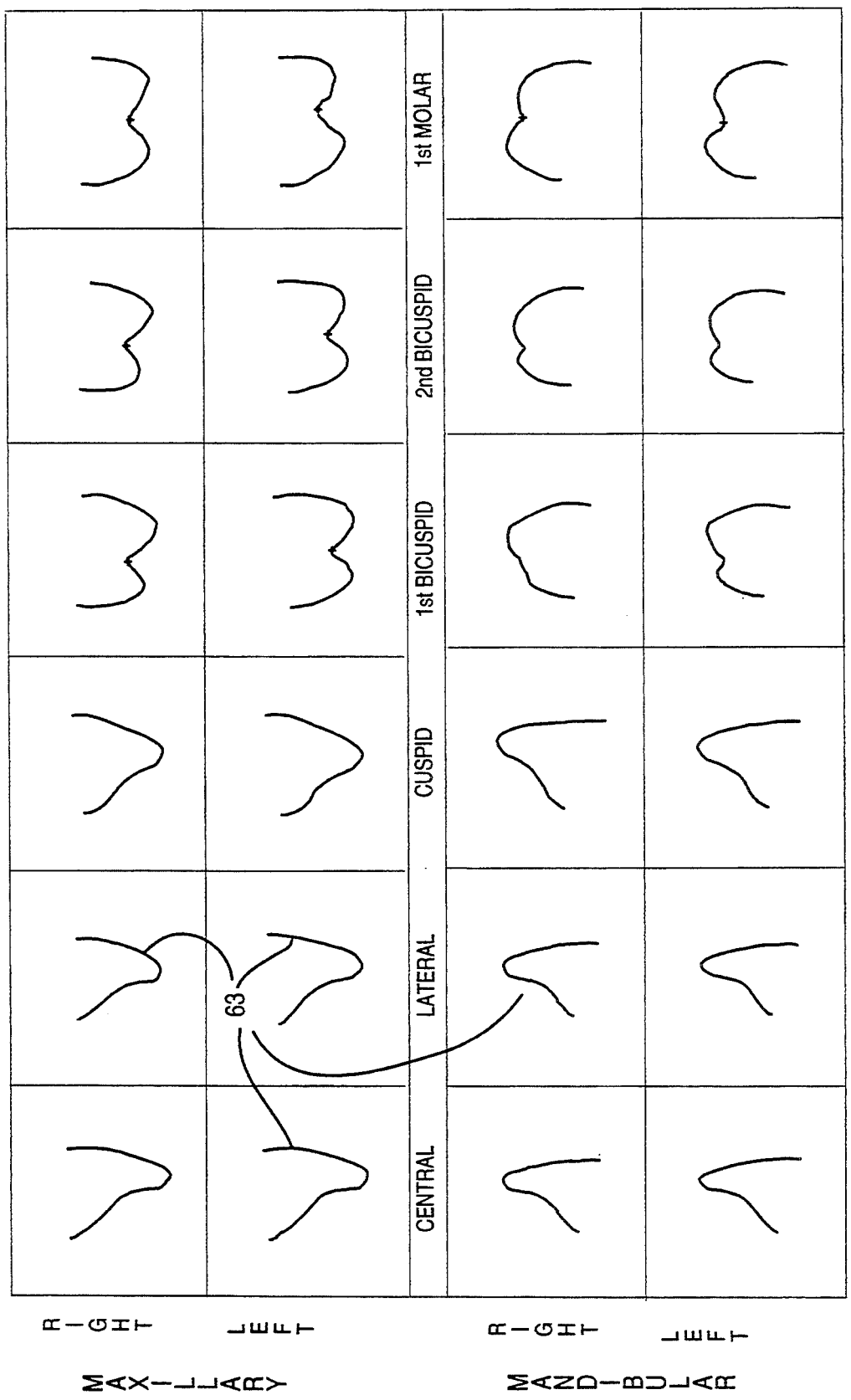

FIG. 5C  SMALL CIRCLE FIRST

FIG. 5B  LARGE CIRCLE FIRST

Spline Seg. No. 1
Circle Seg. Nos. 1 and 2

Spline Seg. No. 2
Circle Seg. Nos. 3 and 4

Spline Seg. No. 3
Circle Seg. Nos. 5 and 6

Spline Seg. No. 4
Circle Seg. Nos. 7 and 8

Spline Seg. No. 5
Circle Seg. Nos. 9 and 10

Spline Seg. No. 6
Circle Seg. No.'s 11 and 12

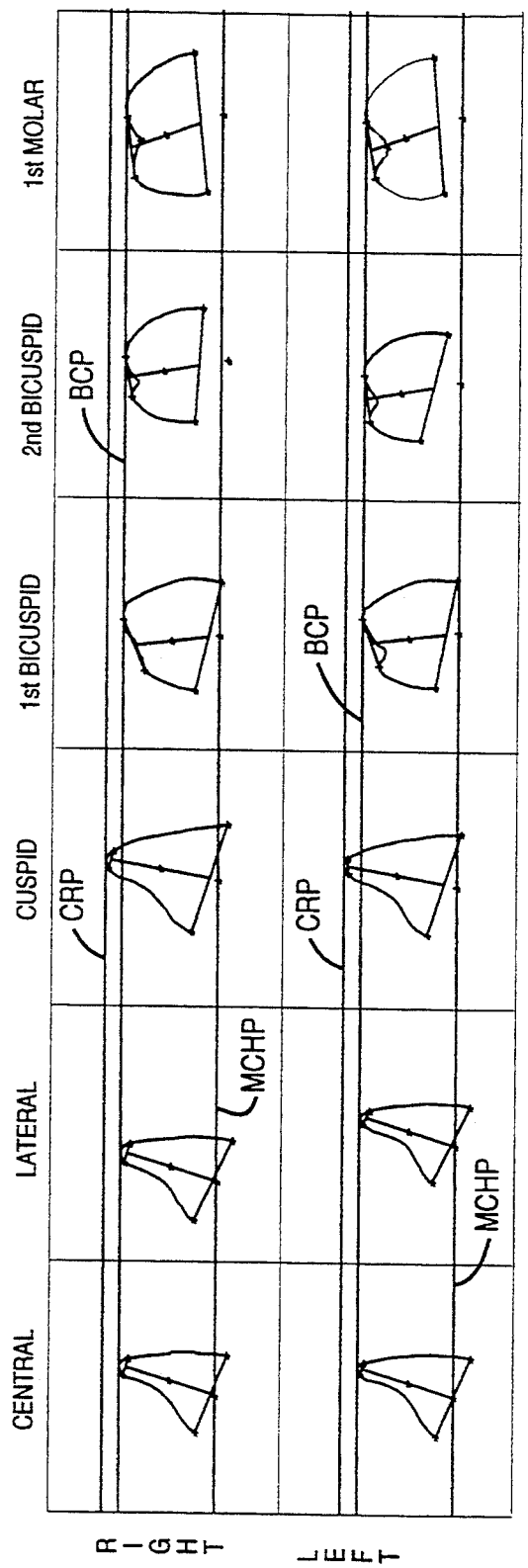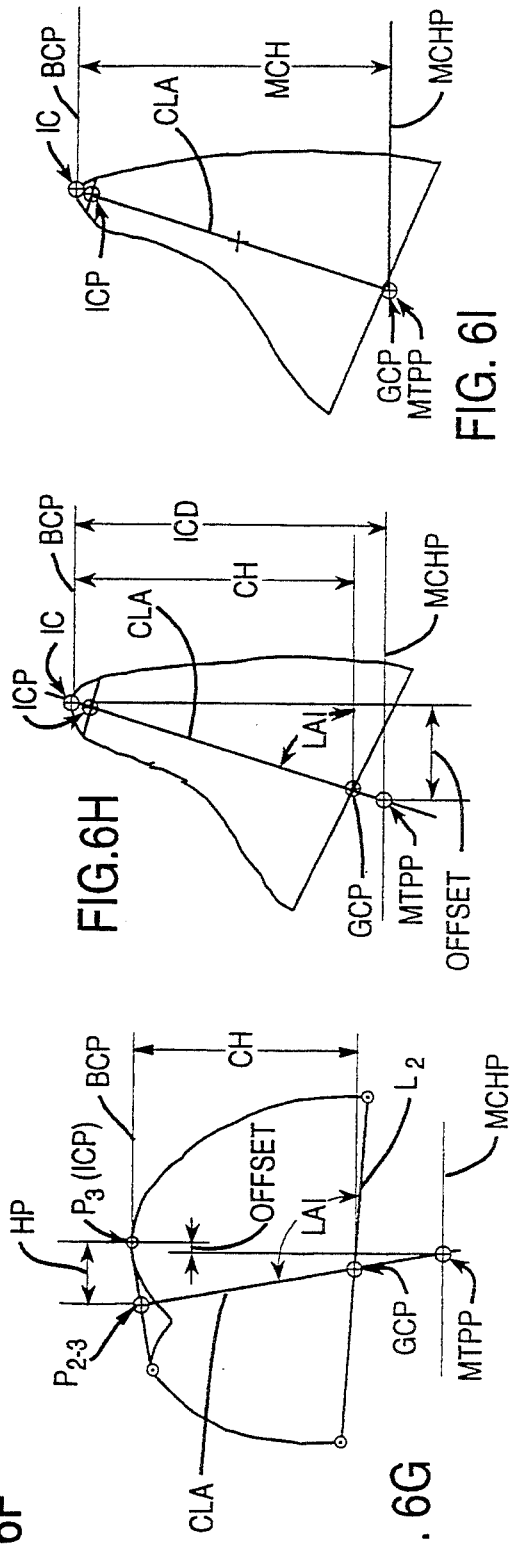

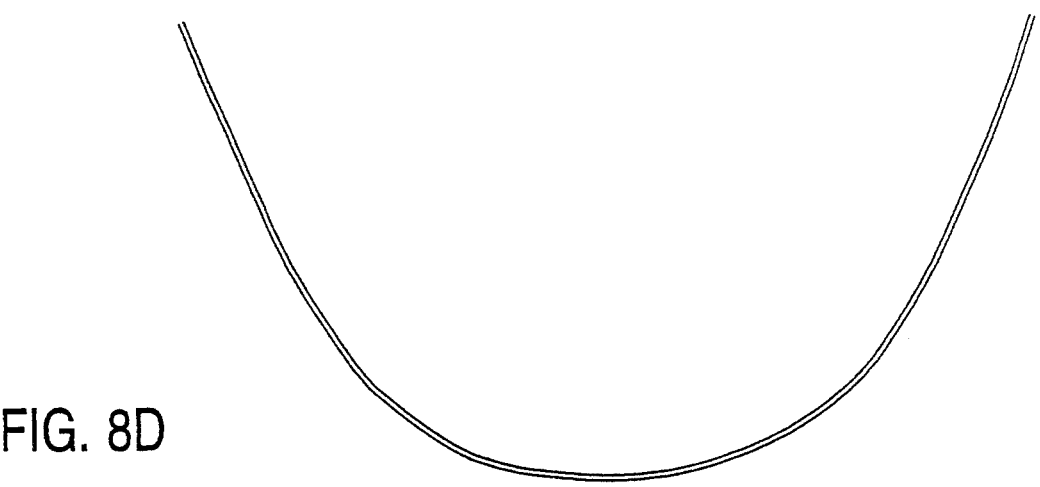
FIG. 8D
FIG. 8E
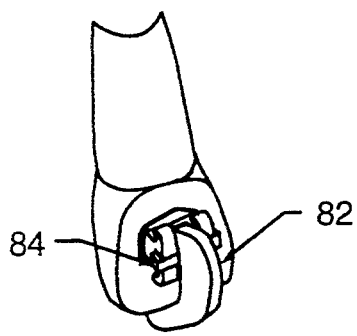
FIG. 8F
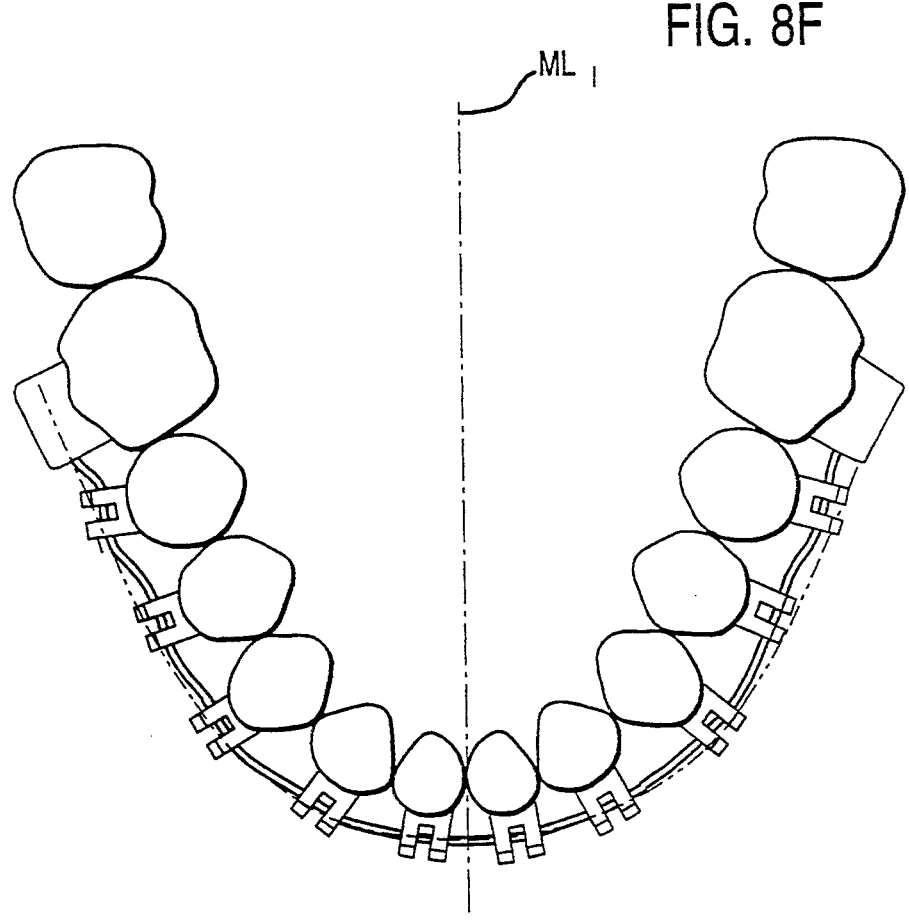

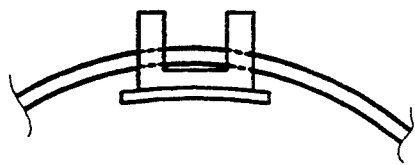
FIG. 8I
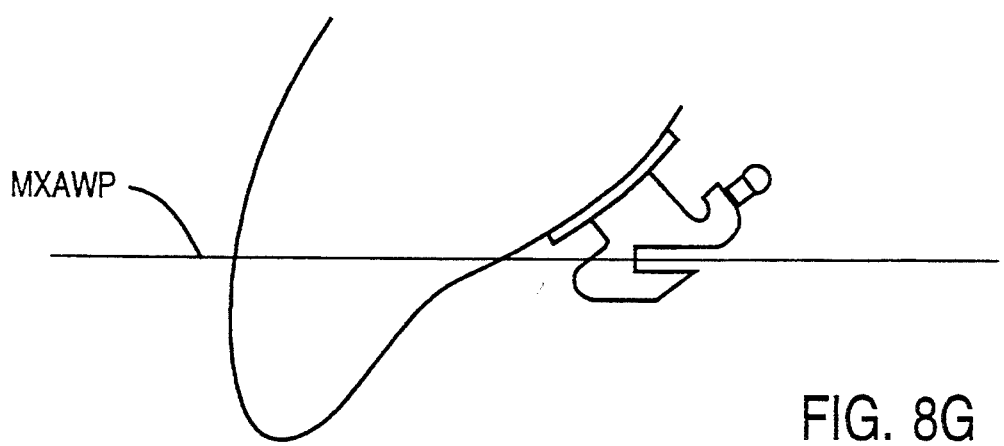
FIG. 8G
FIG. 8H
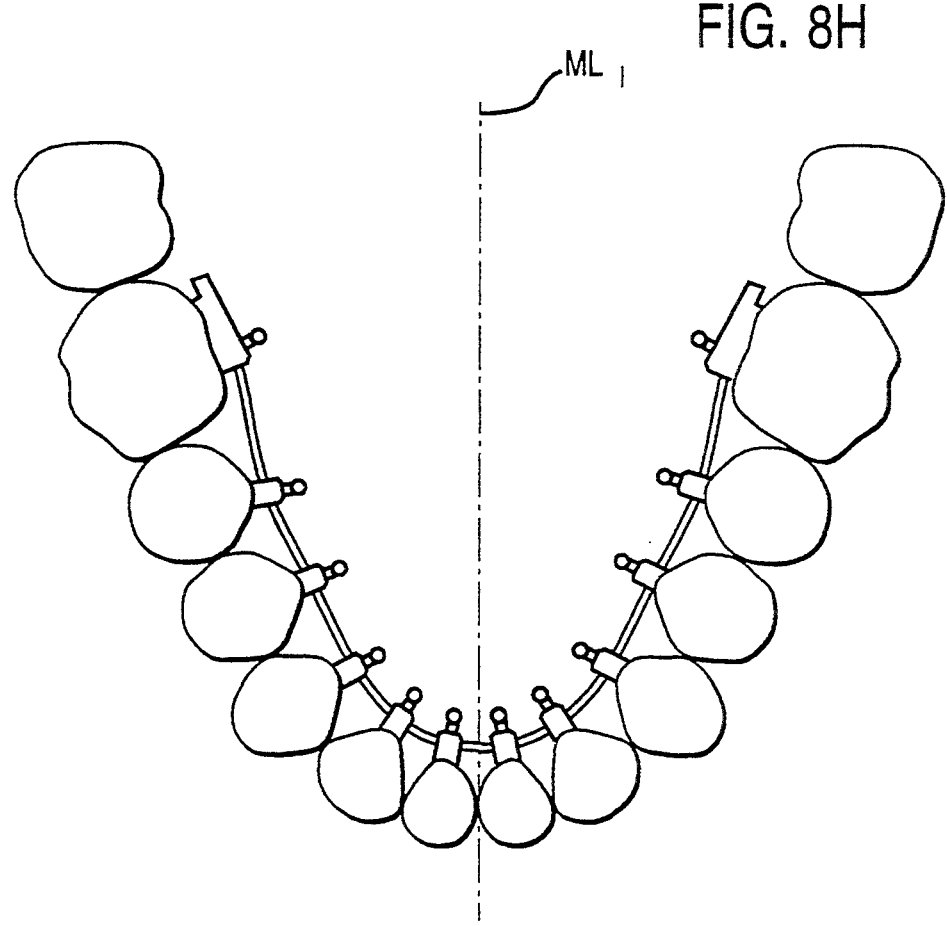

METHOD AND APPARATUS FOR DESIGNING AND FORMING A CUSTOM ORTHODONTIC APPLIANCE AND FOR THE STRAIGHTENING OF TEETH THEREWITH

This application is a continuation-in-part of the following commonly owned and copending U.S. patent applications, each hereby expressly incorporated herein by reference:

Ser. No. 07/875,663, filed Apr. 29, 1992, now abandoned, which is a continuation of Ser. No. 07/467,162;

Ser. No. 07/775,589, filed Oct. 15, 1991, now abandoned, which is a continuation-in-part of Ser. No. 07/467,162; and Ser. No. 07/467,162, filed Jan. 19, 1990, now U.S. Pat. No. 5,139,419.

This application is also related to commonly assigned U.S. patent applications of the same inventors filed on even date herewith and entitled:

CUSTOM ORTHODONTIC BRACKET FORMING METHOD AND APPARATUS,

METHOD AND APPARATUS FOR FORMING JIGS FOR CUSTOM PLACEMENT OF ORTHODONTIC APPLIANCES ON TEETH, AND JIGS FORMED THEREWITH, and

CUSTOM ORTHODONTIC ARCHWIRE FORMING METHOD AND APPARATUS.

FIELD OF THE INVENTION

The present invention relates to the design, manufacture and use of orthodontic appliances for the straightening of teeth, and more particularly, to the automated design, manufacture and use of custom orthodontic appliances based on individual patient anatomy and to the diagnosis of patients therefor and the treatment of patients therewith.

BACKGROUND OF THE INVENTION

The orthodontic treatment of patients has as its fundamental objective the repositioning or realignment of the teeth of a patient in the patient's mouth to positions where they function optimally together and occupy relative locations and orientations that define a pair of opposed and cooperating planar, or nearly planar, smooth arches. The teeth of the two arches, the maxillary arch of the teeth of the upper jaw and the mandibular arch of the teeth of the lower jaw, when in an optimal or ideal position, contact the teeth of the opposite arch along a surface that is usually flat or slightly upwardly concave and commonly referred to as the plane of occlusion.

The treatment applied to patients who have been diagnosed as having teeth insufficiently close to the ideal positions to require orthodontic correction includes an initial or rough procedure to overcome the more serious defects of tooth positioning followed by a finish treatment designed to bring the teeth as closely as possible or practical to their ideal positions. The rough treatment usually involves the movement of certain teeth through the use of any of a number of recognized techniques performed by an orthodontist, and sometimes procedures such as the extraction of certain teeth or surgery on the patient's jaw performed by an oral surgeon.

In the finish treatment, the orthodontist applies an appliance, or set of braces, to the teeth of the patient to exert continual forces on the teeth of the patient to gradually urge them toward their ideal positions. The application of the appliance usually involves the attachment of brackets to the teeth, either with the application of adhesive to the teeth or the securing of bands around the teeth. The brackets are usually each provided with a slot through which an archwire is extended. One archwire is provided for the upper teeth and one for the lower teeth. Typically, the slots in the brackets are of rectangular cross-section and the archwire is of rectangular cross-section. The archwire installed in the slots of the brackets interconnects the teeth, through the brackets, and exerts forces on the teeth to translate or rotate them toward a finish position envisioned by the orthodontist.

It has been recognized in the design and application of orthodontic appliances that an ideally designed and installed orthodontic appliance will present the slots of the brackets in a position to initially receive a preshaped archwire that will elastically deform to exert corrective forces on the teeth to urge them toward their finish positions. When in their finish positions, the archwire of the ideally designed appliance will no longer be elastically deformed, and will no longer exert forces upon the teeth. Achieving this objective has been inhibited by certain problems in the prior art.

One problem presented by the prior art is that current orthodontic products are designed and manufactured to average anatomy. As a result, orthodontists are faced with the need to select what they perceive to be the brackets and archwires of the closest design to those required by a particular patient, and to modify the designs for treatment of the patient. Some of this modification may be performed when the appliance is initially installed, but almost inevitably modification is required during the course of treatment of the patient. This modification may take the form of the replacement of brackets, but most commonly requires a periodic bending and reshaping of the archwire as the treatment progresses. Thus, the treatment of the patient has become a manual feedback system in which the orthodontist monitors the progress of the patient's treatment and then readjusts the appliance, usually by bending the archwires, to correct the forces being applied to the teeth to bring the teeth to their ultimate positions, which are less than ideal. As a result, the patient may be subjected to treatment over a period that is longer than would be necessary if the appliance were initially made to the optimum design. In addition, the time required of the orthodontist for implementation of the treatment may be several times greater than it would be if modification of the appliance were unnecessary. Thus, the orthodontist is able to treat fewer patients and the cost of the treatment to the patient or to the orthodontist is increased.

Location of the connection points for the appliance to the teeth also presents a problem in the prior art. Typically, brackets are bonded to the teeth and then interconnected by the installation of the archwires. This is done when the teeth are in their maloccluded positions, with the orthodontist having only a mental vision of where the finish positions of the teeth will be and where the brackets are to be placed to move the teeth to those finish positions. For more effective use of the appliance and to promote ease in cleaning the teeth, the orthodontist prefers to locate the brackets and archwires away from the gums. If they are placed to close to the tips of the teeth, however, they may interfere with the teeth of the opposite arch as the teeth approach their finish positions.

Another problem of the prior art that has inhibited the selection or design of an ideal orthodontic appliance for the patient is the difficulty in arriving at an expression of the ideal finish position of the teeth. Orthodontists typically make models of the patient's mouth and, with the models and the aid of x-rays, determine a treatment to move the teeth to finish tooth positions. This process is time consuming and presents a source of error and inaccuracy. From the measurements and based on the judgment of the orthodontist, appliance components are selected to implement the prescribed treatment. In reality, the treatment of patients is in many cases more of an art than a science, with results ranging from poor to excellent, and generally variable.

The need for custom manufactured orthodontic appliances and the use of automatic design techniques has been recognized by some, while others have advocated adherence to standard components and manual techniques in view of a perceived lack of practical custom appliance manufacturing and automated appliance design systems of the art.

The development of automated custom appliance design systems has encountered several difficulties. These difficulties have included the task of developing an automated system that includes reliable and efficient decision making algorithms and techniques for automatically determining an ideal finish position of the teeth. Further, these difficulties have included arriving at an expression of appliance geometry in terms that can be efficiently produced by automated appliance manufacturing equipment. Furthermore, the prior art has not provided a way to accurately manufacture an appliance on an individualized basis in accordance with the appliance design. An additional problem in the automated design and manufacture of orthodontic appliances lies in the difficulty in designing the custom design system to take into account the professionally recognized parameters and criteria, derived over many years from the knowledge and experience of the practicing and clinical orthodontist, upon which diagnosis and treatment is based.

Accordingly, there is a great need in orthodontics for a practical, reliable and efficient custom appliance automated design and manufacturing system, and method of providing custom appliances and treating patients therewith.

SUMMARY OF THE INVENTION

A primary objective of the present invention is to provide a practical, reliable and efficient custom appliance automated design and manufacturing system and methods of automatically designing custom orthodontic appliances and treating patients therewith.

It is a particular objective of the present invention to provide an automated custom orthodontic appliance design and manufacturing system that can be easily and reliably used by practicing orthodontists and that will make best use of the skills, knowledge and experience that the orthodontist possesses. It is a further objective of the present invention to increase the accuracy of the orthodontist's treatment, to render the use of the orthodontist's time more efficient, to eliminate sources of error and guesswork from the orthodontist's treatment of patients, and to efficiently, repeatedly and reliably perform automatically the many of the routine steps in the diagnosis, prescription and implementation of orthodontic treatment and in the design and manufacture of orthodontic appliances.

It is a further objective of the present invention to improve the practice of orthodontics by aiding the practitioner in achieving optimal finish treatment of patients and in more accurately determining and precisely achieving the finish placement of a patient's teeth. An additional objective of the present invention is to provide for the accumulation of data from individual patients for the analysis of the data to advance the orthodontic art.

It is still another objective of the present invention to apportion the tasks involved in the design and manufacture of custom appliances most efficiently between orthodontist and appliance manufacturing facility in accordance with the scale and other particulars of the individual practitioner operation.

According to the principles of the present invention, a system and method are provided which depart from traditional design and manufacture by designing orthodontic appliances around the anatomy of the individual patient. Further, unlike current orthodontic products that are designed and manufactured to average anatomy, the orthodontic products of the present invention and the methods of manufacturing and using them are tailored to the individual anatomy of the patient.

In accordance with the preferred embodiment of the present invention, there is provided a computerized system and method with which finish positions of the teeth of a patient are derived from digitized information of anatomical shapes of the patients mouth, an orthodontic appliance is automatically designed from the digitized shape information and the derived tooth finish positions, machine code is generated for production of the orthodontic appliance and communicated to NC machines, and the appliance is automatically fabricated with the machines in response to the machine code.

In accordance with the preferred and illustrated embodiment of the invention, the digitized information is generated from measurements from the mouth of the patient, either taken directly or from a model thereof, and preferably includes information of the shapes of the individual teeth of the patient and of the patient's lower jaw.

In the preferred embodiment, the finish tooth position derivation includes the derivation of one or more archforms, preferably conforming to a skeletal archform defined by the shape of the lower jaw. The appliance is also configured in accordance with the shape of the derived archform, preferably with a mandibular skeletal archform having size and shape conforming to that of the trough of the lower jaw. In the preferred embodiments, additional archforms are constructed using information of the shapes of the individual teeth and the lower jaw skeletal archform to define the positions of the buccal cusps and incisal tips of the mandibular teeth, the marginal ridges of the upper posterior teeth, and the lingual points of occlusion of the upper anterior teeth to position the teeth according to a preferred treatment plan.

In certain preferred embodiments of the invention, the digitized data is taken by measurements of the patient's individual teeth and the data is reduced to certain landmark data that becomes key to effective and efficient arrival at highly preferred finish tooth positions. The individual teeth are arranged on the various derived archforms with mesial and distal contact points of adjacent teeth in contact. The spacing between the opposite contact points of each tooth are preferably extracted from a computerized image formed in horizontal plan views of the patients teeth. Furthermore, relative locations of the incisal tips, marginal ridges, gingival contact points and the external surfaces of the teeth to which the appliance connects, for example, by the mounting of brackets, and which occlude with teeth of the opposite jaw, are determined by digitizing vertical profiles of the surfaces of the crowns of the teeth. This data is reduced to define contact points of the mandibular teeth with the lower jaw, such as the gingival center points, to define crown axes of the teeth, and other parameters that are amenable to manipulation with a simple and reliable algorithm in calculating the finish positions of the teeth. The landmarks also include intercusp and inter ridge spacing measurements that provide a basis for prescribing arch expansion treatment with exactness based on the computer aided calculation of precise finish tooth positions. Further, the tooth position calculations provided improve upon prior orthodontic practice by preserving crown long axis inclination angles and setting the teeth to preferred crown long axis inclination angles for population groups according to seed values that are statistically improved upon by the present invention.

In certain embodiments of the invention, images are digitized to produce the tooth and jaw shape data. Preferably, the images include a scanner which, in one form, generates a video image from which selected points are digitized to produce data from which finish tooth positioning and appliance design is carried out. Alternatively, three dimensional imaging of the teeth and jaw of the patient is carried out with laser or other scanner to form full three dimensional images of the teeth and jaw of the patient. The images may be formed from the patient's teeth and jaw or from a model thereof. Additional data is digitized by taking vertical profiles of the patient's teeth, either by tracing with a computer the three dimensional images generated with other scanners, or by scanning with a mechanical contact probe or with a non-contact probe the individual teeth of the patient, or model thereof. The data may be taken directly from the patient using CAT scans, MRI, positron emission tomography or other technique.

Also in accordance with certain embodiments of the invention, the finish tooth positioning includes the establishment of cuspid rise criteria by rigorous calculations made from measured and statistical anatomical data so that the height of the cuspids and other teeth can be adjusted relative to each other so that the teeth can be positioned to guide the jaws into proper occlusion. With the present invention, numerical relationships are provided for cuspid rise that are an improvement of the prior art.

In accordance with certain preferred embodiments of the invention, an archwire forming machine that is responsive to NC code is driven by signals generated by a computer that reads input data of anatomical shapes of the patient's mouth, is provided to automatically form an arcuate appliance that interconnects the teeth to move them toward their finish positions by rotational and translational forces applied in three dimensions each by the arcuate appliance. Generally, the arcuate appliance is an archwire, and the machine for forming the appliance includes an archwire forming machine that is responsive to NC code is driven by signals generated by a computer that reads input data of anatomical shape of the patient's mouth, preferably of the patient's jaw and teeth, derives the tooth finish positions and archwire and bracket designs that will move the teeth to the calculated finish positions, and generates the machine code to produce the archwire in accordance with the design. Preferably, the archwires have shapes that conform to archforms related to the finish tooth positions, particularly to the shape of the patient's lower jaw, and is represented as a series of segments of a continuous archwire that each have a constant radius of curvature over the length of the segment, and that preferably join adjacent segments in a smooth transition, with the segments tangent where they join.

Further in accordance with certain preferred embodiments of the invention, a bracket fabrication machine, also responsive to NC code, is driven by similar signals from a computer responsive to computer generated finish tooth position calculations and digitized tooth shape data. Preferably, the brackets have bases that mount on computer determined positions on the teeth and have slots to receive archwires that are inclined at computer determined angles. The fabrication of the brackets may include the formation of a slope and/or curvature to the mounting surfaces of the bases of the brackets, or, as with the illustrated embodiment, by cutting custom slots in the brackets. In the preferred embodiment, the design and manufacture of the archwires and brackets are interrelated so that the curve of the archwire is optimized to minimize curvature changes and the brackets are optimize to minimize their profiles, or the distances from the bases to the archwire slots. The calculations provide a basis for the selection of appropriate bracket blanks for the optimized appliance design.

Additionally, in accordance with other aspects of the invention, one or more placement fixtures are manufactured from the input data and the calculated tooth positions for locating points on the teeth, preferably determined by the computer, for the connection of the appliance to the teeth, such as for the mounting of the brackets to the teeth. The fixtures preferably include a set of bracket placement jigs, one for each bracket that is to be mounted on a tooth, to position and hold the bracket to the tooth so that it can be secured thereto in a precise mounting location. The jigs of the preferred embodiment include a tooth profile or three dimensional surface that fits against the tooth to precisely locate the jig on the tooth and hold a bracket at a precise position and inclination thereon so that it can be secured to the tooth with adhesive.

With the present invention, a custom orthodontic appliance is fabricated under the control of a computer directly from data taken from the teeth and/or jaw of a patient or a model thereof. The appliance so formed, when connected to the teeth of the patient, moves the teeth of the patient to precise calculated finish positions without the need for the orthodontist to bend archwires over the course of the treatment. As a result, the orthodontist's time is conserved, the treatment of the patient is achieved in a shorter amount of time and the finish positions of the teeth are more nearly ideal, and consistently so, than those achieved with the procedures of the prior art. Furthermore, the appliance fabricating processes result in the generation of data useful in establishing treatment techniques and criteria that will improve the practice of orthodontics.

Further, movement of the teeth to the finish positions calculated in accordance with the present invention results in far more stable placement of the teeth than with other methods of the prior art which often experience movement of the teeth to inferior positions after the orthodontic treatment is terminated.

These and other objectives and advantages of the present invention will be more readily apparent from the following detailed description of the drawings in which:

BRIEF DESCRIPTION OF THE DRAWINGS

FIGS. 1-1F are diagrams illustrating the preferred embodiments of the system of the present invention, of which:

FIG. 1 is a block diagram illustrating one preferred embodiment of an automated system for the design and manufacture of custom orthodontic appliances for the treatment of patients therewith according to the principles of the present invention.

FIG. 1E is an isometric diagram of one embodiment of a wire forming device of the system of FIG. 1.

FIG. 1F is an isometric diagram of a bracket placement jig forming device of the system of FIG. 1.

FIGS. 2-2Z are flow chart diagrams of the preferred methods of carrying out the present invention, of which:

FIG. 2 is a flow chart of one preferred embodiment of the process of the present invention performed with the system of FIG. 1.

FIG. 2O is a detailed flow chart illustrating the substeps of the maxillary horizontal tooth finish position calculation step of the analysis procedure of FIG. 2B.

Figure 2:
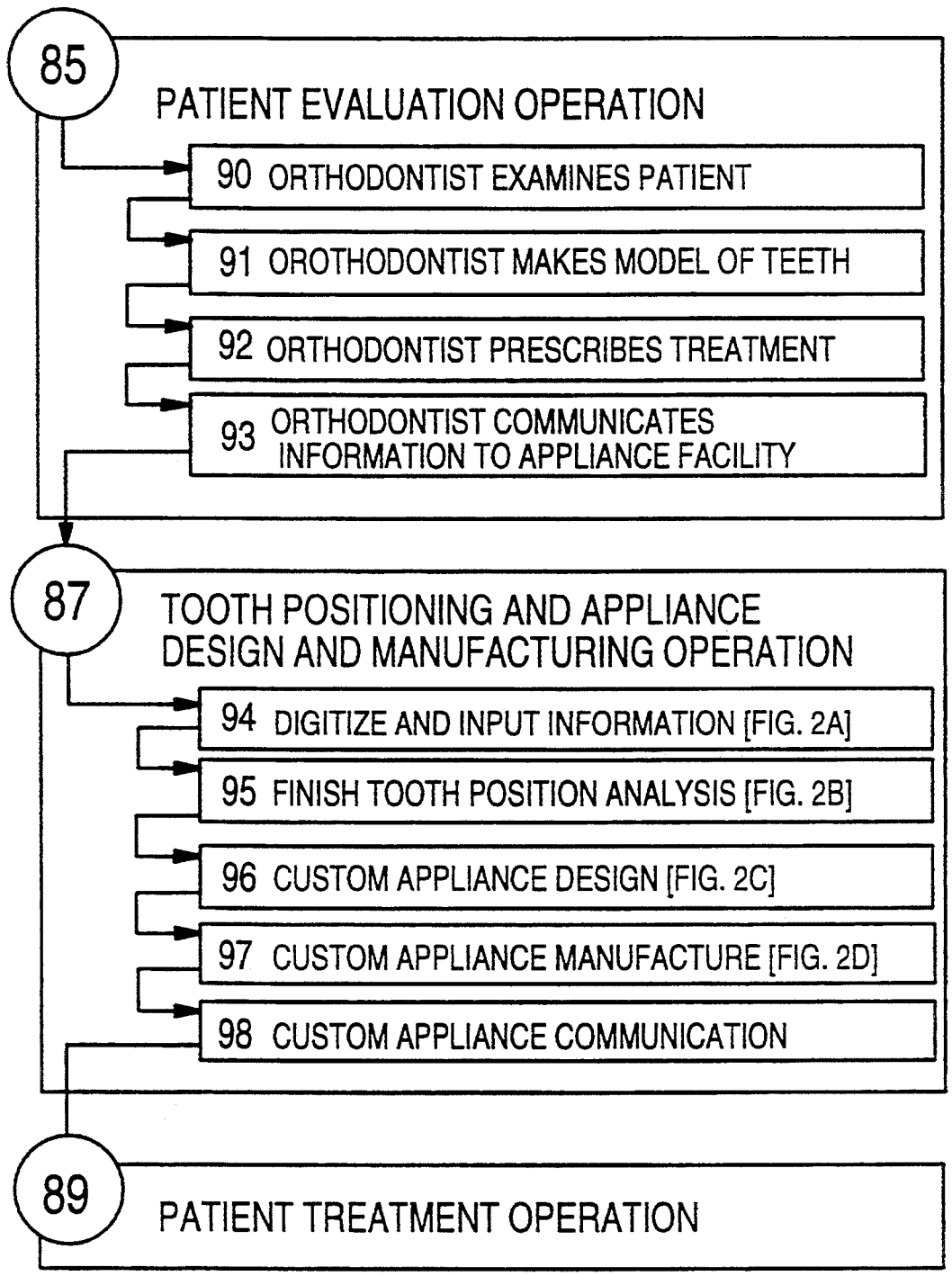
Figure 2A:
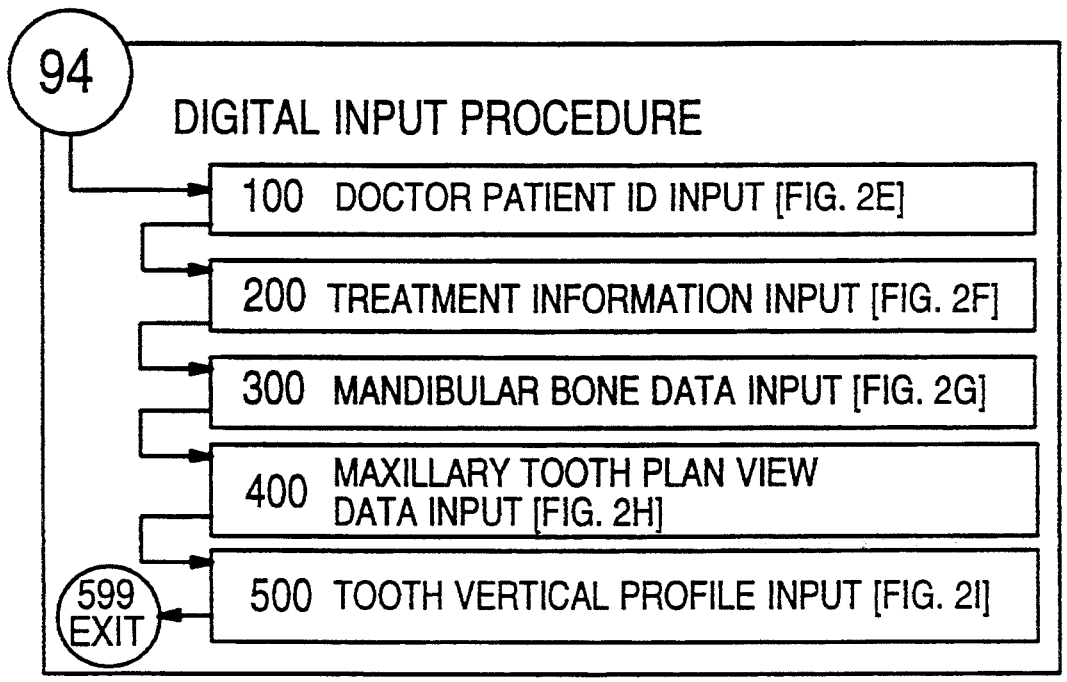
FIG. 2A is a more specific flow chart illustrating the steps of the input procedure of automated tooth positioning and appliance design and manufacturing operation of the process of FIG. 2.
Figure 2B:
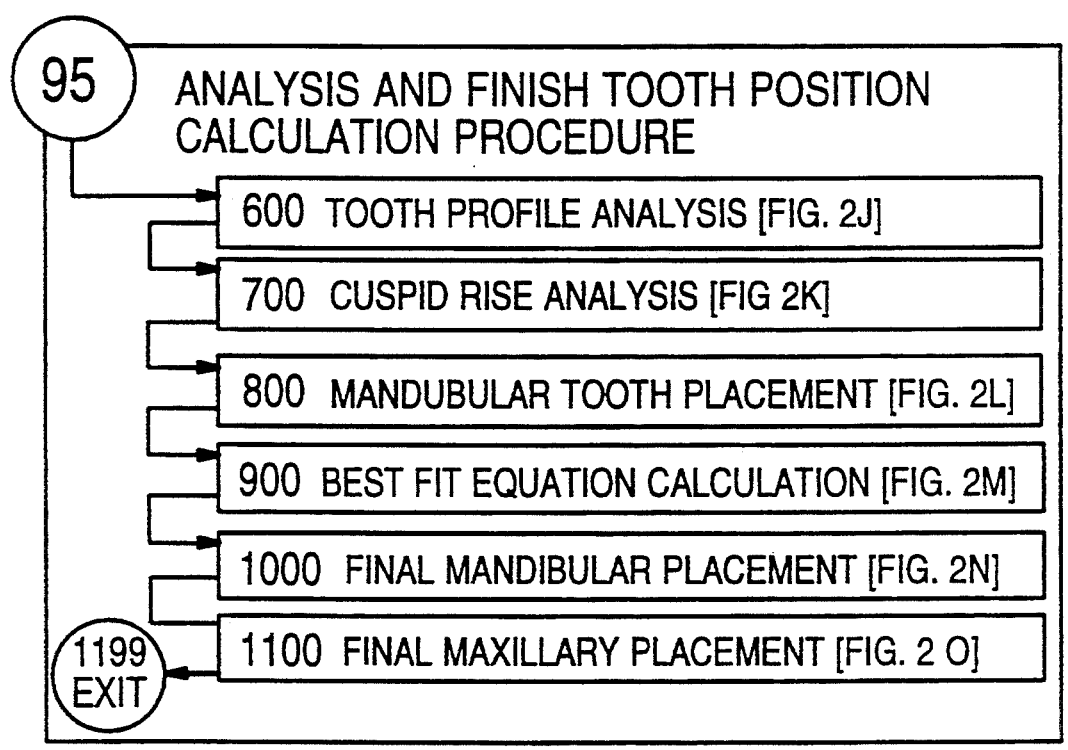
FIG. 2B is a more specific flow chart illustrating the steps of the analysis and tooth finish position calculating procedure of the automated tooth positioning and appliance design and manufacturing operation of the process of FIG. 2.
Figure 2C:
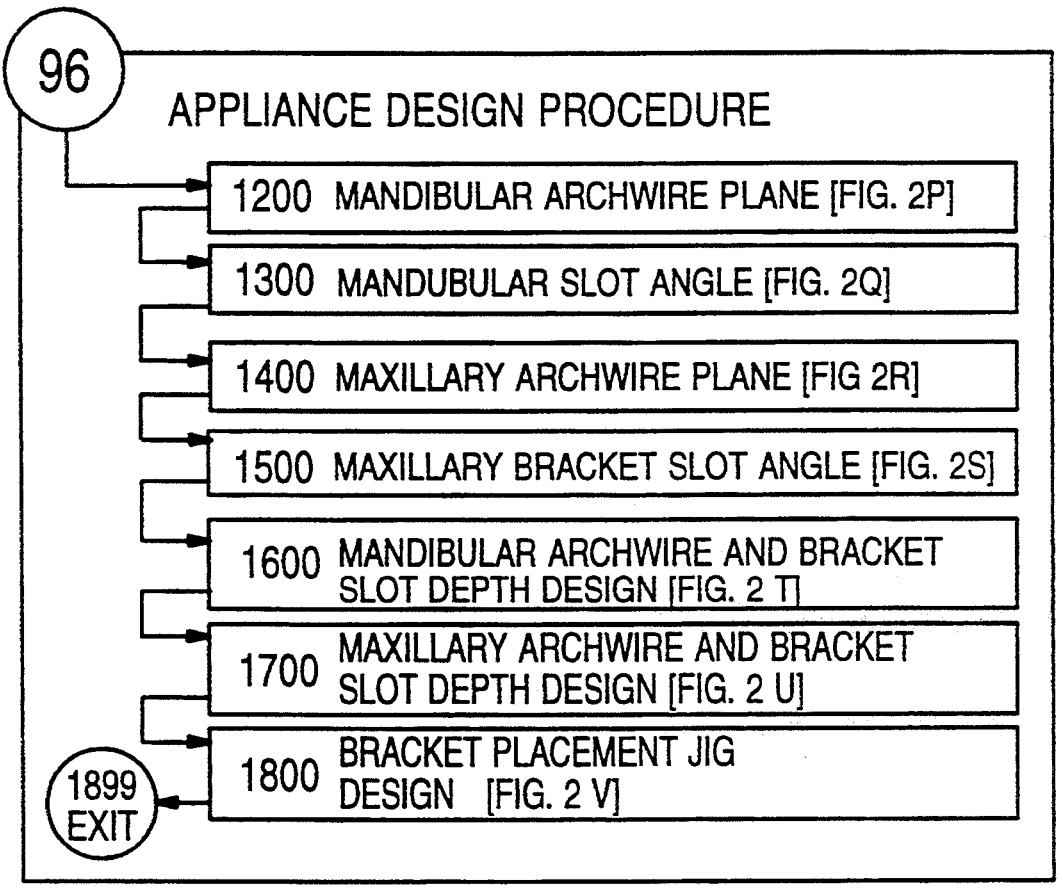
FIG. 2C is a more specific flow chart illustrating the steps of the custom appliance design procedure of the automated appliance design and manufacturing operation of the process of FIG. 2.
Figure 2D:
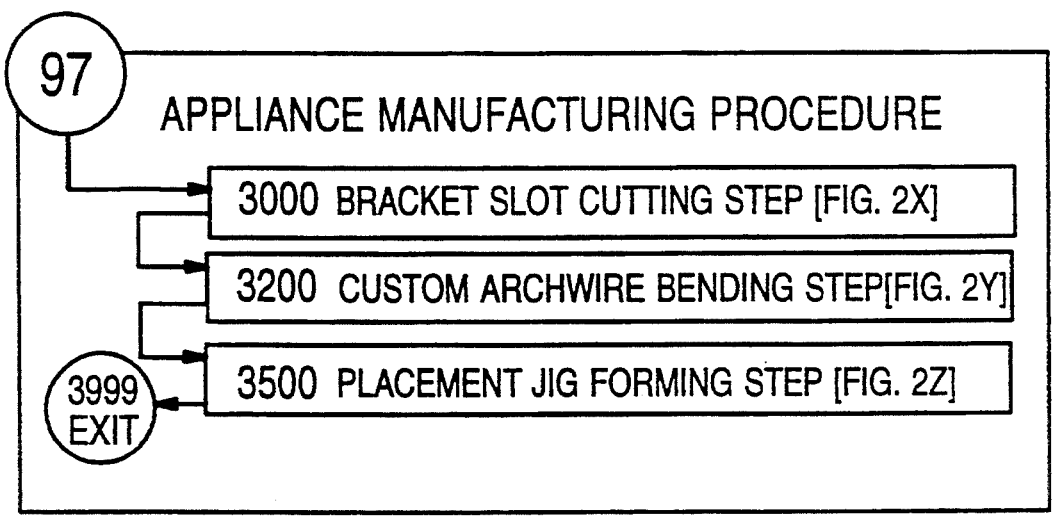
FIG. 2D is a more specific flow chart illustrating the steps of the custom appliance manufacturing procedure of the automated tooth positioning and appliance design and manufacturing operation of the process of FIG. 2.
Figure 2E:
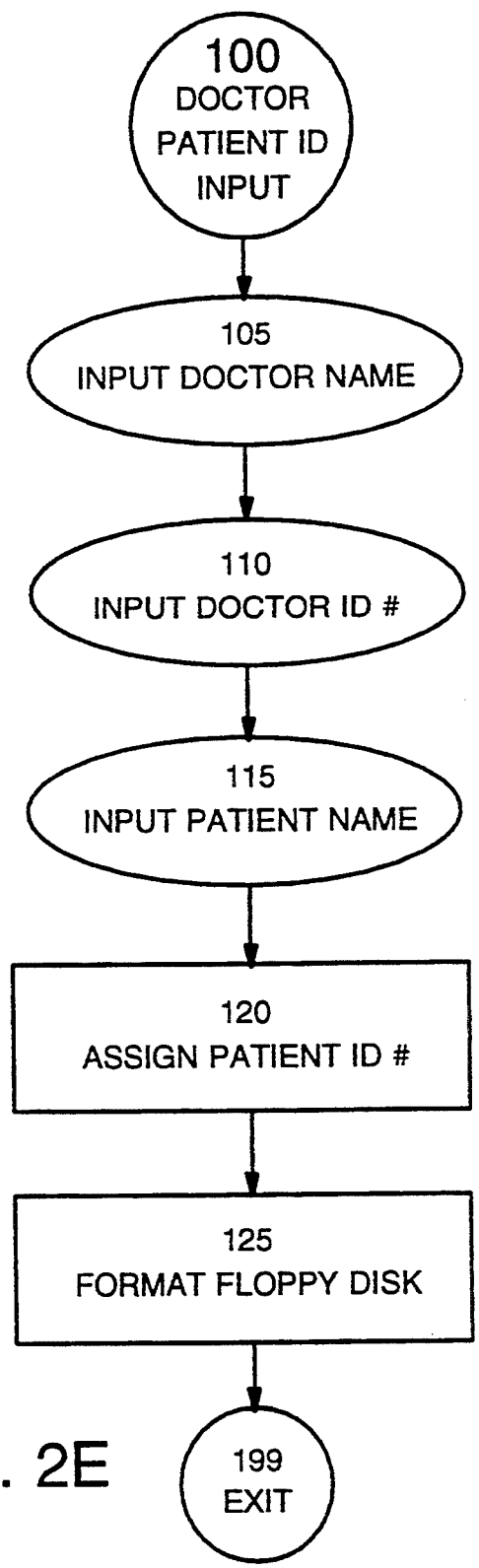
FIG. 2E is a detailed flow chart illustrating the substeps of the identification data input step of the input procedure of FIG. 2A.
Figure 2F:
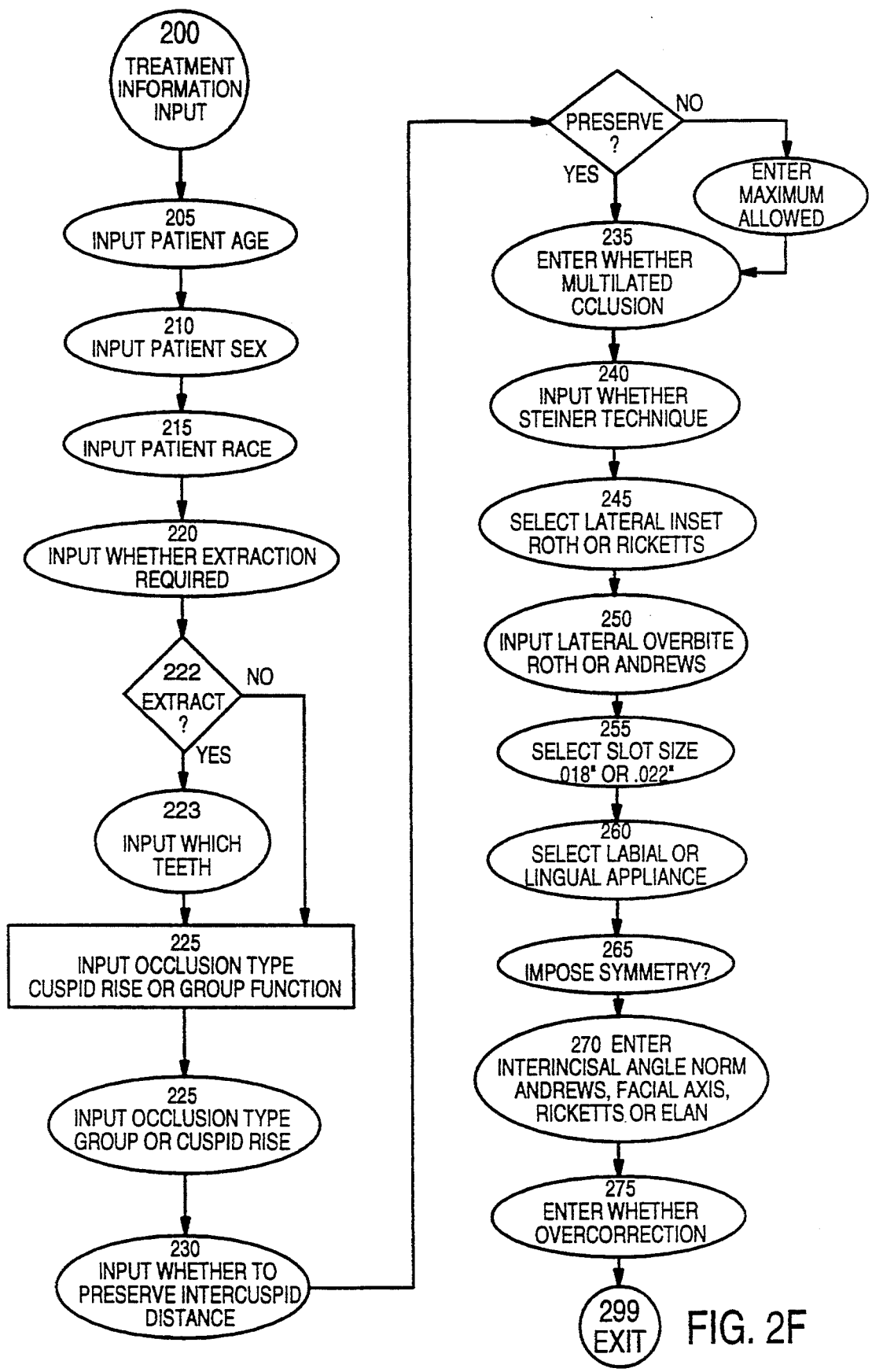
FIG. 2F is a detailed flow chart illustrating the substeps of the patient history and treatment data input step of the input procedure of FIG. 2A.
Figure 2G:
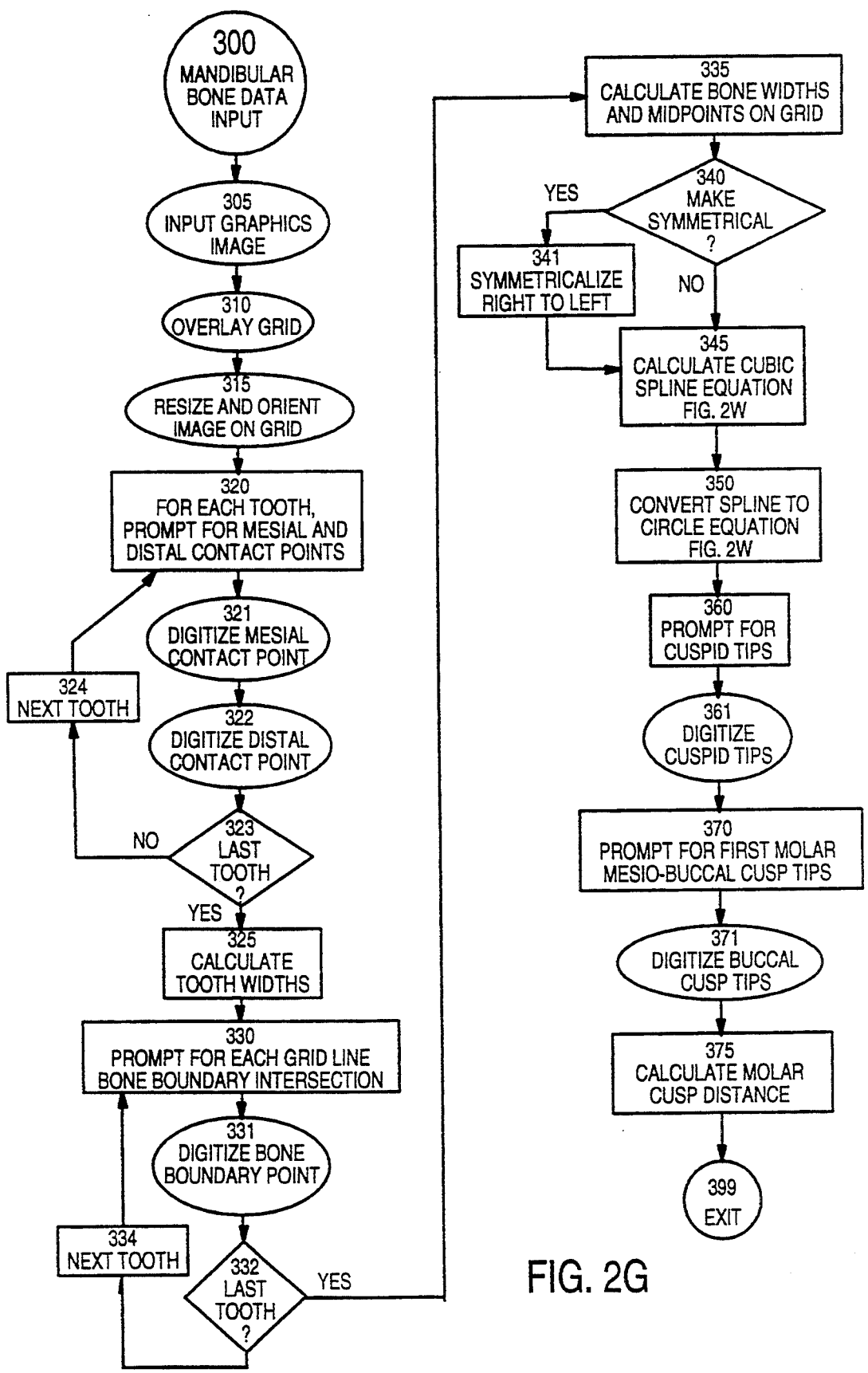
FIG. 2G is a detailed flow chart illustrating the substeps of the mandibular bone and horizontal tooth dimension data input step of the input procedure of FIG. 2A.
Figures 2H, 2I:
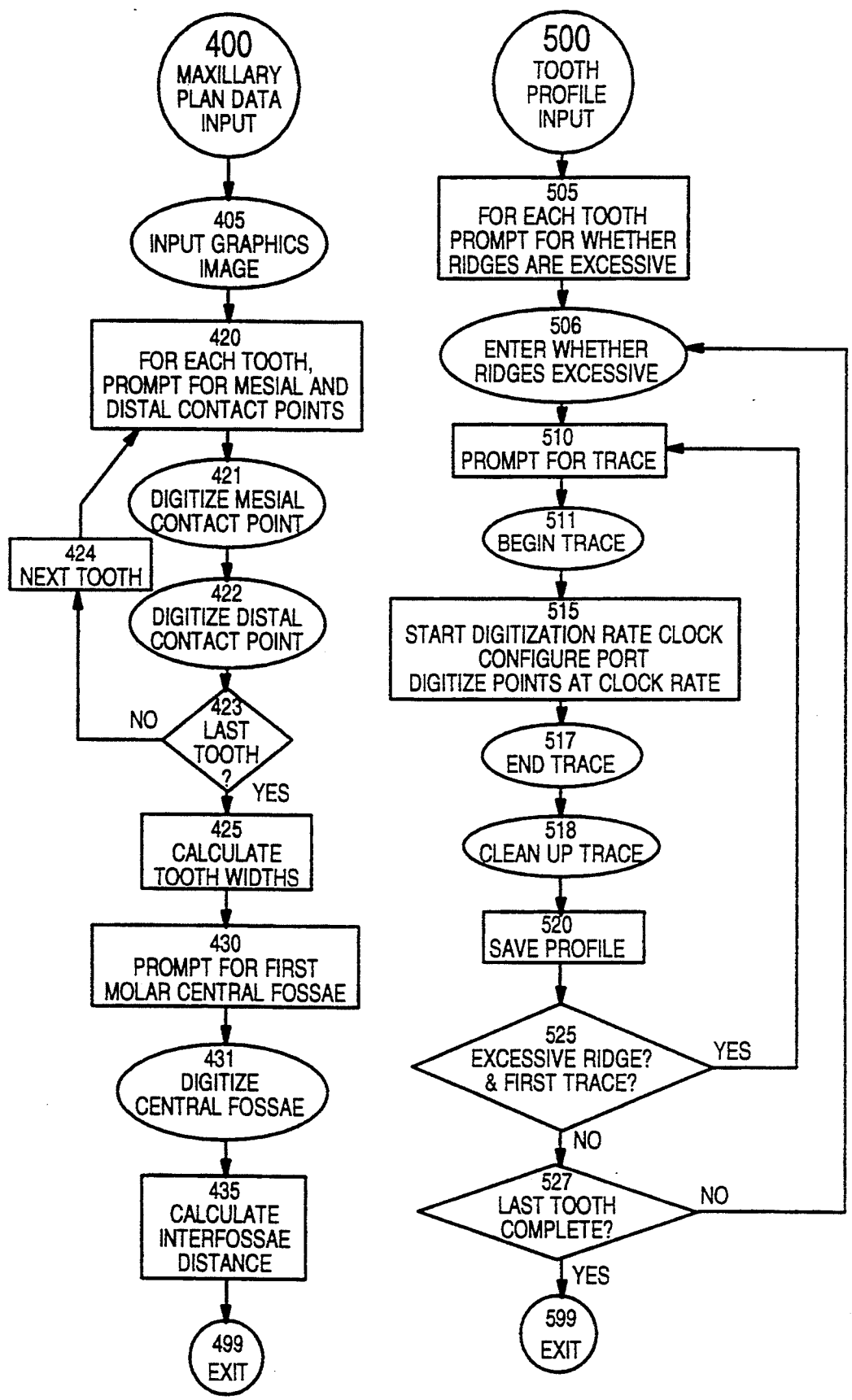
FIG. 2H is a detailed flow chart illustrating the substeps of the maxillary horizontal tooth dimension data input step of the input procedure of FIG. 2A.
FIG. 2I is a detailed flow chart illustrating the substeps of the individual tooth vertical profile data input step of the input procedure of FIG. 2A.
Figure 2J:
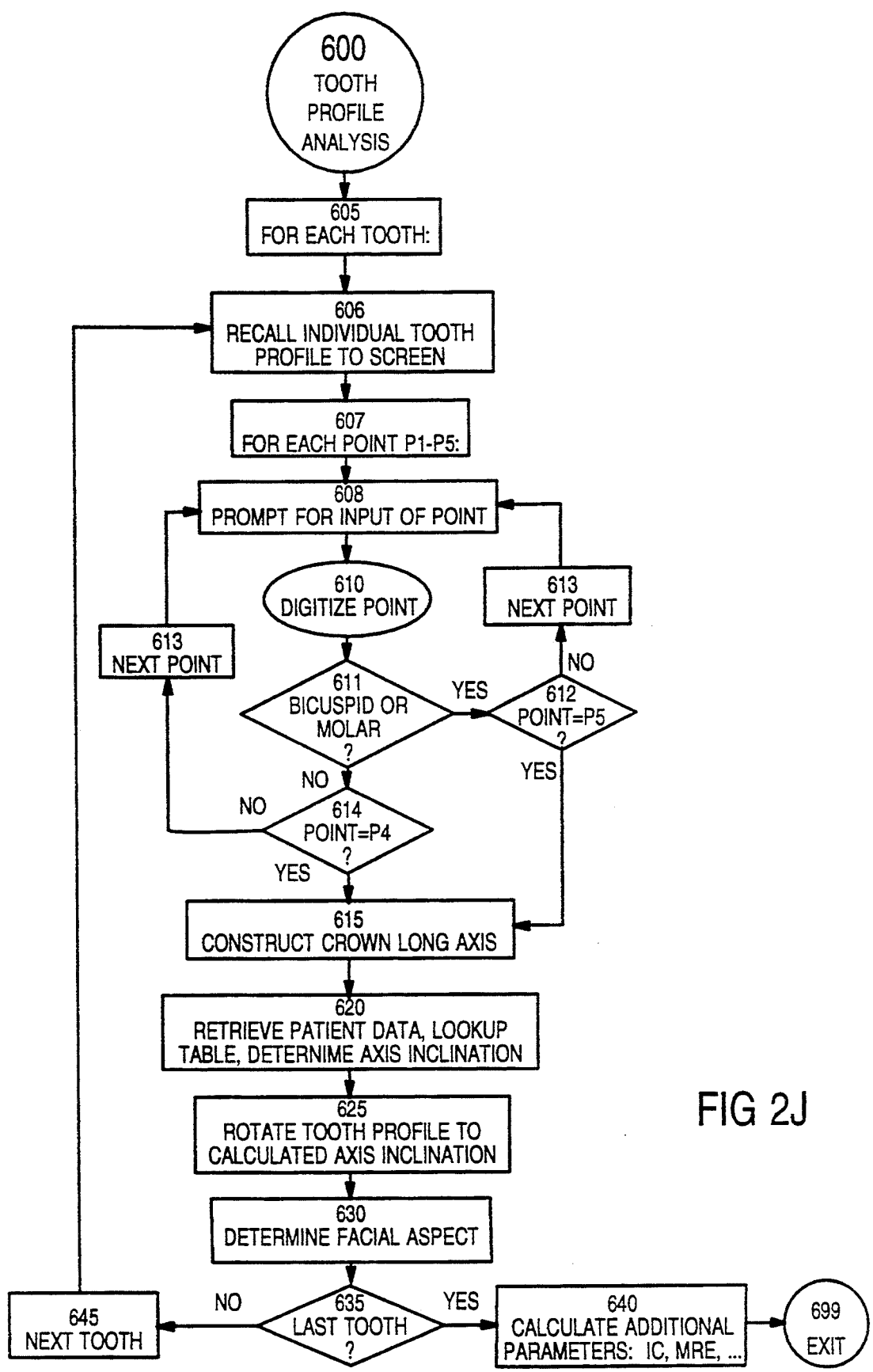
FIG. 2J is a detailed flow chart illustrating the substeps of the individual tooth profile analysis and landmark identification step of the analysis procedure of FIG. 2B.
Figure 2K:
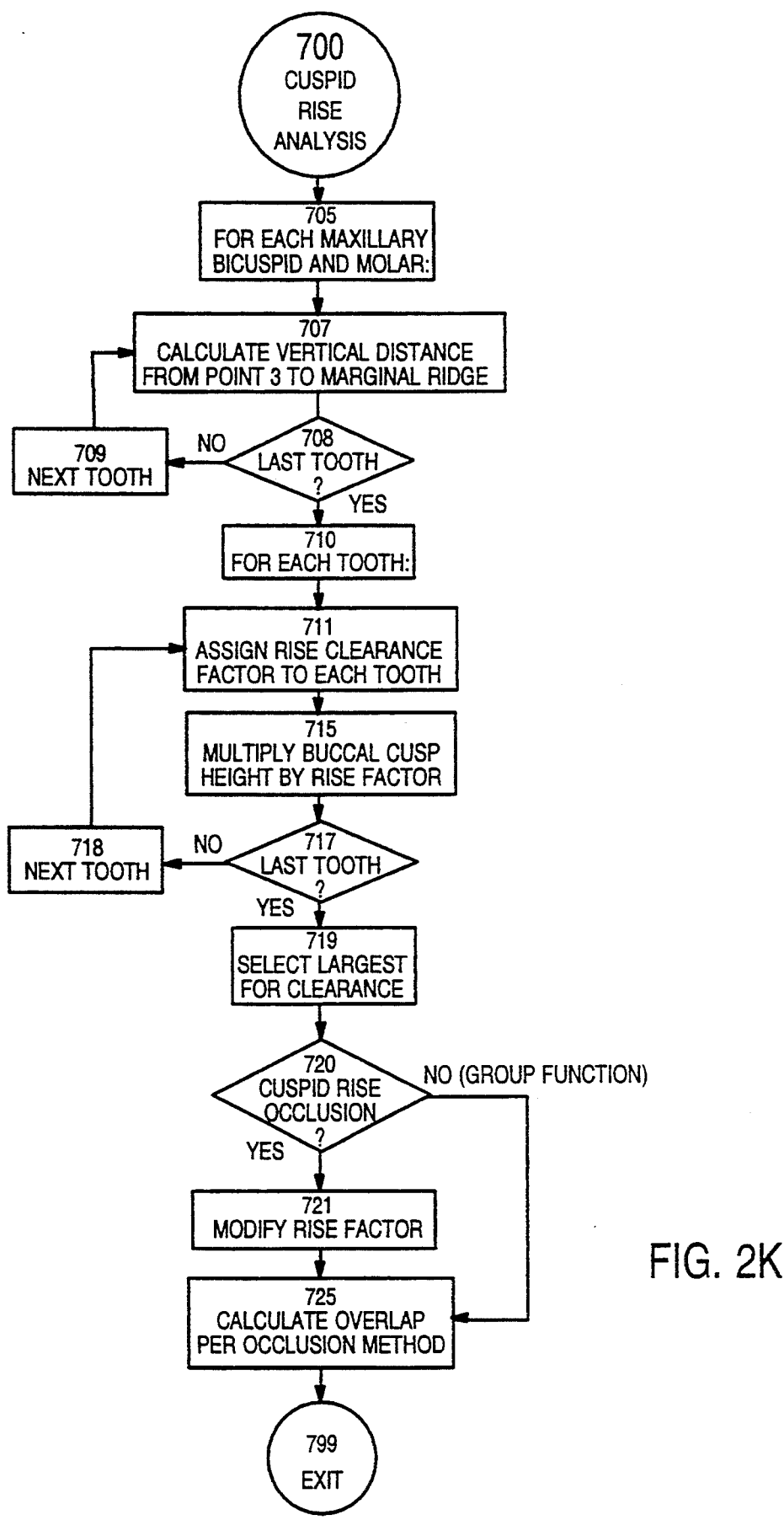
FIG. 2K is a detailed flow chart illustrating the substeps of the cuspid rise calculation step of the analysis procedure of FIG. 2B.
Figure 2L:
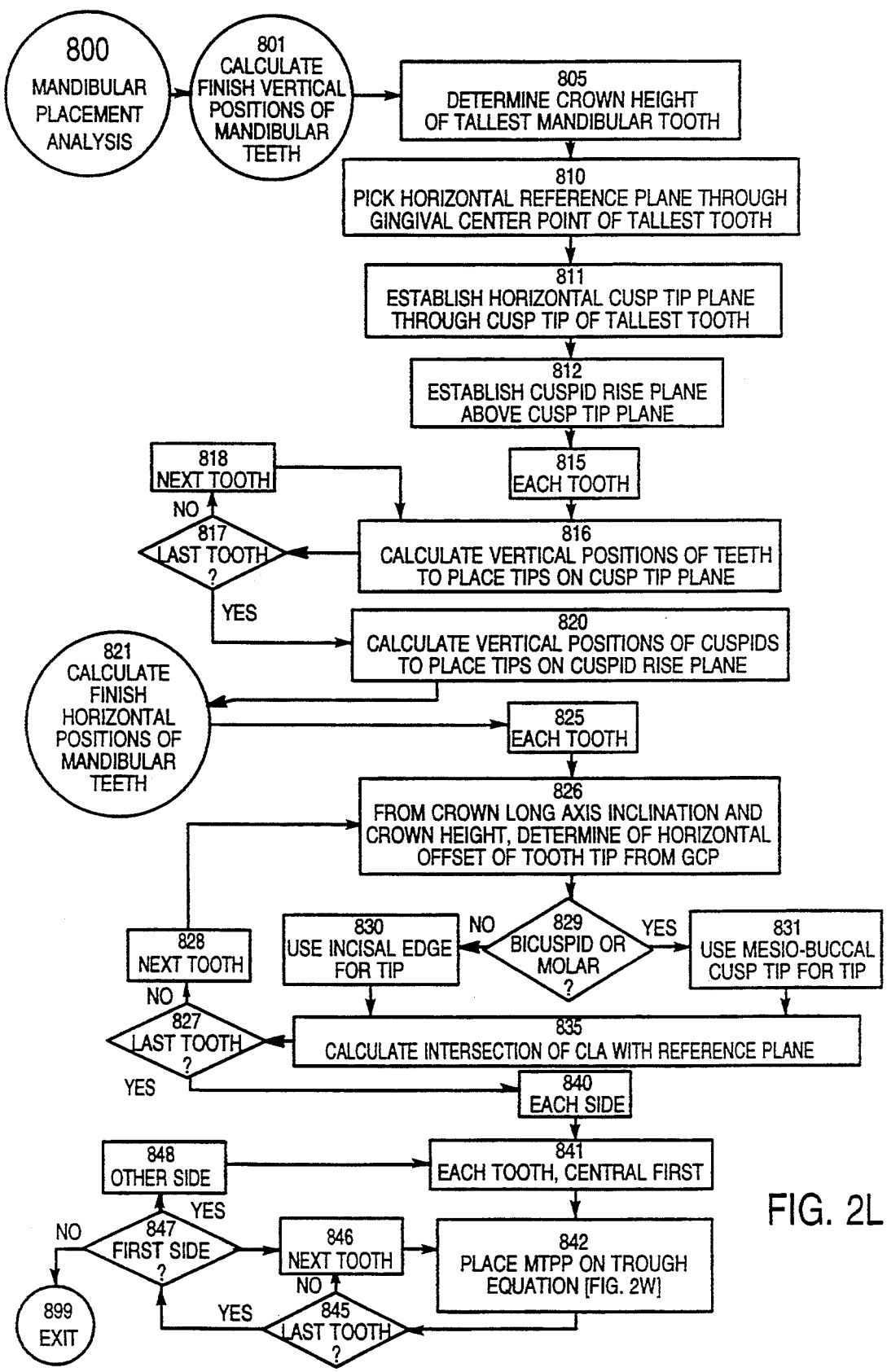
FIG. 2L is a detailed flow chart illustrating the substeps of the mandibular preliminary horizontal tooth finish position calculation step of the analysis procedure of FIG. 2B.
Figures 2M, 2N:
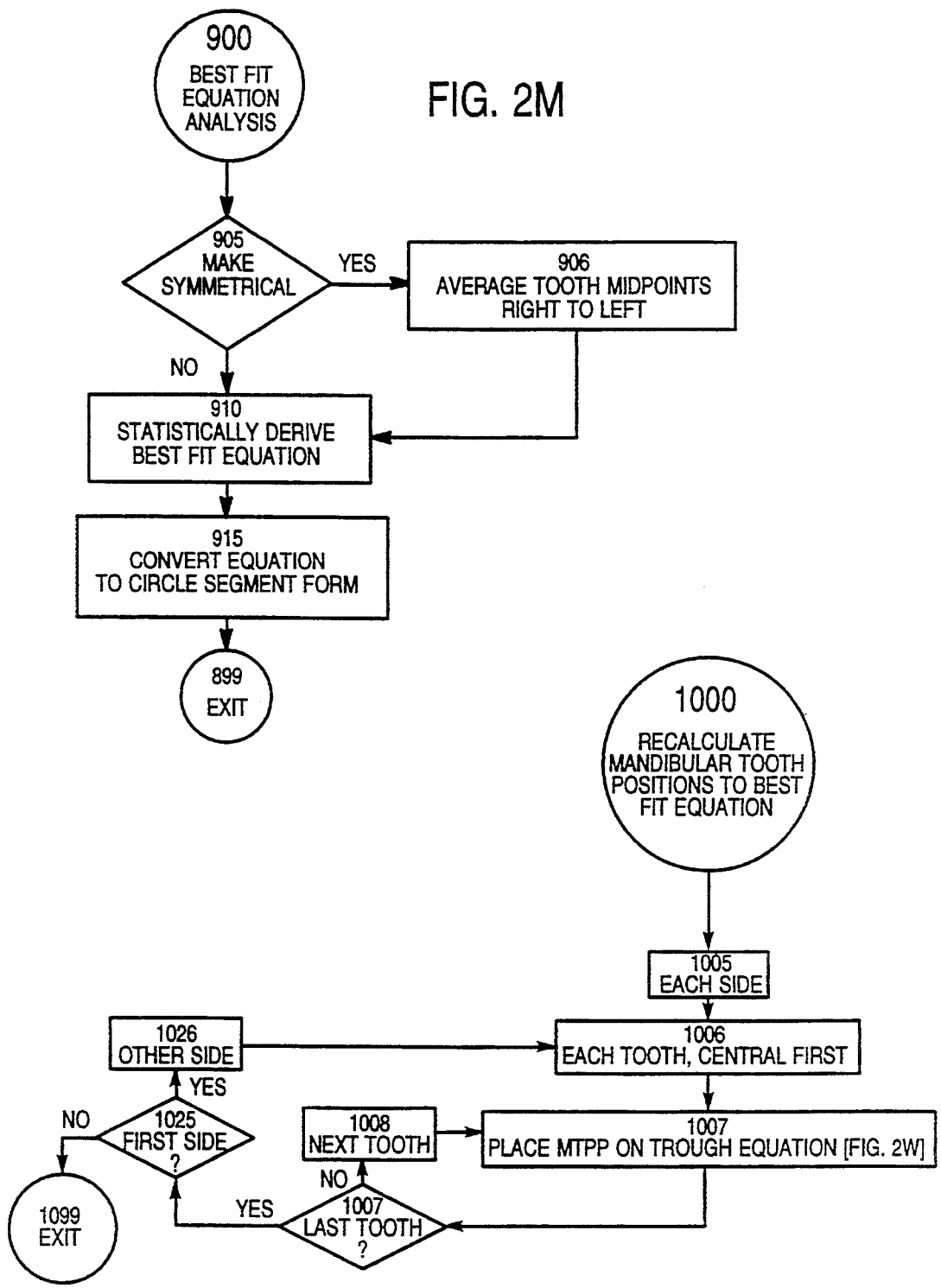
FIG. 2M is a detailed flow chart illustrating the substeps of the best fit mandibular cusp arch equation calculation step of the analysis procedure of FIG. 2B.
FIG. 2N is a detailed flow chart illustrating the substeps of the calculation step of the mandibular tooth finish position on the best fit mandibular cusp arch equation of the analysis procedure of FIG. 2B.
Figure 2:
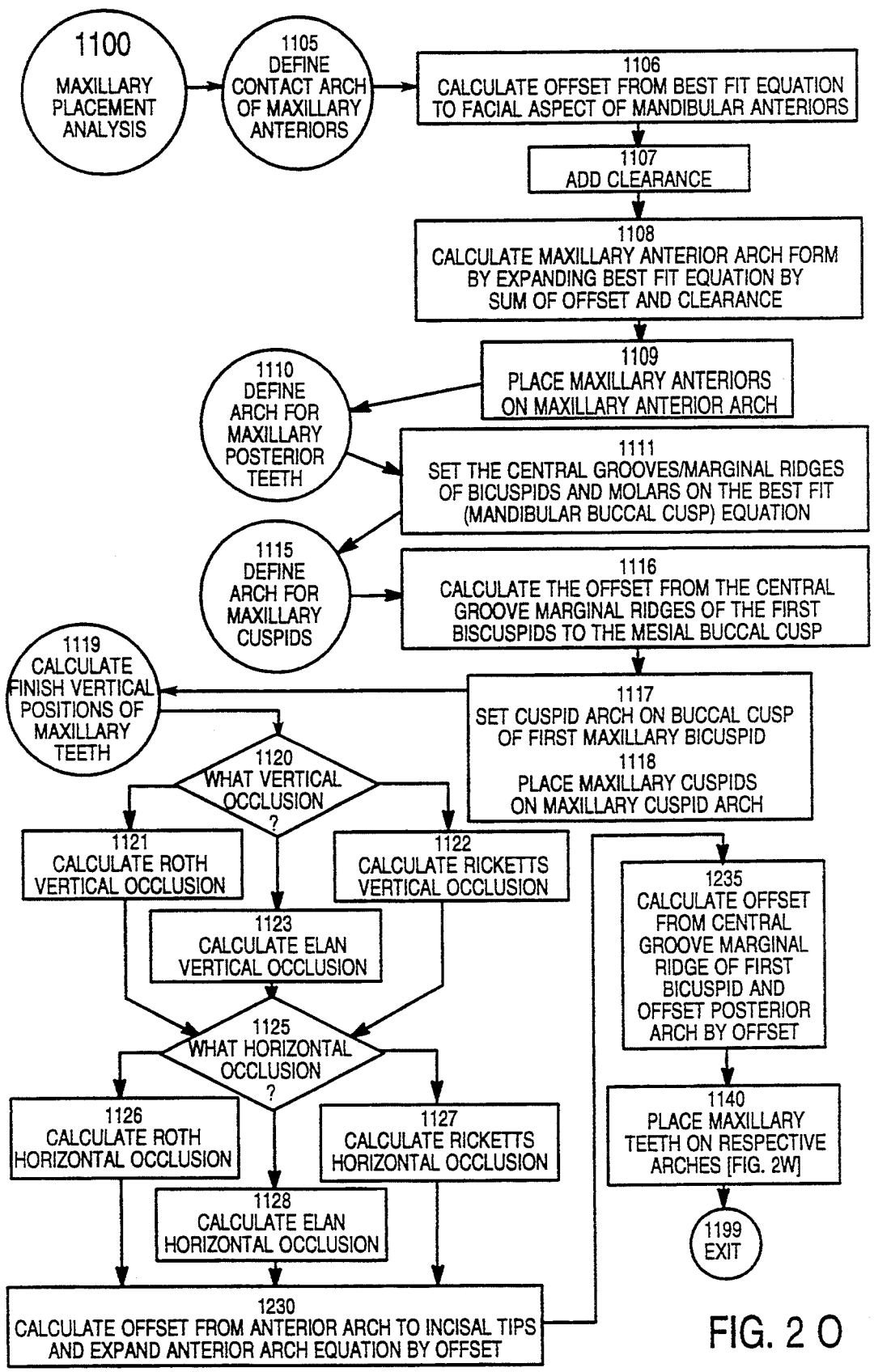
Figures 2P, 2Q:
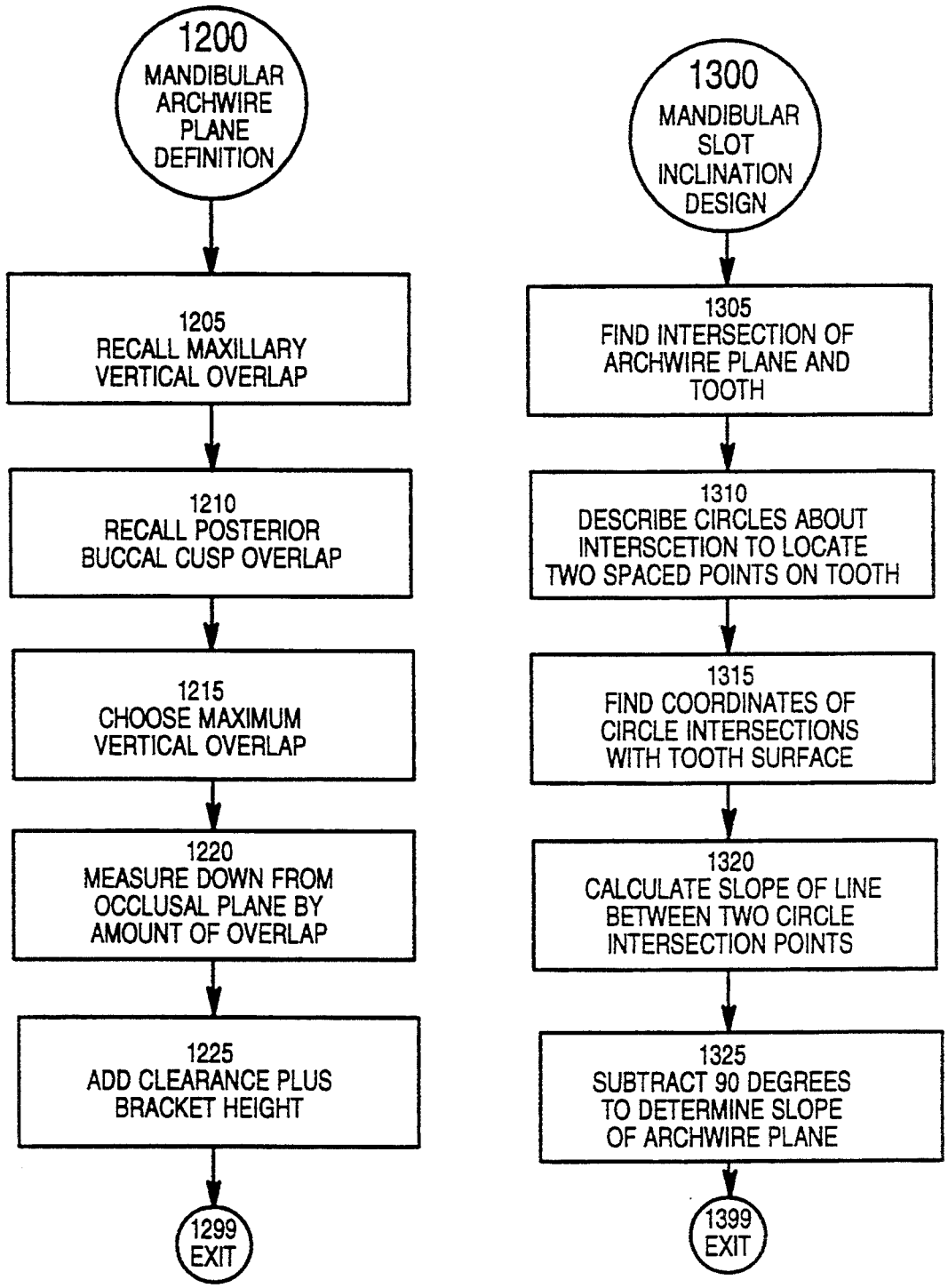
FIG. 2P is a detailed flow chart illustrating the substeps of the mandibular archwire plane calculation step of the appliance design procedure of FIG. 2C.
FIG. 2Q is a detailed flow chart illustrating the substeps of the mandibular bracket slot inclination calculation step of the appliance design procedure of FIG. 2C.
Figures 2R, 2S:
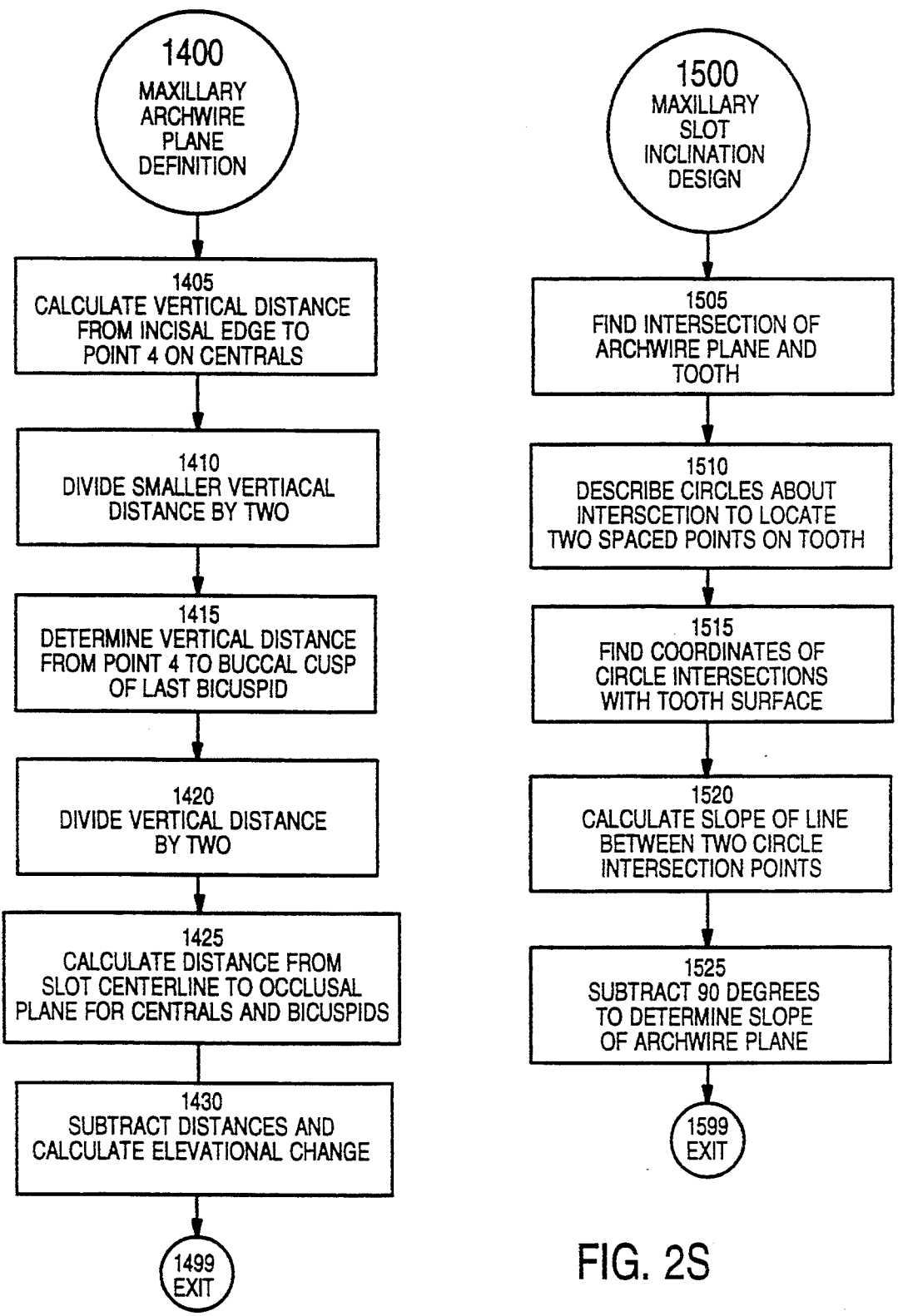
FIG. 2R is a detailed flow chart illustrating the substeps of the maxillary archwire plane calculation step of the appliance design procedure of FIG. 2C.
FIG. 2S is a detailed flow chart illustrating the substeps of the maxillary bracket slot inclination calculation step of the appliance design procedure of FIG. 2C.
Figure 2T:
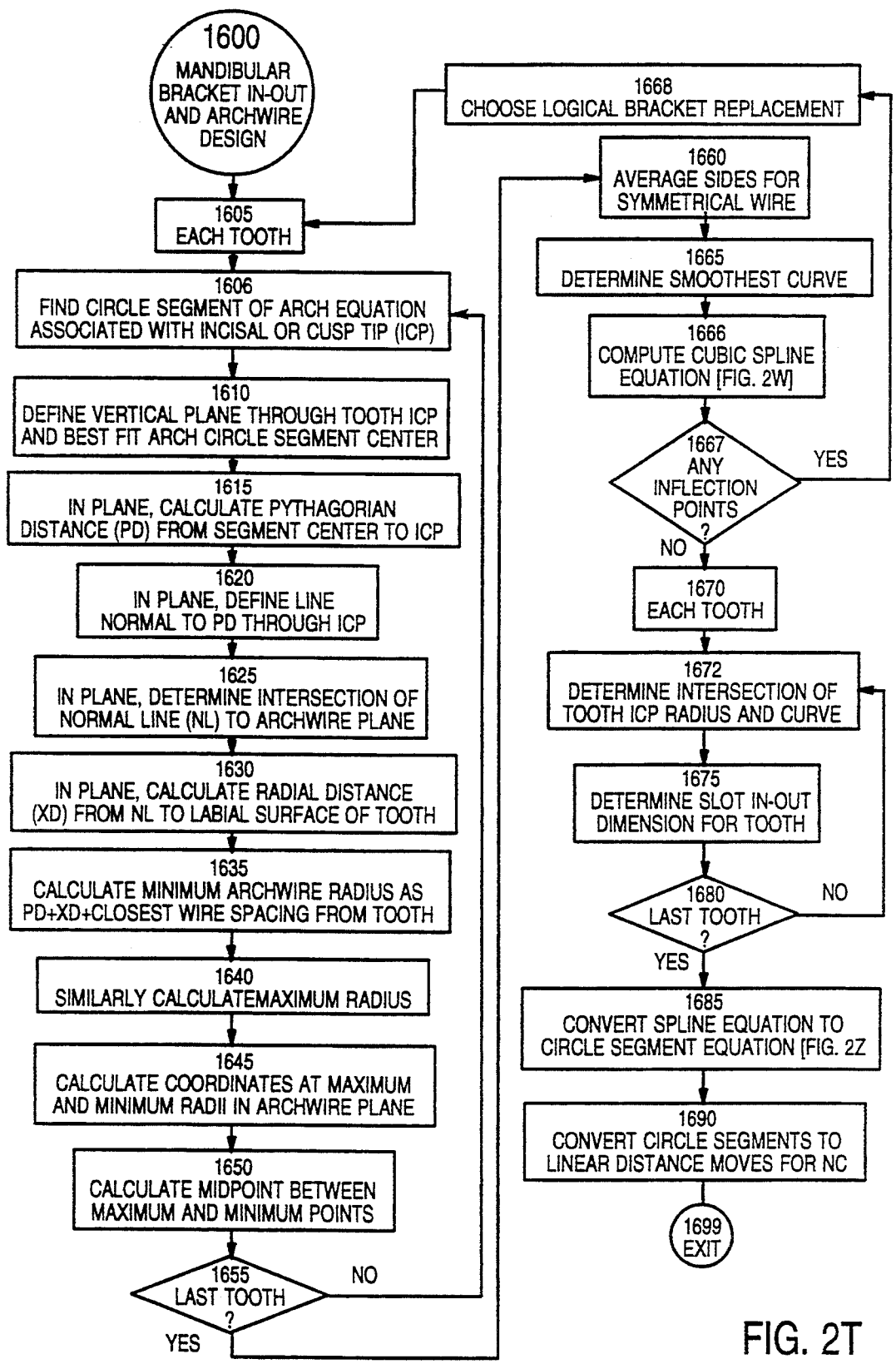
FIG. 2T is a detailed flow chart illustrating the substeps of the mandibular archwire and bracket slot in-out dimension calculation step of the appliance design procedure of FIG. 2C.
Figure 2U:
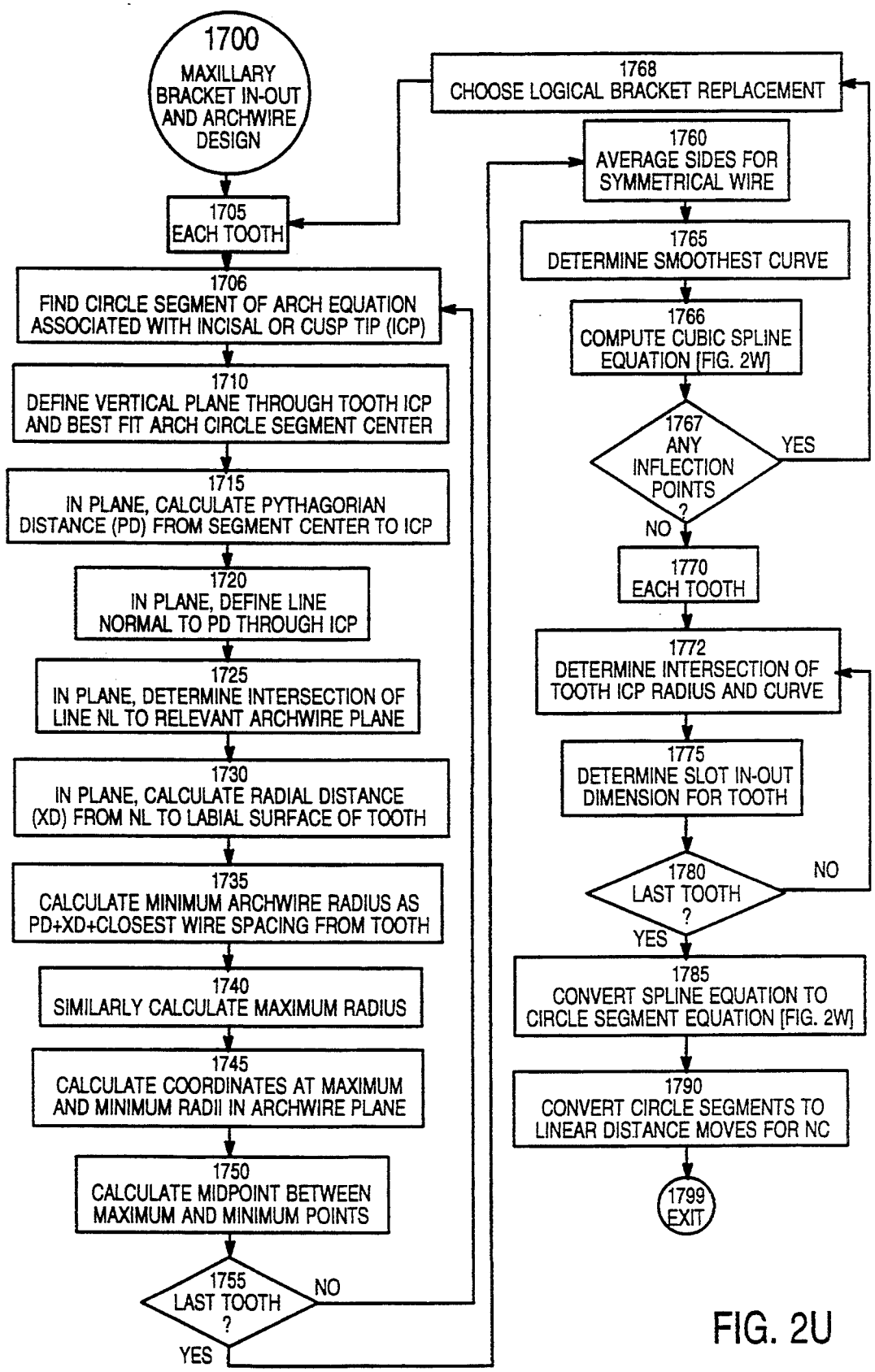
FIG. 2U is a detailed flow chart illustrating the substeps of the maxillary archwire and bracket slot in-out dimension calculation step of the appliance design procedure of FIG. 2C.
Figure 2V:
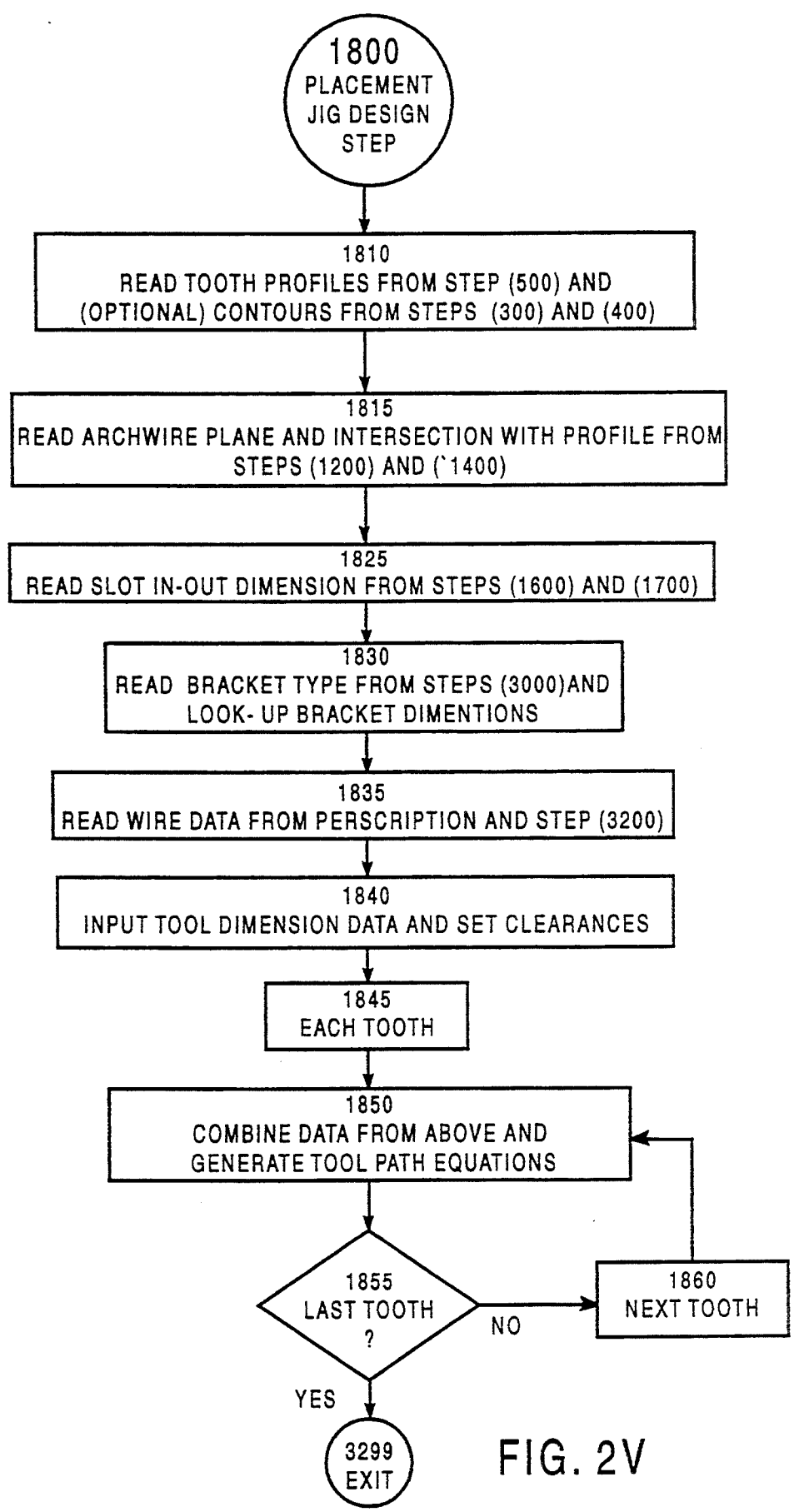
FIG. 2V is a detailed flow chart summarizing the substeps of the bracket placement jig shape calculation step of the appliance design procedure of FIG. 2C that is illustrated in more detail in the flowchart of the jig modification step of FIG. 2Z described below.
Figure 2W:
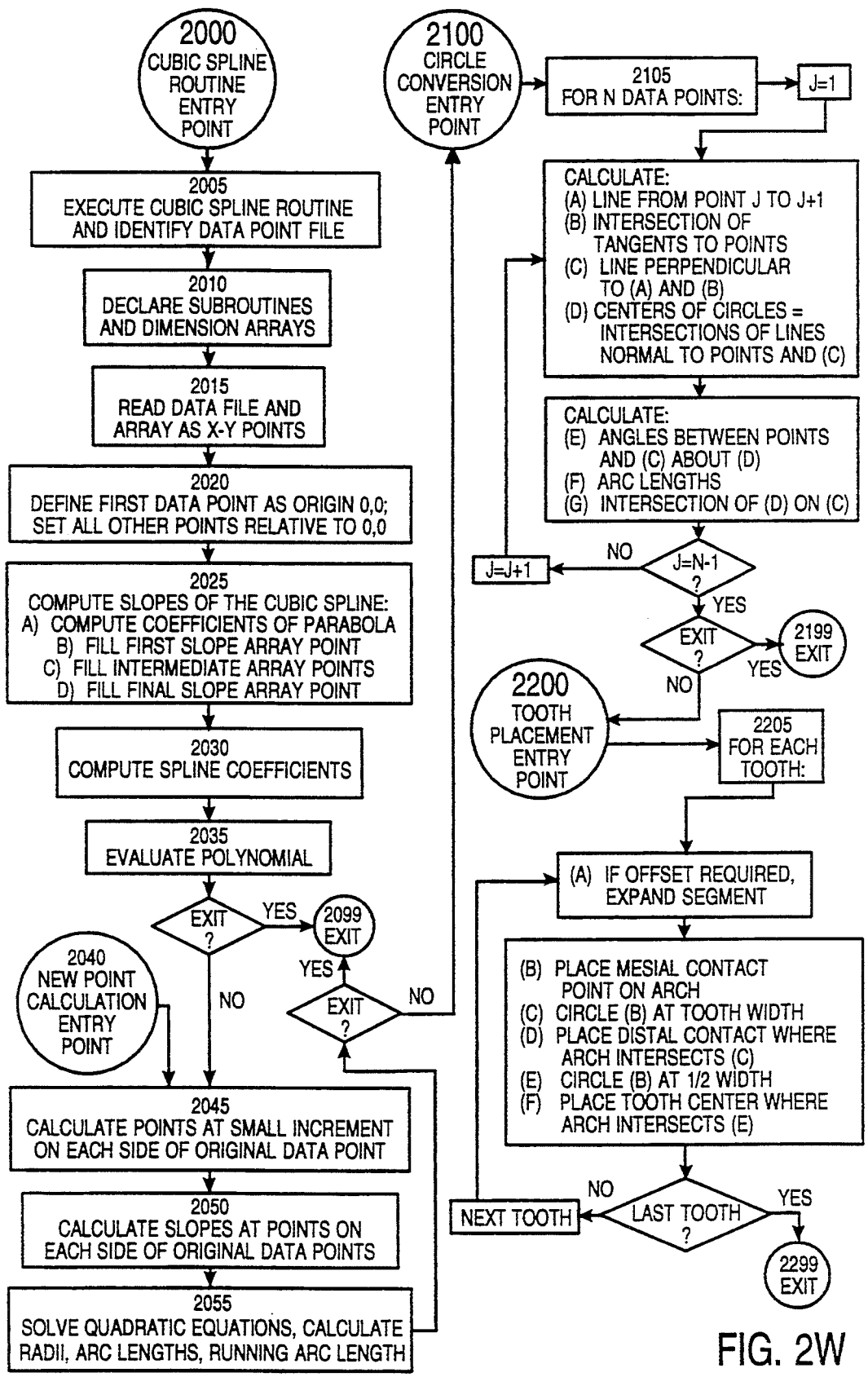
FIG. 2W is a detailed flow chart illustrating the substeps of the cubic spline curve fitting, spline to circle conversion and tooth placement calculation subroutines employed in placing teeth on calculated archforms in certain steps of the tooth positioning and appliance design and manufacturing operation of FIG. 2C.
Figure 2X:
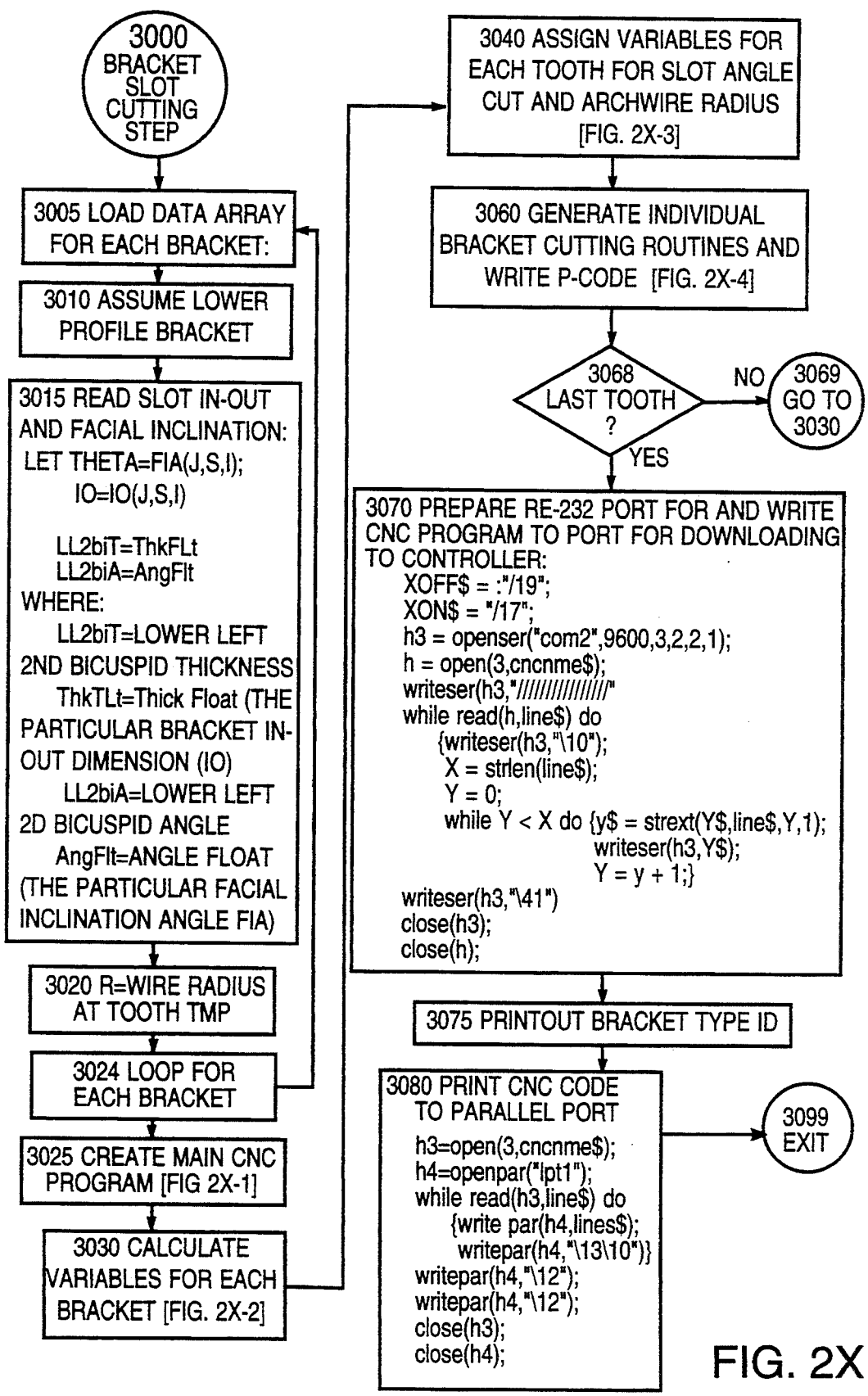
FIG. 2X is a detailed flow charts illustrating the NC code generation and slot cutting substeps of the bracket manufacturing step of the procedure of FIG. 2D, and FIGS. 2X-1 through 2X-4 are more detailed flowcharts illustrating substeps of FIG. 2X.
Figures 1, 2X:
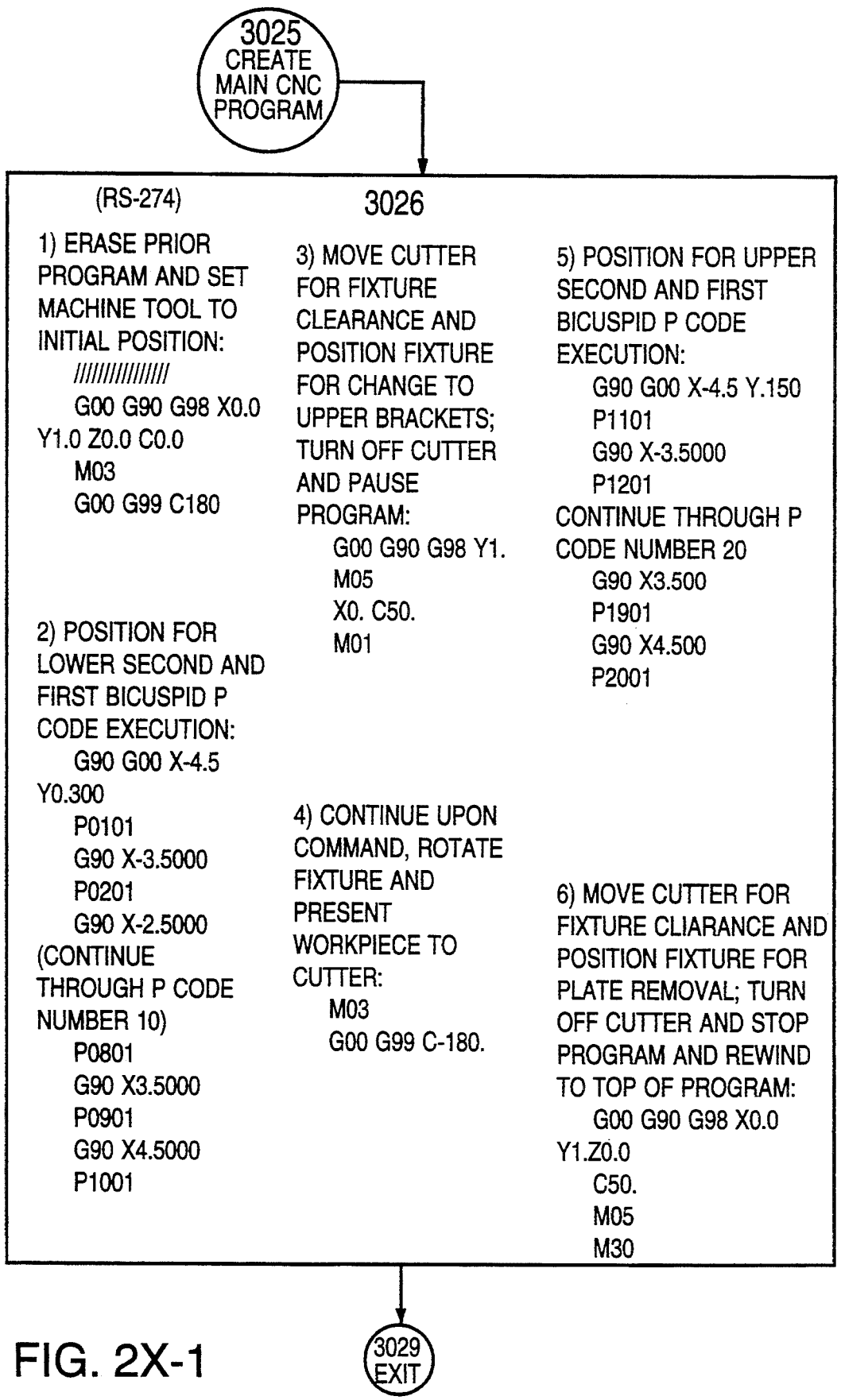
Figures 2, 2X:
Figures 2, 2X, 3:
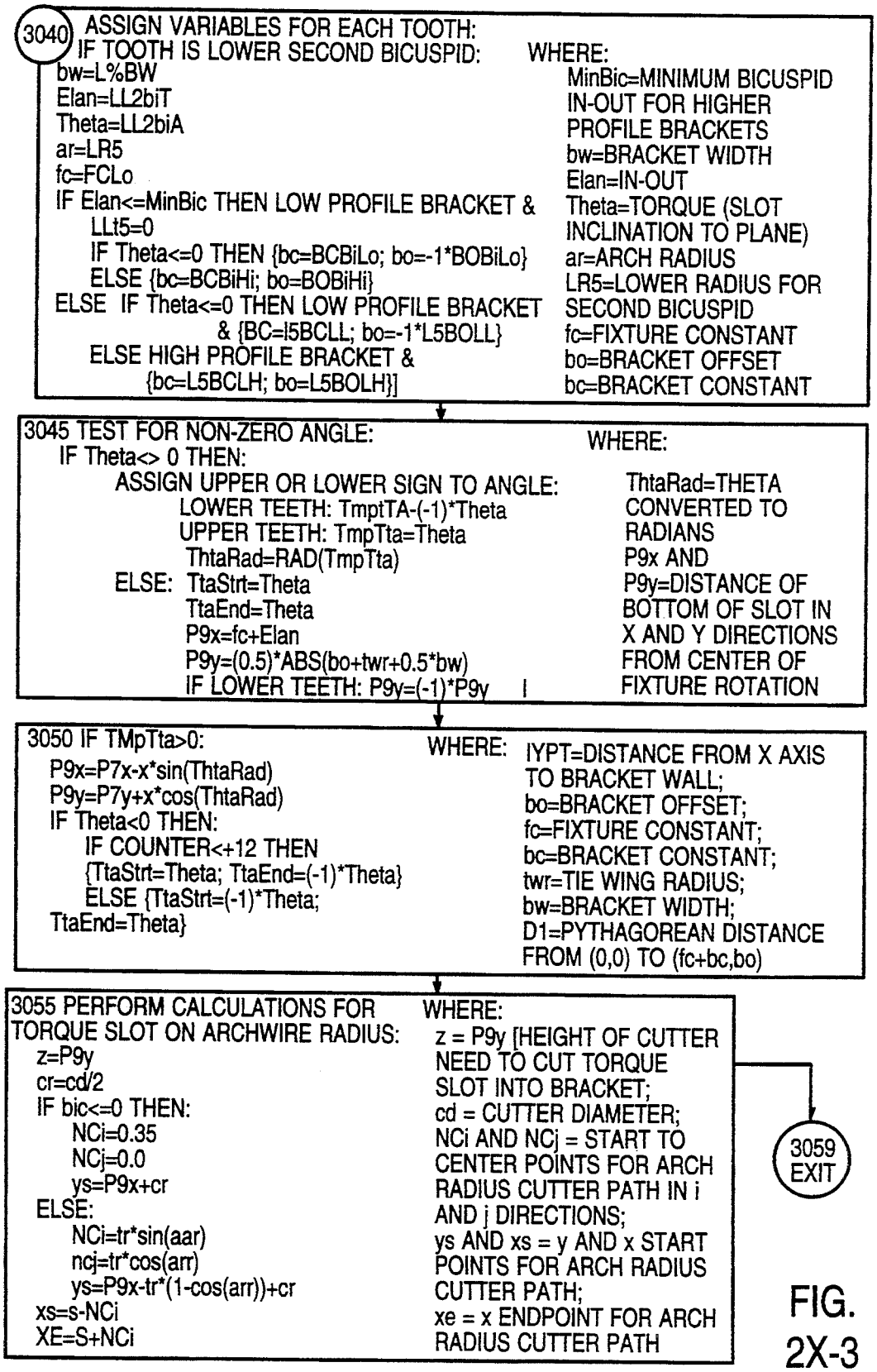
Figure 2Y:
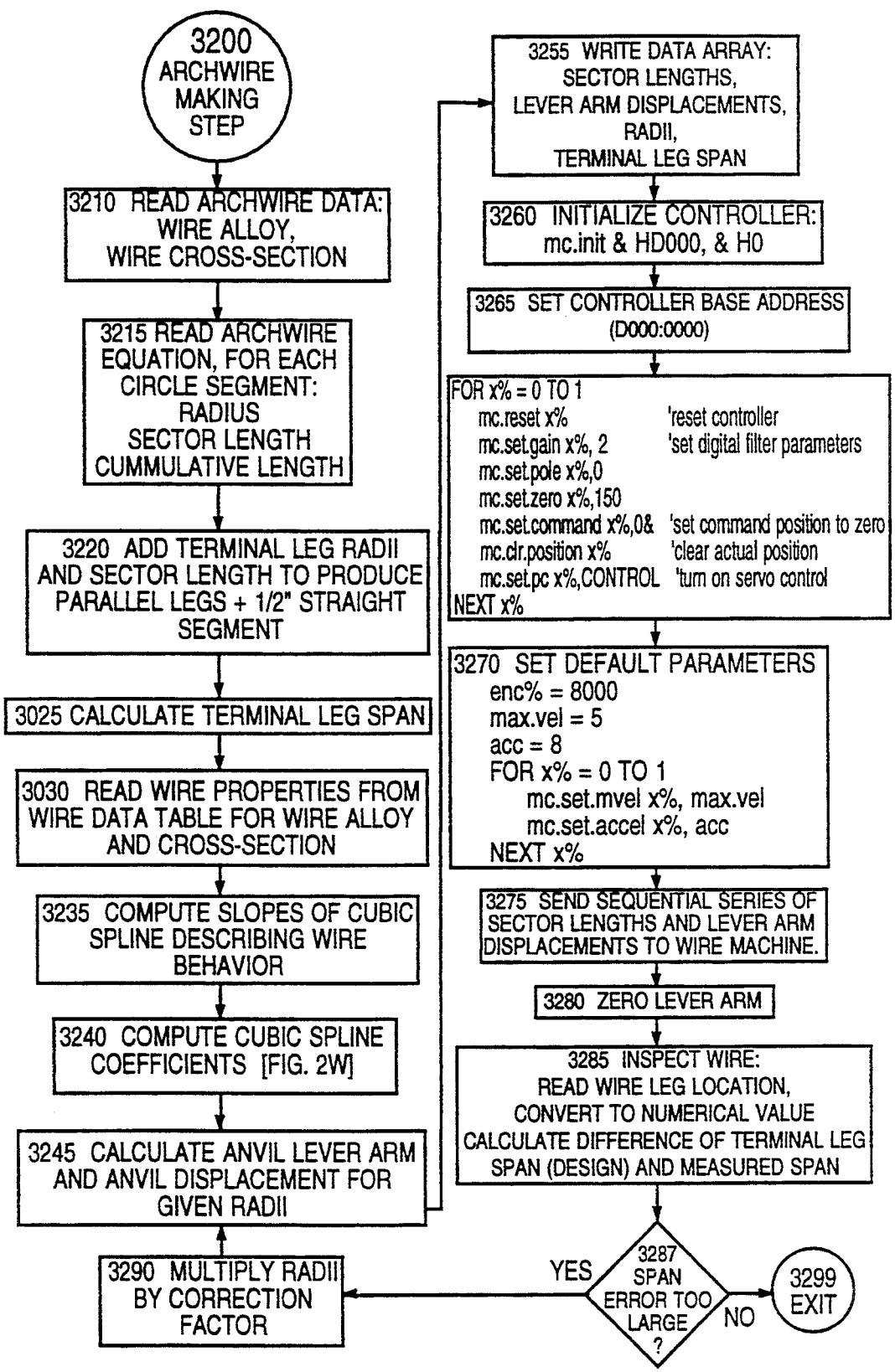
FIG. 2Y is a detailed flow chart of the substeps of the wire bending code generation and wire manufacturing step of the appliance manufacturing procedure of FIG. 2D.
Figure 2Z:
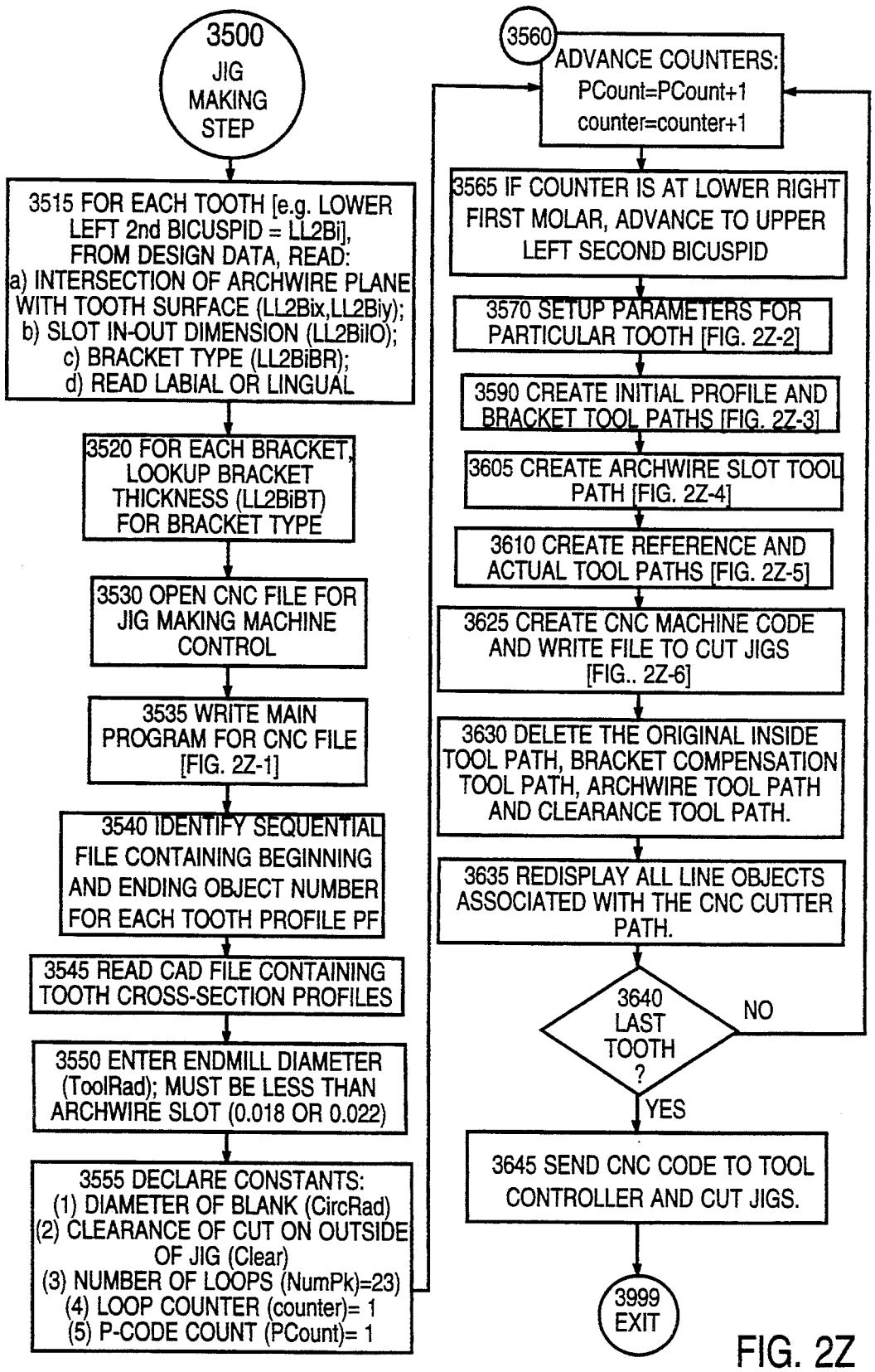
Figures 1, 2, 2Z:
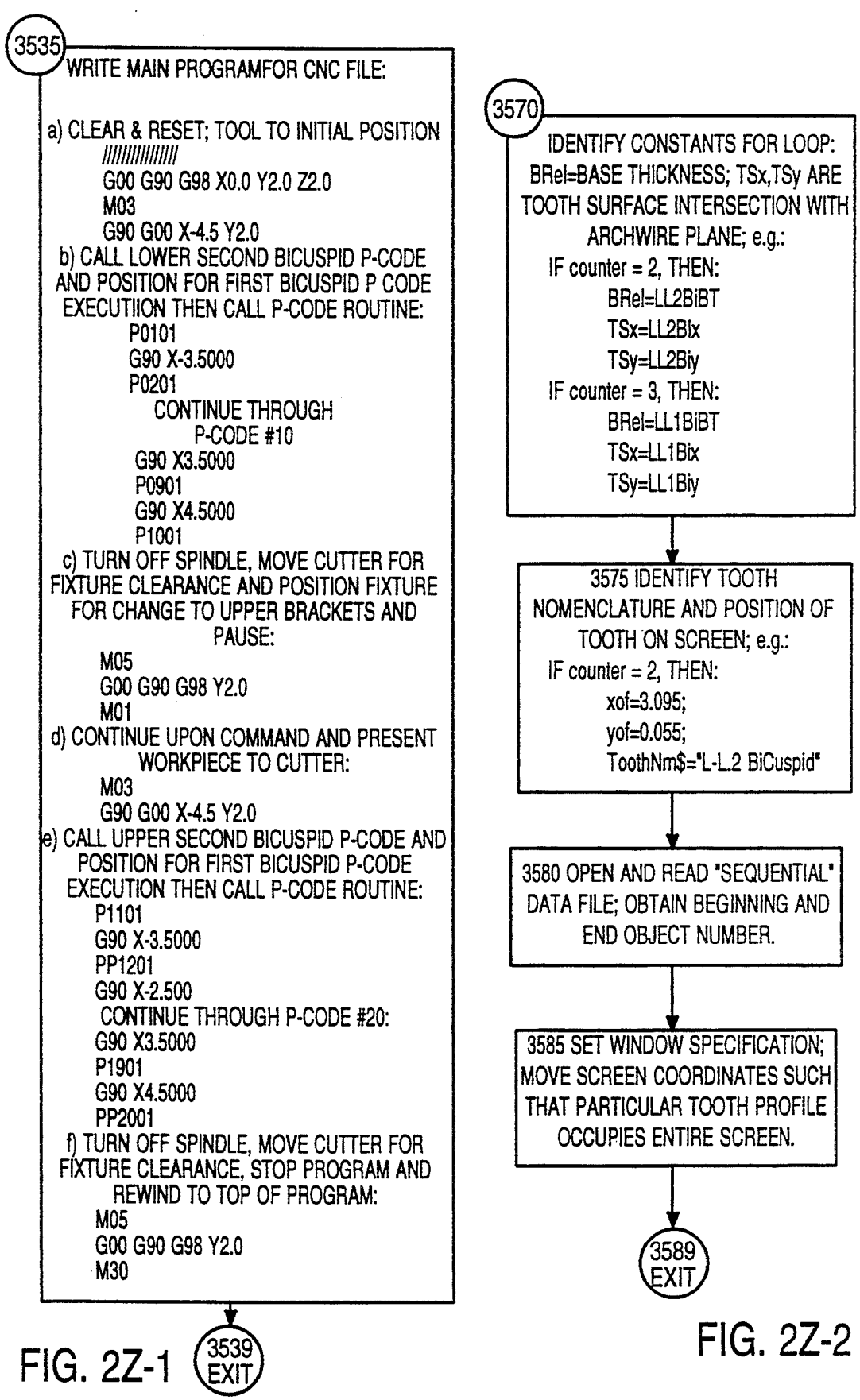
Figures 2, 2Z, 3:
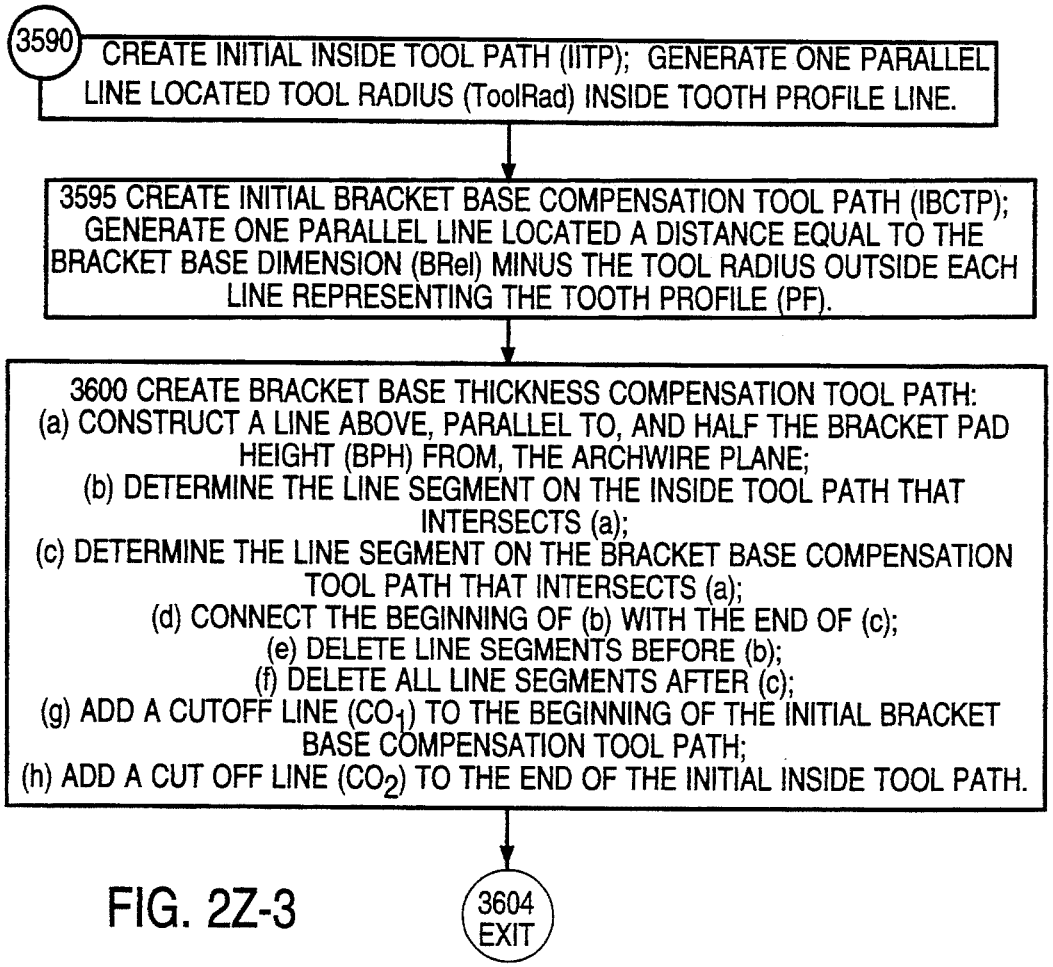

FIG. 2Z is a detailed flow chart illustrating the substeps of the jig manufacturing step of the appliance manufacturing procedure of FIG. 2D. FIGS. 2Z-1 through 2Z-6 are more detailed flowcharts illustrating details of substeps of FIG. 2Z.

Figure 1:
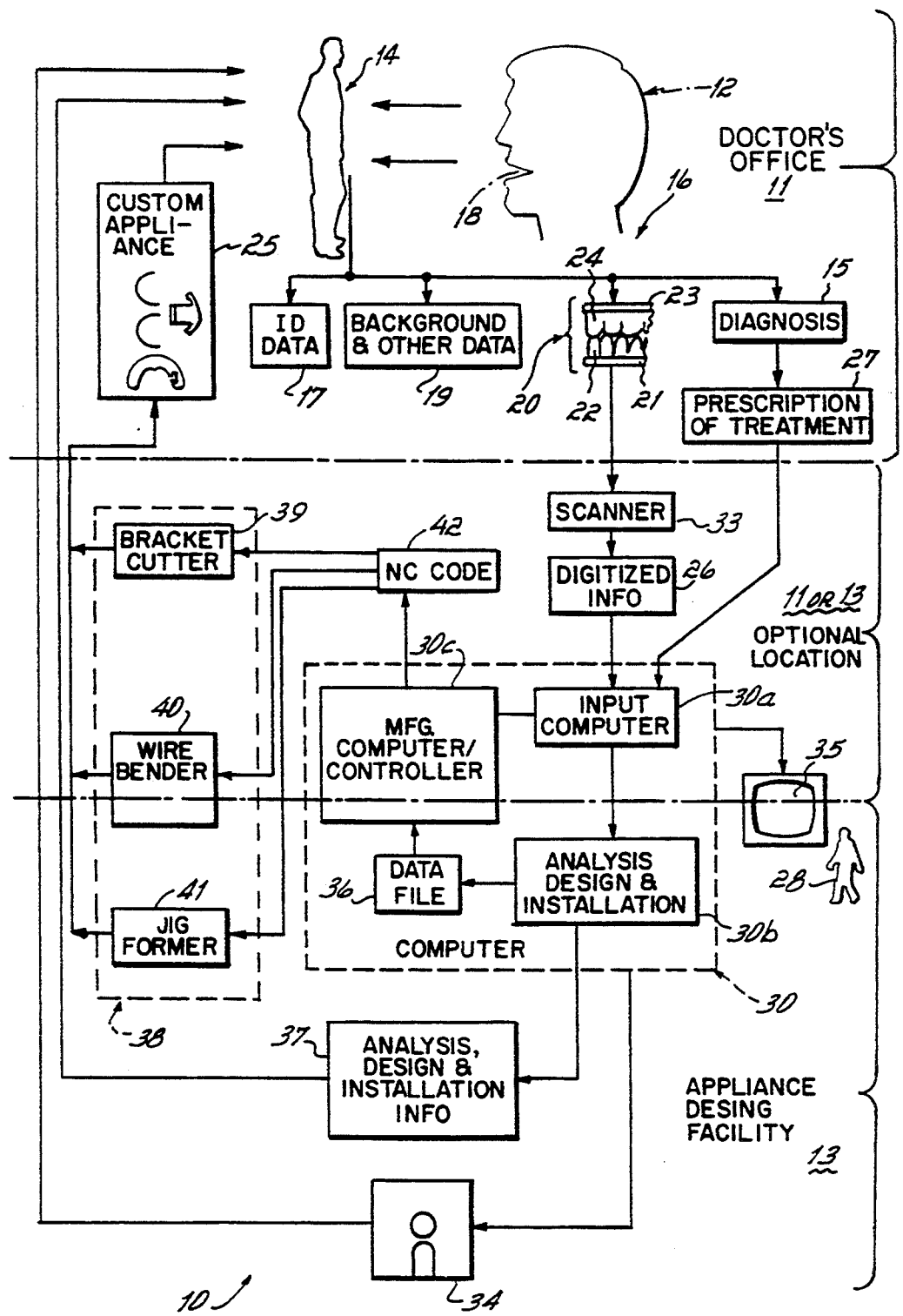
Figure 1A:
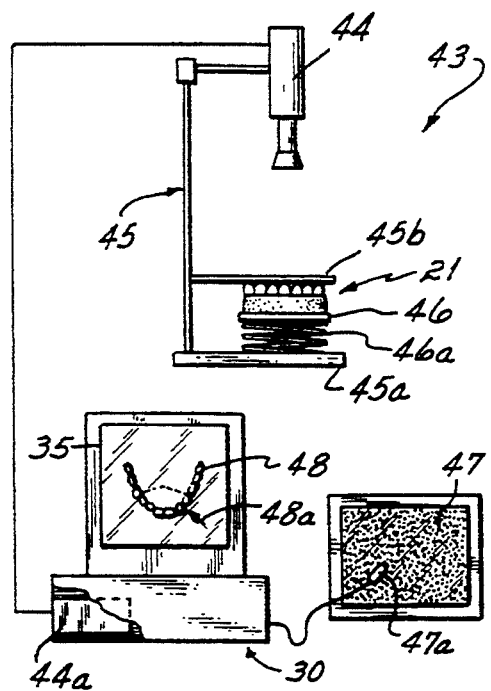
FIG. 1A is an elevational diagram of a video graphics image forming embodiment of the data input portion of one embodiment of the scanner of the system of FIG. 1.

FIGS. 3–3C are illustrations of graphics computer images produced in the input procedure, in which:

FIG. 3 is a an example of a computer display of a video image generated by the scanner of the system of FIG. 1 illustrating in a top plan view a mandibular model produced by the scanner of the type shown in FIG. 1A.

Figure 1B:
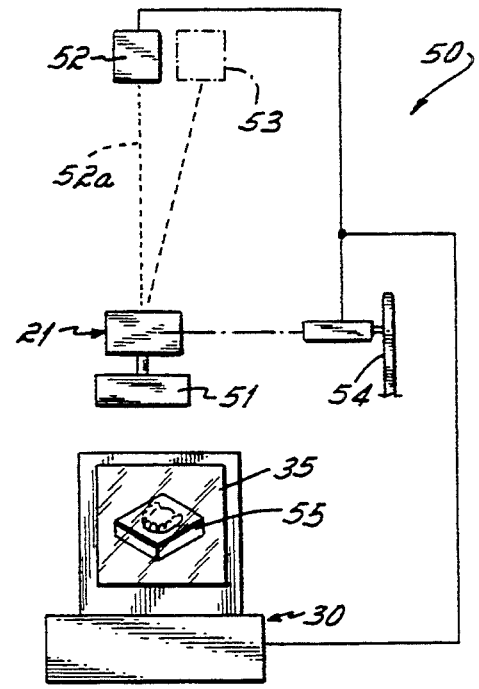
FIG. 1B is an elevational diagram of a laser scanner version of a three dimensional graphics imaging embodiment of a scanner of the system of FIG. 1.
Figure 3:
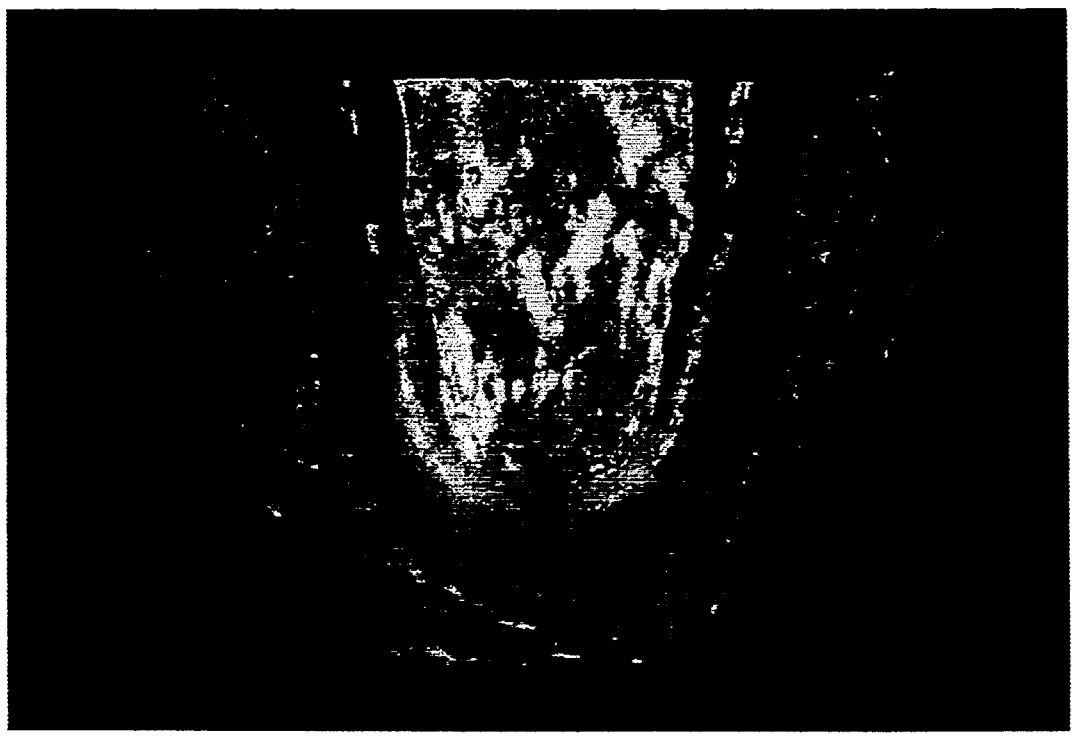
Figure 3B:
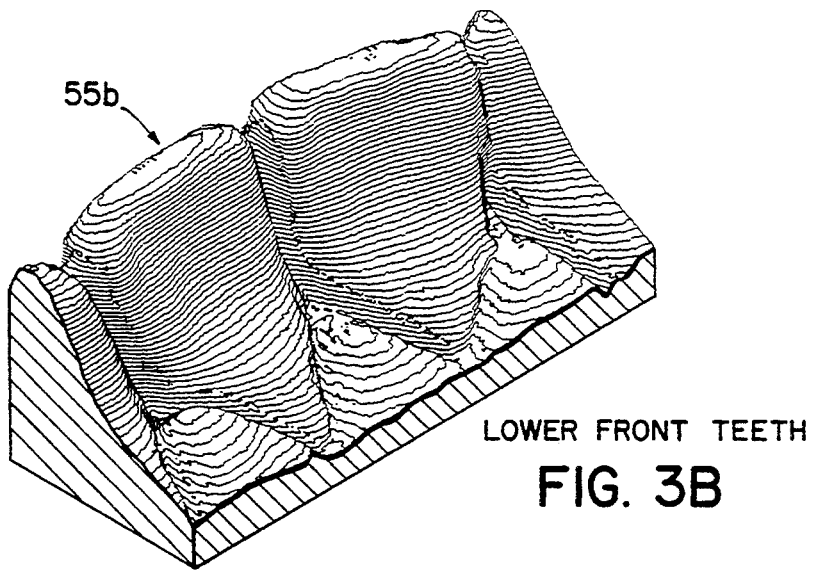
Figure 3A:
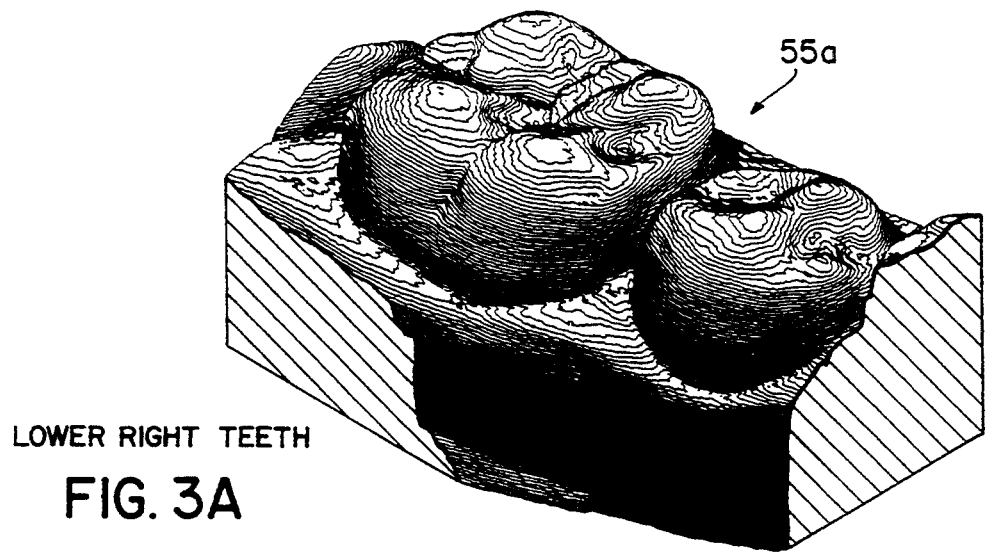

FIG. 3A is a an example of a portion of a three dimensional digital image, illustrated in perspective, and produced by the scanner of the type shown in FIG. 1B.

FIG. 3B is an illustration similar to FIG. 3A of another portion of a three dimensional digital image produced by the scanner of FIG. 1B.

Figure 1C:
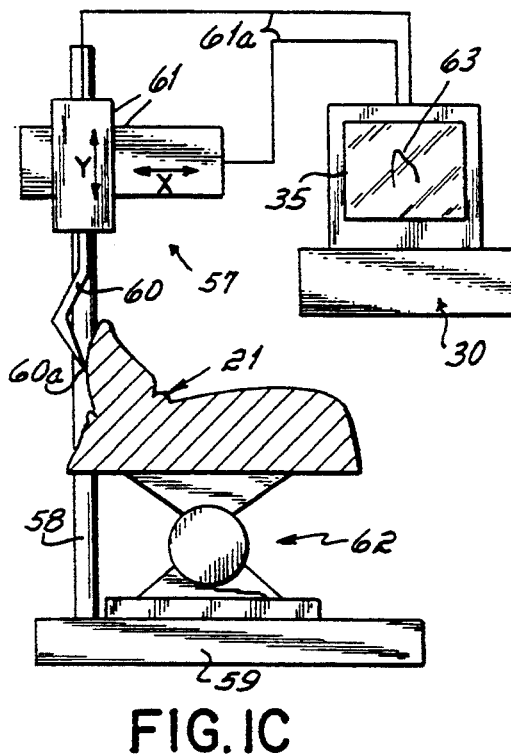
FIG. 1C is an elevational diagram of a mechanical tooth profile probe scanner version of a two dimensional imaging portion of one embodiment of the scanner of the system of FIG. 1.

FIG. 3C is an example of a set of vertical tooth profile images produced by the scanner of FIG. 1C.

Figures 2, 2Z, 3, 4, 5:
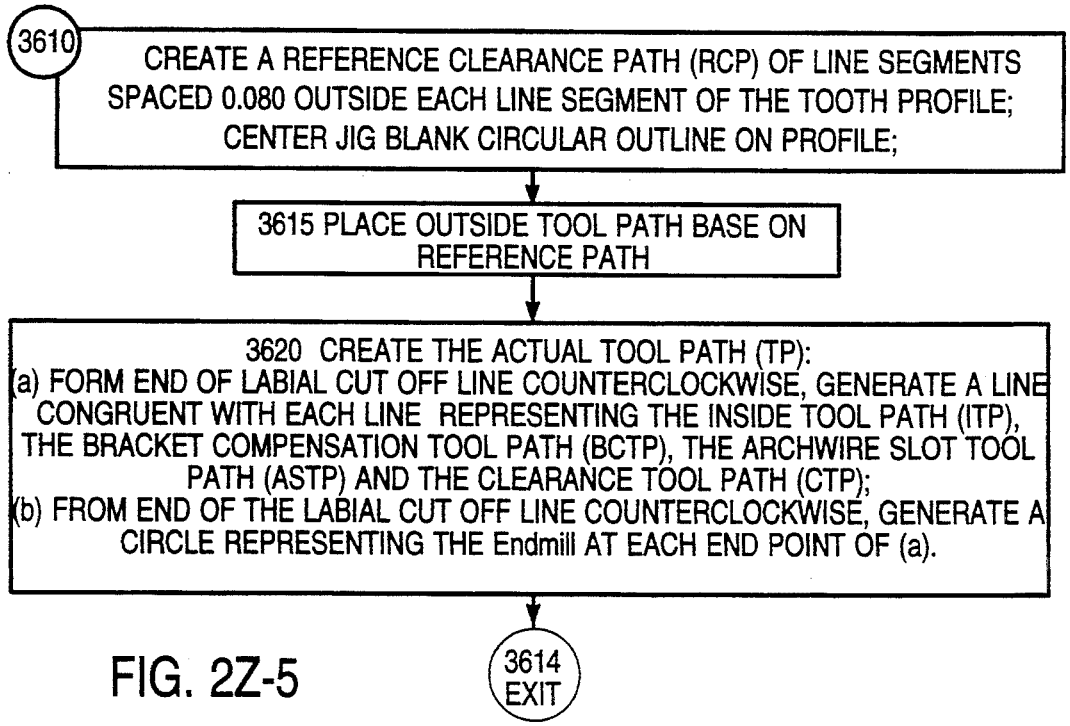
Figure 4A:
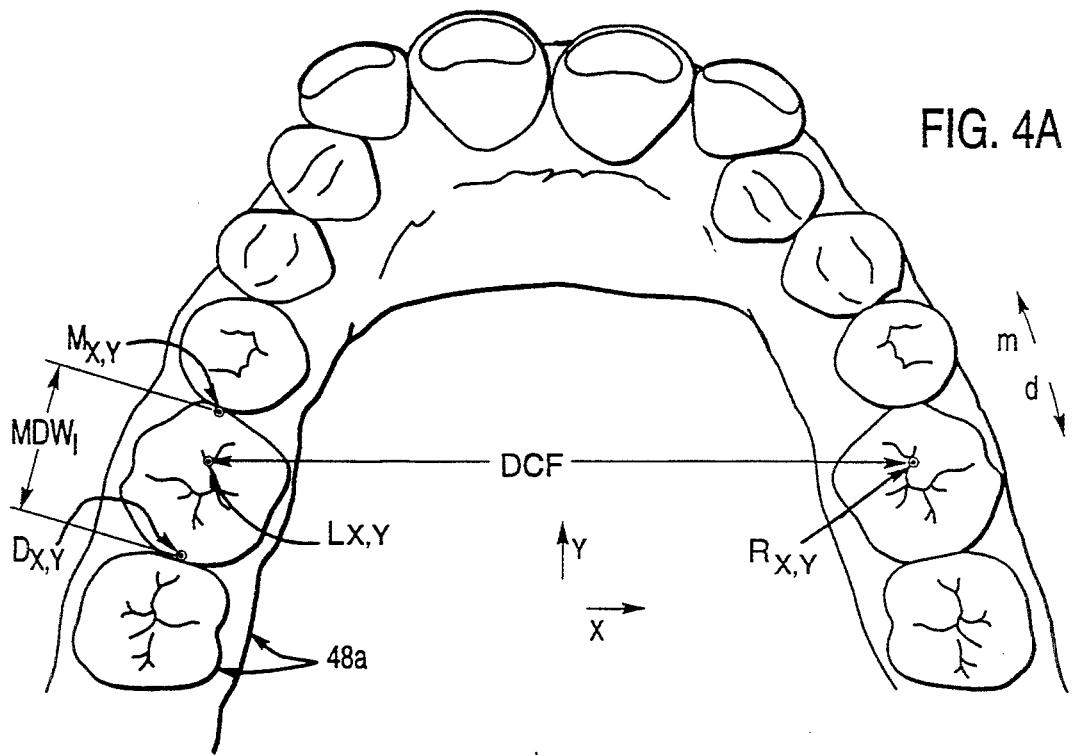
Figure 4:
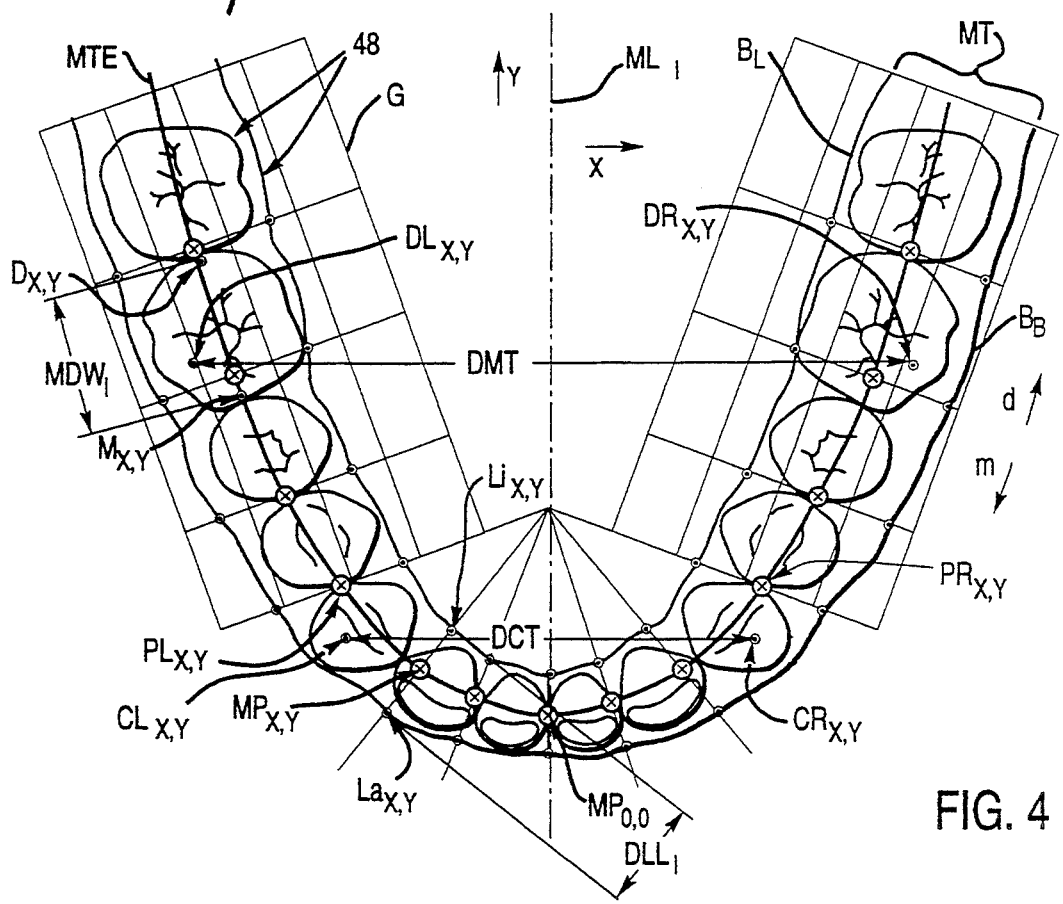
Figure 4C:
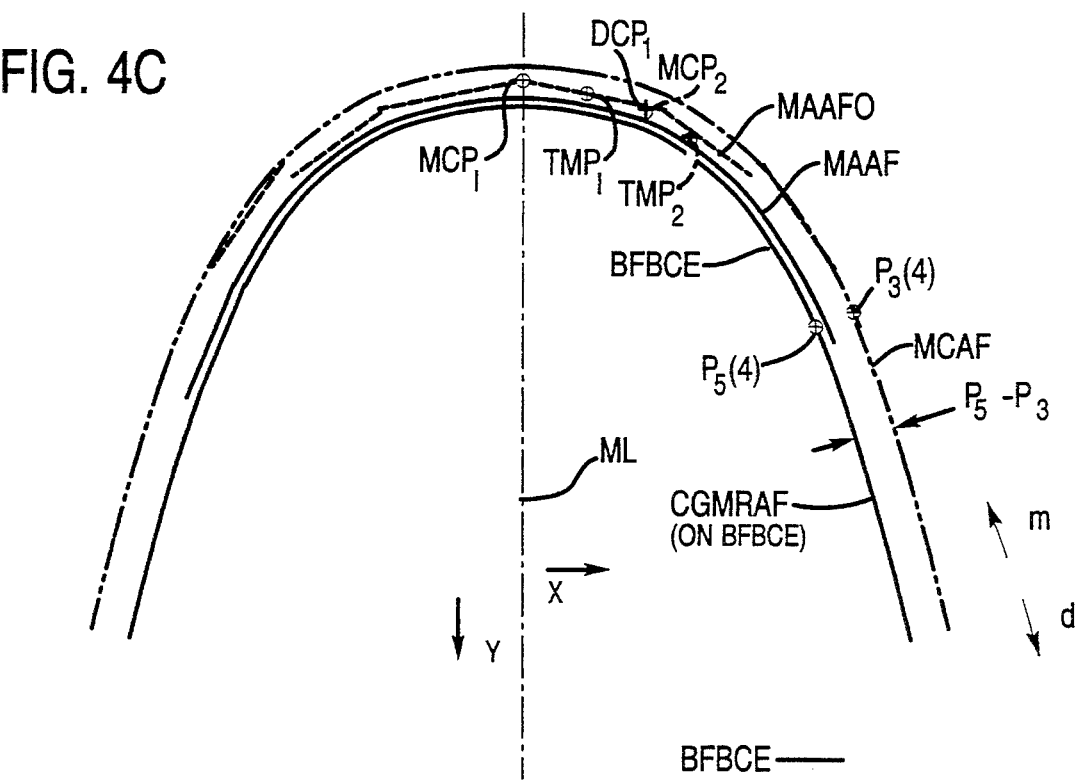
Figure 4B:
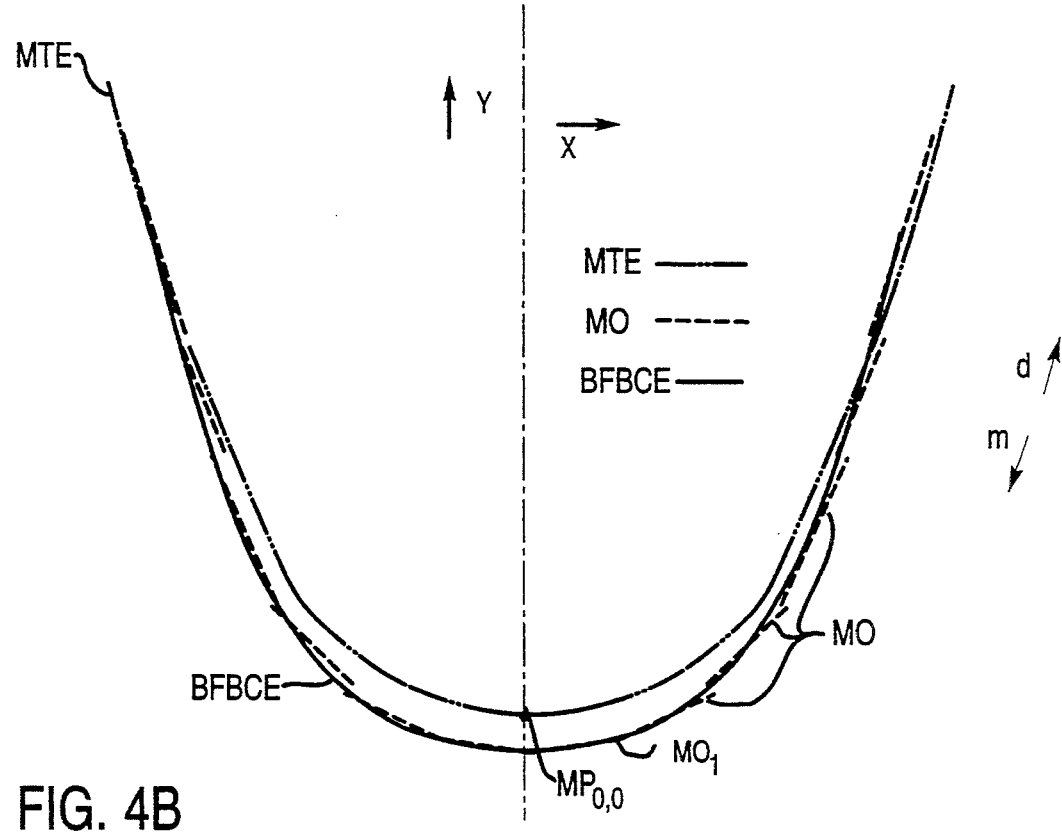
Figure 4D:
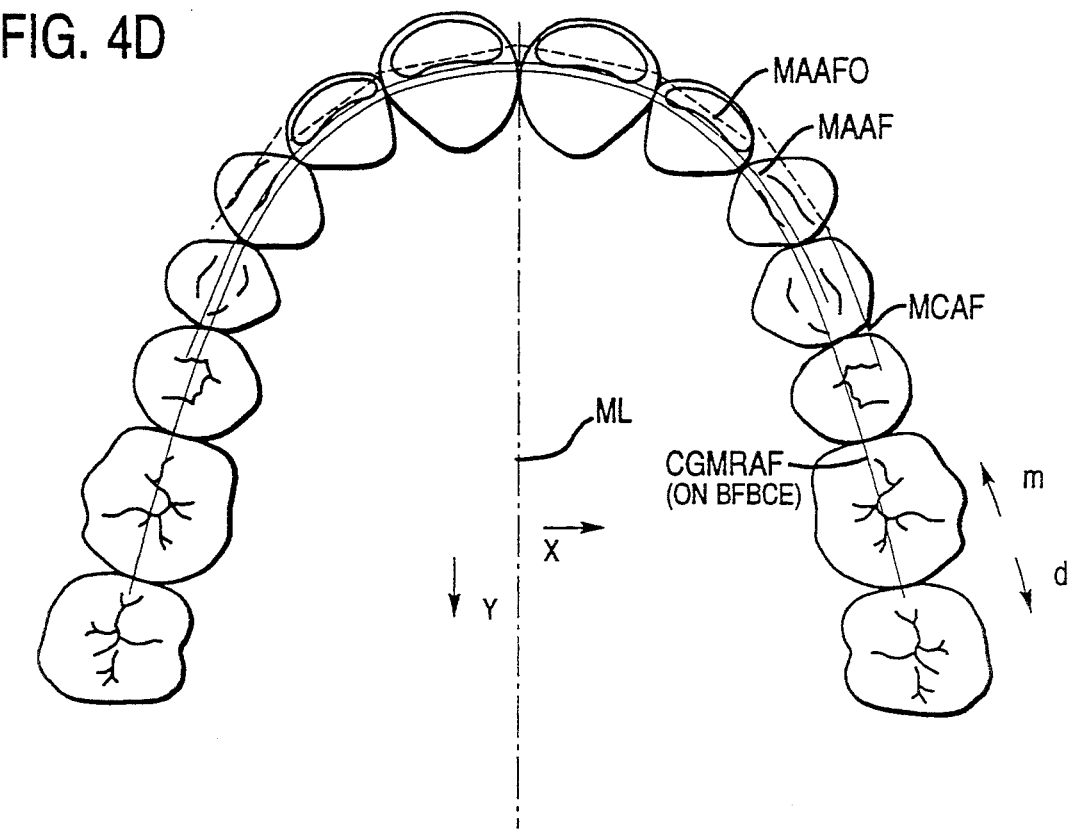
Figure 4E:
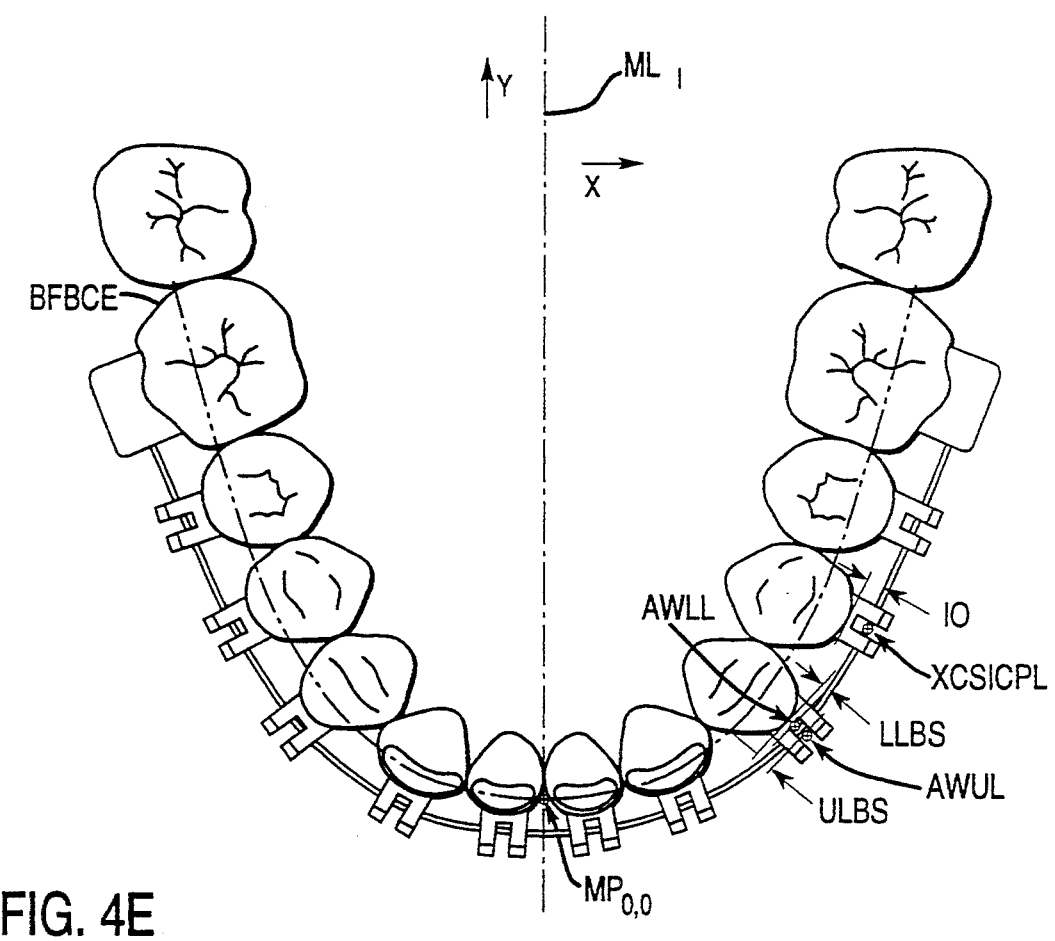

FIGS. 4–4E are plan views of the teeth of the patient on tooth placement archforms at various stages of the tooth position calculation procedure of FIG. 2B, of which:

FIG. 4 is a geometric diagram illustrating a horizontal plan view data input screen showing diagrammatically the video image of FIG. 3 used as a template, with variables relevant to the digitization of data from the mandibular video image marked thereon.

FIG. 4A is a geometric diagram similar to FIG. 4 for the maxillary teeth.

FIG. 4B is a geometric diagram plotting horizontal mandibular archforms calculated through the analysis procedure of FIG. 2B.

FIG. 4C is a geometric diagram plotting horizontal maxillary archforms calculated through the analysis procedure of FIG. 2B.

FIG. 4D is a horizontal plan diagram showing the maxillary teeth in their finish positions.

FIG. 4E is a horizontal plan diagram showing the mandibular teeth in their finish positions and with the custom appliance in place.

Figure 5:
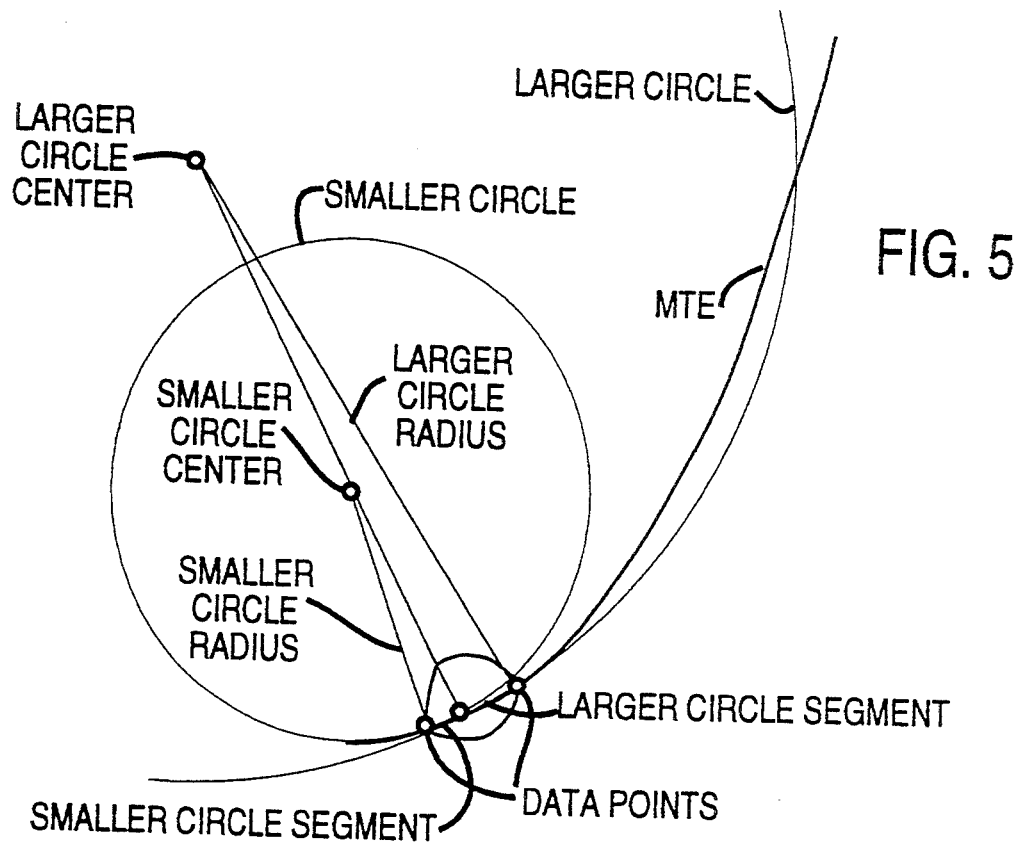
Figure 5A:
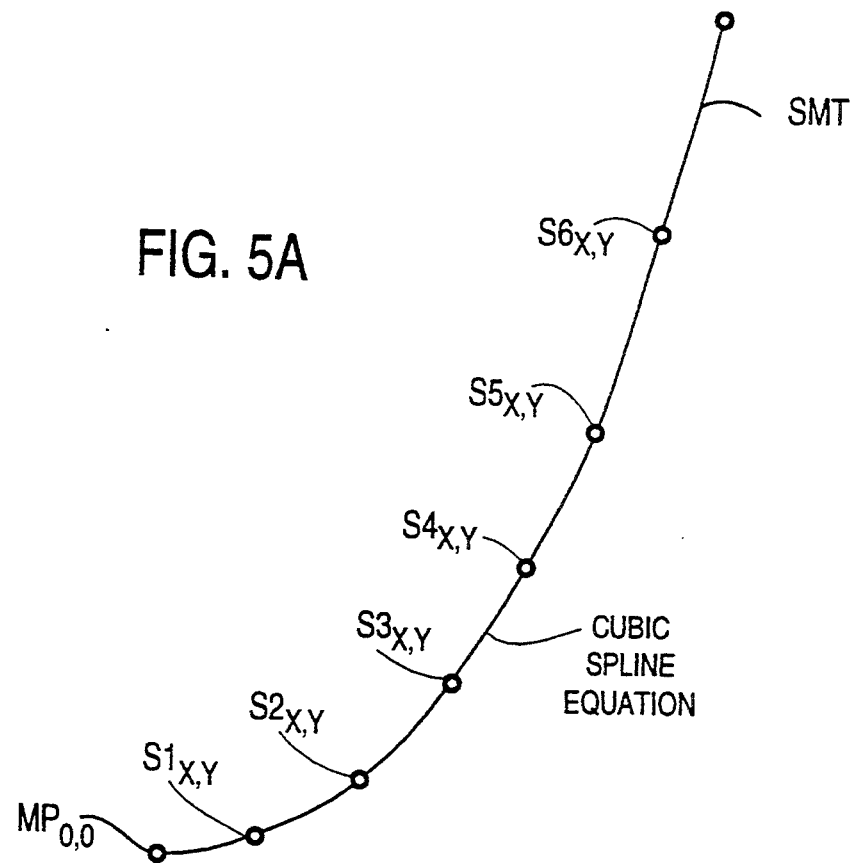
Figure 5D:
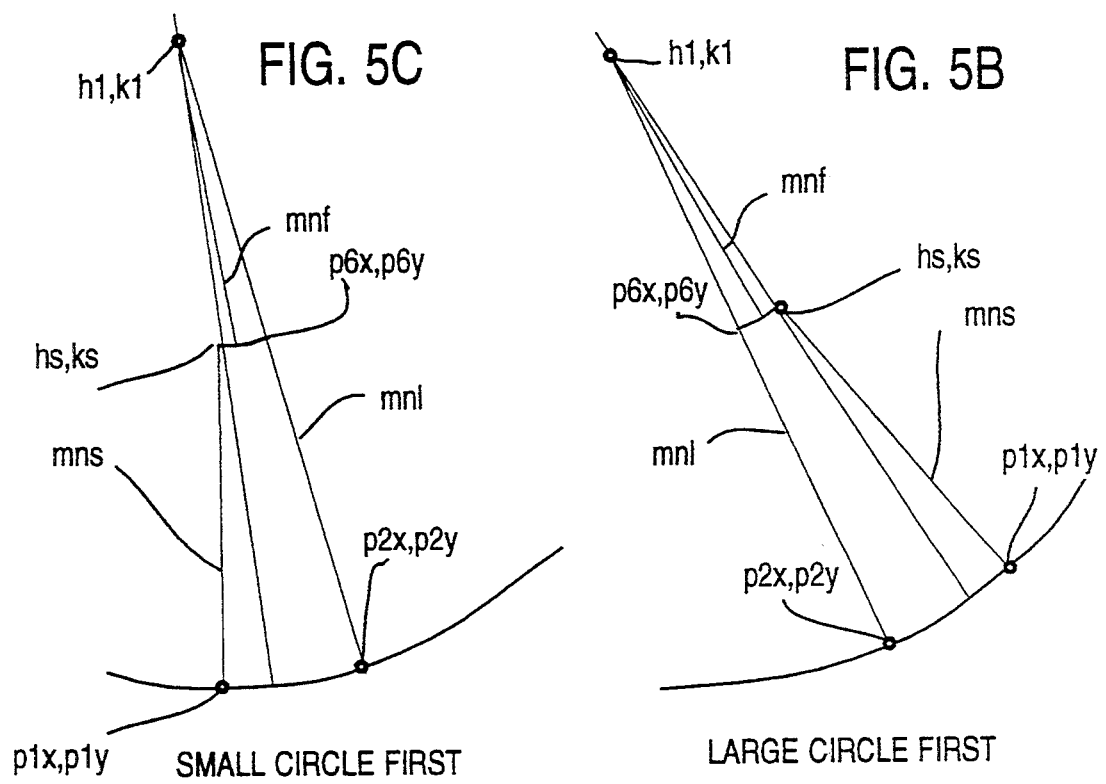
Figure 5D:
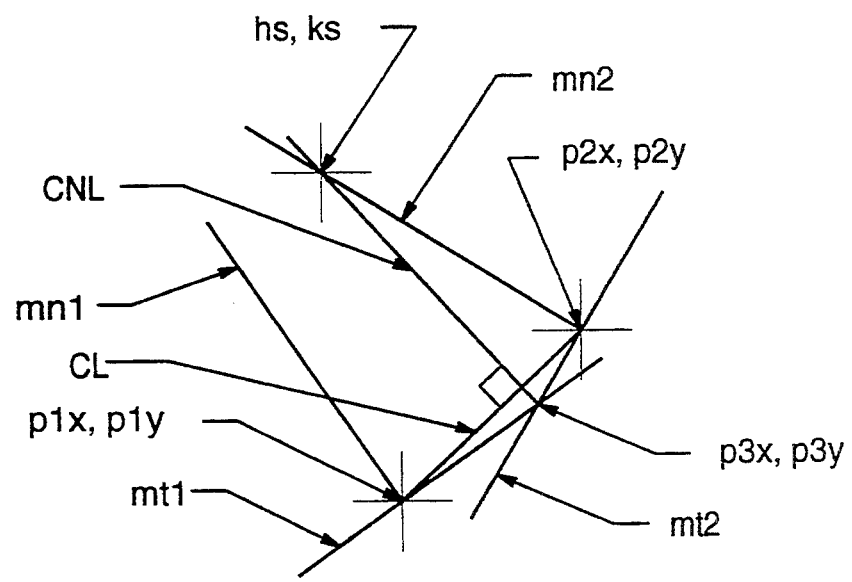
Figure 5E:
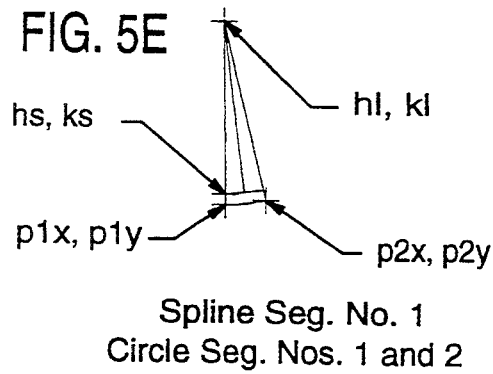
Figure 5F:
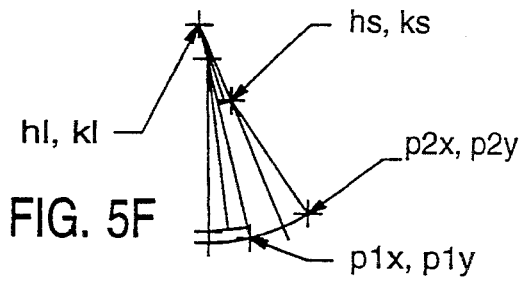
Figure 5G:
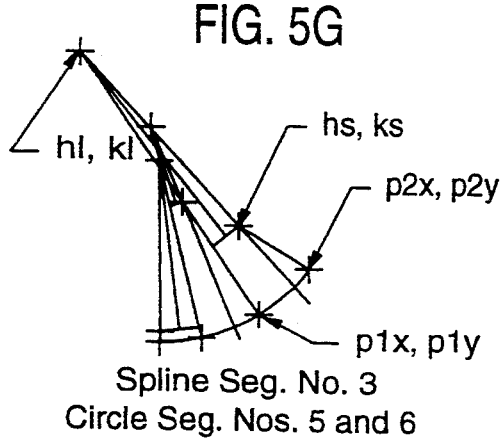
Figure 5H:
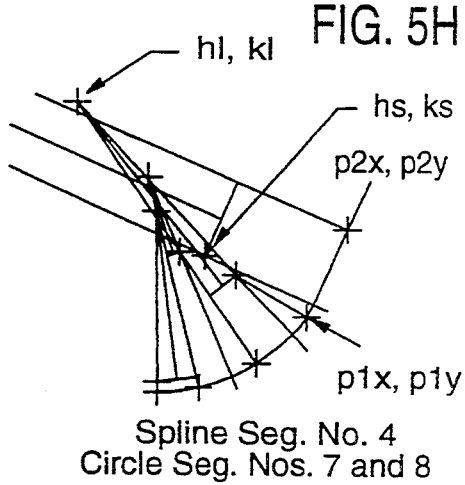
Figure 5I:
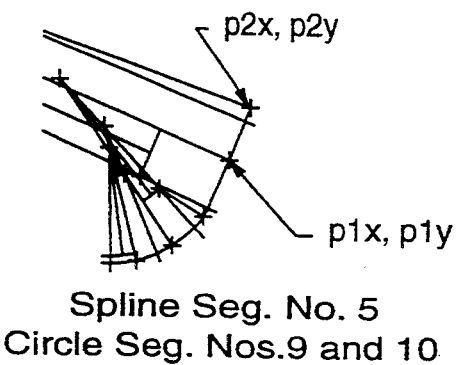
Figure 5J:
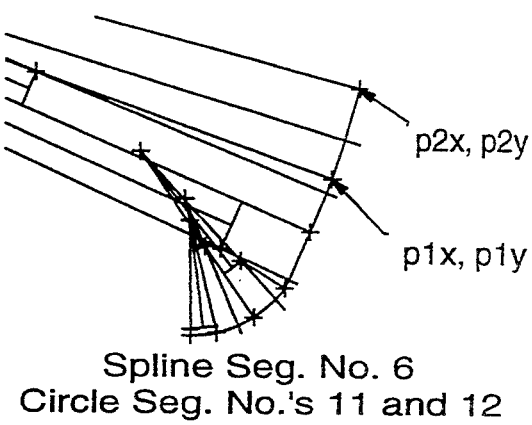
Figure 5K:
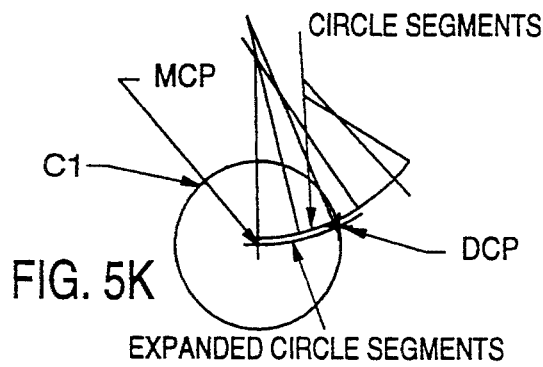
Figure 5L:
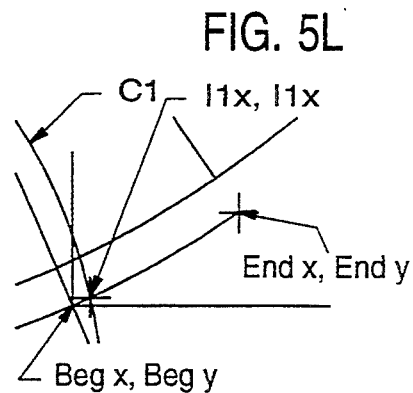
Figure 5M:
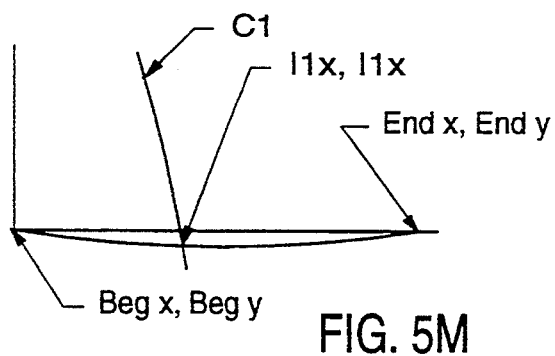
Figure 5N:
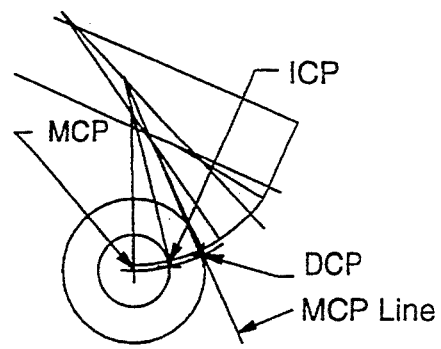
Figure 5O:
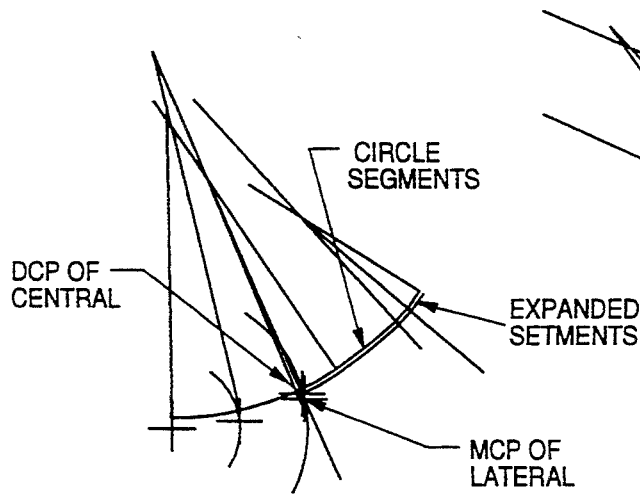
Figure 5P:
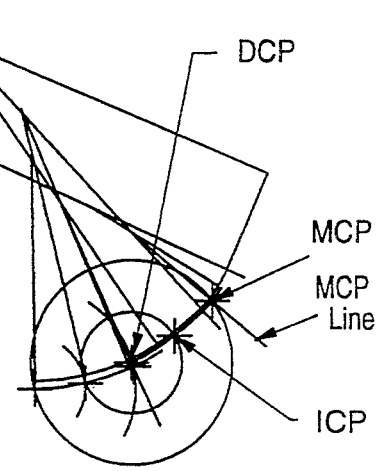

FIGS. 5–5P are mathematical calculation diagrams for reference in connection with spline to circle conversion and tooth placement routines of FIG. 2W, in which:

FIG. 5 is a horizontal plan diagram illustrating the placement of a tooth on an archform equation described in circle segment form.

FIGS. 5A–5J are detailed diagrams of the spline to circle conversion and tooth placement subroutines.

FIGS. 5K–5P are detailed diagrams of the tooth placement subroutine.

Figure 6:
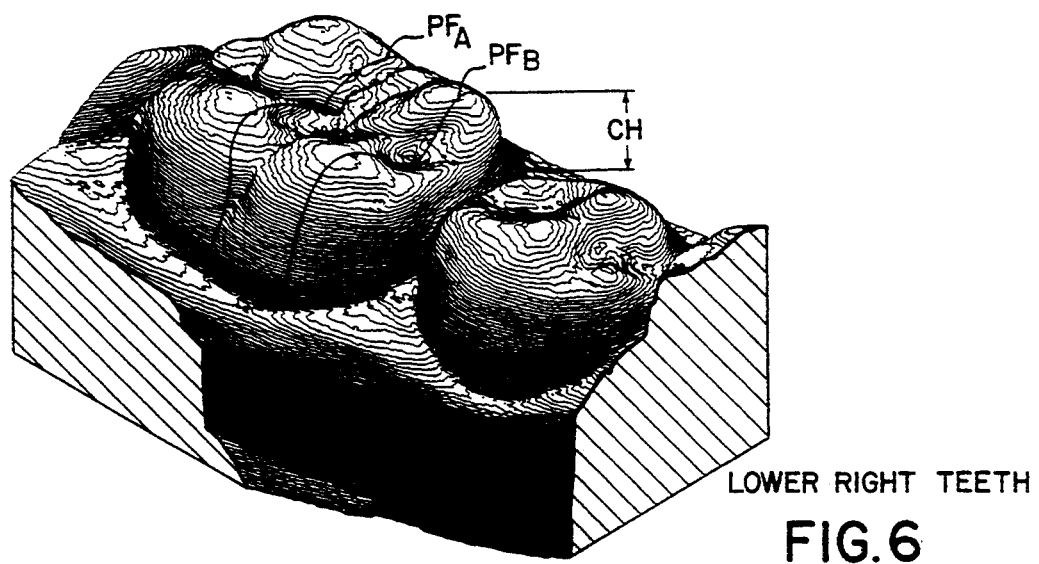

FIGS. 6–6I are diagrams of tooth profiles illustrating landmark determination, tooth inclination and vertical positioning, in which:

FIG. 6 is an isometric image of a three-dimensional computerized representation, similar to FIG. 2B, of a molar showing the locations of alternative vertical labial-lingual profile planes and tooth profiles.

Figure 6A:
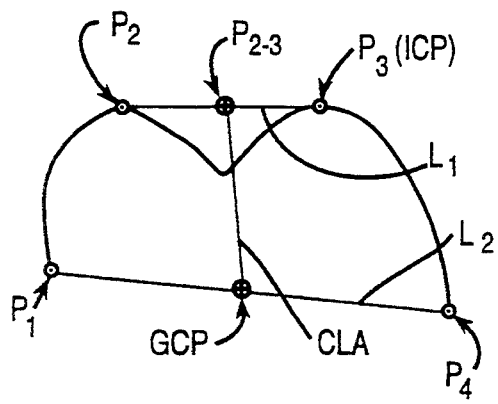

FIG. 6A is a mathematical tooth profile plot as illustrated on the computer screen of a the system of FIG. 1 of a mandibular molar showing selected landmark parameters.

Figure 6B:
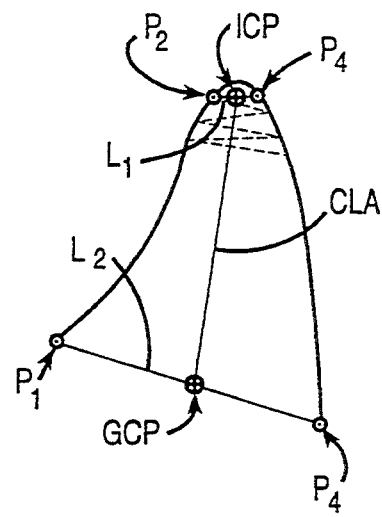

FIG. 6B is a mathematical tooth profile plot, similar to FIG. 6A, of a mandibular cuspid or incisor showing selected landmark parameters.

Figure 6C:
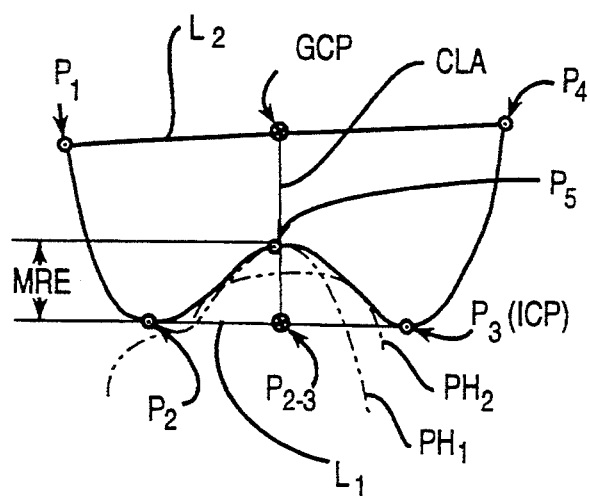

FIG. 6C is a mathematical tooth profile plot, similar to FIG. 6A, of a maxillary molar or bicuspid showing selected landmark parameters.

Figure 6D:
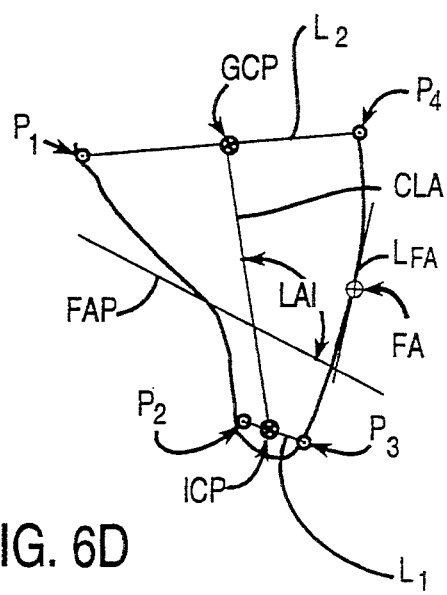

FIG. 6D is a mathematical tooth profile plot, similar to FIG. 6A, of a maxillary cuspid or incisor showing selected landmark parameters relevant thereto.

Figure 6E:
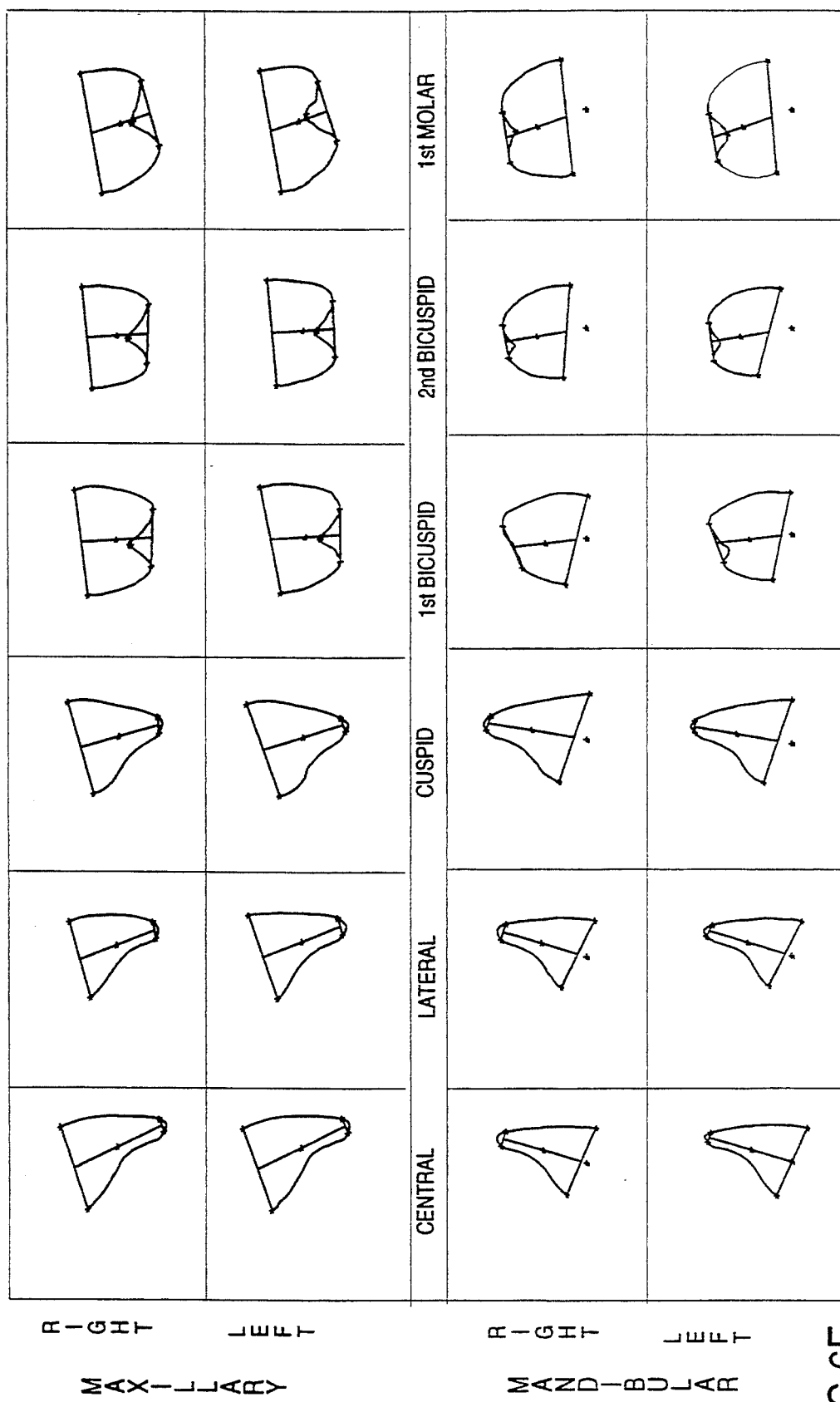

FIG. 6E is representation of a display, similar to FIG. 3C, of an array of mathematical tooth profile plots of all of the teeth, angularly oriented, with landmark parameters marked thereon.

FIG. 6F is representation of a display of an array of mathematical tooth profile plots, similar to a portion of FIG. 6E, of the mandibular teeth with working horizontal placement planes marked thereon.

FIG. 6G is mathematical tooth profile plot, similar to FIG. 6A, of a mandibular posterior tooth with relevant dimensional variables for placement of the tooth marked thereon.

FIG. 6H is mathematical tooth profile plot, similar to FIG. 6B, of a mandibular anterior tooth with relevant dimensional variables for the placement of the tooth marked thereon.

FIG. 6I is mathematical tooth profile plot, similar to FIG. 6H, of a the tallest mandibular tooth.

Figure 7:
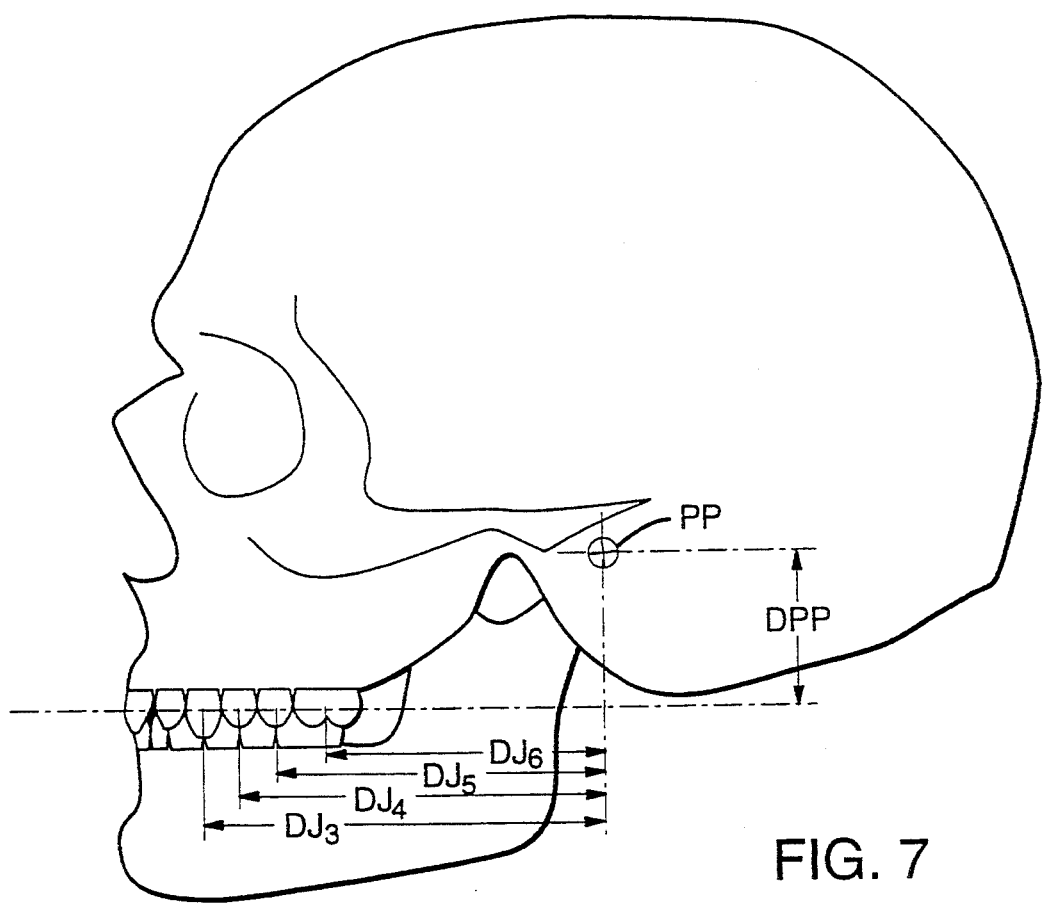
Figure 7A:
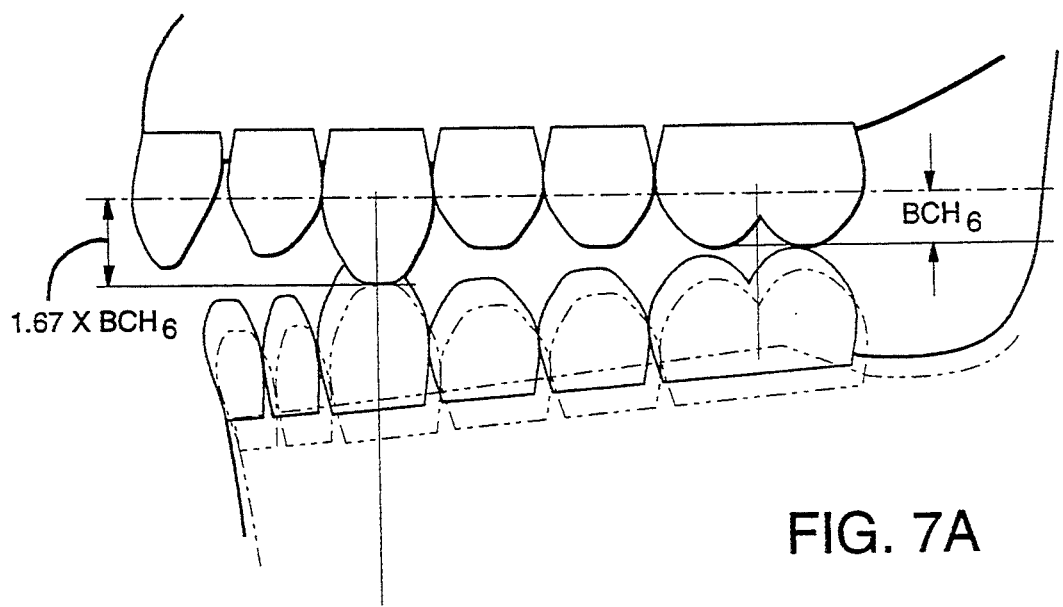
Figure 7C:
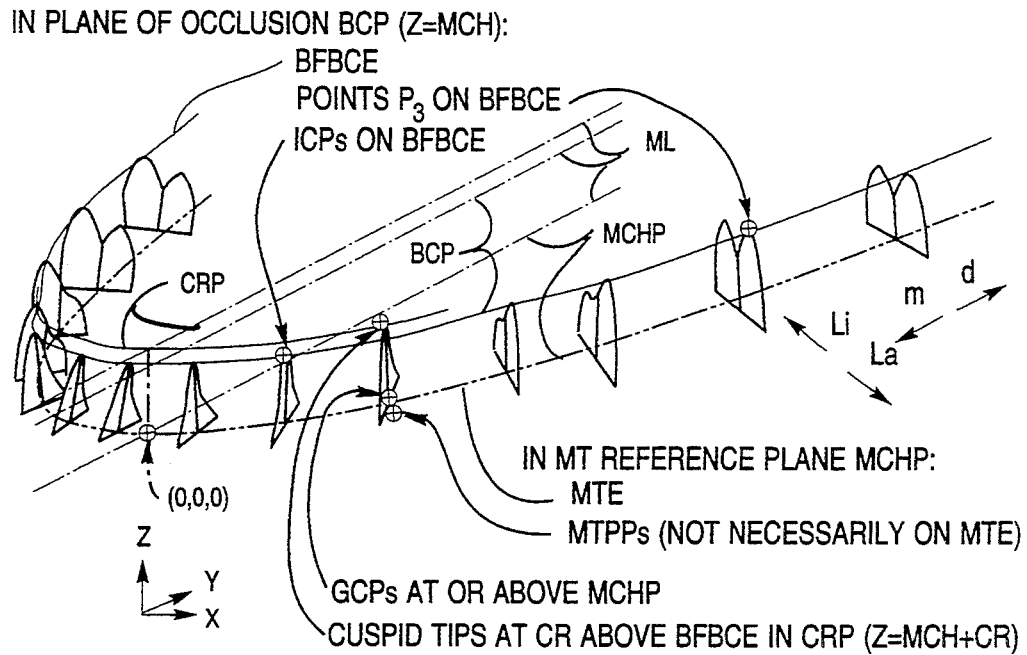
Figure 7B:
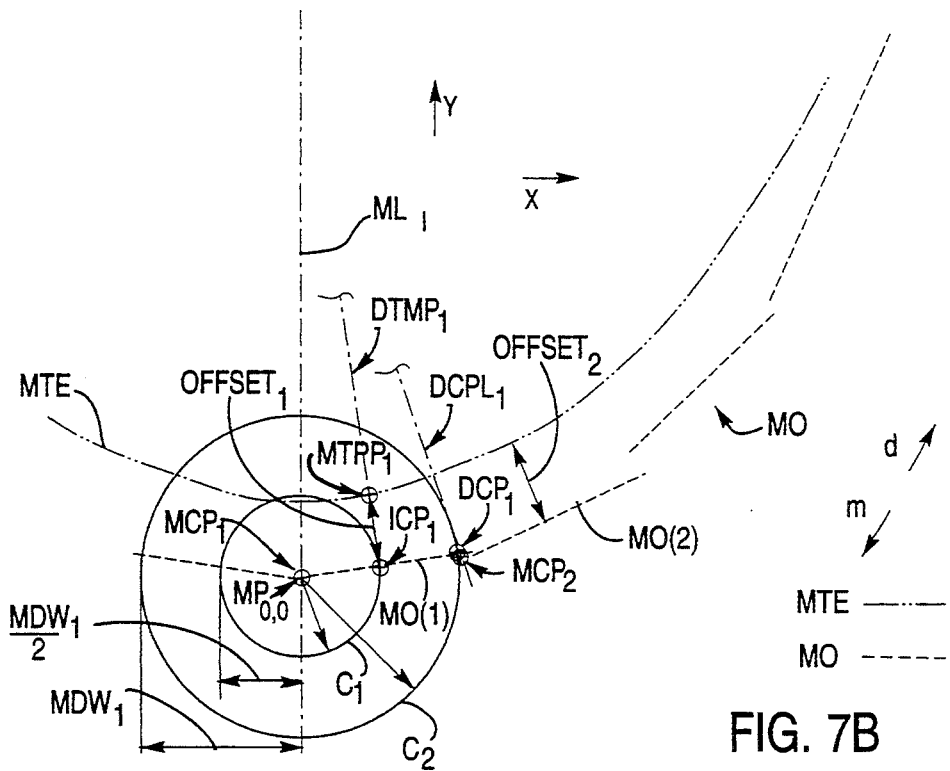
Figure 7D:
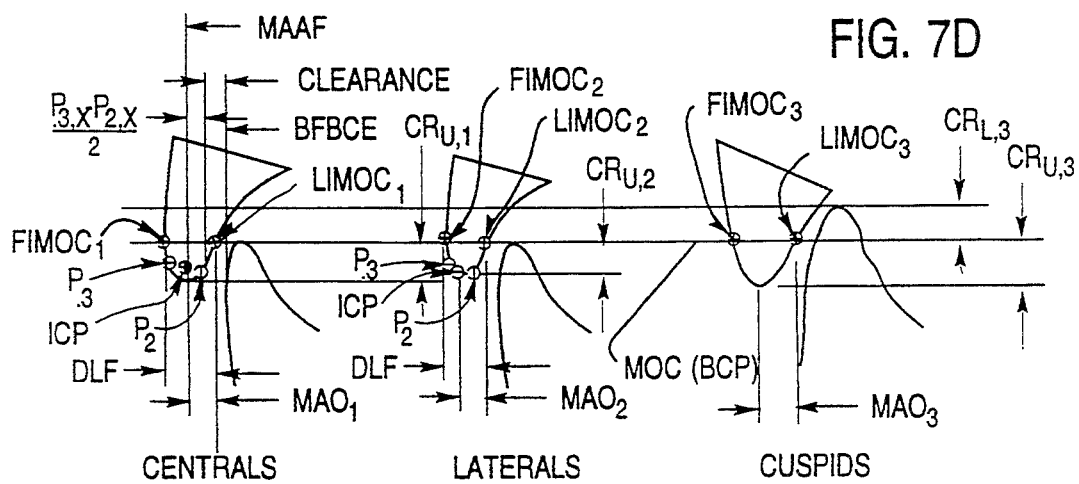

FIGS. 7–7D are diagrams for reference in connection with the finish tooth position calculation, of which:

FIG. 7 is an elevational diagram of the relationship of the jaws of a patient for illustration of cuspid rise occlusion calculation.

FIG. 7A is an enlarged view of a portion of FIG. 7.

FIG. 7B is a plan mathematical diagram illustrating certain of the mathematics of tooth placement on the mandibular offset arch.

FIG. 7C is a perspective diagram illustrating the relationship of the vertical tooth profile planes and relevant horizontal arch planes in the course of tooth finish position calculation.

FIG. 7D is a set of related elevational profiles of mandibular and maxillary teeth showing occlusal and overlap relationships in the course of tooth finish position calculations.

Figure 8:
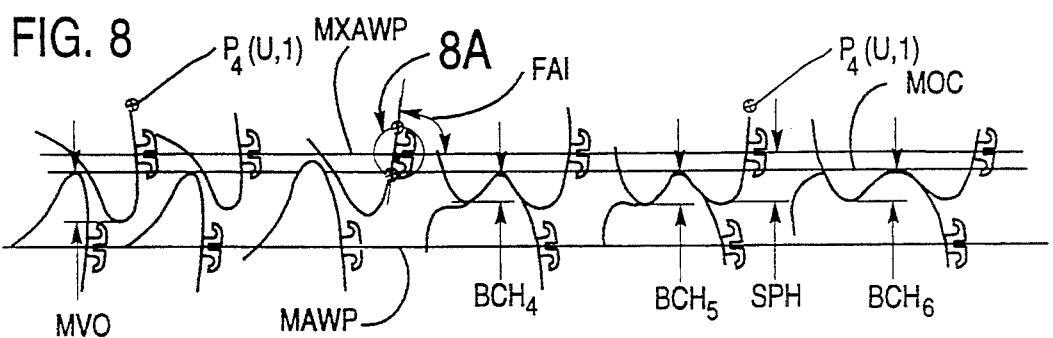

FIGS. 8–8H are diagrams for reference in connection with the steps of the custom appliance design procedure, of which:

FIG. 8 is a diagram similar to FIG. 7D illustrating archwire plane and bracket slot design on positioned teeth.

Figure 8A:
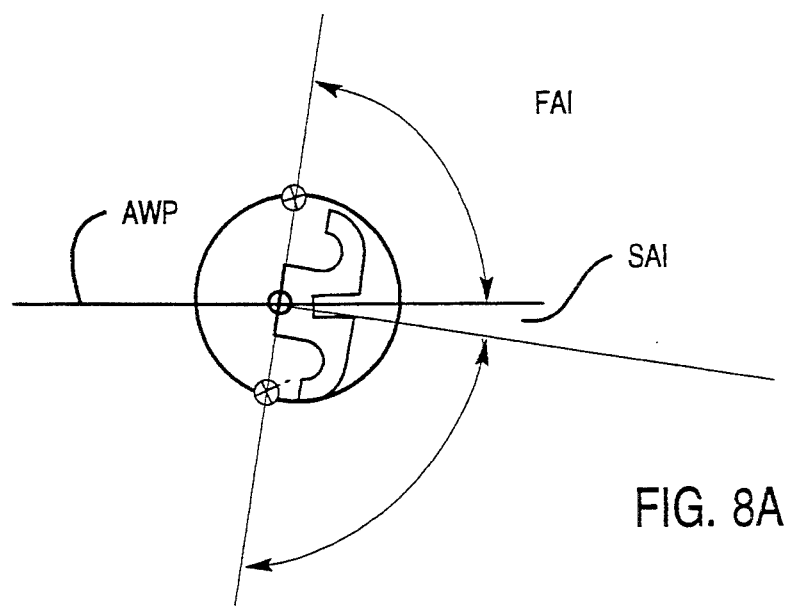

FIG. 8A is an elevational diagram illustrating a bracket and slot configuration in connection with the diagram of FIG. 8.

Figure 8C:
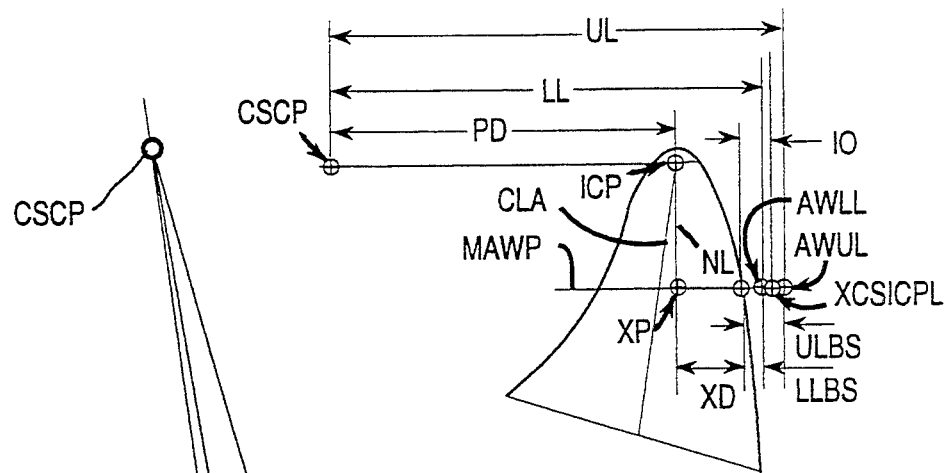
Figure 8B:
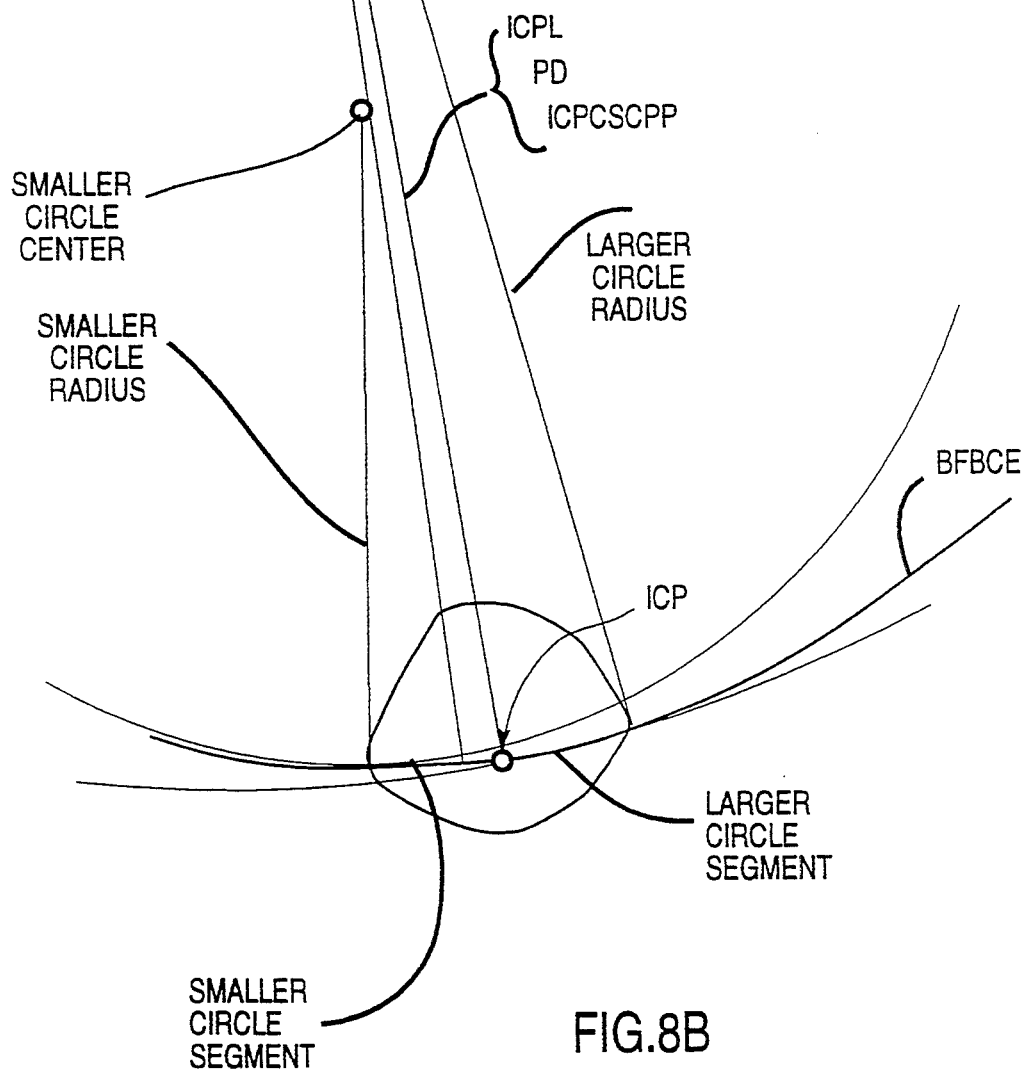

FIG. 8B is a top view illustrating the relation of a tooth to an archform by placement routine of FIG. 2W.

FIG. 8C is a tooth profile diagram illustrating the slot in-out dimension calculation.

FIG. 8D is a perspective diagram illustrating the placement of a custom bracket onto a tooth with the use of a custom placement jig.

FIG. 8E is a plan diagram of a custom archwire for the appliance required to move the mandibular teeth to the finish positions illustrated in FIG. 4E.

FIG. 8F is a plan diagram illustrating the labial installated appliance on the teeth of the patient in their initial positions.

FIG. 8G is a plan diagram, similar to FIG. 8F, illustrating a lingual appliance installed on the teeth of the patient.

FIG. 8H is an elevational diagram illustrating an orthodontic lingual bracket of the appliance of FIG. 8G.

FIG. 8I is a top view of a bracket having a base slot curvature conforming to that of an archwire supported therein.

Figure 9:
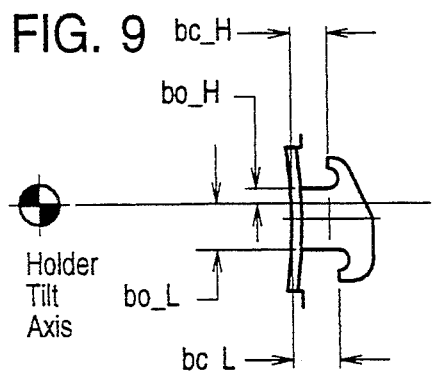
Figure 9A:
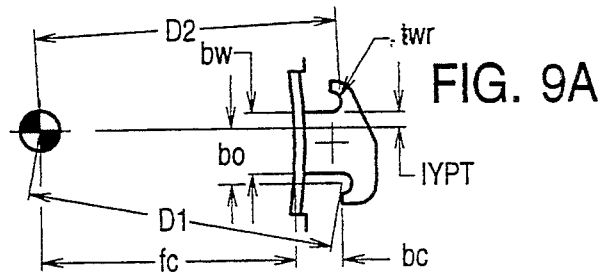
Figure 9B:
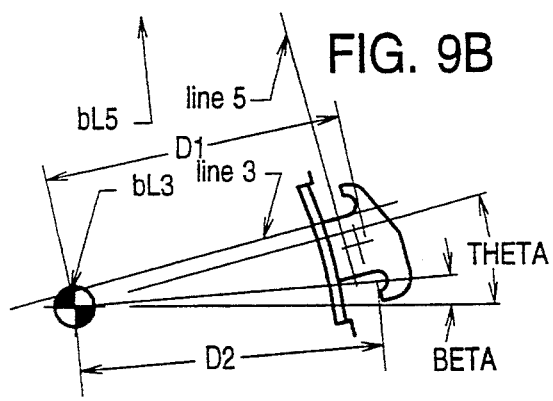
Figure 9C:
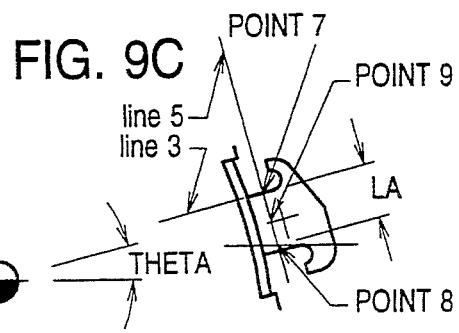
Figure 9D:
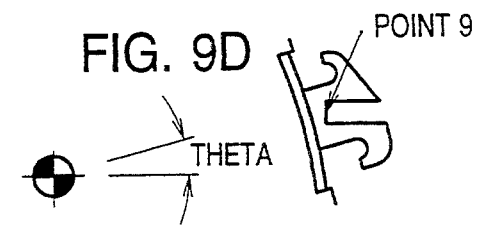
Figure 9E:
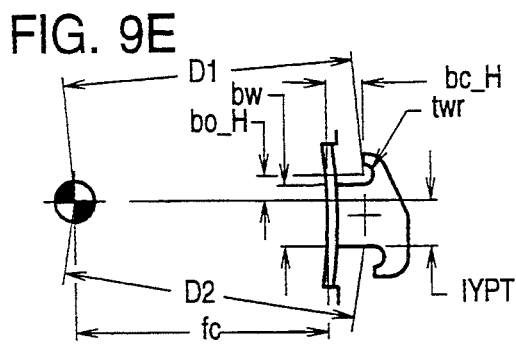
Figure 9G:
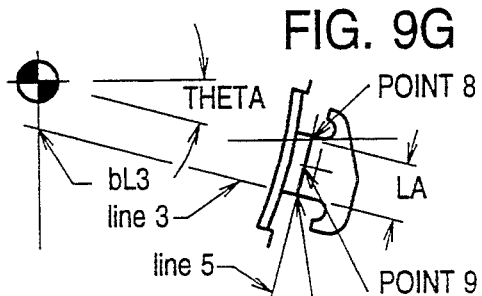
Figure 9F:
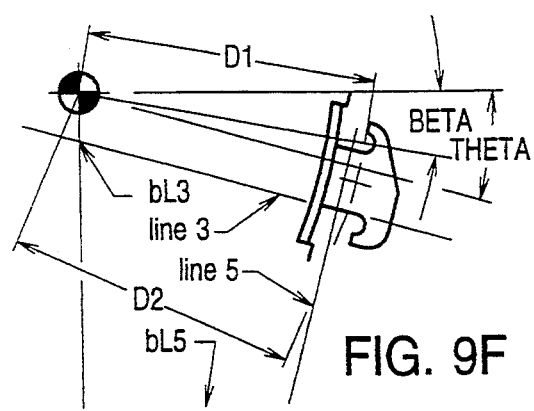
Figure 9H:
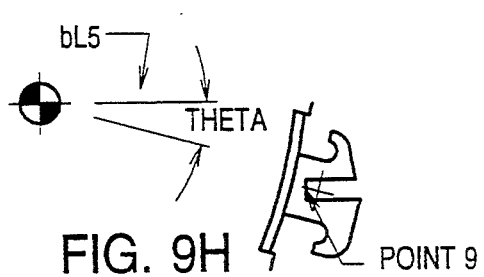
Figure 9I:
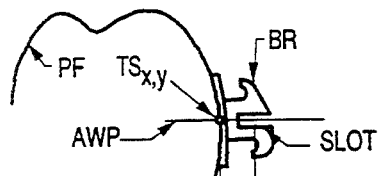
Figure 9J:
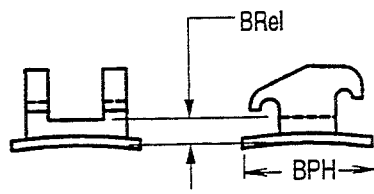
Figure 9K:
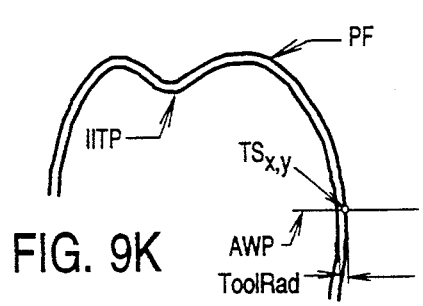
Figure 9L:
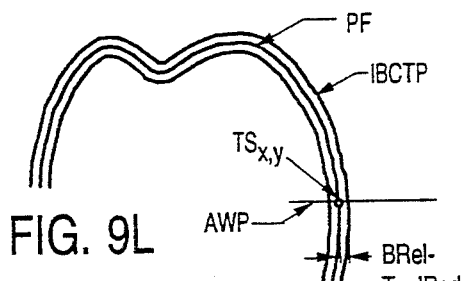
Figure 9M:
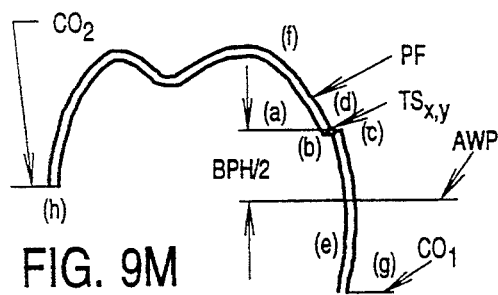
Figure 9N:
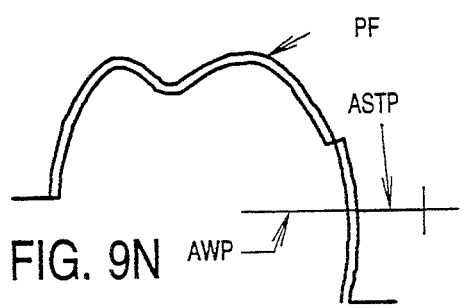
Figure 9O:
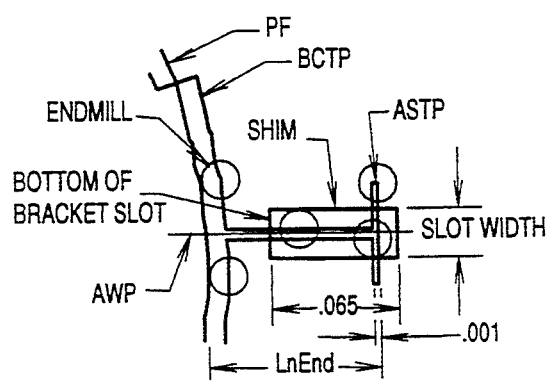
Figure 9P:
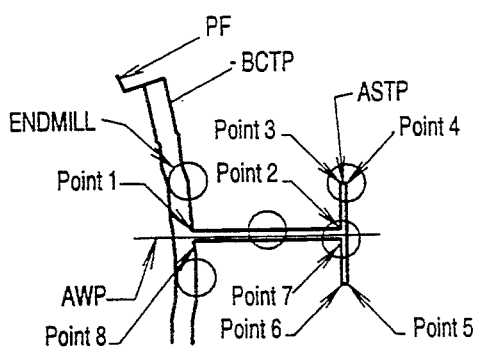
Figure 9Q:
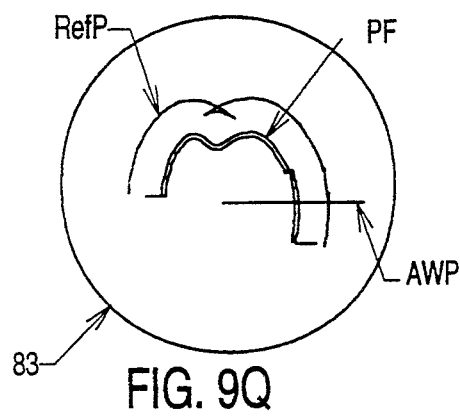
Figure 9R:
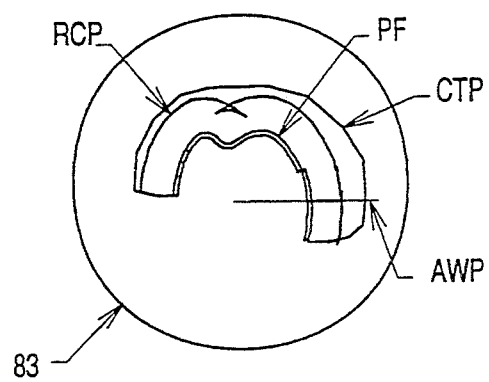
Figure 9S:
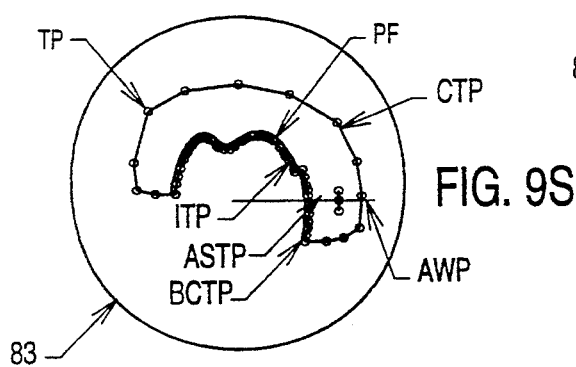
Figure 9T:
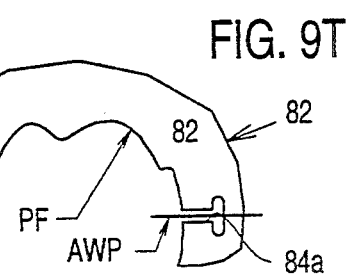
Figure 9U:
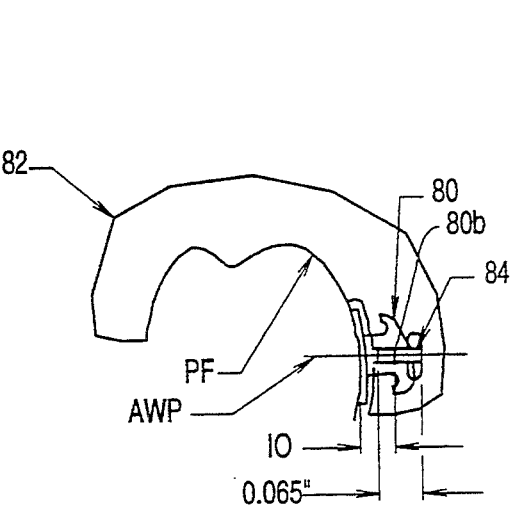
Figure 9V:
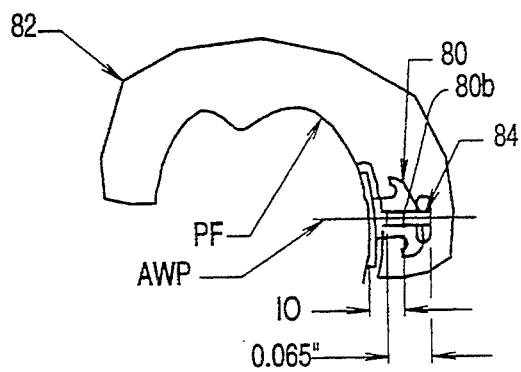
Figure 9W:
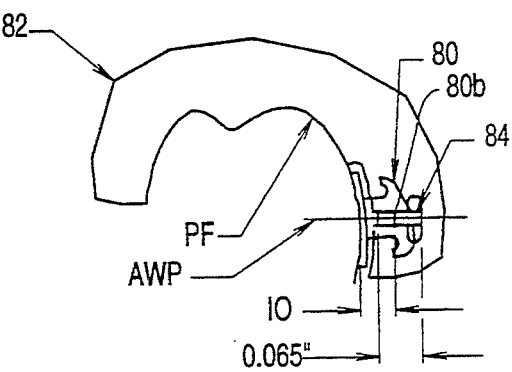

FIGS. 9-9W are diagrams relating to appliance manufacturing steps, of which:

FIGS. 9-9H relate to substeps of the bracket slot cutting code generation and bracket manufacturing step.

FIGS. 9I-9W relate to the substeps of the bracket placement jig manufacturing step.

DETAILED DESCRIPTION OF THE DRAWINGS

The preferred embodiment of the invention provides a system and method for designing and manufacturing orthodontic appliances and for employing the appliances to orthodontically treat patients for the straightening of teeth. Unlike traditional orthodontic products, however, the appliances resulting from the practice of the present invention are designed around the anatomy of the individual patients. It further incorporates in its design criteria the parameters and professional treatment approaches of the treating orthodontists, and applies automated decision making processes in the appliance design that take into account the professionally recognized characteristics and anatomical landmarks of the patients.

The overall configuration of the system 10 is illustrated diagrammatically in FIG. 1. The overall operations of the preferred method of the invention are illustrated in the flowchart of FIG. 2.

In accordance with the preferred embodiment of the invention as illustrated in FIGS. 1 and 2, examination of a patient is performed by an orthodontist at the orthodontist's office for the purpose of assembling the information necessary to determine the patient's condition, prescribe the appropriate treatment, and specify the type of orthodontic appliance to implement the treatment. The information is then communicated to a remotely located appliance design and manufacturing facility where the design of a custom appliance for use in administering the treatment is carried out with the use of computer analysis. The appliance design, together with the information necessary for the orthodontist to install the appliance on the patient is then transmitted back to the orthodontist, who installs the appliance and administers the treatment in accordance with the appliance manufactures instructions and his own professional expertise.

In accordance with alternative embodiments of the invention, digitization of anatomical information for computer input is performed either at the appliance design and manufacturing facility, by the orthodontist at his office, or preferably divided between the two. Similarly, the present invention contemplates the manufacture of the appliance to be performed at either the appliance manufacturing facility, at the orthodontists office, or preferably divided between the two locations and in accordance with the analysis and design provided by the system of the present invention.

The practice of the present invention involves the use of certain system hardware, tangible records of information, and communications paths described below in connection with FIG. 1 and related illustrations, and the performance of operations, procedures and steps described in connection with the flowchart of FIG. 2 and related diagrams, all as set forth in detail below.

Terminology and Conventions

Throughout the description, references are made to tangible elements illustrated in the drawings and to actions performed by hand and by computer. In the description, numbers used to refer to structure or other tangible items illustrated in the drawings of the preferred embodiment appear in conventional form in the text, while numbers that refer to method steps in the illustrated flowchart are enclosed in parentheses in the following description. Letter symbols are used to refer to geometric or mathematical representations of variables, parameters, dimensions and values, input into or calculated by a computer, tie into equations and diagrams illustrated in the drawings, or correspond to computer codes or conceptual items set forth in the disclosure.

Throughout this description, the various teeth of the patient, up to thirty-two in number, may be identified as $T_{J,S,I}$, or $T(J,S,I)$, where J designates the jaw (upper: $J=U$; lower: $J=B$), where S designates the side (patient's right: $S=R$; patient's left: $S=L$), and I designates the tooth by position relative to the jaw centerline as follows:

$I=1$: Central Incisor
$I=2$: Lateral Incisor
$I=3$: Cuspid
$I=4$: First Bicuspid
$I=5$: Second Bicuspid
$I=6$: First (6 year) Molar
$I=7$: Second (12 year) Molar
$I=8$: Third (Wisdom Tooth) Molar The wisdom teeth are, however, customarily not involved in orthodontic procedure and usually are not yet present in the mouth of patients of treatment age. Furthermore, the second molars are often not involved in orthodontic treatment. To simplify the description and drawings, however, these designations are eliminated except where they are necessary to avoid ambiguity. Instead, the description below states verbally when it relates to, for example, the lower jaw (thus making use of the J subscript unnecessary) or where it relates to data or calculations relevant to a particular or either side of a jaw (thus making use of the S subscript unnecessary).

Further, many values are calculated or measured for each tooth I, or for each of a limited group of teeth, as, for example, the mesio-distal width MDW or the mesial and distal extremities $M_{X,Y}$ and $D_{X,Y}$ as in the description of step (300) below. Wherever possible, the I designation is also eliminated and the description instead describes how the variables relate to the various teeth. In addition, where some values such as MDW discussed above relate to a tooth dimension or the distance between two points on a tooth (and may be represented by a scaler value in a computer), other values such as the points $M_{X,Y}$ and $D_{X,Y}$ relate to points M and D, respectively (and may be represented by a pair of X and Y coordinates in a computer). Usually, the subscripts designating the two coordinates are omitted, and where helpful to clarify the description, a single one of the subscripts X or Y may be used, such as with $D_X$ or $D_Y$, to designate that only the X or Y coordinate is employed, for example, in a calculation.

SYSTEM CONFIGURATION

Referring to the system diagram of FIG. 1, an orthodontic appliance manufacturing and patient treatment system 10 is illustrated. The system components are distributed between two locations, a doctor's office 11, and an appliance design and manufacturing facility 13. At the doctor's office 11, a patient 12, who requires orthodontic treatment, is examined by an orthodontist 14, who makes a diagnosis 15 of the condition of the patient and of the treatment, if any, needed. The examination involves the traditional application of the skill, knowledge and expertise of the orthodontist 14, and results in the preparation of detailed records 16 of the anatomy and condition of the mouth 18 of the patient, of the treatment proposed, and of other information necessary to the preparation of an orthodontic appliance.

The records 16 prepared by the orthodontist include a physical model 20 from a mold of the patient's mouth 18, which includes a mandibular model 21 of the patient's lower jaw or mandible 22 and a maxillary model 23 of the patient's upper jaw or maxilla 24. The records 16 also include prescription 27 wherein the orthodontist sets forth a treatment to be applied to the patient and a result to be achieved by the treatment. The prescription 27 may also include a specification of techniques that are to be included in the treatment and a designation of an orthodontic appliance to be employed. The records 16 will further include identification information 17 and patient history information 19.

In the illustrated embodiment of the invention, the records 16 are transmitted to the appliance manufacturing facility 13, at which the finish position of the teeth are calculated and a custom appliance 25 is designed and manufactured. The facility 13 is provided with one or more trained operators 28. In some embodiments, the physical model 20 itself is transmitted in the information 16 to the facility 13. In such cases, one of the primary functions of the operators 28 is to input digital information 26 from the records 16 into a computer 30a. Another function is to operate the same or another computer 30b to design the custom appliance 25, and to operate NC equipment 38 controlled by one of the same or another computer 30c to manufacture the appliance 25. Where the inputing, design and manufacture are performed at the appliance facility 13, the computers 30a, 30b and 30c may be the same computer 30.

In other embodiments of the invention, the orthodontist 14 digitizes data from the model 20, in which case the inputing computer 30 is located at the orthodontist's office 11. In these embodiments, the digitized information 26, rather than the physical model 20, is transmitted to the appliance facility 13. The analyzing and appliance design computer is nonetheless preferably at the appliance facility 13.

The entry of the information into the input computer 30 involves a digitizing of the information 16 to produce the digitized anatomical information 26 in machine readable form for analysis by the analyzing computer 30b. The input computer 30 connected thereto by a scanner 33, which, in the alternative embodiments of the invention, includes equipment that employs one or more video cameras, mechanical probes, laser scanners, ultrasonic scanners, moire image scanners or other forms of imaging or measurement hardware that alone, or in combination with other such components, produce anatomical geometric information that describes the patient's teeth and jaw. The images may be three-dimensional or be made along a plurality of planes or other surfaces that can ultimately be combined to provide information in three dimensions.

The combined information from the scanner 33 of the illustrated embodiment provides a basis for three dimensional analysis of the patient's teeth and from which calculations of finish tooth positions can be made. From the final positional calculations and tooth anatomy data, automatic design and manufacture of the custom orthodontic appliance 25 is carried out. In the illustrated embodiment, the data is imaged in a plurality of differently oriented two dimensional planes in the computer 30, then mathematically manipulated and combined in the computer 30b to construct a three dimensional solution to the tooth positioning and appliance design problems.

In a configuration in which the scanner 33 is connected to a separate dedicated inputing computer 30 is herein described, the functional equivalent of the inputing computer 30 may be included in circuitry within the scanner 33 itself.

Preferably, the digital input process utilizes interactive methods by which an operator 28 uses a pointing device and digitizer to select particularly useful orthodontic parameters from graphics images produced by the scanner 33 on a screen 35 of a display connected to the inputing computer 30.

In embodiments where some or all of the extraction of the digitized anatomical information 26 from the model 20, which may also be derived directly from the mouth 18 of the patient 12, is accomplished by the orthodontist 14 at the orthodontist's office 11, the information 26 is digitized by the orthodontist 14 then transmitted as part of the information 16 to the appliance design center 13. The transmitted information 16 is preferably transmitted from the orthodontist's office 11 to the appliance facility 13 by modem, but may be transmitted in any other available manner.

An analysis and design computer 30b, preferably at the appliance design facility 13, produces an archive diskette 34 that is formatted and written with all of the relevant information of the analysis and the history and prescribed treatment of the patient 14.

The computer 30b at the appliance facility 13 calculates, based on the digitized information 26, the final position of the patient's teeth, and the configuration of the appliance 25 required to move the patient's teeth to this final or finish position. As a result, calculated information for the patient is stored in a patient data file 36. From the calculations the computer 30c produces CNC machine readable code 42 for operating NC manufacturing equipment 38 to produce the appliance 25. An instruction document or file 37 is also produced, either by the computer 30b or the computer 30c, of information to aid the orthodontist 14 in treating the patient 14 with the custom appliance 25.

The manufacturing equipment 38 includes an appliance bracket cutting or forming machine 39 which produces custom brackets for the appliance 25 by cutting slots calculated angles and to calculated depths in slotless generic brackets. The machine 39 may also or alternatively shape the surfaces of the bracket bases. This provides the bracket design option of torquing the teeth by either the bracket slot or base, as may be best for various bracket materials.

The equipment 38 also includes an appliance archwire bending or forming machine 40 which produces custom shaped archwires for the appliance 25 by feeding and bending wire of any one of several available materials and stiffnesses into the custom archwire shape. The equipment 38 may also include a machine for forming patient treatment components and hardware to aid in the manufacture or installation of the appliance 25. In the illustrated embodiment, this includes a machine 41 for the making of bracket placement jigs, which cuts each tooth crown portion of the tooth profile into a plastic form, along with a superimposed cutout of the positioned bracket, for use in accurately installing the custom brackets in their calculated positions on the teeth.

The appliance manufacturing machines 38 may be connected directly to the analyzing computer 30b or one or more may be connected to a separate manufacturing equipment controlling computer or machine controller 30c. The computer 30c may be located at the appliance facility 13 or, together with one or more of the appliance manufacturing machines 38, 40 or 41, be located at the orthodontist's office 11. In one preferred embodiment of the invention, one manufacturing computer 30c and the bracket cutting machine 40 are located at the orthodontist's office, along with the scanner 33 and input computer 30, which may be the same computer as the manufacturing computer 30c, while another manufacturing central computer 30c, which may be the analyzing computer 30b, the wire bending machine 40 and the jig forming machine 41 are located at the appliance facility 13. The optimum distribution of the computers 30, 30b and 30c and the scanner 33 and appliance manufacturing machines 38, 40 and 41 will be determined by the scale of the orthodontist's practice and the orthodontist's preferences. In the illustrated embodiment, the computers 30–30c are IBM PC clones, with Intel 80386 or 80486 microprocessors and equipped with 80387 or 80487 math coprocessors, respectively.

Certain components of the system 10 of FIG. 1 are described below in further detail.

Scanning Assembly 33

Three steps in the information input procedure (82), described below, involve the inputting into the computer 30, for analysis in digital form, of data concerning the shape of the mouth 18 of the patient 12 and of the shapes of the individual teeth therein. In these steps, digitized images and measurement data of the mouth 18 of the patient 12, preferably taken indirectly from the model 20, and digitized to form a three dimensional mathematical model of the patient's mouth 18. The mathematical model includes, in the preferred embodiment of the invention, the definition of certain parameters of the patient's lower jaw and individual teeth, and may include some information of the initial position and orientation of the teeth in the mouth 18 of the patient 12 for evaluating the magnitude of the treatment.

The input information 26 is, in some embodiments of the invention, input as a full three dimensional image, and then simplified by reducing it to a plurality of curves in a plurality of differently oriented planes or fairly flat curved surfaces, each defined in the independent X-Y coordinate system of the respective surface or plane. In subsequent analysis, these planes are oriented, translated and rescaled with respect to each other in arriving at a derivation of the ideal finish positions of the teeth and the design of the custom appliance 25. In accordance with the preferred embodiment of the invention, curves and points on the contours of the jaw and teeth of the patient 12 are expressed in terms of accepted or generally applicable orthodontic parameters so that manual and automated decision making can combine and coordinate the best of orthodontic knowledge and experience with the efficiency and precision of computer analysis to minimize the use of the orthodontist's time, shorten the patient's treatment period and optimize the final treatment result.

The various types of and components of the scanner 33 of various embodiments of the invention are described below.

Video Scanning Data Input Assembly 43:

One preferred form or component of the scanner 33 includes a video imaging assembly 43 as illustrated in FIG. 1A. The video imaging assembly 43 includes one or more video cameras 44 which each produce two dimensional images of the patient's mouth 18, preferably by forming an image of the model 20. When two or more are used together, the video assembly 43 produces stereo images capable of being resolved in three dimensions. In the illustrated embodiment of the invention, a single video camera 44 is employed to produce two dimensional video images of a plan view of the patient's lower or upper jaws 22 and 24, from the models 21 or 23, respectively, in generally horizontal X-Y planes. In accordance with this embodiment, other forms or components of the scanner 33 are preferably employed to produce information in a third dimension as described below.

Referring to FIG. 1A, the video imaging assembly 43 is shown diagrammatically in side elevation at the appliance manufacturer's facility 13. The video imaging assembly 43, in its preferred form, is an operator-computer graphical interface that includes the video camera 44 connected to a video interface board 44a in the input computer 30. The camera 44 is mounted on a stand 45 to face downwardly to form a top plan view one of one of the halves 21 or 23 of the model 20, shown as the mandibular portion 21 in FIG. 3, on a horizontal support 46 attached to a base 45a of the stand 45. The model half 21 or 23 is positioned on the support 46 such that the teeth face upwardly toward the camera 44 and so that the tips thereof lie generally in a horizontal plane that is maintained at a known fixed distance from the camera 44, so that the scale of the image formed by the camera 44 is known. This may be accomplished by mounting the support 46 on springs 46a to urge the model half 21 or 23 upwardly against a transparent horizontal plate 45b.

The input computer 30 has connected thereto a pointing device which may be a mouse 47a or, as shown, a mouse equipped digitizer board 47. The camera 44 produces a graphics image display 48 on the screen 35 of the computer 30, which an operator 28 may align with the assistance of a positioning grid G (FIG. 4A). With the digitizer 47, the operator selects points by positioning a curser 48a on the screen 35 with the mouse 47a. The selection results in the storage of X,Y coordinate data for each of the points selected. The points selected, in the description of the preferred process below, correspond to preselected boundary points of the teeth and, from the mandibular model 21, the lower jaw. From these top view boundary points, tooth and mandibular jaw dimensions are calculated. The calculated dimensions are used in analysis steps to calculate equations for the mandibular bone structure or mandibular trough MT and to calculate from the trough equation and the calculated horizontal dimensions and relative positions of features on individual teeth the finish positions of the teeth.

In the alternative to selecting points from the video image display 48, the same points may be selected in the same manner from a plan view video image of a digitized three-dimensional computerized image of the teeth and jaws, such as an image formed by a laser scanner, moire interference pattern scanner, ultrasonic scanner, stereo video cameras, or other three-dimensional imaging apparatus. Sectional displays $55a$ and $55b$ of such a three-dimensional computerized image made with a laser scanner are shown in perspective in FIGS. 3A and 3B, respectively. Such a laser scanner is described in connection with FIG. 1B below.

Laser Three-dimensional Image Input-Assembly 51:

One preferred form or component of the scanner 33 is the laser generated three-dimensional image forming assembly 50 illustrated in FIG. 1B. Referring to FIG. 1B, one of the halves 21 and 23 of the model 20 is mounted on a support 51 while laser 52 directs a laser beam $52a$ onto the model 21 or 22. The laser beam $52a$ is reflected and the reflected beam is detected by a sensor 53 composed of a photoelectric pixel array which uses a triangulation method to convert a change in position on the sensor into a change in distance between the assembly 50 and the model 21 or 23 mounted to translate parallel to the model 21 or 23 on a support 54 so as to scan the model with the laser beam. Equipment for producing images using laser technology in this manner is commercially available for forming computerized representations in three dimensions of manufactured and other objects. An example of equipment suitable for this purpose are the Cyber Scan TM Measurement System manufactured by Cyber Optics Corporation of Minneapolis, Minn. The images formed by such equipment would preferably include full detailed three-dimensional image data of the patient's lower and upper jaws 22 and 24, taken from the model 20, with the teeth in their original positions. The data is written in standard ASCII files by the equipment described and is readable by the input computer $30a$ into the digitized information files 26.

Illustrated in FIGS. 3A and 3B are two sections of the mandibular digitized model, and include a section $55a$ showing the front mandibular incisors $T_{BR1}$ and $T_{BL1}$ of the patient 12, and a section $55b$ showing the right mandibular second bicuspid $T_{BR5}$ and first molar $T_{BR6}$ of the patient 12. When such images are rotated to a horizontal plan view, a derivation of the same information that is available from the video imager 43 of FIG. 1A may be derived, and points may be selected therefrom for digitization automatically with software, or through an operator/computer interactive process as with the video scanner 43. The three-dimensional image 55 may be rotated into other orientations for the derivation of other information in various planes such as vertical tooth profile information that is derived with the mechanical scanner 57 described below. Additionally, other computerized procedures may be used to automatically derive information from the three dimensional image 55 with or without intervention or interaction by an operator.

Mechanical Probe Digital Scanner Assembly 57:

The scanner may also include, alternatively or in combination with other scanning equipment such as the video scanner assembly 43 of FIG. 1A or the laser scanning assembly of FIG. 1B above, a mechanical probe assembly 57 as illustrated in FIG. 1C. This entire assembly 57 is used in the illustrated embodiment of the invention in combination with the video scanner 43 to derive labial-lingual vertical profiles of the individual teeth of the patient from the model 20 to supplement jaw and horizontal tooth dimensional and shape information derived from a video image produced by the video scanner 43 from the model 20. Alternatively, portions of this assembly can be used to produce the same information from a three dimensional image 55 produced by equipment such as the laser scanning assembly 50.

Referring to FIG. 1C, the probe assembly 57 includes a measurement probe 60 which is moveable over the individual teeth of the model 21 to produce an electrical signal that is digitized for computer input of point locations or profiles of the surfaces of the teeth in separate X-Y for each tooth. In the illustrated embodiment of the process of the invention, the information 26 preferably derived from the model 21 includes the tooth profiles curves $PF_1$ in a labial-lingual plane viewed in a mesial-to-distal direction.

The probe assembly 57 further includes a magnetic base 59 upon which is mounted the model 20, and from which extends an upstanding vertical support 58 on which the probe 60 is mounted. The probe tip $60a$ is freely rotatable about a vertical axis on which its tip lies, while the probe itself is hooked to allow the tip to track recesses in the surfaces of the teeth of the model 21. The probe 60 is mounted on the support 58 to move in X and Y directions in a vertical plane preferably that extends through the support 58 and the probe 60. In this manner, the probe tip $60a$ is positioned to scan the surface of a tooth of the model 21 along this plane. The probe 60 is linked to the support 58 through a pair of orthogonal measurement position transducers 61, which respectively generate electrical analog measurements of the positions of the tip of the probe 60 along respective ones of the X-Y orthogonal coordinates. The outputs of the transducers 61 are connected to circuitry that generates a sequence of periodic readings of the transducer measurements of the probe tip positions which are then digitized. These outputs are sent in along lines $61a$ connected to input computer 30, preferably to a serial port thereof.

In use, a half of the model 20, for example, the mandibular model 21, is mounted upon the magnetic base 59 on a steel surveyor's mount 62 which slides on the base 59 when lightly urged, but which otherwise holds its place thereon for precise positioning. The mount can be raised, lowered or tilted for and for leveling. In operation, the probe 60 is manually moved by an operator 28 or automatically to scan the surface of each selected tooth of the model 21 to produce profile curves PF of a section of each tooth as illustrated in FIG. 3C. The profile PF may be generated by any one of a number of commercially available off-the-shelf CAD/CAM or illustration software packages, such as VERSACAD TM available from Prime Computers, Inc. of Bedford, Mass. The computer programs described in the flowcharts herein is written for use with VERSACAD TM in CPL TM, the programming language of therefor. The video images 63 of the profiles PF are displayed on the screen 35 and the digitized profiles are stored as part of the input information 26 in non-volatile memory of the computer 30.

With the curves such as the profile PF so formed, an operator can, with the use of the pointing device 47, select, by positioning the cursor on the formed profile on the screen 35, point parameters of the tooth, the coordinates of which can be thereby input digitally into the computer 30.

Appliance Manufacturing Equipment 38

The manufacturing equipment 38 of the preferred embodiment of the invention includes: an appliance bracket cutting or forming machine 39 that custom forms the bracket bases to mount to the teeth and cuts archwire slots in the brackets at precise calculated positions and angles; an appliance archwire bending or forming machine 40 that precisely bends archwires to a shape that will cooperate with the custom brackets to apply corrective forces to the teeth until they are in their calculated finish positions; and a bracket placement jig forming machine 41 that manufactures bracket placement jigs that conform to the contours of the patient's teeth, as recorded in the profiles PF. These jigs are used by the orthodontist to precisely place the custom brackets at calculated positions on the teeth.

The manufacturing equipment 38 is controlled by NC computer generated programs based on the data from the digitized input information files 26 and the calculated patient data files 36.

Figure 1D:
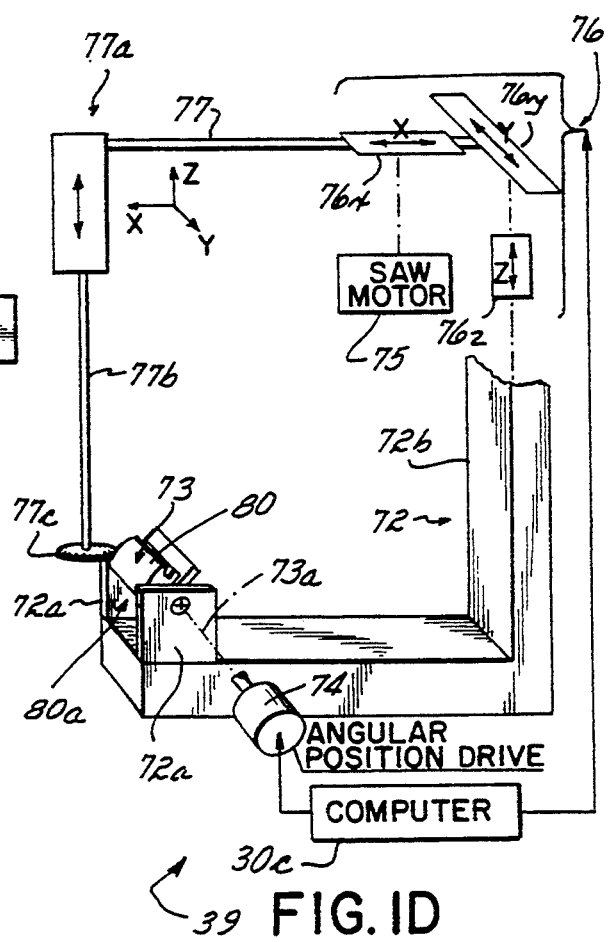
FIG. 1D is an isometric diagram of one embodiment of a bracket cutting device of the system of FIG. 1.

Bracket Cutting Machine 39:

Referring to FIG. 1D, a bracket slot cutting machine 39 is illustrated. The machine 39 includes a stationary base 72 on which is fixed a pair of upwardly extending workpiece support brackets 72a to the top of which is pivotally mounted a workpiece or bracket support 73. On the support, a full set 80a of brackets 80 for the custom appliance 25 is mounted, prearranged in an assembly or cartridge of twenty or twenty-four brackets. The support 73 pivots about an axis 73a extending between the brackets 72a. Connected to the axis 73a is an angular positioning motor 74 which positions the support 73, and the brackets 80 mounted thereto, to any angular orientation with respect to the horizontal. The motor 74 has an input connected to the computer 30c to set the inclination to the slot inclination angle of the bracket design in response to NC command codes.

Also fixed to the base 72 and extending upwardly therefrom is a saw support bracket 72b. To the top of the support bracket 72b is a saw drive motor 75 and a set of three saw blade positioning linear drive actuator 76, including an X-drive actuator 76x, a Y drive actuator 76y, and a Z drive actuator 76z through which a saw support arm 77 is supported to move respectively in the X, Y and Z directions, that is, in an X direction horizontally perpendicular to the axis of rotation 73a of the bracket holder 73, in a Y direction horizontally parallel to the axis of rotation 73a of the workpiece holder 73, and in a vertical Z direction. The actuators 76 have inputs connected to the computer 30c to receive positioning signals from the computer 30c to cut arcuate slots in the X-Y plane of the machine 39 in response to NC commands generated in accordance with a custom appliance design.

At the remote end of the moveable arm 77 is a slot cutter assembly 77a, drivably linked to the motor 75. The assembly 77a has extending downwardly therefrom a rotatable cutter blade drive shaft 77b, which has fixed to the lower end thereof a circular slot cutter blade 77c. The blade 77c lies in the horizontal X-Y plane and is of the thickness of the slot needed for the thickness of archwire selected. The archwires are typically rectangular in cross-section so that they are able to exert torque on the bracket, which accordingly will be provided by the saw blade 77c with a slot of rectangular cross-section. The base of the slot will be cut, in accordance with the command signals from the computer 30c, at an angle in the X-Y plane of the machine 39 that is tangent to the final curve of the archwire that it will receive. The base of the slot will be convex to accommodate the curve of the wire in the horizontal plane. The base of the slot will be convex to accommodate the curve of the wire in the horizontal plane. The inclination of the bracket slot is achieved by the angle of the support 73 in response to control signals from the computer 30c. The computer 30c is programmed to account for changes in elevation of the bracket 80 due to the offset of the brackets from the support axis of rotation 73a.

Wire Bending Machine 40:

The wire bending apparatus 40 is illustrated diagrammatically in FIG. 1E. Primary control of the apparatus 40 is preferably by an IBM PC clone, preferably with an 80386 or 80486 microprocessor with a math coprocessor, and with motion controller board 65 installed. The controller board 65 is, for example, an MC300 Motion controller 3-axis card manufactured by Motion Engineering, Inc. The MC300 is a dedicated motion control card which sends and received signals to and from MC-OLS stepper interfaces 66a and 66b. MC-OLS stepper motor interfaces 66a and 66b send control signal commands to the stepper motor power supplies 67a and 67b, such as Compumotor S-Drive stepper power supplies #88- 011483D, regarding rate and direction of motion of the motors.

The power supply 67a has an output connected to wire feed rollers 68, positioned on opposite sides of a wire guide 68a, which guides archwire 69 to feed it from a continuous coil supply. The power supply 67b has an output connected to a wire bending roller assembly or wire anvil 70.

The controller 66b additionally is adapted to receive feedback signals regarding position from a disc encoder 70a, such as a Dynapar/Veeder Root #E1000A76500, which monitors the position of wire forming roller 70b, providing closed loop control of a wire bending roller 70b. The roller is driven by a wire anvil motor 70c, such as a Compumotor #S/SX 57-102, through a drive screw 70d, such as an Industrial Devices Corp. Electric cylinder #X995A-2-M56-MT1-200-PS. The screw 70d converts the angular position of the motor 70c into linear motion of the roller 70b to deflect and bend the wire 69 as it is fed through the guide 68a by the rollers 68.

By coordinating the anvil 70 and the wire feed 68, formed archwires 64 of any planar shape are fabricated. The rollers 68 pinch the wire, forcing it to advance into the anvil 70. The roller 70b of the anvil 70 moves up and down varying the radius and thus controlling the radius to which the wire is permanently deformed. If the formation of archwires with inflection points, that is that have bends in opposite directions, a second anvil would be provided opposite the wire 69 from the anvil 70 and controlled in synchronism therewith.

A wire position sensor 71 is provided that inspects the finished archwire by comparing the width of the formed wire 64 to the desired width. The sensor 71 is mounted with respect to the anvil 70 and feed rollers 68 to detect the position of the formed archwire 64 when it is at the end of its forming cycle. This measurement provides a feedback signal that provides compensation for material property variations that effect the formed shape and the amount of overbending required. The sensor 71 sends information back to the computer 30c as to whether the wire 64 is acceptable or over-bent or under-bent. If the wire is either over or under-bent, the computer 30c calculates the correction required and incrementally modifies the signals through the interfaces 66a and 66b to provide compensation to progressively correct successive archwires 64 until the result of the signal from the sensor 71 is deemed acceptable by the computer 30c.

Bracket Placement Jig Forming Machine 41:

The bracket jig forming equipment 41 is preferably a standard NC mill configured as illustrated in FIG. 1F. The machine 41 includes the standard mill 81, having a downwardly projecting rotary tool head 81a on which is mounted an endmill tool 81b of, for example, 0.020 inches in diameter, where 0.022 inch archwire is used, and, for example 0.016 inches in diameter where 0.018 inch archwire is used.

The mill 81 is either connected to an controller which will have been loaded with CNC program code 42 prepared by the computer 30c or will be directly connected to the computer 30c. The mill 81 is provided with a tool support 81c to which a set of circular ABS plastic jig blanks 83, usually twenty or twenty-four in number, are fed by a feeding mechanism 81d, equipped with a magazine 81e of the sets 83a of jig blanks 83. The tool head 81a is moveable vertically to bring the tool 81b into contact with the blanks 83 and horizontally in the X-Y directions in accordance with the tool path instructions from the code 42.

GENERAL OPERATIONS AND PROCEDURES

In the preferred and illustrated embodiment of the invention, the overall configuration of which is illustrated diagrammatically in FIG. 1, the full custom system 10 is operated to produce the orthodontic appliance 25 based on the individual anatomy of the patient 12. One preferred method of the invention is represented by the operations and procedures illustrated in the flowchart of FIGS. 2.

The method of the present invention, in its preferred embodiment, includes three general operations. The first operation, is (85) a patient evaluation operation performed by the orthodontist 14 at the doctor's office 11 on the patient 12. This operation includes the traditional professional diagnosis and general prescription of treatment. According to the present invention, the evaluation operation (85) is followed by (87) a computer aided analysis and appliance design and manufacturing operation performed, preferably at least in part, at the appliance facility 13 to produce the custom appliance 25, and in turn followed by a patient treatment operation (89), which includes treatment of the patient 12 by the orthodontist 14 at the doctor's office 11, with the installation and use of the appliance 25.

(85) Patient Evaluation Operation

Referring to the system diagram of FIG. 1 and the flow chart of FIG. 2, the orthodontic evaluation operation (85) is performed at a doctor's office 11. The operation (85) includes the procedures (90) of the examination of a patient 12, (91) the preparation of the model 20 of the patient's mouth and teeth, (92) the prescription by the orthodontist 14 of treatment, (93) and communication the appliance facility 13.

The examination procedure (90) the patient 12, who requires orthodontic treatment, is examined by an orthodontist 14, who makes a diagnosis 15 of the condition of the patient and of the treatment, if any, needed. Based on the diagnosis 15, the orthodontist or doctor 14 assembles the information 16 that is necessary to implement the prescribed treatment.

In assembling the information 16, the orthodontist 14 (91) prepares a model of the patient's mouth 18, usually a physical model 20 from a mold of the patient's mouth, in its initial condition at the time of the diagnosis 15. The model 20 includes the mandibular model 21 of the patient's lower jaw or mandible 22 and the maxillary model 23 of the patient's upper jaw or maxilla 24.

Then, further based on the diagnosis 15, the orthodontist 14 (92) prescribes a particular treatment and generates a prescription 27 in a tangible record form.

The orthodontist 14 then (93) communicates the information 16, for example, by transmitting the model 20, the prescription for treatment 27, a record of information 17 identifying the doctor 14 and the patient 12, together with information 19 containing statistical and historic data of the patient 12, to an appliance design facility 13, at some remote location. At the appliance design facility 13, the information 16 is digitized and input into the computer 30 for analysis.

Alternatively, the orthodontist 14 may convert the information 16 to digital computer readable form and transmit the digitized information to the appliance design facility 13. In this alternative, the system 10 would be configured with the input computer 30 located at the orthodontist's office 11, and the orthodontist 14 or assisting personnel would perform portions of an data input procedure (94) described below.

(87) Analysis, Design and Manufacture Operation

When the information 16, which includes, for example, the model 20, the prescription 27 and the information 17 and 19, are received either at the appliance system manufacturer 13 or is ready to be digitized at the orthodontist's office 11, (87) an analysis, finish tooth position calculation, and orthodontic appliance design and manufacturing operation is begun. In the operation (87), the information 16 is processed and the custom appliance 25 for moving the patient's teeth to an optimum final or finish position in accordance with treatment prescribed by the orthodontist 14 is produced.

The operation (87) includes the procedures of (94) inputing into a computer the information 16 from the orthodontist 14, in digital form, (95) analyzing with the aid of computer 30b the input digitized information to arrive at the finish position of the teeth, (96) designing with a computer a custom orthodontic appliance in accordance with the computer analysis, (97) manufacturing the custom appliance 25 in accordance with the computer assisted design with the aid of computer controlled machinery, and (98) communicating the custom appliance 25 and accompanying instructions to the orthodontist 14.

In accordance with certain embodiments of the present invention, some or all of the appliance manufacturing step (97) can be performed at the facilities 11 of the orthodontist 14, in which case the communicating step (98) would involve the communication of machine readable code, in lieu of some or all of the completed custom appliance 25, from the design facility 13 to the orthodontist 14.

(94) Input Procedure:

In the input procedure (90) is illustrated in the flowchart of FIG. 2A. In the procedure (94), the received information 16 is input, in the illustrated embodiment by operator 28 at the design facility 13, into a computer 30 in digital form. Even where the inputing is performed by operator at the design facility 13, some information 16, such as the information 17 and 19, may be supplied by the orthodontist 14 in machine readable form and input directly into the computer 30. The input procedure (94) includes five steps (100)–(500), the substeps of which are described in detail in connection with the flowchart details of FIGS. 2E–2I below. The steps of the input procedure (90), in the illustrated embodiment, also include certain substeps that are part of the function of the analysis step (92) but are more conveniently performed at the time of the information is entered into the computer.

The input steps (100) and (200) involve the entry of background information assembled by the orthodontist 14. In the input steps (300), (400) and (500), tooth and jaw positions and profiles are defined in terms of orthodontic parameters and landmarks that can be later analyzed by computer to best implement the orthodontic knowledge, skill and experience embodied in the prescription 27 and of the orthodontic profession while efficiently automatically producing a optimum result. These steps of the input procedure (90) include:

(100) The inputing of the doctor-patient identification information 17 in digital form into the computer 30a:

This information is used to identify the records of the patient and the products produced.

(200) The inputing of patient background information 19 in digital form into the computer 30a:

This information is used in part in the calculating the finish position of the patient's teeth in accordance with genetic characteristics. Sex and race, for example, are used to assign certain seed values such as the inclination of the axes of the individual teeth of the patient 12 to an arch plane in step (625), which is used to determine an offset for tips of the teeth from the jaw bone or gum line.

This information also includes diagnostic determinations and treatment option decisions made by the orthodontist 14, such as determinations to extract teeth, or employ optional treatment norms.

(300) The inputing into the computer 30, from a top view image of the patient's mandibular model 21, the mandibular jaw shape and tooth dimensional information:

In implementing a treatment to correct the tooth alignment of the patient 12, the mandible 22 is the logical starting point because it is a solid bone and has relatively little pliancy. By contrast, the maxilla or upper jaw 24 is composed of segments held together by sutures which do not fuse until mid or late teens. Furthermore, these sutures can be separated by the orthodontist even after the point of initial fusion by simple and commonly known clinical techniques. These anatomical factors require that the orthodontist 14 make relatively small changes in the mandibular bone 22 and the preponderance of skeletal changes in the maxilla 24. For this reason, the position of the mandibular trough MT therefore taken as a constraint on the positions of the roots of the lower teeth.

In step (300) information is input for use, in part, to define from the patient's lower jaw bone the shape of the mandibular trough MT, which serves as the first constraint in arriving at the finish position of the teeth. In one embodiment, this is accomplished by superimposing a predefined grid G on a video or graphics image of the mandibular trough (from FIG. 3) in the manner illustrated in FIG. 4. In addition, the distances between the mesiodistal extremities, or mesiodistal widths MDW, that is, their contact points with adjacent teeth, in a horizontal plane, are input. These determine the total length of the dental arch and the relative center-to-center spacings of the teeth along the arch.

A mandibular trough equation MTE is derived, and may be converted to a symmetrical equation SMT. As a starting point toward calculating finish tooth position, the mesio-distal widths of the mandibular teeth are mathematically placed on the trough equation.

This is explained more fully below in connection with FIG. 4.

In the above and in many archform calculations below, a cubic spline equation form is used initially in fitting a curve to data points, then converted to a circle segment equation that provides advantages in the analysis and design process and in the final calculations needed to operate NC manufacturing equipment. This is explained below in connection with FIGS. 5 et seq.

Measured initial contra-lateral cusp spacing data are generated for use by the orthodontist 14 in evaluating the custom design and treatment parameters resulting from the final calculations below.

In some embodiments, horizontal profile data of the lower jaw may be input in this step, additional landmarks in the horizontal plane may be identified, or full three-dimensional images of the teeth and lower jaw may be made, for example, as discussed in the descriptions of FIGS. 1A–1C above.

(400) The inputing into the computer 30, from a bottom view image of the patient's maxillary model 23, maxillary tooth dimensional information:

The shape of the maxilla, which is made of a segmented bone, is a variable capable of being altered orthodontically in response to final tooth position calculations as set forth below. Therefore, its initial shape and initial maxillary tooth position is relevant only in evaluating the feasibility of the amount of alteration required and the type of treatment to be used.

In step (400), information is input into the computer 30c of maxillary jaw shape and tooth dimensional information from the maxillary model 23. This information is used in part to determine the mesiodistal widths MDW of each upper tooth, in a horizontal plane, and to determine the total length of the dental arch and the relative center to center spacings of the teeth along the arch.

Measured initial contra-lateral cusp and central groove/fossa spacing data are generated for use by the orthodontist 14 in evaluating the custom design and treatment parameters resulting from the final calculations below.

As with step (300) above, in some embodiments, horizontal profile data of the upper jaw may be input in this step, additional landmarks in the horizontal plane may be identified, or full three-dimensional images of the teeth and lower jaw may be made, for example, as discussed in the descriptions of FIGS. 1A–1C above. In these embodiments, techniques such as those described in step (500) may be employed in the horizontal plane in steps (300) and (400).

(500) The inputing of individual tooth elevational profile information from the two halves of the model 20:

The tooth profile information can be generated using computer analysis or interactive computer imaging from three-dimensional images, if employed, as illustrated in FIG. 3A formed with scanners such as illustrated in FIG. 1B, or with the use of the probe assembly 57 of FIG. 1C from the physical model 20 of the jaw. Use of the probe assembly 57 is herein described.

Rapid reduction of tooth shape information to important dimensions and landmark data for efficient and realizable calculations of finish tooth position is achieved by imaging carefully selected profiles of the teeth. Profiles are produced by outlining the tooth crown surfaces along a vertical plane or other similarly oriented surface that extends in a labial-lingual direction generally perpendicular to the arch of the teeth in the respective jaw. For the single cusp anterior teeth, this surface is generally a surface bisecting the tooth and the crown long axis CLA of the tooth. For multiple cusp teeth, the same generally applies except modification or displacement of the surface is intelligently made on some teeth to pick up the highest cusp or a marginal ridge that is relevant to development of the proper occlusion.

For most calculations, as set forth in the detailed explanation below, the tooth features profile can be assumed to be on a plane through the tooth centerline, even when they are not. With the features selected herein, such assumptions result in errors that are still much smaller than those accepted in conventional methods. In other calculations, the precise position of a feature must be considered, and provision for such considerations are made in the certain embodiments of the invention.

For each tooth, profile data is taken in separate X-Y coordinates that relate only to the selected surface or plane. In the course of the analysis and calculation of finish tooth position, these planes are separately translated and reoriented with respect to those of the other teeth and those of the trough and archforms, in several steps, until the ultimate interplane relationships are established.

(95) Analysis and Tooth Positioning-Procedure:

The computer analysis procedure is illustrated in the flowchart of FIG. 2B. In the computer analysis procedure (95), the digitized information input by the input procedure (94) is analyzed to calculate the finish position of the teeth, so that the custom appliance 25 can be designed in computerized design procedure (96) and manufactured in computer controlled manufacturing procedure (97). The analysis procedure (95) includes six steps and subroutines (600)–(1100), the substeps of which are described in detail in connection with the flowchart details of FIGS. 2J–2O below. These steps include the following:

(600) The dental analysis step in which the orthodontic landmarks of the teeth are identified:

A minimum number of points on the tooth profiles are selected that are sufficient for determining the contact points between teeth that are relevant to finish tooth position calculation and appliance design. These points are selected such that the calculations made from them are relatively insensitive to measurement errors in the input of the data in step (500). From the selected points, for each tooth, other parameters are derived, including an incisal center point ICP, a gingival center point GCP and the crown long axis CLA through the ICP and GCP, as explained below in connection with step (600) and FIG. 6 et seq.

In order to determine the relationship between the crown long axes and archwire planes, twenty-four of each crown type were removed from a set of orthodontic casts and sectioned along the mid-sagittal plane. These crowns were then mounted and projected at twenty times magnification on an optical comparator. Tracings were then made of these profiles. As a result, a procedure was determined for use to establishing the crown long axis inclination angles to produce the desired occlusion, and seed values were tabulated that and correlated with data such as the sex and race of the patient as entered in step (200). As a result of this analysis, preferred crown long axis inclination angles are produced with the present invention that are an improvement over the facial inclination angles employed in the prior art.

From the tabulated data, angles of inclination LAIs of the crown long axes CLAs of each of the teeth of each jaw are set relative to the plane that contains the mandibular trough equation MTE. This plane is parallel to a facial axis plane FAP used in clinical studies through a clinically defined facial axis FA of a tooth. These LAIs are later used to determine the horizontal offsets from the MTE of the tips of the lower teeth in step (1000) below, as well as the maxillary tooth placement in step (1100). The rotation of the inclination angle places new Y coordinates of each of the tooth profile planes established in step (500) parallel, and the X axes of these planes parallel to the same plane but of with their relative horizontal orientations and relative vertical positions yet to be determined. Once the teeth are rotated to their finish inclinations, precise crown heights, incisal and cusp tip locations, and other points and contours of the tooth surface are precisely defined for intertooth contact and appliance design and positioning calculations.

As an example, for the maxillary bicuspids and molars, a marginal ridge elevation MRE is determined for later use in calculations relative finish positions of the upper and lower teeth.

(700) The cuspid rise determination step in which the occlusion of the upper and lower teeth is defined:

The orthodontist 14 will have selected the technique to be used to guide the teeth of the patient into occlusion as the jaws come together. Depending on the selected occlusion technique, either all or part of the occlusion is brought by a rise of the cuspids above that of the other teeth, to thereby initiate contact between the upper and lower teeth which aligns the two arches as the jaw closes. Most orthodontists prefer to accomplish this with the rise of the cuspids.

From anatomical studies, data is employed and the amount of cuspid rise, or other cusp rise if selected, that is necessary to clear the buccal cusp height BHC of the teeth, which is determined from the landmark data of step (600).

(800) The mandibular tooth placement step in which the plane of the mandibular teeth is defined and the teeth are positioned with respect to the mandibular trough:

The step (800) accomplishes the preliminary mathematical construction of the mandibular occlusion. This step first calculates the positions of the mandibular teeth to place their tips in an occlusal plane pending final refinement of the placement.

The starting point for the mandibular tooth placement is to assume tooth positions that place the teeth with their crown long axes CLAs intersecting the plane of the mandibular trough on the mandibular trough equation MTE. This satisfies the condition that the mandibular teeth are set in the bone of the lower jaw. The CLAs of the teeth are also inclined at the seed value angles LAIs established in step (600).

Next, the positions of the teeth are adjusted vertically to place the tips of all of the mandibular teeth, except the cuspids, in the same plane. The tips of the mandibular cuspids are set to extend above the plane of the tips of the other mandibular teeth by a distance according to the cuspid rise criteria selected, preferably by setting the distance equal to one third of the total cuspid rise, as calculated in step (700).

Then, a horizontal OFFSET from the MTE, generally in the labial direction, is calculated trigonometrically for each mandibular tooth from its crown height above the mandibular trough and its long axis inclination angle LAI. This calculation results in a mandibular trough offset equation MO, which is an outward radial expansion of the MTE. The MTE was defined in the form of a series of circle segments in step (300). The expanded MO equation is a discontinuous arch constructed by adding the respective OFFSET of each tooth to the radius of the circle segment of the MTE with which the midpoint of the width of the tooth is associated.

The teeth are then placed on the offset equation MO beginning with the placement of the central with its mesial contact point on the mandible centerline and the tooth midpoints on the MO. Then moving distally, the remaining teeth on the same side of the mandible are placed on the MO with their mesial contact points MCP in contact with the distal contact point DCP of the previous tooth. The same procedure is employed for the teeth on the other side of the mandibular arch.

An alternative further refinement would consider the vertical position on the teeth of their widest points and, considering the also the inclinations of the teeth, make a trigonometric adjustment so that the tooth contact points are spaced by the tooth widths MDW at the height of their actual widest points, rather than assuming the teeth contact in the plane of their tips.

(900) The best fit cusp step in which the best fit equation is derived for mandibular arch:

In this step, a continuous curve is derived using statistical methods to produce a best fit buccal cusp equation BFBCE from the disconnected line segments of the MO. This is also illustrated in FIG. 4A. In the embodiment described below, a Bezier equation is used. A cubic equation is then generated from resulting data points that define the best fit equation. The cubic equation of the BFBCE is then converted to circle segment form as with the MTE above.

(1000) The mandibular teeth placement step in which the positions of the mandibular teeth are calculated for placement on the best fit arch equation:

The positions of the lower teeth are then recalculated to move the teeth horizontally, parallel to the MOC, such that the incisal center points ICP lie on the BFBCE. For incisors and cuspids, the ICPs are the tips of the teeth in the profile planes of steps (500) and (600). For the bicuspids and molars, the ICPs are the buccal cusp tips of the teeth. For purposes of placement of the teeth on the BFBCE or other archform, the ICPs are assumed to lie midway between the mesial and distal contact points of the respective teeth. Accordingly, tooth placement is achieved by moving the teeth normal to the circle segment associated with these ICPs. This recalculation of position has the effect of moving the roots of the teeth normal to the arch associated with their ICPs, either labially or lingually, such that their ICPs fall on BFBCE, when viewed from above.

This placement is the finish position of the mandibular teeth.

(1100) The maxillary placement step in which the maxillary arch is derived for occlusion with the placed mandibular teeth:

This step fits the positions of the maxillary teeth to the already positioned mandibular teeth. The maxillary teeth have not yet been positioned with respect to any equation, but the inclination angles of their dimensions and crown long axes CLAs have been determined in step (600). This positioning involves setting the tips of the maxillary teeth on the BFBCE, with certain modifications to the equation and the placement criteria to account for the way the different types of teeth occlude.

In adjusting maxillary tooth positions, the cuspids, the anterior teeth and the posterior teeth are treated separately to bring their relevant contact surfaces into three different respective arches that are then aligned relative to each other.

Since the anterior teeth do not occlude incisal edge to incisal edge, the BFBCE is modified to take into account the distance from the BFBCE to the labial contact points of the mandibular incisors and laterals, plus a horizontal or labial clearance, with the maxillary teeth. This defines the points of occlusion with the maxillary anteriors, at the intersection of their lingual surfaces with the plane of occlusion MOC. These points lie in a maxillary anterior contact arch form MAAF. This equation is calculated by expanding the BFBCE, by enlarging the radii of the circle segments of which it is made up, to account for these tooth dimensions and the clearances.

The vertical positioning of the maxillary anteriors and cuspids is then performed based on the vertical occlusion methods that have been prescribed, establishing an overlap for the incisors and cuspid rise as determined in step (700). This defines the vertical position of the maxillary cuspids and anteriors with respect to the MOC, and thereby defines the incisal overlap or overbite.

Placement of the maxillary posterior teeth places the intersections of the marginal ridges and the central grooves from steps (400) to (600) the cusps of the mandibular teeth with which they will occlude. The maxillary tooth movements needed to achieve this occlusion are applied to calculate a central groove marginal ridge arch form CGMRAF by modifying the BFBCE. The cusp tips of the maxillary cuspids are placed between the archforms of the incisors and of the posteriors, for example, by averaging the distance from the BFBCE to the MAAF and to the buccal cusp of the first maxillary bicuspid, by placing the cuspid mesial and distal contact points in contact with the adjacent teeth, by calculating a clearance as was done for the incisors or by some other criteria. The archforms for the maxillary tooth placement are illustrated in FIG. 4B.

The vertical positioning of the remaining teeth takes into account the occlusion and other prescription information input in step (200). The remaining calculations are set forth in detail below.

(96) Appliance Design Procedure:

The appliance design procedure (96), as illustrated in the flowchart of FIG. 2C, calculates the dimensions of the appliance components in a form capable of being translated into NC codes for operating NC machinery for production of the appliance components, such as the brackets and archwires and also placement jigs for installing the brackets in the proper positions on the teeth of the patient. In the appliance design procedure (96) includes the following steps (1200) through (1800), which are further illustrated in the detailed flowcharts of FIGS. 2P-2V:

(1200) The mandibular archwire plane step in which the plane of the archwire for the mandibular teeth is defined in relation to the teeth of the mandible:

Where labial brackets are to be applied, as illustrated in FIG. 8, a plane is selected for the mandibular archwire that avoids interference with the mandibular archwire and brackets with the maxillary teeth, which overlap on the labial side of the mandibular teeth. Where lingual brackets are to be applied, this step is performed to define a maxillary archwire plane to avoid interference between the lingually mounted maxillary archwires and brackets with the mandibular teeth that overlap on the lingual side of the maxillary teeth.

This step involves the selection of the archwire plane and defines it in mathematical relation to the MOC. Once defined, the bracket positions on the teeth are determined such that the archwire slots will lie within the dimensional limits of the bracket. Where possible, it is preferable that the archwire lie in a literally flat plane and be symmetrical about the midline of the arch. As such, the archwire will be properly shaped for installation with either side facing upward.

(1300) The mandibular slot inclination step in which the angles of the slots of the mandibular tooth brackets of the appliance are calculated:

The slot inclination angle for the mandibular brackets is calculated from the angle between the mandibular archwire plane and the angle of the mandibular tooth surface to which the base of the bracket is to be mounted. The slot inclination angle may be achieved by cutting the full angle into the slot, by inclining the bracket base, or by both of these methods.

(1400) The maxillary archwire plane step in which the plane of the archwire for the maxillary teeth is defined in relation to the teeth of the maxilla:

The maxillary archwire plane in the case of labial appliances, and the mandibular archwire plane in the case of lingual appliances, has few constraints on its position and may be selected based on cosmetic considerations. It is usually selected as a plane midway on the crown of the maxillary teeth. It is therefore normally not parallel to the mandibular archwire plane. Once defined, the bracket positions on the teeth are determined such that the archwire slots will lie within the dimensional limits of the bracket.

(1500) The maxillary slot inclination step in which the angles of the slots of the maxillary tooth brackets of the appliance are calculated:

The slot inclination angle for the maxillary brackets is calculated from the angle between the maxillary archwire plane and the angle of the maxillary tooth surface to which the base of the bracket is to be mounted. The slot inclination angle may be achieved by cutting the full angle into the slot, by inclining the bracket base, or by both of these methods.

(1600) The mandibular archwire and bracket in-out dimension calculation step in which the slot depth and bracket geometry is calculated for the mandibular tooth brackets:

For each bracket, the deepest and shallowest slot depths is determined to develop a window into which the archwire must pass, as illustrated in FIG. 8A. Then the smoothest archwire curve that will pass between the depth limits is determined. The smoothest curve is considered to be one with the least variation in radius changes along the curve, and preferably with no inflection points. A cubic spline equation is used to fit the points and the equation is then converted to one of circle segment form.

(1700) The maxillary archwire and bracket in-out dimension calculation step in which the slot depth and bracket geometry is calculated for the maxillary tooth brackets:

As with the mandibular slot depth calculations, for each maxillary bracket, the deepest and shallowest slot depths is determined to develop a window into which the archwire must pass. Then the smoothest archwire curve that will pass between the depth limits is determined. Here to, the smoothest curve is considered to be one with the least variation in radius changes along the curve. A curve with no, or the least number of inflection points is preferred. A cubic spline equation is used to fit the points and the equation is then converted to one of circle segment form.

(1800) The bracket placement jig designing step in which placement jigs are designed for use in properly positioning the custom designed brackets on the patient's teeth:

After the brackets and archwires are completely defined as in the above steps, with the depth and angle of the slots finalized for in the positioning of the brackets on the teeth and the shape of the desired archwires are described mathematically, bracket placement jigs are designed that will be used to assist the orthodontist in placing the brackets at the proper locations on the teeth. The designing of the jigs, in the preferred embodiment, is carried out in the software that generates the NC machine code in the performance of the jig manufacturing step (3500) below. This deferring of the jig design allows for consideration of appliance hardware modifications that may be made in the course of the bracket and archwire forming steps (3000) and (3200), respectively.

The provision of the bracket placement jigs furthers a goal of the practice of orthodontics to treat cases to occlusal perfection with the least amount of effort, discomfort and time expended. The portion of this goal that can be accomplished by appliance design and manufacture has been described above. While the individualized appliance geometries thus defined will be fabricated, the ability to place the bracket portion of the appliance system on the teeth with sufficient accuracy to allow the appliance system to deliver the desired orthodontic relationship, heretofore not realized clinically, is provided as follows: The brackets are placed according to the three criteria:

1. Height: The height is established so that the appliance causes the upper and lower teeth to contact each other in the prescribed manner.
2. Mesio-Distally: The mesio-distal location is established so that the mesial and distal ridges of the teeth are parallel to the archform for that patient.
3. Long Axis: The bracket is aligned relative to the long axis of the tooth so that the appliance system tips the tooth to the desired angle relative to the archwire.

From the vertical profile data of step (500), and horizontal or three dimensional profile data of steps (300) and (400), the shape and size of each tooth is extracted, including particularly the profile in a mesio-distal view at the height of contour or along a plane perpendicular to the greatest prominence of the central developmental lobe of each tooth. Additionally, the geometry of the archwire slot has been accurately related to the respective teeth. This geometry includes the intersection of the archwire plane with the tooth profile curve, the slot inclination angle and the slot in-out dimensions. In addition, the wire size and bracket geometry information are assembled, and tool size and clearance information are taken into account.

With this information, a bracket placement jig is designed for NC controlled manufacture to position the slot, and thereby the bracket, precisely on the tooth.

In FIG. 8D, a plastic jig 82 is shown which engages the walls and bottom of the bracket slot fully. Additionally, the portion of the jig 82 contacting the tooth designed to be formed to precisely fit the known contour of the tooth, as determined by the profiles input in step (500). This assures that the bracket slot and hence the bracket is placed at precisely the correct height when bonded to the tooth.

Brackets are placed so that the slots are not necessarily perpendicular to the long axis of the tooth but at varying degrees of cant. The jig 82 accomplishes this goal by the use of an adapter 84 that fits into the bracket slot 82b and a coplanar slot 84a (FIG. 9T) to engage the plastic blade jig 82, as illustrated in FIG. 8D. The jig design substeps, which are preferably performed in step (3500) and included in the detailed flowchart of the jig manufacturing step of FIG. 2Z, are summarized in the flowchart of FIG. 2V. The design is converted into CNC code in step (3500) for controlling the jig forming machinery 41 primarily to cut a contoured surface that conforms the profiles of the tooth so that the jig fits in a precise position on the tooth to position the bracket for adhesion to the teeth.

In installation performed in the treatment operation (89), the jig 82 is lined up with the long axis of the tooth crown when viewed from either the front or facial surface of the tooth and from the biting or occlusal surface. A plastic blade form of jig 82 offers visual reference to the height of contour of the tooth and alignment of the bracket with the marginal ridges.

(97) Appliance Manufacturing Procedure:

The appliance manufacturing procedure (97), as illustrated in the flowchart of FIG. 2D, entails the generation of controller codes for NC machinery to produce the brackets, archwires and bracket placement jigs designed in the appliance design procedure (96), and the manufacture of the appliance components with the use of the machinery controlled by the codes. The procedure (97) includes the steps of:

(3000) Controlling and operating the bracket forming machinery 39 to produce the custom brackets:

The bracket manufacturing procedure of the preferred embodiment involves the generation of NC code for the bracket slot cutting mill 39 of FIG. 1D, as illustrated in the flowchart of FIG. 2X. The step involves the geometric relating of the tooth profile information PF for each tooth, and other tooth contour information of the shape of the surface of the tooth to which the bracket is to be attached from steps (300) and (400), and the archwire plane, slot inclination angle and slot depth information from steps (1200) through (1700). In addition, the bracket forming step performs the function of selecting the bracket blank from which the bracket is to be fabricated. The bracket blank is made up of a base or pad that is attached to the tooth and an outwardly projecting support into which an archwire slot is formed.

The preferred embodiment includes the forming of brackets by cutting custom slots in bracket blanks while preserving the base inclination angle. Brackets could be alternatively fabricated by inclining the bracket bases or pads. Additionally, bracket bases may be contoured to conform to the surfaces of the teeth, or a bonding agent may fill the space between the bracket base and the tooth. Furthermore, while in the preferred embodiments, a mechanical cutter blade forms the bracket, other means such as wire EDM, machining, casting or stereo lithography may be employed.

(3200) Controlling and operating the Wire-bending machinery 40 to produce the custom archwires:

The software that operates the computer 30c to drive the wire bending apparatus 40 reads data files generated for the mandibular and maxillary archwires in steps (1600) and (1700) respectively. Also read by the computer 30c are data on the characteristics of the unformed wire 69, including that relating to the material of which the wire is made, as well as its cross-sectional shape and dimension. The file that is read contains coordinated data regarding calculated archwire segment lengths and radii which cumulatively describes geometrically the desired archwire shapes. As explained above, the archwires consist of a sequence of tangential arc segments with each segment a particular length and radius.

The arch forming software determines the position of the roller 70b of the anvil 70 that is required to produce a given radius in the particular wire material and cross-section by going to a look-up table, previously derived and stored in a file accessible by the computer 30c, containing constants necessary to correct for each wire material and cross-section. The anvil 70 is driven to the desired position to produce the required radius and the feed roll motor 70c is driven to create the desired length of wire at that radius. By adjusting the position of the anvil roller 70b and length of wire fed for with the roller 70b so adjusted, archwires 64 of the calculated final sequential tangential radii are fabricated.

(3500) Controlling and operating the jig forming machinery 41 to make custom placement jigs for the location of the brackets on the patient's teeth:

The machine control codes for controlling the jig forming machinery 41 are produced directly from the tooth profiles generated in step 500 and from the archwire plane location of steps (1200) and (1400), the slot inclination steps (1300) and (1500), and the slot in-out dimensions from the steps (1600) and (1700). As stated above, the jig design step (1800) is preferably performed in the course of, and is described herein as part of, the jig manufacturing step.

The profile data, which represents the profile curves with a fairly high resolution of data points is a series of straight line segments for developing the codes for driving the NC equipment. Tool and bracket dimensions and design clearances are also taken into account, and CNC codes are generated to cut jigs from circular plastic wafers on a standard CNC mill using a small carbide endmill tool. The details of the substeps of the step (3500) are included in the flowchart of FIG. 2Z.

(98) Appliance Transmission Procedure:

One of the ultimate objectives is to place the custom orthodontic appliance 25 into the hands of the orthodontist 14, along with the tools and information necessary for the proper installation of the appliance 25 in the mouth of the patient 12 to treat the patient by moving the patient's teeth to the calculated finish positions. This is best understood by reference to FIG. 1.

Referring to FIG. 1, as set forth above, the configuration of the preferred system 10 will vary depending on the nature and scale of the orthodontist's practice. Preferably, all or much of the appliance design portion of the procedure (87) takes place at an appliance design facility 13, although in a large scale orthodontic clinic, the entire process could be carried out at the patient treatment location. Usually, however, the functions performed in the design computer 30b, or design portion of the computer 30, are carried out at the appliance facility 13, together with some of the manufacturing functions performed by the manufacturing control computer 30c and the appliance manufacturing equipment 38.

In the configuration where, as illustrated, some or all of the appliance 25 is made at the appliance facility 13, the custom appliance 25 is transmitted to the orthodontist 14. Along with the appliance 25 is communicated documentation in the form of a hard copy printout of information 37 generated by the design computer 30b, which could also include documentation of the input data that made up the data 26 and the prescription information 27, and a printout of parameters recorded by the manufacturing computer 30c.

The transmitted appliance 25 includes a set of archwires 64, as illustrated in FIGS. 8E and 8F, a complete set of custom brackets 80, as illustrated in FIGS. 8D and 8F, and the placement jigs as illustrated in FIGS. 8D and 9T through 9W. Along with the jigs 82 are included a set of adapters 84 that are used to align the slots 80b of the brackets 80 with coplaner slots 84a of the jigs 82. The appliance and the bracket placement jigs therefor are similar in the case of lingual appliances, a bracket for which is illustrated on a tooth in FIG. 8G while the lingual appliance is shown positioned on the mandibular teeth in FIG. 8H.

In addition, custom archwires 64 are transmitted to the orthodontist 14. These archwires include archwires in the exact form, as illustrated in FIG. 8E, to move the teeth to their finish calculated positions, as illustrated, for example for the lower teeth, in FIG. 4D. In FIG. 4D, the archwire 64 is shown in the unstressed state (or having nominal residual stress sometimes motivating some orthodontists to prescribe overcorrection) that it will attain when the appliance 25 has moved the patient's teeth to the calculated finish positions. This is the same shape as the archwire of FIG. 8E shipped to the orthodontist 14. This finish archwire will be of a material and stiffness determined to be appropriate for the final positioning of the teeth. Depending on the severity of the initial malpositioning of the patient's teeth, however, less stiff archwires, or temporary archwires may be desired for beginning the orthodontic treatment. Thus, additional archwires 64 of various properties but in the shape shown in FIG. 8E will be provided the orthodontist 14. In addition or in the alternative to the provision of these additional archwires, an actual size drawing or template having thereon the shape shown in FIG. 8E will be provided the orthodontist 14 to enable him to form archwires for preliminary treatment and rough positioning.

In alternative configurations, information may be sent from the design computer 30b in machine readable form, for example by diskette 34 or modem, to a manufacturing computer 30c to which is attached one or more of the appliance component manufacturing machines 38.

(89) Patient Treatment Operation

The patient treatment involves, first, the assembly of the respective bracket 80, jig 82 and adapter 84 combinations, as illustrated in FIG. 8D, and the application of the brackets 80 thereby to the patient's teeth. This involves the application of adhesive to the area generally in the center of the face of the tooth, either labial or lingual, to which the brackets 80 are to be applied. This is illustrated in FIG. 8D, for example, with the application of a bracket 80 to the labial face of a maxillary incisor $T_{U,1}$. The assembly is positioned on the tooth with the blade of the jig 82 positioned on a generally vertical labial lingual cross section through the approximate center of the tooth, in the plane that may be said to contain the crown long axis CLA of the tooth.

When the bracket adhesive has set, the bracket placement jig 82 is removed by first sliding out the adapter 84 mesiodistally and then sliding the jig 82 off of the incisal edge of the tooth, leaving the bracket in the calculated position.

Then, with the brackets 80 set on the teeth the archwire 64 is installed. Often, the first archwire installed will be one of lower stiffness than the final archwire. In the example of FIG. 8F, the mandibular teeth in their initial position as illustrated in FIGS. 4 and 4A are shown. The brackets 80 are positioned on the teeth in the exact same positions as shown in the calculated finish position diagram of FIG. 4D. Because the teeth are not yet in this ideal finish position, the archwire 64, when inserted into the archwire slots and tied to the brackets 80, will be stressed into the elastically deformed condition shown in FIG. 8F. This stressed condition of the archwire 64 operates, without the need of the orthodontist to artfully bend the wire, to apply the forces to the teeth to urge them toward the ideal positions of FIG. 4D. This force will continue to be applied until the teeth have moved to the finish positions. In some prescribed forms of treatment, the wire and brackets are designed to move the teeth to a slightly overcorrected position to allow for a relaxation movement of the teeth when the appliance 25 is removed.

DETAILS OF STEPS OF APPLIANCE ANALYSIS, TOOTH POSITION CALCULATION, AND APPLIANCE DESIGN AND MANUFACTURING OPERATION (87)

The analysis, design and manufacturing operation (87), as stated above, includes the (94) input, (95) analysis, (96) design, (97) manufacturing, and (98) transmission procedures of a computerized custom designed appliance manufacturing operation. The steps of those procedures, as outlined above, include the following:

Digitized Input Procedure (94)

The input of digitized information includes the (100) input of patient and doctor identifying information, (200) the input of patient background information, (300) the input of digitized information of the horizontal dimensions of the mandibular teeth and the mandibular bone, (400) the input of horizontal dimensions of the maxillary teeth, and (500) the input of vertical labial-lingual profile information of each of the individual teeth.

(100) Identification Information Input Step:

The first step in the procedure (82), as illustrated in flowchart of FIG. 2A, is (100) to input the doctor-patient identification information 17. This step (100), as illustrated in the detailed flowchart of FIG. 2E, includes the substeps, performed by an operator 28 in response to prompts for text input at a terminal of the computer 30, of (105) input of the doctor's name, (110) input of the doctor's identification number, and (115) input of the patient's name. Then, the computer 30 (120) assigns a patient identification number. With this information, (125) a patient-specific floppy disk or diskette 34 is automatically formatted.

(200) Patient Background Input Step:

The next step in the information input procedure (94), as illustrated in FIG. 2A, is (200) the entry, in response to prompts, of the patient background information 19, and the prescribed treatment information 27 from the doctor. This step, as illustrated in the detailed flowchart of FIG. 2F, involves the substeps of (205) entering, from the background information 19, the patient's age as numerical data, and selecting (210) the patient's sex and (215) the patient's race from options on the screen. Then, from the prescription information 27, the data are entered, by selecting choices from multiple choice prompts, from information such as the following:

(220) Whether or not the treatment is to include an extraction, and if so, which teeth are to be extracted;

(225) Whether the occlusion type is a group function or a cuspid rise, and if a cuspid rise, whether averages or individual head film is to be used;

(230) Whether the prescribed procedure is to preserve lower intercuspid distance or allow expansion, and if expansion is to be allowed, how much expansion;

(235) Whether or not the occlusion is mutilated;

(240) Whether a Steiner compromise is to be allowed to accommodate skeletal discrepancy;

(245) Whether a Roth or Ricketts inset is to be used on upper laterals, and if so which;

(250) Whether a Roth or Andrews upper lateral overbite is indicated, and if so, which;

(255) Which is the preferred slot size, from traditional sizes 0.018" or 0.022" (0.45 mm or 0.55 mm), or other available size, or which 0.20" (0.50 mm) would often be acceptable;

(260) Whether the case is to be treated with labial or lingual appliances;

(265) Whether the case is to be diagnosed using symmetry or not;

(270) How inter-incisal angle is to be determined, using the Andrews Norms, the Parallel Upper Central to Facial Axis Norm, or Ricketts Norm.

(300) Mandible Digitized Video Input Step:

The forming of the computerized mathematical model of the teeth of the patient 12 begins with (300) the inputing of video or other graphics top view image of the patient's lower jaw, including the teeth, as illustrated in the detailed flowchart of FIG. 2G. Such an image as input by the video scanner 43, is illustrated in FIG. 3.

The step (300) includes the digitizing and processing of the data of the widths of the mandibular teeth and size and shape of the mandibular bone or bone of the lower jaw 22 of the patient 12 from the horizontal plan view of the lower jaw as in FIG. 4. The mandible 22 is composed of hard or cortical bone on the external surface and soft or cancellous bone in the interior. This bone is not as orthodontically alterable as is the maxilla. Since the lower teeth must remain in the mandible, determination of its shape and boundaries is made so that a skeletal arch can be defined to be used as a starting point in the calculation of the finish position of the teeth.

The lower teeth must lie on the mandible 22 in an arch that may be defined as the mandibular trough MT, as illustrated in FIG. 4. The roots of the lower teeth of the patient are contained within the mandibular trough MT, which is defined as the space between boundaries $B_L$ and $B_B$ of FIG. 4. The outer, or buccal, and inner, or lingual, boundaries $B_B$ and $B_L$, respectively, are preferably digitized by interactive selection by the operator 28 from an image 48 of the cortical bone of the mandible 22 on the screen 35. Furthermore, the mandibular teeth must lie in the arch in contract with one another. They each occupy a portion of the arch equal to the distances between their mesial and distal contact points with the adjacent teeth. These tooth extremities are also preferably digitized by interactive selection from the image 48.

To (300) input data of the patient's mandibular teeth and lower jaw 22, as illustrated in the detail flow chart of FIG. 2G, (305) a video graphics image 48 (FIG. 3) of mandibular model 21 is first input to the screen 35 of the computer 30c. Then (310) a grid G is overlaid on the video image of the mandibular 22 as illustrated in FIG. 4. The grid G is presents grid lines that intersect the image 48 on the screen. The operator 28 (315) resizes the grid G, if necessary, and orients the image relative to grid G to define X,Y coordinates with a Y axis on a midline ML of the lower jaw 22 and an X axis perpendicular to the Y axis through a selected intersection point or origin 0,0, preferably set at the mesial contact points of the lower central incisors.

Next, the computer 30 prompts the operator sequentially to select each point, first for the individual tooth contact points, then the jaw bone boundaries. With the pointing device 47, (320) the operator 28 moves the cursor on the screen 35 and selects (e.g., clicks with a mouse on) the prompted point, thereby initiating the software for digitizing the X,Y cartesian coordinates of the mesial and distal extremities $M_{X,Y}$ and $D_{X,Y}$, respectively, for each mandibular tooth. The mesial extremity $M_{X,Y}$ of a tooth is the point on its surface closest the midline ML along the mandibular arch (the mesial direction m) while distal extremity of a tooth is the point on its surface closest the rear of the mouth along the mandibular arch (the distal direction d). From the X,Y coordinates of $M_{X,Y}$, and $M_X$ and $M_Y$, and of $D_{X,Y}$, $D_X$ and $D_Y$, (325) the mesio-distal width $MDW_I$ of each tooth I, on each side of the mandible 22, is calculated using Pythagorean theorem:

$$MDW = \sqrt{(M_x + D_x)^2 + (M_Y + D_Y)^2}$$

where:
$M_X$ is mandibular X coordinate.
$M_Y$ is mandibular Y coordinate.
$D_X$ is distal X coordinate.
$D_Y$ is distal Y coordinate.

These widths are then summed to calculate the total length MAL required of the arch to accommodate the mandibular teeth. Since all of the teeth will be finally positioned to be in contact with the adjacent teeth, this length remains a constant length of any arch on which the mandibular teeth are placed in the calculations.

Then, by moving the pointing device 47 to the intersections of the lines of the grid G with the visible boundaries $B_B$ and $B_L$ and selecting the intersection points, data is input for determination of the shape of the mandibular trough MT. The point selection function can be made with conventional available CAD/CAM, imaging or illustration software and the pointing device 47. (330) From the selected intersections of the lines of the grid G with the mandible boundaries $B_B$ and $B_L$, cartesian coordinates $La_{X,Y}$ and $Li_{X,Y}$ of labial and lingual limits, respectively, of cortical bone on both sides of mandibular jaw are generated. The X,Y coordinates La and Li so chosen are digitized as above on the boundary lines $B_L$ and $B_B$ of the cortical bone, between and interproximate the teeth.

After the points La and Li are chosen representing the cortical bone limits, (335) midpoint coordinates $MP_{XY}$ are calculated between each of the individual labio-lingual pairs of La and Li. Also, calculated are the bone width distances between each of the respective labio-lingual pair DLL, as follows:

$$MP_X = La_X + \frac{Li_X - La_X}{2} \; ; MP_Y = La_Y + \frac{Li_Y - La_Y}{2}$$

-continued $$DLL = \sqrt{(La_X + Li_X)^2 + (La_Y + Li_Y)^2}$$

where:
$La_X$ is labial X coordinate of point La.
$La_Y$ is labial Y coordinate of point La.
$Li_X$ is lingual X Coordinate of point Li.
$Li_Y$ is lingual Y coordinate of point Li.

These midpoints $MP_{X,Y}$, one of which is the designated origin $MP_{0,0}$, lie on an arch that describes the size and shape of the center of the cancellous portion of the mandibular bone 22.

At this point, the beginning of the analysis for the calculation of the finish positions of the teeth is carried out. The coordinates of points $MP_{X,Y}$ are recalculated relative to a new origin 0,0 at the calculated midpoint between the mandibular centrals, to normalize the mandibular trough equation to its own independent midpoint when calculated below. The sum of the individual mandibular tooth widths MDW equals the total dental length or mandibular arch length MAL contained in the mandibular trough equation MTE that will be constructed through the points $MP_{X,Y}$. MAL is referred to as the arch perimeter.

At this stage, (340) the midpoints are typically averaged right to left to eliminate any asymmetry that may be present due to slight measurement errors. If, however, the patient has been diagnosed by the orthodontist 14 to be of asymmetrical anatomy, the averaging process is not performed. Such a determination will have been made by the orthodontist 14 in the examination procedure (90) described above and specified of the prescription 27 in step (265) of the procedure (92) described above. An advantage of the averaging process is that, when used, it assists the final positioning of the teeth symmetrically about the midline ML and will make it easier for an archwire to be produced that is symmetrical from right to left, and thus can be made such that it can be installed in inverted orientation.

The midline ML shown in FIG. 4 is the axis of such symmetry corrections. These corrections for each point $MP_{X,Y}$ are calculated as follows:

$$S_X = MP_X + \frac{PR_X - PL_X}{2} \; ; S_Y = MP_Y + \frac{PR_Y - PL_Y}{2}$$

where:
$S_{X,Y}$ is the symmetricalized point $MP_{X,Y}$
$MP_{X,Y}$ is mid-point of mandibular trough
$PR_{X,Y}$ is a point $MP_{X,Y}$ on the right side
$PL_{X,Y}$ is the corresponding point on left side of the trough With the completion of this symmetricalization process, a mathematical equation MTE, which describes the size and shape of the mandibular trough according to steps (345), (350) and (355), is derived by fitting a curve to the points $MP_{X,Y}$. Preferably, this curve is derived by fitting a series of cubic equations, such as a cubic spline equation, to pass smoothly through the points, for example, through the averaged midpoints $S_{X,Y}$. The cubic equations allow the determination of the slope of the curve at each of the midpoints.

The cubic equations are then preferably converted in form to a series of segments of tangent circle equations with slopes equal to the slopes of the cubic spline at the midpoints, and equal to the slopes of the adjacent circle segments at the segment end points, or their points of intersection, along the curve. To fit a cubic equation with quadratics, two circles CS and CL are used to describe each segment of the MTE between midpoints, as illustrated in FIG. 5. This allows a smooth curve consisting of tangential circles to represent the mandibular trough.

The cubic equation calculations are preferably those performed by (345) calculating cubic spline parameters required to pass a smooth curves through symmetricalized midpoints $S_{X,Y}$ as illustrated in FIG. 5A. This includes (350) calculating the slope of the cubic spline curve at each symmetricalized mid-point $S_{X,Y}$ or $S_{X,Y}$, and (355) calculating a series of tangential circle equations whose slopes are equal at the mid-points and at points of intersection along the curve.

(345) The cubic spline method preferred uses a cubic, or third degree, polynomial to interpolate between each pair of data points $S_{X,Y}$. A different polynomial is used for each interval, and each one is constrained to pass through the original data with the same slope as the data. (350) The slopes of the cubic equation are computed by solving the slope of a parabola that passes through each data point and its two nearest neighbors points. The cubic spline method is described in more detail in the discussion of the cubic spline subroutine (2000) below.

(355) Any point on the cubic spline equation can now be calculated by using a cubic spline interpolation. Using this, the cubic spline equation is subjected to a circle segment conversion by which the form of the equation MTE is converted to a series of circle segments that interconnect tangentially. Once the spline equation is derived, the slopes at each data point are calculated using the point slope method. These slopes are utilized to derive, between each pair of data points on the spline equation, the description of two circle segments, each from one of two circles as illustrated in FIG. 5, to convert the MTE to a series of circle Segments throughout its length. This facilitates the setup of the teeth, the description of the configuration of archwires, and the generation of NC code for the manufacture of the appliance. The spline-to-circle conversion routine is described in further detail under routine (2100) below.

The input procedure continues. (360) Cartesian coordinates are input for right and left mandibular cuspid cusp tips CR and CL, respectively, as illustrated in FIG. 4. (365) A distance DCT between the cusp tips CR and CL of the two mandibular cuspids is then calculated:

$$DCT = \sqrt{(CR_X + CL_X)^2 + (CE_Y + CL_Y)^2}$$

where:
$CR_X$ = right cuspid X coordinate.
$CR_Y$ = right cuspid Y coordinate.
$CL_X$ = left cuspid X coordinate.
$CL_Y$ = left cuspid Y coordinate.

This information is used to calculate if and how much the mandibular intercuspid distance is to be altered, and to evaluate whether the calculated final position is acceptable. Similarly, (370) cartesian coordinates or right and left mesio-buccal cusp tips, MR and ML, respectively, of mandibular first molars are calculated, and (375) the distance between these points DMT is calculated:

$$DMT = \sqrt{(MR_X + ML_X)^2 + (MR_Y + ML_Y)^2}$$

where:
$MR_X$ = right first molar cusp X coordinate.
$MR_Y$ = right first molar cusp Y coordinate.
$ML_X$ = left first molar cusp X coordinate.
$ML_Y$ = left first molar cusp Y coordinate.

This information is used to determine if and how much the mandibular intermolar distance is to be altered.

(400) Maxilla Digitized Video Input Step:

As with the mandibular jaw information described in connection with FIG. 4, (400) a computer image is made from input in the same manner from the upper model 23 of the maxillary jaw 24 of the patient 12, as illustrated in the flowchart detail of FIG. 2H. This involves the substeps of (405) inputing a video image 48a of maxillary model 23 to the computer screen 35. The image 48a is illustrated in FIG. 4A. With the maxilla, it is not necessary to overlay the grid G on maxillary image on the screen, since the bone of the maxilla is a variable that will be altered orthodontically to accommodate the finish positions of the teeth. The orientation of the axes and position of the origin are immaterial to the calculation of the relative distances such as MDW of the teeth. Only the scale must be maintained. As with the mandibular information, the image of the maxillary jaw 24 is displayed at a scale predetermined by the scanner 33. The scale is involved in the calculation of the maxillary tooth widths MBW.

(420) Cartesian coordinates of mesial and distal extremities $M_{x,y}$ and $D_{x,y}$ of each maxillary tooth are then input as with the mandibular teeth and (425) the mesiodistal width MDW of each maxillary tooth is calculated using Pythagorean theorem, thus:

$$MDW = \sqrt{(M_X + D_X)^2 + (R_Y + L_Y)^2}$$

where:
$M_X$ is mesial X coordinate.
$M_Y$ is mesial Y coordinate.
$D_X$ is distal X coordinate.
$D_Y$ is distal Y coordinate.

This information is used first to determine whether the maxillary and mandibular teeth are correct in proportion to the mesiodistal widths MDW of the other. If the proportions are incorrect, a tooth size discrepancy TDS is said to exist, and the information is recorded to report to the orthodontist. The MDW's of the maxillary teeth are later used to place the maxillary teeth upon the mandibular arch.

Next, (430) coordinates of the central fossae of right and left maxillary first molars are input. Then, (435) the distance between central fossae DCF is calculated as follows:

$$DCF = \sqrt{(R_X + L_X)^2 + (R_Y + L_Y)^2}$$

where:
$R_X$ is right side central fossa X coordinate.
$R_Y$ is right side central fossa Y coordinate.
$L_X$ is left side central fossa X coordinate.

$L_Y$ is left side central fossa Y coordinate.

This information is recalculated after the tooth finish positions are calculated to coincide with the DMT spacing of the mandibular first molars, and compared with this initial measurement as an indicator of whether the intermolar width will be changed by treatment and the amount of such change, if any.

(500) Digitized Probe Tooth Profile Input Step:

The next input step (500) involves an analysis of the dentition, as illustrated in the detailed flowchart of FIG. 2I. In this step, selected profiles of each of the teeth are generated from either the model 20, or from a digitized three dimensional representation of the patient's teeth or the model 20 as illustrated in FIGS. 3A and 3B. In the illustrated embodiment, the use of the probe assembly 57 of FIG. 1C is used in this step.

Where the full three dimensional scan has been employed in step (300), as could be produced with the use of the laser image generator (FIG. 1B), or as could be produced with moire image generator or other technique, a digitized computer model is produced. From such a computer model, which is an electronic version of the model 20 in the form illustrated in FIGS. 3A and 3B, planes or other cross-sections through the teeth are selected that contain extremities of the teeth. The three dimensional images may be displayed on the screen 35 and profiles generated either with the pointing device 47 in a manner similar to the use of the mechanical probe described below, or automatically using available CAD or illustration imaging software. Whether the profiles are generated from a physical model 20 or an electronic version thereof, much of the input step (500) and/or the landmark selection step (600) may be similarly employed.

In the preferred use of the information from the probe assembly 57, a single digitized profile curve PF is constructed for each tooth in a generally vertical plane extending in an approximately labial-lingual orientation generally along the central developmental lobe perpendicular to the marginal ridges. While other profiles can be taken, the need to do so is reduced by intelligent plane selection made with an understanding of tooth anatomy, depending on the data required by the tooth positioning and appliance design criteria employed. The selection of the profile plane is illustrated in FIG. 6 where a first profile $PF_A$ through the center of the tooth is shown as missing the buccal cusp tip which is the maximum crown highpoint of the tooth. Profile $PF_B$ is then selected to include the buccal cusp, and the ridge of the profile is found to generally align with the lowpoint of $PF_A$. Alternatively, the profile may be non-planar to pick the important features of both planes. As such, the profile produced will be comparable to a projection onto a plane of the relevant tooth extremities.

The step (500) of analysis of the dentition includes, first (505) examination, by the operator 28 of the computer 30a, of the marginal ridges of the upper central and upper lateral teeth. If ridges are excessive, a determination is made to take a profile twice with the probe 60, once by smoothing the teeth, for example with wax, for arch coordination and once without smoothing for placement jig geometry. Otherwise, a single profile taken across the buccal cusp will contain information of the crown height of the tooth as well as approximating the profile of the tooth through its mesiodistal center with accuracy that is usually sufficient. Then, (510) a determination is made as to whether one or two traces of maxillary incisor teeth are to be input as in step (505) above.

(515) The computer 30a is configured to receive sequential cartesian coordinate pairs through an RS-232C serial port representing tooth profile anatomy from the orthogonally positioned displacement transducers 61. (520) The computer 30a prompts the operator 28 to enter the profiles of each tooth sequentially. In response to the prompts, data points of each tooth are input, beginning with lower left molar T(B,L,6) and ending with upper right molar T(U,R,6), and a display 63 of profile $PF_1$ image is generated. The output circuits associated with the transducers 61 are configured to digitize data values at periodic time intervals as the probe 60 is moved across the teeth from the time the probe first starts to move across the tooth until the operator enters a command or key stroke indicating that the scan is complete. Then (525) the input profile data of each of the teeth is stored in memory by the computer 30. The resulting profiles $PF_1$ are illustrated in FIG. 3C. These profiles, at this stage, are not related to the positions of the teeth within the mouth or with respect to other teeth. Thus, each of the X-Y coordinates of the individual tooth profiles are independent of each other. In step (600) below, the coordinate axes of each tooth will be oriented with respect to each other, and thereafter, in later steps (800)–(1100), the coordinates of each profile are translated vertically for proper occlusion and horizontally for placement on their respective arches.

(95) Analysis and Finish Tooth Position Calculation Procedure

The calculation of the finish positions of the teeth, as illustrated in the flowchart of FIG. 2B, includes (600) determining the relative positions of geometric landmarks on the surfaces of the teeth and establishing the axis inclinations of the teeth, (700) calculating cuspid rise, (800) initially positioning the mandibular teeth vertically and in relation to the mandibular trough, (900) calculating a best fit cusp tip equation for the mandibular teeth, (1000) calculating the finish positions of the mandibular teeth on the best fit equation, and (1100) calculating the finish positions of the maxillary teeth on three arches related to the best fit equation.

(600) Tooth Landmark Identification Analysis Step:

After the individual teeth have been digitized, the inputing of tooth shape data (94) is complete, with the digitized information 26 stored a file. Then, referring again to the flowchart of FIG. 2, (95) the input data 26 is analyzed to develop or derive further parameters for calculating the final positions of the teeth and for (96) the design of the appliance 25. In the tooth positioning analysis (95), as illustrated in the flowchart of FIG. 2B, (600) a tooth profile analysis is made in which, for example, certain anatomical landmarks are chosen, depending on the tooth to be analyzed. The details of the tooth profile analysis are illustrated in the flowchart of FIG. 2J.

In the tooth profile analysis step, (605) individual images 63 of the profile curves $PF_I$ of each tooth (FIG. 3C) are recalled separately to the screen of the computer 30b for selection of the landmarks.

Using the displayed images 63 of the profile curves $PF_I$, (610) specific landmark points are chosen, first on the mandibular molars and bicuspids. The selected points are digitized as illustrated in FIG. 6. The selected points are:

Point P₁: The Lingual (tongue side) gum/tooth intersection.

Point P₂: The prominence of the lingual cusp.

Point P₃: The prominence of the buccal (cheek side) cusp.

Point P₄: The buccal gum/tooth intersection.

From these landmarks, (615) the crown long axis CLA of each molar and bicuspid profiled is determined. The determination is made by constructing a first line L₁ between points P₂ and P₃ and a second line L₂ between points P₁ and P₄. The crown long axis CLA of a tooth is the line between the midpoints of L₁ and L₂.

Line L₁ is constructed through point P₂ and point P₃ by the following equation:

$$\frac{Y - Y_2}{X - X_2} = \frac{Y_3 - Y_2}{X_3 - X_2}$$

where:

$X_2, Y_2$ = X and Y coordinates of point $X_3, Y_3$ = X and Y coordinates of point Line L₂ is constructed through point P₁ and point P₄ by the following equation:
where:

$$\frac{Y - Y_1}{X - X_1} = \frac{Y_4 - Y_1}{X_4 - X_1}$$

$X_1, Y_1$ = X and Y coordinates of point P₁.

$X_4, Y_4$ = X and Y coordinates of point P₄.

A point equidistant between points P₂ and P₃ along line L₁ is then calculated and defined as P₂₋₃:

$$P_{2-3x,y} = \frac{X_2 + X_3}{2} ; \frac{Y_2 + Y_3}{2}$$

where:

$X_2, Y_2$ = X and Y coordinates of point P₂.

$X_3, Y_3$ = X and Y coordinates of point P₃.

A point equidistant between points P₁ and P₄ along line L₂ is also calculated and defined as the Gingival Center Point GCP:

$$GCP_{X,Y} = \frac{X_1 + X_4}{2} ; \frac{Y_1 + Y_4}{2}$$

where:

$X_1, Y_1$ = X and Y coordinates of point P₁.

$X_4, Y_4$ = X and Y coordinates of point P₄.

The line defining the crown long axis CLA is constructed using the following equation:

$$\frac{Y - Y_{2-3}}{X - X_{2-3}} = \frac{Y_{GCP} - Y_{2-3}}{X_{GCP} - X_{2-3}}$$

where:

$X_{2-3}, Y_{2-3}$ = X and Y coordinates of the center point P₂₋₃.

$X_{GCP}, Y_{GCP}$ = X and Y coordinates of gingival center point $GCP_{X,Y}$.

For molars and bicuspids, point P₃, the buccal cusp tip, is defined as the Incisal Center Point ICP.

Similarly, (610) the anatomical landmarks and crown long axis CLA for the mandibular cuspids, laterals and central teeth are determined, as illustrated in FIG. 6B.

The points P₁ through P₄, as labeled in FIG. 6B, are selected as follows:

Point P₁: The lingual gum/tooth intersection.

Point P₂: The lingual aspect of the incisal edge.

Point P₃: The buccal aspect of the incisal edge.

Point P₄: The facial gum/tooth intersection.

As with the bicuspids and molars, lines L₁ and L₂ are constructed. The landmarks in the cases of the teeth as illustrated in FIG. 6B, are chosen because they are relatively tolerant to operator error in selection. This can be seen by the set of broken lines that are possible alternatives to L₂ in FIG. 6B. From these landmarks (615) the crown long axis CLA is determined as defined above, by connection of the midpoints of L₁ and L₂.

The next step in the analysis is the determination of maxillary dentition for each upper molar and bicuspid. (610) Anatomical landmarks are identified and chosen as illustrated in FIG. 6C, which requires (612) the selection of a fifth point, P₅, defined as follows:

Point P₁: The lingual gum/tooth intersection.

Point P₂: The prominence of the lingual cusp.

Point P₃: The prominence of the buccal cusp.

Point P₄: The buccal gum/tooth intersection.

Point P₅: The mesial marginal ridge of the tooth at central groove.

Referring to FIG. 6C, from the landmarks, (615) the crown long axis CLA of each applicable maxillary tooth is determined.

The (610) anatomical landmarks for the maxillary cuspids, laterals and central teeth are determined as illustrated in FIG. 6D. The points labeled P₁ through P₄ are selected, as follows as illustrated in FIG. 6D.

Point P₁: The lingual gum/tooth intersection.

Point P₂: The lingual aspect of the incisal edge.

Point P₃: The buccal aspect of the incisal edge.

Point P₄: The facial gum/tooth intersection.

From each of these sets of landmarks, the crown long axis CLA of each such tooth is also determined as described (615) above.

This completes the loop (620) for all of the teeth.

Next, as further illustrated in FIG. 6D, (620) seed values for setting the crown long axis inclinations LAI of the teeth. Initially, such seed values may be derived from analyses that identified the facial axis plane FAP through the facial axis point FA of the tooth (the midpoints of the height of the clinical crowns along the facial axes of the clinical crowns) as described by Dr. Lawrence Andrews. It is, however, contemplated that CLA seed values for various population groups will be statistically derived in the course of the practice of the present invention, and will produce improved treatment results.

The seed values shown in Table 1 below are typical for caucasian males. These seed values for tooth LAI, tabulated in degrees from the horizontal lingual (−X) axis, will vary to reflect known variations due to such things as sex, The preferred seed values are shown in Table 1 below are typical for caucasian males. These seed values will vary to reflect known variations due to such things as sex, race or treatment plan.

TABLE 1

| Tooth Type | Maxillary Crown LAI | Mandibular Crown LAI |
|---|---|---|
| Central | 117 | 107 |
| Lateral | 112 | 107 |
| Cuspid | 108 | 100 |
| 1ˢᵗ Bicuspid | 94 | 83 |
| 2ⁿᵈ Bicuspid | 94 | 80 |

TABLE 1-continued

| Tooth Type | Maxillary Crown LAI | Mandibular Crown LAI |
|---|---|---|
| 1st Molar | x | x |
| 2nd Molar | x | x |

The computer images as summarized in FIG. 3C for each tooth (630) are then rotated so that the CLA is oriented at the angle LAI, the long axis inclination angle, to the mandibular trough plane MT according to the Values in Table 1. This computes the final inclinations of the teeth that will be preserved in the calculations below. This produces the oriented profiles PF summarized in FIG. 6E.

In the analyses of Andrews referred to above, the LAIs were established with a line $L_{FA}$ drawn tangent to the facial surface at FA, and line representing the relative inclination of the archwire plane drawn through FA point. The angle between the lines was established at the inclinations reported by Andrews for patients with no skeletal discrepancies. The angle LAI between the crown long axis CLA and a line representing the maxillary arch plane in which lies the mandibular trough equation MTE is related to the facial inclination angles of Andrews' studies by taking into account statistically the thicknesses and contours of the teeth. Table 1 above was derived, after statistical processing, to produce the seed value used for the final inclination of the crown long axis in preferred occlusal design.

Once the tooth profiles have been rotated to the inclination angles LAI, certain precise vertical dimensions and extremities can be determined. From the digitized profile curves, which are stored in memory in the form of a series of closely spaced points, the precise incisal tip IC, as illustrated in FIGS. 6F, 6H and 6I, are identified on the cuspids, laterals and centrals.

Additionally the elevation of the marginal ridge $P_5$ is identified. The marginal ridge elevation MRE, which is the vertical distance from $P_3$ to $P_5$, is identified on the maxillary posterior teeth because they are the centric stops for the buccal cusps of the mandibular molars and bicuspids. In other words, point $P_3$ on the mandibular molars and bicuspids contacts point $P_5$ on the maxillary molars and bicuspids when the teeth are together, as illustrated in phantom line $PH_1$, in FIG. 6C. For a more precise placement in a less common case where the maxillary ridge is narrow in relation to the mandibular tip (phantom line $PH_2$), a more detailed three dimensional analysis of the tooth shape can take into account additional correction needed. The calculation of MRE (FIG. 6C) is made after rotation of the teeth to their proper LAI inclinations so that MRE will be a vertical distance, where LAI is measured relative to the plane of the dental arch. The MRE is used as the buccal cusp height BCH in the calculation of cuspid rise and archwire plane placement as described below in the discussion of FIGS. 7A and 8, respectively.

(700) Cuspid Rise Determination Step:

The next step of the analysis procedure (87) is (700) the calculation of cuspid rise, illustrated in detail in the flowchart of FIG. 2K.

Most orthodontists currently desire a cuspid rise occlusion, in which, in lateral movement of the lower jaw, the cuspids cause the other teeth to disclude or to come apart. In order for this to happen, the overlap of the cuspids must be greater than that of the other teeth when the teeth are together. This is complicated by the fact that the cuspids (I=3) are close to the front of the mouth and are therefore further from the condyle or pivot point PP of the jaw than are the posterior teeth (I>3), as illustrated by distances $DJ_I$ in FIG. 7. This results in the teeth closer to the back of the mouth moving less than the cuspids on opening. This differential rate of movement must be included in the calculation of cuspid rise or the back teeth will remain in contact after the cuspids have cleared each other. Also, the distance DPP from the occlusal plane to the pivot point PP of the condyle of the jaws must be considered, as illustrated in FIG. 7. A failure to provide for this distance results in what is known as working interferences.

According to the preferred embodiment of the present invention, where cuspid rise is prescribed to control occlusion, the contribution of cuspid rise is distributed between the maxillary and mandibular cuspids, with two parts of the cuspid rise provided by the maxillary cuspids and one part by the mandibular cuspids. This distribution is applicable where occlusion is solely to be a cuspid rise function. Where occlusion is to be a group function, as specified by the orthodontist 14 in the prescription 27, the distribution between the upper and lower teeth is generally equal.

In the substeps performed in the calculation of the cuspid rise (700), illustrated in detail in the flowchart of FIG. 2K, the first substep is (705) to acquire the initial vertical distance or buccal cusp height BCH from $P_3$ to the marginal ridge for each of the right and left maxillary first bicuspids T(U,4), second bicuspids T(U,5), first molars T(U,6), and second molars T(U,7), as illustrated in FIG. 6C. This is the marginal ridge elevation MRE calculated for each of these teeth in substep (615) of step (600). Then, from anatomical study, (710) the cuspid rise vertical height CR required to clear each respective pair of teeth is determined by first computing the values in Table 2, which are derived from the jaw dimensions DPP and $DJ_I$ in FIG. 7. required to clear each respective pair of teeth is determined by first computing the values in Table 2.

1.67×BCH of T(U,7)
1.50×BCH of T(U,6)
1.36×BCH of T(U,5) and
1.20×BCH of T(U,4).

TABLE 2

Then, (715) from the products of the buccal cusp height BCH for each such tooth multiplied by the rise factor listed above, the largest value is selected. This selected product is the cuspid rise required to clear the most prominent cusp and provide group function occlusion. This is illustrated as $BCH_6$ in FIG. 7A for the case where the first molars are the last to clear.

(720) If the group function has been selected in the prescription 27 provided by the orthodontist 14, the calculated rise is used as is. If cuspid guidance has been selected in the prescription 27 of the orthodontist 14, the calculated cuspid rise factor must further be modified to give typically 0.5 to 0.75 mm of clearance over the largest rise factor by multiplying the buccal cusp height BCH for each tooth by the rise factor listed above and selecting the largest figure, then adding 0.5 to 0.75 mm additional cuspid overlap to obtain and adjusted cuspid guidance cuspid rise.

(725) Calculation of cuspid overlap or cuspid rise CR for maxillary and mandibular cuspids is preferably as follows: If group function has been selected, mandibular rise equals 50% total group function rise, and maxillary rise equals 50% of the total group function rise. If cuspid function has been selected, mandibular rise equals 34% of the total cuspid guidance rise, and maxillary rise equals 66% of the total cuspid guidance rise.

(800) Mandibular Tooth Placement Step:

The next step in the analysis procedure (87) is (800) the mathematical construction of the mandibular occlusion to calculate the position of the mandibular teeth. The details of this step are illustrated in the flowchart of FIG. 2L. The first calculation places the tips of the mandibular teeth on an occlusal plane pending final refinement of the placement, as diagrammatically illustrated in FIG. 6E. In this step, the inclinations of the mandibular tooth crown long axes CLA are preserved, and the teeth are moved upward along their CLA's until their tips are in alignment with the plane of the top of the tallest tooth. The CLA's are placed to intersect the MTE below the tooth GCP. Because the teeth are inclined at different LAIs, or long axis inclination angles, the tooth tips will each be differently offset from the MTE, and thus not in a smooth arch.

The substeps of the mandibular placement step (800), illustrated in the flowchart of FIG. 2L, are as follows:

(805) The tallest mandibular tooth, with the exception of the cuspids, is identified. In FIG. 6F this is illustrated as the left mandibular central. The tallest tooth is the tooth with the greatest crown height CH. The crown height CH is the distance, in the Y direction (with the teeth profiles oriented as described in step (600), from the GCP, the point of intersection of line $L_2$ and crown long axis CLA, to highest point on buccal cusp, e.g. $P_3$ (for posterior teeth) as illustrated in FIG. 6F and (for the anterior teeth) to either the incisal center point ICP or, preferably to the incisal tip IC, as illustrated in FIG. 6G. The crown height CH of the tallest tooth, shown as the left mandibular central incisor in FIG. 6F, is the maximum crown height MCH of the mandibular teeth.

Then, (810) three parallel planes are established:

a) an MCH reference plane MCHP parallel to the X-axis, and passing through an origin 0,0, set at the GCP of the tallest tooth (FIGS. 6F and 6I);

b) a Buccal Cusp Plane BCP parallel to X-axis and passing through coordinates 0, MCH on the tallest tooth (FIGS. 6F and 6I); and c) a Cuspid Rise Plane CRP parallel to X-axis and passing through coordinates 0, where CR is the cuspid rise calculated in step (700), where the cuspid rise option has been selected.

With the planes defined, (815) the oriented mandibular teeth are placed such that the highest point on buccal cusp tip $P_3$ or incisal tip IC of each contacts the buccal cusp plane BCP, for all teeth except the cuspids, as illustrated further in FIG. 6F. The BCP thereby is established as the occlusal plane MOC. The reference plane MCHP is set equal to the plane of the mandibular trough MT. This sets the GCP of the tallest tooth on the MT, with the GCP's of the remaining mandibular teeth above it. It also sets the occlusal plane MOC a distance MCH from the mandibular trough MT. The absolute highest point on a tooth crown is preferably used to align the teeth with the BCP. Such a point can be determined by additional point selection in step (500), such as by the direct selecting of the point IC for the precise incisal tip, or preferably by calculating the highest point directly from the profiles of FIG. 3C or from three dimensional images as in FIGS. 2A, 2B after rotation of the teeth to their final inclination angles LAI, at the end of step (600).

The next stage in this step is to establish the mandibular component of cuspid rise. This involves (820) vertically moving the cuspida by, for example, sliding the cuspids along their crown long axes, such that the cuspid cusp tips are at the appropriate height above the mandibular occlusal plane, that is, in the plane CRP.

At this stage, the vertical positions of the mandibular teeth relative to each other are calculated, providing a basis for relating the Y coordinates of the individual mandibular tooth profiles with respect to each other as illustrated in FIGS. 6F and 7C.

Then, with the mandibular teeth vertically positioned, the teeth are horizontally set at temporary positions with respect to the MTE, which lies in the plane of the mandibular trough MT (MCHP). This horizontal positioning, in effect, relates the X axes of the individual tooth profiles in a horizontal in-out direction with respect to the mandibular arch and special mesiodistally along the mandibular arch.

Because the preferred goal, however, is to position the tips of the teeth in the smoothest arch in an occlusal plane MOC rather than their gingival aspects in a smooth arch at the mandibular trough MT, (825), a horizontal distance OFFSET for each tooth is calculated, based on the tooth and the crown long axis inclination LAI determined in step (600). This offset is the horizontal distance from the MTE to the tooth tips when their GCP's are placed on the MTE.

For mandibular centrals and laterals and cuspids, the OFFSET is calculated by dividing, by the tangent of LAI, the vertical distance from (1) the intersection of crown long axis CLA and the incisal tip IC to (2) the intersection of CLA and maximum cusp height reference plane MCHP. The vertical distance may be calculated from the IC to the MCHP (equal to the Y coordinate of point IC, producing the incisal center vertical distance ICD.) For mandibular laterals and centrals, ICD equals MCH. For mandibular cuspids, ICD equals the mandibular cuspid rise component, which is MCH+(Total CR)/3 when cuspid rise function occlusion has been selected. The calculation of the OFFSET for centrals, laterals and cuspids would thus be as follows for the incisors and laterals:

$$\text{OFFSET} = \text{ICD}/\tan(\text{LAI})$$

(831) For mandibular bicuspids and molars, referring to FIG. 6F, the OFFSET is calculated as the horizontal distance from point $P_3$ to the intersection of the CLA and the MCHP as follows:

$$\text{OFFSET} = [\text{MCH}/\tan(\text{LAI})] + \text{HD}$$

where HD equals the horizontal distance from point $P_3$ to incisal center point ICP.

Then, (835) the mandibular trough placement point MTPP is defined as the intersection of MCHP and CLA, as illustrated in FIGS. 6G and 6H. For the tallest tooth, MTPP is its GCP, as illustrated in FIG. 6I. The MCHP is at the level of the mandibular trough and contains the MTE. The MTPP is the point on the tooth that is initially placed on the MTE.

Next, referring to FIG. 7B and 7C, the teeth are placed with their MTPP's on the mandibular trough, one side at a time. To achieve this, (840) the subroutine (2200) is called twice, once for the left side, and once for the right side, as follows:

The mandibular trough equation MTE is first adjusted for the mandibular centrals to increase the radii by the amount of the central OFFSET for that particular tooth, as defined above, to form a mandibular trough offset curve MO(1) of FIG. 4B. The radii of the MTE referred to are those of the MTE defined in the circle segment form of the equation generated in step (300) with the spline to circle conversion routine (2100). Since the OFFSETs of the teeth differ, the MO may be viewed as a discontinuous equation when constructed in this manner, made up of segments, each containing the tip of one tooth and spaced labial-lingually from the MTE by the amount of the individual tooth's OFFSET.

Beginning with the left side, the central is placed, as illustrated in FIG. 7B, by placing its mesial contact point MCP at the intersection of the midline ML with the offset curve MO for the tooth. This has the effect of the placing MTPP of the tooth, which is the intersection of the CLA with the MCHP or MT, on the MTE and the incisal tip IC of the tooth on $MO_1$. The tooth placement on the circle segment form of an equation is explained in detail in the description of the tooth placement routine (2200) below. In the placement of the central, a circle $C_1$ is constructed with a radius equal to the mesiodistal width $MDW_1$ of the central tooth and with the center of the circle $C_1$ at the mesial contact point MCP of the tooth at intersection of the midline ML with the offset curve $MO_1$. Then, circle $C_2$ is constructed with a radius equal to MDW/2 and with its center coincident with the center of circle $C_1$. Then, the intersections of trough offset curve MO with the circles $C_1$ and $C_2$ are found, its intersection with the circle $C_1$ being the distal contact point DCP of the tooth and its intersection with the $C_2$ being the tooth midpoint TMP of the central tooth. The tooth midpoint TMP is here defined as the midpoint of the mesiodistal width of the tooth placed on an archform, which is the intersection of the archform with a vertical labial-lingual plane that contains the CLA. This mid-point TMP of the central tooth on the MO is the approximate position of the incisal tip IC.

Determining the intersections of the circles with the offset trough curve MO, or expanded mandibular trough, requires identification of which circle sector lines (FIG. 5) the circles $C_1$ and $C_2$ intersect. These are identified by comparison of the X coordinates of the intersections with the X coordinates of the distal contact points DCP of each of the central teeth to determine which segments of the trough equation will be used, as explained more fully in the description of the tooth placement routine (2200) below.

Finally, a distal contact point line DCPL is constructed for the central tooth through the DCP, at the intersection of circle $C_1$ with the MO, and through the center of the identified circle segment of the MO, the expanded MTE, on which the DCP of the tooth lies. This line lies along a radius of the circle segment of the MO curve through the distal contact point of the central tooth. Similar lines DTMP are constructed for the center of the tooth TMP.

(845) For each of the remaining mandibular teeth on the same side of the arch, in distal sequence, a new mandibular trough offset $MO_f$ is calculated, by expanding the MTE with radii of curvature increased by the amount of the next tooth's OFFSET and with center of the circles $C_1$ and $C_2$ moved labially or outwardly from the MTE along the prior tooth's distal contact point line DCPL by the amount of the current this tooth's OFFSET. This is the MCP for the next tooth. Circle $C_1$ for the tooth is constructed with a radius equal to the mesiodistal width of the tooth and with its center at their center point MCP. Circle $C_2$ is constructed with a radius equal to MDW/2 and with centers coincident with circles C1.

For bicuspids and molars, the tooth midpoints TMP can be considered as their points $P_3$. Then, as with the central, the intersections of MO and circles $C_1$ and $C_2$ are calculated for these teeth. The distal contact points DCT of these teeth are at the intersections of MO for the tooth and the respective $C_1S$. The centers of the teeth TMP are at the intersections of MO for the tooth and the respective circles $C_2$. The MO sector segments which the circles intersect are identified. Selection of the segments is made by comparing the X and Y coordinates of intersections to X and Y coordinates of distal contact points DCPs. Finally, a distal contact point line DCPL is constructed from selected segment center to the plane DCP. The same is done for the centers of the teeth TMP.

(848) The substeps (842) are repeated for all of the remaining mandibular teeth on the same side of the arch. Then, (849) substeps (840)–(848) are repeated for the teeth on the opposite side of arch.

(900) Best Fit Mandibular Arch Equation Step:

The above step (800) leaves the crown long axes CLA of the mandibular teeth intersecting the MCHP reference plane, which is at the level of the mandibular trough MT at or just below the gingival center points GCP of the teeth, along the mandibular trough equation MTE. The discontinuous offset equation MO, however, contains the approximate tips of the teeth in the occlusal plane MOC, with the teeth irregularly offset as represented by the discontinuous MO lines in FIG. 4B. To place the tips of the teeth into an ideal arch, (900) a final equation for better placement of the buccal cusp tips and incisal edges of the mandibular teeth in a continuous arch is developed. The development of the best fit equation is illustrated in the detailed flowchart of FIG. 2M.

When viewed perpendicularly to the occlusal plane as in FIGS. 4B and 7B, it can be seen that the buccal cusp tips and incisal tips of all of the individual teeth do not lie along either the mandibular trough equation or the same geometrical expansion of that equation. In fact, due to small anatomical variations, it is unlikely that the tips will fall on any smooth curve when the tooth CLAs intersect a smooth curve at the mandibular trough in the MCHP and the LAIs are preserved. To remedy this, the equation is statistically developed that best fits the cusp tips and incisal edges of the individual teeth; a Best Fit Buccal Cusp Equation BFBCE. In the formulation of the equation, the coordinates of the right and left tooth midpoints TMP, the ICPs or ICs in FIG. 7B, are preferably averaged. The equation BFBCE may be obtained (910) by use of polynomial or other bezier or least square statistical techniques to arrive at a best fit equation. These are available in any of a number of off-the-shelf software packages.

Such a BFBCE equation is plotted in FIG. 4B. Once the BFBCE is determined, it may be (915) converted to a circle segment equation in a manner such as with the spline to circle conversion routine (2100). This equation provides a basis for moving the teeth labially or lingually from the discontinuous offset equation MO to place the tips of the mandibular teeth in a smooth arch in the occlusal plane CP, as illustrated in FIG. 7C. To do this, in the next step the profile planes will be translated bodily in their own horizontal X-directions (which is an X-Y movement in the coordinates of the horizontal planes), moving their MTPPs off of the MTE in the MCHP (or MT).

(1000) Mandibular Best Fit Arch Placement Step:

After statistically deriving a best fit equation BFBCE, (1000) positions of the individual mandibular teeth are calculated to translate then facially, either labially or lingually, so that their tips fall on the best fit curve. This step is illustrated in detail in the flowchart of FIG. 2N.

To achieve this, (1005) the mesiodistal contact point of the mandibular central, the point MCP, as in FIG. 7B, is first placed on the intersection of the midline ML with the BFBCE in the same manner as it was placed on the MO in step (800). Then (1010) circles C1 and C2, as defined above, for the tooth are constructed and their intersections with the BFBCE curve are found. As with the placement in step (800) above, the intersection of $C_1$ with BFBCE is the distal contact point DCP of the tooth, and the intersection of $C_2$ with the BFBCE curve, is the center point TMP (which aligns with IC) of the tooth. This, in effect, moves the tooth normal to the circle segment of the BFBCE associated with the TMP. Then, (1015) new circles $C_1$ and $C_2$ are constructed with centers at the distal center points DCP and (1020) substeps (1005) and (1015) are repeated for all teeth on the same side of the mandibular arch. Then, (1025) steps (1005) through (1020) are repeated for the teeth on the other side of the mandibular arch. The placement uses the tooth placement routine (2200), the description of which below explains in detail the placement of the mandibular teeth on the BFBCE.

This step bodily translates the teeth in a generally horizontal direction, and rotates the teeth of the mandible about their CLAs to place incisal edges and cusp tips, as determined in step (800), on the BFBCE. With the completion of this step the finished positions of the mandibular teeth are calculated and the mandibular occlusion is finalized. At this point the mandibular occlusion can be envisioned as an ideal setup cast in stone, to which the maxillary occlusion will be fitted and related.

The finish positions of the mandibular teeth are illustrated in FIG. 7C in which the X-Y coordinates are those of the horizontal arch planes. A vertical Z coordinate, perpendicular to the horizontal X-Y plane, is aligned with the Y axes of the individual tooth profile planes. The X coordinates of the profile planes are aligned with the labial-lingual directions La-Li in FIG. 7B.

(1100) Maxillary Tooth Placement Step:

The construction of occlusion requires (1100) the fitting of the maxillary teeth to the already positioned mandibular teeth. This is accomplished by deriving a modified best fit buccal cusp equation BFBCE for the maxillary teeth in the step illustrated in detail in the flowchart of FIG. 2O. Unlike with the mandibular teeth, with the maxillary teeth, the cusp tips of the posterior teeth and incisal edges of the anterior teeth are not set in a single arch. The maxillary teeth are rather set: (1) with the central groove-marginal ridge points of the maxillary bicuspids and molars on the BFBCE, (2) with the maxillary anteriors spaced labially off of the BFBCE to allow for incisal overlap and a clearance between the lingual surfaces thereof and the labial surfaces of the mandibular teeth, and (3) with the cuspid tips in the arch generally between the first maxillary bicuspid and the lateral incisor. The arches on which the maxillary teeth are placed as illustrated in FIG. 4C, as explained above.

For the maxillary incisors, the modification of the BFBCE first involves an averaging the distances from point $P_2$ to point $P_3$ on the mandibular incisor incisal edge, and dividing by two, to locate the arch that will contain the labial surface of the tooth adjacent the incisal center point ICP of the tooth, which is generally the point $P_3$. This produces a uniform distance from the best fit equation to the contact point of the facial surface on the labial side of the mandibular anterior teeth with the facial point on the lingual side of the maxillary anterior teeth. An additional distance, of typically one-quarter millimeter, is added to the averaged distance to provide a slight Clearance between the upper and lower anterior teeth. This is illustrated in FIG. 7D.

The maxillary anterior dentition is set for vertical position relative to the occlusal plane MOC according to occlusion criteria selected to provide a predetermined overlap. From the cuspid rise calculation of step (700), the vertical positions of the maxillary cuspids are known relative to the mandibular occlusal plane MOC. For maxillary laterals and centrals, the vertical positions provide the overlaps according to the prescribed criteria, putting their lingual facial contact points with their mandibular counterparts on the MOC plane. All teeth are inclined at the prescribed crown long axis CLA inclination values LAI from Table 1 in step (600).

In the (1100) placement of the teeth of the maxilla, or upper jaw 24, with respect to those of the mandibular, or lower jaw 22, (1105) three arch forms are mathematically defined. These are (1106) the maxillary anterior arch form MAAF, (1110) the central groove marginal ridge arch form CGMRAF, and (1115) the maxillary cuspid arch form MCAF, as illustrated in FIG. 4B. The MAAF is established to position the maxillary incisors with respect to the BFBCE so that their lingual faces contact or clear the labial faces of the mandibular incisors. The CGMRAF is established separate from the MAAF because the maxillary bicuspids and molars contact their mandibular counterparts with their central groove marginal ridge intersection points juxtaposed on the mandibular buccal cusps. The MCAF is established separate from the MAAF and the CGMRAF because the cuspids have a still different relation to their mandibular counterparts.

(1106) Location of the MAAF relative to the BFBCE requires a circle segment radius expansion of the BFBCE equation such that the lingual surfaces of the maxillary incisors, after being adjusted vertically to provide a predetermined overlap, will contact the labial face of the mandibular incisors at points spaced labially from the BFBCE with the predetermined Clearance. This expansion is calculated as the average distance between points $P_3$ and $P_2$ on the four maxillary incisors and adding the predetermined Clearance of typically 0.25 mm. This expansion, so calculated, is added to the BFBCE circle segment radii to define the maxillary anterior contact arch form MAAF. The MAAF is thus also expressed as a circle segment equation.

The calculation of the amount of circle segment radius expansion of the BFBCE needed to define the MAAF is made at the midpoint of the mesiodistal width of either maxillary central, $TMP_1$ in FIG. 4C. This would be the intersection with BFBCE of circle $C_2$ in FIG. 7C. The tooth is placed on the maxillary contact arch form equation MAAF such that the mesial contact point of the tooth is on intersection of the midline ML and the maxillary contact arch form MAAF (FIG. 4C). (1108) The MAAF is defined as follows with respect to upper laterals and centrals:

$$MAAF = BFBCE + \Sigma \frac{P_{3X} - P_{2X}}{\{t\}\{Avg\}} + \text{Clearance}$$

where:
t=number of teeth (4),
Avg=2 (to find midpoint), and
Clearance=0.25 mm, typically.

$P_2$ and $P_3$ are points on the maxillary central as defined in step (600). As described above, the crown long axes CLA of these teeth are angulated relative to the occlusal plane at the crown long axis seed values stated in Table 1.

(1109) The tooth placement proceeds in accordance with the tooth placement routine (2200) described below. The placement positions the lingual faces of the central teeth on the MAAF, with the central mesial contact point $MCP_1$ on ML. The midpoint $TMP_2$ of the mesiodistal width of the next maxillary tooth is then placed on the maxillary contact arch equation MAAF such that the mesial contact point $MCP_2$ touches a line normal to the curve MAAF and through the distal contact point $DCP_l$ of the previous tooth. This procedure applies on one side of the occlusion up to the cuspid. The other maxillary side is constructed similarly.

The next substep in the construction of the maxillary occlusion is (1110) the definition of the location of the arch for horizontal placement of the posterior teeth. The teeth are again set at the LAI values of Table 1 from step (600). (1111) The intersections of the marginal ridge and the central groove, which, if not separately selected in step (600) may be taken as point $P_5$ in FIG. 6C, are placed over the buccal cusp of the appropriate mandibular tooth whose cusps were previously positioned on the best fit buccal cusp equation BFBCE. Thus, the CGMRAF coincides with the BCBFE as shown in FIG. 4B.

For the maxillary cuspids, (1115) the cusp tips are placed on some smooth arch between the he MAAF and the CGMRAF. Preferably, their tips are placed on the BFBCE expanded by the average of the distances therefrom to the incisal tip of the lateral and to the buccal cusp tips of the first maxillary bicuspids. This labial distance from this point to the buccal cusp tip of the first bicuspid may alternatively be used to place the distal contact point of the cuspid, with its mesial contact point in contact with the distal contact point of the lateral. The point to which the BFBCE must be expanded to locate the buccal cusp tip of the first bicuspid for the two above alternatives is $P_{3X}(U,4)-P_{5X}(U,4)$. The cuspids will thereby be spaced out from the BFBCE by the average of a distance equal to the horizontal or X distance from $P_5$ to $P_3$ on the first maxillary molar, as illustrated in FIG. 6O, and the MAAF.

Alternatively, the cuspids may be placed with their mesial contact points $MCP_3$ on the MAAF and with their distal contact points DCP in line with the mesial contact points or with the buccal cusp tips of the first maxillary bicuspids.

A third alternative in placing the cuspids is to use the same criteria for clearance with the mandibular teeth used for the definition of the MAAF. Following the determination of the MCAF, the cuspids placed adjacent the laterals with the tips thereof on the MCAF, followed by the successive placement of the posterior teeth with the marginal ridges thereof on the CGMRAF (BFBCE), all according to routine (2200).

In relating the profile and archform drawings and equations above, it should be noted that the X dimension of the profiles on which $P_3$ and $P_5$ are defined are vertical planes, and that the X direction in these planes corresponds to the labial direction in the horizontal planes of the archforms, as was explained for the mandibular teeth in connection with FIG. 7C. Thus, addition of an X component of a point on a tooth profile to an archform curve results in a labial expansion of the archform, or an increase in the radius of the corresponding circle segment of the archform circle series equation.

At this point, information from the prescription 27 from the orthodontist 14 is retrieved to determine (1120) which maxillary anterior vertical occlusion method has been selected. The methods may include, for example, (1121) Roth occlusion, (1122) Ricketts occlusion, or (1123) the preferred method, referred to by the inventors as Elan occlusion. These are discussed below.

Where (1121) Roth occlusion has been selected, the maxillary cuspids will extend a distance $CR_{U3}$ equal to the cuspid rise CR below the occlusal plane MOC, and for laterals and centrals, the teeth will extend a distance $CR_{U2}$ equal to 0.5 the cuspid rise beyond the occlusal plane, as illustrated in FIG. 7D. From step (725), the treatment is selected to apply either group function or cuspid rise function, and the respective cuspid rise quantities for maxillary cuspids are determined. From the lowest point on buccal (facial) cusp, a distance is measure vertically upward equal to 0.5 CR to find the intersection of occlusal plane MOC and central and lateral teeth. If two profiles were taken, the profile that includes marginal ridges is used. The intersections of MOC with each maxillary incisor are defined as follows:

Facial intersection with MOC=FIMOC,
Lingual intersection with MOC=LIMOC,
The distance from LIMOC to FIMOC, DLF, is computed as follows:

$$DLF = |X_{FIMOC} - X_{LIMOC}|$$

where LIMOC is the contact point with MAAF.

Where (1122) Ricketts occlusion is prescribed, the maxillary cuspids also extend below the MOC by a distance $CR_{U3}$ equal to the cuspid rise CR. The laterals are positioned such that the tips are the distance $CR_{U2}$ of 1.0 mm above the cuspid tips, and the distance $CR_{U1}$ is such that the tips of the centrals are 0.5 mm above the cuspid tips. From step (725), in which either group function or cuspid rise function were selected, the respective cuspid rise quantities are applied for the maxillary cuspids. Then, from lowest point on buccal (facial) cusp, a distance of 1.0 mm is measured upward on the laterals and a distance of 0.4 mm is measured upward on centrals to find the intersection of MOC with the central and lateral teeth. If two profiles were taken, a profile that includes the marginal ridges is used. A line is then constructed through the points on the buccal cusps parallel to the MOC. The intersections with the teeth are defined as follows:

Facial intersection with MOC=FIMOC

Lingual intersection with MOC=LIMOC

Distance DLF from LIMOC to FIMOC
= $|X_{FIMOC} - X_{LIMOC}|$ where LIMOC is contact point with MAAF.

Where (1123) Elan occlusion has been selected, the maxillary cuspids will extend a distance $CR_{U3}$ equal to 0.67 of the cuspid rise CR below the occlusal plane MOC, laterals extend a distance $CR_{U2}$ equal to 0.33 of the cuspid rise CR below the plane MOC, and the centrals extend a distance $CR_{U1}$ equal to 0.50 of the cuspid rise CR below the plane MOC. As with the above, from step (725), in which either group function or cuspid rise function were selected, the respective cuspid rise quantities are applied for the maxillary cuspids. Then, from the lowest point on buccal (facial) cusp, a distance of 0.33 of the cuspid rise CR is measured upward on the laterals, and a distance of 0.50 of the cuspid rise CR is measured upward on the centrals, and the intersection of the teeth with the plane MOC is found. If two profiles were taken, a profile that includes marginal ridges is used. The MOC plane and the intersections with the teeth are defined as follows, as illustrated on the cuspid in FIG. 7D:

Facial intersection with MOC=FIMOC.

Lingual intersection with MOC=LIMOC.

Distance DLF from LIMOC to FIMOC
= $|X_{FIMOC} - X_{LIMOC}|$.

LIMOC is contact point with MAAF.

The (1125) elected horizontal occlusion is selected. If (1126) the Roth maxillary anterior horizontal occlusion has been selected, no further changes are required. This results in the lingual surfaces of the teeth forming a smooth arc. If (1127) the Ricketts maxillary anterior horizontal occlusion has been selected, changes are made to cause the labial surfaces of the teeth to form a smooth arc. This requires finding the largest DLF, or LIMOC-FIMOC distance for the centrals, subtracting the other LIMOC-FIMOC distances of the incisors from this largest distance, adding the respective differences to each tooth to extend the LIMOC point lingually along line LIMOC-FIMOC, and establishing a new point at which the LIMOC is to intersect the MOC.

If (1128) the Elan horizontal occlusion is selected, which is the preferred and illustrated embodiment, the horizontal tooth placement proceeds as set forth below. Because, given the overlap of the maxillary incisors, the labial-lingual thicknesses of the anterior teeth are greater in the plane of occlusion than the distance $P_3 - P_2$ used to calculate the MAAF and the MCAF, offsets must be calculated and the maxillary teeth placed again on the offset versions of these archforms.

First, in calculating the positions of the teeth to provide the horizontal occlusion, (1130) a distance is calculated from LIMOC to ICP for the maxillary centrals and the laterals. This distance is referred to as the maxillary anterior offset MAO, thus:

$$ICP = \frac{X_2 + X_3}{2}; \frac{Y_2 + Y_3}{2}$$

-continued
$$MAO = |LIMOC_X - ICP_X|$$

(1135) The maxillary first bicuspid offset MBO is calculated:

$$MBO = |P_{5X} - P_{3X}|$$

(1140) The maxillary tooth positions are then recalculated, one side at a time, with respect to the offset maxillary arch forms defined above that contain the buccal cusp tips and incisal edges of the maxillary teeth. This is achieved by sending the relevant parameters to the placement routine (2200) and calculating placement in the same manner as shown in FIG. 7B for the mandibular teeth. For the maxillary centrals, (1141) MAAF is adjusted such that the MAAF radii are increased by the amount of the MAO. This curve is now called maxillary contact archform offset MAAFO and is illustrated in FIG. 4C.

Calculation of the positions of the maxillary incisors on the MAAFO, preferably in accordance with the tooth placement routine (2200), closes the spaces between the teeth that results from expanding MAAF to MAAFO.

The intersection of MAAFO and the arch midline ML is the mesial contact point MCP of the tooth. A circle $C_1$ is constructed with a radius equal to the mesiodistal width MDW of the central incisor. Its center is at the intersection point of MAAFO and ML. The intersection of the circle $C_1$ with MAAFO is the distal contact point DCP. Then, circle $C_2$ is constructed with a radius equal to MDW/2, that is half the mesiodistal width MDW. Its center is coincidental with that of $C_1$. The intersection of the circle $C_2$ with the MAFFO curve is the mid-point of tooth TMP and the incisal center point ICP.

The intersection of MAAFO and circles $C_1$ and $C_2$ are then constructed. The curve defined by MAAFO and the intersection of circle $C_1$ is the distal contact point DCP. The intersections of MAAFO and MAAFO circle segment lines are found. The X coordinates of the intersections are compared to the X coordinates of DCP to determine which segment's center will be used.

A distal contact point line DCPL is constructed from the selected segment center to the DCP. Similarly a center of tooth line TMPL is constructed from the sector center to the TMP. Thus, the tooth LIMOC is on MAAF and the tooth mesiodistal width line is on the MAAFO arch. The location of FIMOC is accordingly determined by adding DFL to the MAFFO circle segment radius through the TMP.

The MAAFO, like the MO for the mandibular teeth, is discontinuous, with the archform being offset differently for the different maxillary teeth. Accordingly, for the maxillary laterals, the prior MAAFO is replaced with the MAAF adjusted such that the MAAF radii are increased by amount of MAO for lateral. The tooth's MCP is the tooth's MAO distance from the MAAF along the prior tooth's distal contact point line DCPL. Circle $C_1$ is constructed with a radius the mesiodistal width of the tooth and with a center at the tooth's MCP. The intersection of $C_1$ with the MAAFO is the tooth's DCP. Circle 2 is constructed with a radius equal to half of the tooth's MDW and with a center coincident with that of circle $C_1$. The intersection of circle $C_2$ with MAAFO is the tooth's ICP.

Then, the intersections of MAAFO and the MAAFO sector lines are found. The X and Y coordinates of intersections are compared to the X and Y coordinates of DCP to determine which segment's center will be used. A distal contact point line DCP is constructed from the selected segment center to the DCP. Similarly a center of tooth line TMPL is constructed from the sector to the TMP.

For the maxillary cuspids, the prior MAAFO is eliminated. A new arch form, the maxillary cuspid arch form MCAF, is computed to place the cuspid between the lateral and the first bicuspid. In one preferred approach, the MCAF is constructed offset from the BFBCE by the average of the OFFSETs of the first bicuspid and the lateral, as calculated in substep (1135) above. With exception of a new arch radius, the cuspid is placed as above.

For the maxillary bicuspids and molars, the arch form CGMRAF, which is the BFBCE, is offset by MBO. CGMRAF is adjusted by adding MBO for the respective teeth. The cuspid tips on the MCAF, which was offset from the BFBCE to align with the buccal cusp tips of the first bicuspids in (1115) above, are thus in line with the posterior buccal cusp tips. From the cuspid DCP, circles $C_1$ and $C_2$ are constructed and DCPLs are established. This sequence is repeated for remainder of the teeth, completing the relation of the maxillary and mandibular occlusions. The finish positions of the maxillary teeth are illustrated FIG. 4D.

At this point, the final positions of the maxillary teeth have been calculated, and thus, the finish positions of all of the teeth.

Appliance Design Procedure (96)

The appliance design procedure includes the steps of (1200) determining the location of the mandibular archwire plane relative to the calculated finish positions of the mandibular teeth, (1300) calculating the angle of each mandibular bracket slot relative to the mounting surface of the respective tooth, (1400) determining the location of the maxillary archwire plane relative to the calculated finish positions of the maxillary teeth, (1500) calculating the angle of each maxillary bracket slot relative to the mounting surface of the respective tooth, (1600) calculating the shape of the mandibular archwire and the slot in-out dimension of each mandibular bracket, (1700) calculating the shape of the maxillary archwire and the slot in-out dimension of each maxillary bracket, and (1800) calculating the contours of bracket placement jigs for each tooth.

(1200) Mandibular Archwire Plane Step:

The next step is (1200) to establish the position of the archwire plane for the mandibular teeth, which is illustrated in detail in the flowchart of FIG. 2P. The archwire plane can be located in an infinite number of vertical positions since the brackets and archwire will be designed to accommodate any chosen location. Since the overlap of the maxillary teeth is known, for labial bracket placement, the mandibular archwire plane is set to provide bracket clearance for the maxillary teeth in the finished occlusion. For lingual bracket placement, this consideration is given to the maxillary archwire plane instead, in step (1300) below.

Since the maxillary teeth do not pose a bracket interference dilemma with labial bracket placement, the brackets can be positioned for ease of placement, cosmetic considerations and gingival health. This applies to the mandibular bracket positioning where lingual bracket placement is used. Typically, these brackets are located more centrally than the brackets of the other arch.

More particularly, as illustrated in the flowchart of FIG. 2P and FIG. 8, (1200) to establish the archwire plane, (1205) the selected vertical occlusion and respective vertical overlap from MOC for cuspids, laterals and centrals is recalled from (1110). Then, (1210) with the information from (705), the buccal cusp height BCH is recalled for each bicuspid and molar. Next, (1215) the maximum BCH or anterior vertical overlap is chosen as the maximum vertical overlap MVO. Then, (1220) a distance equal to the MVO is measured downward from the MOC. Finally, (1225) half of the bracket height (typically 3.0 mm) plus an additional 0.75 mm is added for occlusal clearance. This defines the mandibular archwire plane MAWP. This places brackets as occlusal as possible with an 0.75 mm clearance from the worst case from the maxillary occlusion.

(1300) Mandibular Slot Inclination Step:

Once the archwire planes have been defined with respect to the teeth, as illustrated in the flowchart of FIG. 2Q, (1300) the angle between the bracket mounting surface of the teeth and archwire plane is determined. This angle minus 90° is the facial torque or inclination angle to be formed into the brackets. This also defines the bracket slot placement height which is the distance from the top of the incisal edge to the archwire plane. This distance is calculated perpendicular to the archwire plane.

Slotless bracket bodies (vanilla brackets) have now been positioned appropriately. A smooth archwire is then designed such that it will pass through the bodies of the brackets. The archwire must not cut too deeply into the bracket or pass even partially outside the face of the brackets. Brackets are chosen having different heights according to need. Without modifying buccal tube assemblies, standard bracket distances from the tooth surface to the center of the slot may be used as a seed values. The archwire equation is then mathematically derived from cubic spline and tangential circle techniques as previously described and provided in the routines (2000) and (2100). Both archwires are developed similarly.

Bracket angle determination (1300), more particularly, is achieved by (1305) taking the intersection of the MAWP and labial (buccal) surface of each mandibular tooth in the case of labial appliances, and the intersection of the MAWP with the lingual surface of each tooth in the case of lingual appliances. Then, (1310) circles are constructed with centers at the intersections and with diameters that represent the occluso-gingival (vertical) dimensions of the bracket bonding pad (typically 3.0 mm). Then, (1315) X,Y coordinates of the circle intersections with labial (buccal) tooth surface are taken, and, with the equations:

$$R^2 = (X_1 - h)^2 + (Y_1 - K)^2$$

$$Y_2 = mX_2 + b_2$$

$$Y_3 = mX_3 + b_3$$

(1320) The slopes between the points of intersection are calculated to produce the facial inclination angle FIA, where:

h,k = coordinates of circle center

X₁,Y₂,b₂ = definition of first line segment

X₃,Y₃,b₃ = definition of second line segment

Then, as illustrated in FIG. 8A for labial appliances, π/2 radians are then subtracted to produce the slot inclination angle SIA:

$$FIA = \frac{Y_2 - Y_3}{X_2 - X_3}$$

$$SIA = FIA - \pi/2$$

(1400) Maxillary Archwire Plane Step:

The next step is (1400) locating the maxillary archwire plane as illustrated in the flowchart of FIG. 2R and diagram of FIG. 8. For the maxillary centrals, this involves (1405) finding the vertical distance from incisal edge to point P₄. (1410) The smallest value is selected and divided by two to produce the slot placement height for the maxillary centrals. (1415) For terminal maxillary bicuspids the vertical distance from buccal cusp to point P₄ is found. (1420) Again, the smallest value is selected and divided by two. This produces the slot placement height SPH for the terminal maxillary bicuspids.

For maxillary centrals, (1425) the Y value of FIMOC is subtracted from the Y value for the slot placement height SPH. This is the distance from MOC to the slot centerline. For terminal maxillary bicuspids, (1430) the Y value of MOC is subtracted from the Y value for the slot placement height SPH. This is the distance from MOC to the slot centerline. Then, (1435) the SPH for the terminal bicuspid from SPH for the maxillary centrals. This is elevation change DH of the maxillary archwire relative to the MOC from the centrals to the terminal maxillary bicuspids. (1440) The elevation of the maxillary archwire MXAWP from the MOC, or archwire height AHT on each tooth, is calculated as follows:

AHT = K + DH + SPH − MOCy + Vertical overlap
from (1110)

where K is the conversion factor from Table 3.

TABLE 3

| Tooth Type | Non-Extraction | Extraction (e.g. 2nd Bicuspid) |
|---|---|---|
| Maxillary Central | 0.0 | 0.0 |
| Maxillary Lateral | −0.19 | −0.28 |
| Maxillary Cuspid | −0.42 | −0.62 |
| Maxillary First Bicuspid | −0.68 | −1.00 |
| Maxillary Second Bicuspid | −1.00 | NA |
| Maxillary First Molar | −1.32 | −1.46 |

(1500) Maxillary Slot Inclination Step:

Once the archwire plane is determined, as illustrated in the flowchart of FIG. 2S, (1500) the slot inclination angle SAI for each of the maxillary tooth brackets is determined in a manner similar to the slot inclination determination step for the mandibular brackets (1300). This step (1505) begins by finding the intersection of the maxillary archwire plane MXAWP with the labial or buccal surface of each maxillary tooth. Then, (1510) circles are described, for each maxillary tooth, having centers at this intersection point and having diameters equal to the occluso-gingival, or vertical, dimensions of the bracket bonding pad, which is typically 4.0 mm.

From these circles, (1515) X,Y coordinates of the intersections of the circles with the labial or buccal tooth surface are found, as follows:

$$R^2 = (X_1 - h)^2 + (Y_1 - k)^2$$

$$Y_2 = mX_2 + b_2$$

$$Y_3 = mX_3 + b_3$$

Where:
h,k = coordinates of the circle center
X₁,Y₁ = possible coordinates on the circle
X₂,Y₂,b₂ = definition of a first line segment
X₃,Y₃,b₃ = definition of a second line segment Then, as illustrated in FIG. 8A, (1520) π/2 radians are then subtracted to produce the slot inclination angle SIA:

$$FIA = \frac{Y_2 - Y_3}{X_2 - X_3}$$

$$SIA = FIA - \pi/2$$

(1600) Mandibular Archwire and Slot Depth Step:

The next step, as illustrated in the flowchart of FIG. 2T, is (1600) to determine the mandibular archwire and bracket in-out dimension. First, (1605) the circle segment of the BFBCE with which the ICP of the right central is associated is determined, as illustrated in FIG. 8B. Then, (1610) the incisal center point and circle segment center point plane ICPCDCPP is created normal to the arch planes. An incisal center point line ICPL is struck that will pass through the ICP and a particular circle segment center point CSCP associated with the tooth. Then (1615) the Pythagorean distance PD from CSCP to ICP is determined. Then, (1620) viewing the tooth in the ICPCSCPP, as illustrated in FIG. 8C, a line NL is struck normal to the BFBCE plane through the ICP, which is the intersection of CLA and BFBCE. Next, (1625) still viewing the tooth in this plane, the intersection point XP of NL and MAWP is determined.

Still viewing the tooth in the ICPCSCPP, (1630) the X distance XD to the labial surface of the tooth from the XP is determined, and (1635) PD is added to XD and the lower limit of the bracket slot LLBS. The LLBS is a distance associated with the particular bracket that will be placed on this tooth. It is the deepest slot allowable for that bracket. Then, the lower limit LL is calculated thus:

LL = PD + XD + LLBS

Similarly, (1640) PD is added to the XD and the upper limit of the bracket slot ULBS. The ULBS is also a distance associated with the particular bracket that will be placed on this tooth. It is the shallowest slot allowable for that bracket. The, the upper limit UL is calculated thus:

UL = PD + XD + ULBS

(1645) Then, viewing the mandibular occlusion in a plan view and moving out along the ICPL from its CSCP by the nn distance, X and Y points, AWLL$_{X,Y}$, are determined relative to an origin at the intersection of BFBCE and the mandibular midline ML.

Then, (1650) viewing the mandibular occlusion in a plan view and moving out along the ICPL from its CSCP by the UL distance, X and Y points, $AWUL_{X,Y}$ are determined relative to the intersection of BFBCE and the mandibular midline ML. Then, (1655) the mid-point of $AWLL_{X,Y}$ and $AWUL_{X<Y}$ is found and steps (1605) through (1650) are then repeated for all mandibular teeth.

Then, (1660) the average mid-point and distance from right to left is calculated to force mandibular archwire symmetry:

$$S_X = MP_X + \frac{PR_X - PL_X}{2}$$

Where:

$S_{X,Y}$ is the symmetricalized point.

$$S_Y = MP_Y + \frac{PR_Y + PL_Y}{2}$$

MP is the mid-point of BCBCE.
PR is a point on the right side of the midline.
PL is a point on the left side of the midline.
The smoothest curve SC that will pass between all $AWLL_{X,Y}$ and $AWUL_{X,Y}$ points is then determined, as illustrated in FIG. 4E. This is accomplished by the following procedure:

a) The mid-point of each $AWLL_{X,Y}$ and $AWUK_{X,Y}$ pair is found.

b) Then, as described above, a cubic spline equation is passed through these points.

c) The existence of any inflection points is determined.

d) The curve with the least variation in radius changes along the curve is considered the smoothest curve. Preferably, it has no inflection points. If there are one or more inflection points, a logical alternative bracket solution will be derived based upon where the inflection occurred.

Then, (1665) the intersection point XSCICPL of the mandibular right central's ICPL is determined as well the smoothest curve as defined above in substep (1660). Next, (1670) the in-out IO of that particular tooth is determined as the distance along ICPL from ICP to XSCICPL minus that tooths' XD. Then, (1675) steps (1665) and (1670) are repeated until all in-out dimensions are calculated.

Finally, (1675) all XCSICPL points are passed into the cubic spline routine (2000) and to circle routine (2100) and (1680) all circle segment information gathered therefrom are converted to linear distance LD moves needed to bend the appropriate wire, as will be further explained in connection with the wire bending step (3200) below. The bracket slot cutting is described in connection with step (3000) below.

(1700) Maxillary Archwire and Slot Depth Step:

The next step, as illustrated in the flowchart of FIG. 2U, is (1700) to determine the maxillary archwire and bracket in-out dimension. As with the mandibular determination step (1600), (1705) the circle segment of the BFBCE with which the ICP of the right central is associated is determined. The step is similar to that for the mandibular slot in-out dimension calculation of FIGS. 4E and 8C, except that the maxillary centrals and laterals are associated with the MAAF rather than the BFBCE, the maxillary cuspids are associated with MCAF, and teeth posterior to the cuspid are associated with the BFBCE.

The calculation proceeds with (1710) the incisal center point and circle segment center point plane ICPCDCPP being created, with a line being struck that will pass through the incisal center point line ICPL which will pass through the ICP and a particular circle segment center point CSCP associated with the tooth. The plane passing through the ICP and the CSCP and normal to the mandibular trough MT is the ICPCSCPP. Then (1715) the Pythagorean distance PD from CSCP to ICP is determined. Then, (1720) viewing the tooth in the ICPCSCPP, a line NL is struck normal to the BFBCE through the intersection of CLA and BFBCE. Next, (1725) still viewing the tooth in this plane, the intersection point XP of NL and MAWP is determined.

Still viewing the tooth in the ICPCSCPP, (1730) the X distance XD to the labial surface of the tooth from the XP is determined, and (1735) PD is added to XD and the lower limit of the bracket slot LLBS. The LLBS is a distance associated with the particular bracket that will be placed on this tooth. It is the deepest slot allowable for that bracket. Then, the lower limit LL is calculated thus:

LL=PD+XD+LLBS

Similarly, (1740) PD is added to the XD and the upper limit of the bracket slot ULBS. The ULBS is also a distance associated with the particular bracket that will be placed on this tooth. It is the shallowest slot allowable for that bracket. The, the upper limit UL is calculated thus:

UL=PD+XD+ULBS (1745) Then, viewing the mandibular occlusion in a plan view and moving out along the ICPL from its CSCP by the LL distance, X and Y points, $AWLL_{X,Y}$, are determined relative to the intersection of BFBCE and the mandibular midline ML. Then, (1750) viewing the mandibular occlusion in a plan view and moving out along the ICPL from its CSCP by the UL distance, X and Y points, $AWUL_{X,Y}$ are determined relative to the intersection of BFBCE and the mandibular midline ML. Then, (1755) The mid-point of $AWLL_{X,Y}$ and $AWUL_{X,Y}$ is found and steps (1705) through (1750) are then repeated for all mandibular teeth.

Then, (1760) the average mid-point and distance from right to left is calculated to force mandibular archwire symmetry:

$$S_X = MP_X \frac{PR_X - PL_X}{2}$$

Where:

$$S_Y = MP_Y \frac{PR_Y + PL_Y}{2}$$

$S_{X,Y}$=the symmetricalized point.
MP=the mid-point of BCBCE.
PR=a point on the right side of the midline.
PL=a point on the left side of the midline.
Then the smoothest curve SC that will pass between all $AWLL_{X,Y}$ and $AWUL_{X,Y}$ points is determined. This is accomplished by the following procedure:

a) The mid-point of each $AWLL_{X,Y}$ and $AWUK_{X,Y}$ pair is found.

b) Then, as described above, a cubic spline equation is passed through these points.

c) The existence of any inflection points is determined.

d) If there are no inflection points, this is considered the smoothest curve. If there is an inflection point, a logical alternative bracket solution will be derived based upon where the inflection occurred. The relevant information necessary to determine a new pair of $AWLL_{X,Y}$ and $AWUL_{S,Y}$ and their midpoints is undertaken. It should be noted that there are varying LLBS and ULBS possibilities available for each tooth. Then, (1765) the intersection point XSCICPL of the mandibular right central's ICPL is determined as well the smoothest curve as defined above in substep (1760). Next, (1770) the in-out of that particular tooth is determined as the distance along ICPL from ICP to XSCICPL minus that tooths' XD. Then, (1775) steps (1765) and (1770) are repeated until all in-out dimensions are calculated.

Finally, (1775) all XCSICPL points are passed into the spline to circle program and (1780) all circle segment information gathered therefrom are converted to linear distance LD moves needed to bend the appropriate wire, as will be further explained in connection with the wire bending step (3200) below. The bracket slot cutting is described in the discussion of step (3000) below.

(1800) Placement Jig Design Step:

With the shapes of the individual teeth determined, their finish positions calculated, and the brackets designed and their places on the individual teeth determined, the information necessary for the design of bracket placement jigs to aid the orthodontist in positioning the brackets in their proper positions on the individual teeth is available. In the preferred embodiment of the invention, the design of the placement jigs is carried out in the software associated with the jig manufacturing step (3500) described below, following a loading of the appropriate files with the necessary data from the calculations described above into the manufacturing control computer 30c. An abbreviated presentation of the jig design substeps is set forth in the flowchart of FIG. 2V.

Referring to FIG. 2V, (1805) a file containing data of the individual tooth profiles, the archwire plane location including data relating each of the tooth profiles to the relevant archwire plane, the bracket profiles relevant to each tooth, and the bracket design data including the slot size, inclination and depth, are prepared. Then, (1810) the tools that will form the jig are determined, and (1815) clearances are established. Then, (1820) data needed for instructions to cut an internal profile into each jig is assembled to hold a bracket and to locate the bracket at the proper position on the tooth by precise fitting of the jig over the tooth profile along a labial-lingual plane through the tooth midpoint TMP.

The details of the jig design step, as it is performed along with the jig manufacturing step, is described in detail in connection with the description of the flowchart of FIG. 2Z under step (3500) below.

Subroutines

Three subroutines are used in calculating various archforms and calculating the positions of the teeth thereon. These are (2000) the cubic spline equation curve calculation subroutine, (2100) the spline equation to circle segment equation conversion subroutine, and (2200) the tooth placement subroutine. These are illustrated in the flowchart of FIG. 2W.

(2000) Cubic Spline Equation Fitting Subroutine:

In the cubic spline interpolation, symmetrical data points are interpolated and a cubic spline equation is derived. As illustrated in FIG. 5A, a symmetrical mandibular trough or cubic spline equation SMT is shown for one side of the lower jaw. In FIG. 5A, the point $M_X$, $M_Y$ represents the intersection of the curve and the midline ML. The points $SI_X, SI_Y$ for $I=1$ to 6 represent the symmetricized points $X_{ML}$ referred to above.

The cubic spline method uses a cubic (3rd degree) polynomial to interpolate between each pair of data points. A different polynomial is used for each interval, and each one is constrained to pass through the original data points with the same slope as the data. At these points, slopes are computed by finding the slope of the parabola that passes through each data point and its two nearest neighbors.

The iterations necessary to compute the cubic polynomial are as follows:

1) For each data point, the X and Y coordinates are made equal to zero and all other data points evaluated relative to this new original.

2) The slopes of the cubic spline are computed by first computing the coefficients of the above described parabola, then a first point of a slope array is filled followed by the remaining points through the final slope array point.

3) The spline coefficients are computed.

4) The polynomial is evaluated.

These steps are described in *Science and Engineering Programs*, Apple II Edition, Edited by John Heilborn, and published by Asborne/McGraw-Hill. Copyright, 1981, McGraw-Hill, Inc., and incorporated herein by reference.

Once the polynomial has been evaluated, it is possible to acquire additional data points. A Y value can be determined for any given X value, with the constraint that additional data points be within the upper and lower limits of the original X values. The following iterations are performed before circle conversion:

1) Determination of X and Y points on each side of the original data points. This is done by taking X points that are one thousandth (0.001) to each side of original X data points. Then X values two thousandths (0.002) less than the last data point are taken. Then Y points are determined for each arrayed X point by evaluation of the polynomial equation discussed above. Then the Y points of the array are calculated.

2) The slope array is then filled with slopes corresponding to data points on either side of the original data points.

3) The slope of the curve at each of the original data points is calculated. This involves retrieving X and Y points on either side of original data points, and calculating the slope at the original data points using the Point Slope method according to:

$$\text{SLOPE} = \frac{Y_2 - Y_1}{X_2 - X_1}$$

Where:

SLOPE = the slope of the curve at that point.

$X_1$ = the X point 0.001 to left of original data point.

Y1 = the Y point associated with X1.
X2 = the X point 0.001 to right of original data point.
Y2 = the Y point associated with X2.

The slope is calculated using the arrayed point that is 0.002 less than the last data point and the last data point, and the slope is calculated using the point slope method as all array slopes are calculated.

(2100) Circle Segment Conversion Subroutine:

The circle segment conversion typically fits two circle segments into one spline segment. A spline segment is defined as the interpolated cubic spline equation which describes the shape of the curve between two original data points. A circle segment is defined as the arc associated with a beginning point, or end point, and the slope of tangency at that point. Two configurations of circle segments are possible when converting a spline segment into two circle segments, one where the first circle is larger than the second (FIG. 5B) and the other where the first circle is smaller than the second circle FIG. 5C, the variables in which are identified below. The iterations necessary to convert a spline segment into two circle segments are illustrated in FIG. 5D in which:

$P1_X,P1_Y$ = the beginning point of spline segment
$P2_X,P2_Y$ = end point of spline segment
MT1 = tangent slope of spline at point $P1_X,P1_Y$
MN1 = normal slope of MT1
MT2 = tangent slope at point $P2_X,P2_Y$
MN2 = normal slope of MN2
$P3_X,P3_Y$ = intersection of a line through point $P1_X,P1_Y$ with a slope of MT1 and a line though point $P2_X,P2_Y$ with a slope of MT2
CL = a Cord Line, a line connecting points $P1_X,P1_Y$ and $P2_X,P2_Y$
CNL = a Cord Normal Line, a line normal to CL through $P3_X,P3_Y$
hs,ks = the center of the smaller of the two circle segments The iterations to convert a spline segment into two circle segments are, as follows:

1) Determine MN1 and MN2. They are the negative inverse of MN1 and MT2, respectively.
2) Determine the intersection point $P3_X,P3_Y$.
3) Determine the slope of the CL.
4) Determine the slope of CLN.
5) Determine the distance from $P1_X,P1_Y$ to $P3_X,P3_Y$. This is defined as test one.
6) Determine the distance from $P2_X,P2_Y$ to $P3_X,P3_Y$. This is defined as test two.
7) Test to determine which length is smaller. If the test one result is shorter than the test result, the smaller circle is associated with $P1_X,P2_Y$, otherwise, the smaller circle is associated with $P2_X,P2_Y$.
8) Rename the variable associating to the size of the circle. See FIG. 5B in which:
$P1_X,P2_Y$ = the beginning point of spline segment
$P2_X,P2_Y$ = the end point of spline segment
MNS = the normal slope of small circle segment, equivalent to MN1 or MN2 depending on the relative results of test one and test two
MNL = normal slope of large circle segment
hs,ks = the center of the smaller of the two circle segments
hl,kl = the center of the larger of the two circle segments
$P6_X,P6_Y$ = a distance, defined by the radius of the small circle, to a point along MNL from the spline segment point associated with it
MNF = is the slope of the final line 9) Determine the intersection of the line described by slope of CNL and passing through $P3_X,P3_Y$ and the line described by MNS through the spline segment point associated with it. The intersection point of these two lines is the center of the smaller circle hs,ks.
10) Determine the Pythagorean distance from the small circle center hs,ks to the spline segment points associated with it. This distance is the radius of the small circle rs.
11) Move along the line described by MNL and passing through the spline segment point associated with it by the radius of the smaller circle rs. This point is $P6_X,P6_Y$.
12) Strike a line from $P6_X,P6_Y$ to hs,ks.
13) The negative inverse of the slope of the line from $P6_X,P6_Y$ and hs,ks is mnf.
14) Determine the midpoint of the line from $P6_X,P6_Y$ to hs,ks.
15) Determine the intersection of the line described by a slope of mnf and passing the point described in step 14 and the line described by MNL and through the spline segment point associated with it. The intersection point of these two lines is the center of the larger circle hl,kl.
16) Determine the Pythagorean distance from the large circle center hs,ks to the spline segment points associated with it. This distance is the radius of the larger circle rl.
17) The intersection of the two circles is defined as the intersection of the line going through the large circle center hl,kl and the small circle center hs, ks and either of the circles. At this point the tangency of the two circles are equivalent.
18) Accommodate an arc length calculation dependent upon which spline point is closer to $P3_X,P3_Y$.
If the test one result is greater than that of test two, then:

Theta1 = ATN(m) − ATN(MSl)

Theta2 = ATN(MLl) − ATN(m)

otherwise:

Theta1 = ATN(msl) − ATN(m)

Theta2 = ATN(m) − ATN(mll)

where:

$$m = \frac{kl - ks}{hl - hs}$$

Theta1 = the arc angle of the smaller circle

Theta2 = the arc angle of the larger circle.

19) Calculate arc length for each segment.
s1 = rs (Theta1)
s2 = rl (Theta2)
where:
s1 = arc length of smaller segment
s2 = arc length of larger segment
20) Calculate the running arc length.

21) Continue distally until all spline segments are converted.

FIGS. 5E–5J illustrate the building of the mandibular trough data points into circle segments.

(2200) Tooth Placement on Curve Subroutine:

The individual tooth placement upon an equation is required in many steps of the tooth finish position calculation procedure (94). The preferred method is described here in connection with the first occurrence in the procedure for the placement of the mandibular teeth.

There are four alternative equations upon which teeth can be placed: the mandibular trough MT equation, the maxillary anterior arch form MAAF equation, the maxillary cuspid arch form MCAF equation, and the central groove marginal ridge arch form MGMRAF equation. All occlusion equations will have been converted to circle segments before teeth are placed upon them. A typical tooth placement is illustrated in FIG. 5N, in which:

DCP = Distal Contact Point
ICP = Incisal Center Point
MCP = Mesial Contact Point
MCPL = is the Mesial Contact Point Line.

The DCP is the point at which the tooth contacts the proceeding tooth. The ICP is the center of the tooth being placed. The MCP is the point at which the tooth contacts the preceding tooth. The MCPL is defined as the line through the DCP of the tooth being placed and the center of the circle segment associated with the DCP. The MCPL is the line upon which the DCP of the proceeding tooth will be found.

The iterations to place the teeth onto the circle segments are:

1) Determine the offset distance for the mandibular central tooth on the side of the jaw under consideration.

2) Expand all circle segments about their centers by the offset amount.

3) Determine the intersection of the first circle segment and the midline. This is the mesial contact point MCP of the central, as illustrated in FIG. 5K.

4) Place the first circle $C_1$, whose radius is the mesio-distal width of the tooth, at MCP, as illustrated in FIG. 5K.

5) Determine which circle segment in the distal direction circle $C_1$ intersects and identify the intersection point. This is accomplished by performing an iteration which begins by transferring the coordinate system to the beginning point of the circle segment, as illustrated in FIG. 5L, in which:

$X_{BEG}, Y_{BEG}$ = beginning coordinates of the circle segment
$X_{END}, Y_{END}$ = End points of the circle segment
$X_{INT}, Y_{INT}$ = coordinates of circle intersection
X and Y axes are oriented at $Y_{BEG}, Y_{BEG}$.

The two following circle equations are then solved simultaneously:

$$R_1^2 = (x - h1) + (y - k1)$$

$$R_2^2 = (x - h2) + (y - k2)$$

Where:
h1,k1 = the center coordinates of the first circle
h2,k2 = the center coordinates of the second circle
$R_1$ = the radius of the first circle $C_1$
$R_2$ = the radius of a second circle $C_2$
X,Y = coordinates of possible intersection points The following solutions are possible:

(1) two real solutions which are labeled $X1_{INT}, Y1_{INT}$ and $X2_{INT}, Y2_{INT}$, respectively.

(2) imaginary solutions, which are discarded, whereupon the next circle segment is evaluated. If intersections are real, the circle segment is rotated, as illustrated in FIG. 2M, such that $X_{END}, Y_{END}$ is placed on the X axis. Then, $X_{BEG}, Y_{BEG}$ is subtracted from the rotated X intersection point $X1_{INT}$ or $X2_{INT}$, and rotated $X_{END}$ is subtracted from the rotated X intersection point $X1_{INT}$ or $X2_{INT}$. If the signs of the results of the two subtractions are opposite, the rotated intersection point is tested for a value less than zero. If it is not less than zero, the other rotated intersection point is tested to determine if it is valid. The testing continues until a segment is found such that the subtractions produce opposite sign results and the associated rotated Y intersection point is less than zero. This is the distal contact point DCP of the tooth, as illustrated in FIG. 5N.

6) Construct a line which passes through the DCP and the center of the circle segment that intersects $C_1$.

7) Place circle $C_2$, whose radius is one half the mesio-distal width MDW of the tooth, at the MCP.

8) Determine which circle segment in the distal direction intersects circle $C_2$ and identify the intersection point. This is the incisal center point ICP of the tooth, as illustrated in FIG. 5N.

9) Eliminate all expanded circle segments.

10) Determine the offset distance for the mandibular lateral.

11) Expand all circle segments about their centers by the offset amount.

12) Determine the intersection point of the expanded circle segment ECS associated with the DCP MCP Line. The intersection point defines the mesial contact point MCP of the lateral, as illustrated in FIG. 5O.

13) Place circle $C_1$, whose radius is the mesio-distal width MDW of the lateral, at the current MCP point.

14) Determine which circle segment in the distal direction circle $C_1$ intersects and identify the intersection point, which is the DCP of the lateral.

15) Construct a line which passes through the DCP and the center of the circle segment that intersects $C_1$.

16) Place circle $C_2$, whose radius is one half the mesio-distal Width MDW of the tooth, at the MCP.

17) Determine which circle segment in the distal direction intersects circle $C_2$ and identify the intersection point. This is the incisal center point ICP of the tooth, as illustrated in FIG. 5P.

18) Continue distally until all teeth are placed.

19) Perform the same iterations for the co-lateral side of the arch.

(97) Appliance Manufacturing Procedure

The appliance manufacturing procedure (97) includes the steps of (3000) manufacture of the custom brackets, (3200) manufacture of the custom archwires and (3500) manufacture of custom placement jigs for placement of the custom brackets on the patient's teeth. These steps are described in detail below for the embodiment in which all of the manufacturing is carried out at the appliance design facility 13.

(3000) Bracket Manufacturing Step:

The bracket manufacturing step (3000) produces the custom brackets, preferably by selecting bracket blanks and cutting a torque slot in the bracket for the archwire 64. This utilizes the modified CNC mill 40 illustrated in FIG. 2D. The bracket slot cutting step is illustrated in the detailed flowchart of FIG. 2X.

Referring to FIG. 2X, the bracket manufacturing step (3000) begins with the computer 30c (3005) loading the data for each bracket from the patient data file 36.

For each tooth and bracket, as a default or initial selection, (3010) low profile brackets are assumed. Then, the slot angle FA/and the slot in-out dimension IO are read. Also, (3020) the radius of the archwire at the tooth midpoint is determined.

Then, (3025) a main CNC program is created and (3030) the program loops to generate the code for the cutting of each bracket, beginning with the calculation of the variables for the bracket, (3040) assigning the variables for each bracket to (3045)–(3050) set the cutting of the slot at the appropriate angle by rotating the bracket support 73 and setting the cutter 77c to a cooperating height Z and horizontal X position. If the position of the slot lies outside of the area of the bracket, a bracket of the appropriate higher profile is called for by the program, and loaded, either automatically or by an operator. The code is then generated (3055) to control the path of the cutter in the Y direction to cut the archwire radius in the slot bottom. (3060) then, the NC code is combined with the calculated variable values for the tooth and bracket and a subroutine is generated for the bracket, with (3065) the P-codes subroutines written the file. (3068) The program loops until codes for all of the brackets are complete.

Then, (3070) the CNC code is preferably downloaded to an NC controller and the brackets are formed by the cutting of the slots in the series of bracket blanks, and (3080) a report is written.

(3200) Archwire Manufacturing Step:

The archwire manufacturing step (3200) produces the archwire 64, as illustrated in FIG. 2E, preferably that is symmetrical about its archwire midline AML, having the appropriate terminal leg span TLS, formed of a series of circle segments.

As illustrated in the flowchart of FIG. 2Y, the archwire manufacturing step (3200) executes a program with the manufacturing control computer 30c to generate a CNC code to operate the wire forming machine 40. The program begins by (3215) opening one or more files from the calculated patient data 36 and reads therefrom the wire alloy and the wire cross-section prescribed, and an array of data that contains a series of j sets of data including the radius and sector length of each circle segment of which the archwire curve is formed, and the calculated total cumulative archwire length. To the archwire equation, (3220) a radii and sector lengths are added to produce a one half inch of straight segment at each end of the wire to form parallel terminal leg extensions. Then, calculating the cumulative slopes and sector lengths of the wire along the equation, (3225) the terminal leg span TLS is calculated.

Based upon the wire type selected, (3230) one of several data files or tables are read. For rectangle wire, for example, four files would include: (1) 0.022" thickness stainless steel (SS), (2) 0.025" thickness SS, (3) 0.022" thickness titanium molybdenum alloy (TMA), and (4) 0.025" thickness TMA. Other files are provided for round wires of various diameters and types.

Then, using the cubic spline subroutine (2000), (3235) the slopes of the cubic spline equation describing wire behavior are calculated by: (1) computing the coefficients of a parabola, (2) filling the first point of a slope array, (3) filling the intermediate points of the slope array, and (4) filling the last point of the slope array. Then, (3240) the cubic spline coefficients are calculated. Then, (3245) he vertical displacement of the bending lever arm LA (FIG. 2E) between the contact points of the roller 70b with the wire 69 and the contact point of the rollers 68 with the wire 69 is determined for each circle segment of the archwire equation, and data added to the array.

Then, (3255) temporary variables are defined for the sector length, lever arm displacement, radius and terminal leg span across the straight segments of the archwire, (3260) the controller card 65 of the computer 30c is initialized, (3265) the controller base address is set, and (3270) default parameters are set. Then, (3275) a sequential series of sector lengths and lever arm displacements are sent respectively (1) through the circuits 66a and 67a to the drive of the feed rolls 68, and (2) through the circuits 66b and 67b to the anvil assembly 70.

When all of the circle segments have been formed, (3280) the lever arm displacement is zeroed and (3285) the wire leg location is read by the sensor 71. This reading converted to a numerical value in the computer 30b and any difference in the actual measured terminal leg span and the desired terminal leg span TLS is calculated. If (3290) the difference is out of tolerance, a correction is made and another wire is formed.

(3500) Jig Manufacturing Step:

The jig manufacturing step (3500) produces bracket placement jigs custom designed for each tooth to aid in the placement of the custom designed brackets in the proper positions on the teeth so that the custom designed archwire will, when installed in the custom designed and custom placed brackets, move the teeth to their calculated finish positions.

The information necessary for the design of the custom placement jigs is contained in the patient data file of from the calculations made in the appliance design procedure (96) and in the tooth profile data file of digitized information read in step (500), in the illustrated embodiment of the invention. The design of the custom jigs involves, primarily, an assembly of the information already generated, and, in the preferred embodiment, takes place in the course of generating the code for control of the NC controlled manufacturing equipment 41 that produces the jigs.

In the preferred and illustrated embodiment, the jig manufacturing equipment 41 is a standard CNC mill equipped with a small carbide endmill tool of, for example, 0.020 inches in diameter (FIG. 1F). The jigs themselves 82 are made from circular ABS plastic wafers 83 of approximately one inch in diameter and approximately 0.040 inches in thickness, though considerable variation in size is acceptable.

The jig manufacturing step (3500), as illustrated in the detailed flowchart of FIG. 2Z, begins with the execution of a program or routine in the manufacturing computer 30b and the input of parameters identifying the patient or case. Upon beginning of the execution of the program, (3515) the file of patient data 36 generated in the tooth position calculation and analysis procedure (95) and the appliance design procedure (96) is opened and information is read for each tooth, as illustrated in the diagram of FIG. 9I, in relation to a tooth profile PF. The variables read are (a) the intersection of the archwire plane and the labial (or lingual, if prescribed) surface of the tooth TS, which is in the form of a pair of X,Y coordinates $TS_{X,Y}$ in the tooth profile vertical-labial/lingual plane, (b) the slot in-out dimension Elan or IO, (c) the type of bracket, which provides access to the appropriate place in a lookup table of bracket dimensions, such as bracket base thickness BRel and bracket pad height BPH, and (d) the torque slot width, 0.018 or 0.022 from the prescription.

Then, (3520) the bracket data file is opened and the bracket base thickness read, as illustrated in FIG. 9J. Then, a file name is assigned, (3530) a CNC file is created, and (3535) a CNC "main" program is written to it, as set forth, for example, in the flowchart of FIG. 2Z-1.

Then, (3540) a sequential file is identified that contains the beginning and ending object number for each tooth profile, and (3545) a CAD program file containing the tooth profiles $PF_1$ is loaded. The profiles PF, as illustrated in FIG. 3C, are made up of a series of closely spaced points in the profile plane, each represented by X,Y coordinates, connected by straight line segments to define the profile curve PF. The endmill tool diameter Endmill is also entered, which must be less than the archwire diameter or archwire slot width (0.018 or 0.022). Constants are declared, including the diameter of the jig blank 83, the cut clearance on the outside of the jig, the number of loops, set at 23, and the counter initial settings.

Then, (3560) the CNC P-code is generated for each tooth, by looping through substeps (3560) through (3639) until the code for each of the jigs 82 is generated. The loop begins by (3560) incrementing the tooth and P-code counters by 1. The loop begins with the lower left bicuspid, as brackets are usually not used on the molars, and proceeds left to right. Thus, (3565), when the incrementing of the counter advances the count to the lower right molar, (3565) the counter is advanced to skip to the upper left bicuspid.

Then, (3570) the parameters for the particular tooth are set up as illustrated in the flowchart detail of FIG. 2Z-2. This is followed by creating the profile and bracket clearance compensation tool paths ITP and BCTP, respectively, as illustrated in the flowchart detail of FIG. 2Z-3. This involves (3590) the creation of an initial inside tool path line IITP made up of a series of straight line segments, one parallel to each of the line segments of the tooth profile curve, spaced a distance equal to the tool radius on the inside of the profile curve, as illustrated in FIG. 9K, (3595) the creation of an initial bracket base compensation tool path line IBCTP made up of a series of straight line segments, one parallel to each of the line segments of the tooth profile curve, spaced a distance equal to the bracket base dimension minus the tool radius outside of the profile curve, as illustrated in FIG. 9L, and (3600) creation of the final bracket base compensation tool path (d) to cut from the inside tool path line to the base compensation line at the top of the bracket base pad to cut off the jig at the bottom of the pad, as illustrated in FIG. 9M ("top" and "bottom" being used as an example for the lower teeth, and being opposite for the upper teeth).

Next, (3605) the archwire slot tool path ASTP is created as illustrated in the flowchart detail of FIG. 2Z-4, which can be understood from the sequence set forth in the flowchart with reference to the diagrams of FIGS. 9N, 9O and 9P. Then, as set forth in the flowchart detail of FIG. 2Z-5, (3610) a reference tool path RefP is created on an image of a jig blank 83, as illustrated in FIG. 9Q, and with reference to it, (3615) the outside jig boundary cutout CTP is added as illustrated in FIG. 2R, and (3620) the actual tool path TP is then generated as illustrated in FIG. 9S.

Then, (3625) the CNC machine code is generated, as illustrated in the detailed flowchart of FIG. 2Z-6, and written to the output file. Then, (3630) the variables are reset, (3635) the final results are displayed, and (3640) the program loops back to substep (3560) until all of the bracket jig code have been generated. Then, (3645) the completed CNC file is Sent to the controller of the CNC mill and a pallet of wafers 83$a$ (FIG. 1F) is cut into a set of bracket placement jigs 82. An example of one of the jigs is illustrated in FIGS. 9T through 9W.

What is described above includes the preferred embodiments of the invention. Those skilled in the art will appreciate that additions to and modifications of the system and method of the invention, and the detailed manifestations thereof, may be made without departing from the principles of the inventive concepts set forth herein.

Accordingly, the following is claimed:

1. A method of fabricating a custom orthodontic appliance to position teeth of a patient to preferred finish positions in the mouth of the patient, the method comprising the steps of:

sensing anatomical shapes from the mouth of the patient;

digitizing the sensed anatomical shapes from the mouth of the patient, and producing thereby signals containing digitized anatomical shape data including three dimensional tooth shape data representing the shapes of individual teeth of the patient;

deriving an ideal dental archform by processing the digitized anatomical shape data contained in the signals with a digital computer programmed to produce a digitized mathematical archform model that is at least in part dependent on the ditized anatomical shape data;

deriving, with the computer, tooth finish positions from the digitized anatomical shape data and the digitized mathematical archform model to mesio-distally space the teeth along the derived ideal dental archform and to position and orient the teeth relative to the derived ideal dental archform to positions and orientations based at least in part upon the three dimensional tooth shape data for the individual teeth;

establishing an appliance connection point on each of a plurality of the teeth;

designing a custom orthodontic appliance, with the computer from the digitized three dimensional tooth shape data, the established appliance connection points and the derived tooth finish positions, such that the custom orthodontic appliance has an appliance configuration dimensioned to interconnect the teeth at their respective connection points with the teeth in the derived tooth finish positions;

producing machine readable control signals containing geometric information correlated to the results of the appliance designing step; and automatically fabricating a custom orthodontic appliance with a machine responsive to the machine readable control signals to shape the appliance according to the geometric information contained in the control signals so as to form the custom orthodontic appliance having the designed appliance configuration.

2. The method of claim 1 wherein:

the appliance configuration is such that the fabricated custom orthodontic appliance, when connected to the teeth at the appliance connection points, exerts substantially no tooth moving forces on the teeth when the teeth are in the derived tooth finish positions, and otherwise urges the teeth toward the derived finish positions in an arch corresponding to the digitized mathematical archform model.

3. The method of claim 1 further comprising the step of:

determining from and relative to the derived tooth finish positions and the digitized anatomical shape data, with the aid of the computer, at least one archwire plane;

the appliance connection point establishing step including the step of calculating bracket location data defining the locations on the teeth of the connection points in part in relation to the determined archwire plane;

the custom orthodontic appliance designing step including the step of designing, in part from the calculated bracket location data, the appliance configuration that includes a bracket configuration for each of a plurality of brackets, one for connection to each tooth at the appliance connection point thereon, and that includes an archwire configuration for at least one archwire connectable to each bracket, such that the at least one archwire will lie in the at least one archwire plane when the teeth are in the derived tooth finish positions; and the appliance fabricating step including the steps of automatically fabricating brackets and automatically fabricating at least one archwire having the appliance configuration.

4. The method of claim 3 wherein:

the anatomical shape digitizing step includes the step of digitizing, for each tooth, tooth profile data including a series of digitized data points representing the shape of the surface of a tooth at least along a profile thereof, extending generally vertically and labial-lingually;

the connection point establishing step includes the step of locating a mounting point for each bracket on the surface of a respective tooth along the profile thereof at the intersection of the respective archwire plane with the profile; and the bracket designing step includes the step of designing, for each tooth, from the series of digitized data points representing the shape of the surface of the tooth, the located bracket connection points, the determined archwire plane locations and the derived tooth finish positions, a bracket configuration that includes a bracket slot, having a depth, inclination and shape, such that, when fabricated brackets are installed at the respective bracket mounting points, fabricated archwires are mounted on the installed brackets, and the teeth have arrived at their respective derived finish positions, substantially no tooth urging force is exerted by the archwires through the brackets and on the teeth.

5. The method of claim 4 further comprising the steps of:

designing appliance placement jig configurations from the tooth profile data, each having a jig surface that will conform to the surface of a respective tooth for facilitating the location of the connection point thereon and the mounting of the bracket thereat;

producing the machine readable information at least in part in accordance with the designed appliance placement jig configurations; and automatically fabricating appliance placement jigs with a machine in response to the machine readable information to conform to the designed appliance placement jig configurations.

6. The method of claim 1 wherein the teeth include mandibular teeth and maxillary teeth and wherein:

the anatomical shape digitizing step includes the steps of the digitizing the shape of the lower jaw of a patient and producing thereby digitized lower jaw shape data, and digitizing the shapes of mandibular teeth of the patient and producing thereby three dimensional tooth shape data of individual mandibular teeth; and the archform deriving step includes the step of deriving, with the computer, a mandibular skeletal archform from the digitized lower jaw shape data and producing the digitized mathematical archform model based at least in part on the mandibular skeletal archform;

whereby the tooth finish position deriving step includes the step of deriving the tooth finish positions based on the three dimensional tooth shape data and the derived mandibular skeletal archform to arrange the teeth with respect to the mandibular skeletal archform.

7. The method of claim 6 wherein:

the tooth shape digitizing step includes the step of digitizing, on each mandibular tooth, locations of contact points with adjacent mandibular teeth, locations of tooth intersections with the jaw, and locations of tips thereon, and producing thereby individual three dimensional mandibular tooth shape data, the tips including incisal edges for incisors and cuspids and buccal cusp tips for teeth distal to the cuspids; and the finish tooth position deriving step includes the step of deriving, with the computer, mandibular tooth finish positions from the three dimensional mandibular tooth shape data and the derived mandibular skeletal archform, the mandibular tooth finish positions being calculated to place adjacent mandibular teeth in mutual contact, to align each mandibular tooth approximately on the mandibular skeletal archform at the lower jaw, and to place tips of mandibular teeth mesial and distal of the cuspids approximately at the same height in an occlusal plane, and on a smooth arcuate curve related to the mandibular skeletal archform.

8. The method of claim 6 wherein:

each tooth has a crown, a root and a long axis extending generally vertically through the center of the crown, intersecting a gingival center point where the crown meets the root, and wherein:

the lower jaw shape digitizing step includes the step of digitizing mandibular trough data points defining a mandibular trough in which mandibular tooth roots are to be confined;

the mandibular skeletal archform deriving step includes the step of fitting a smooth continuous mandibular trough curve to the digitized mandibular trough data points and producing a digitized representation of the mandibular trough curve;

the mandibular tooth finish position deriving step includes deriving positions which center each mandibular tooth by placing the long axis thereof approximately on the mandibular trough curve near the gingival center point of the tooth, and which place the tips of the mandibular teeth on a second smooth continuous curve derived by adjusting the mandibular trough curve; and the custom orthodontic appliance designing step includes defining the appliance configuration by a series of digital values derived from the second smooth continuous curve.

9. The method of claim 8 the step of deriving the second smooth continuous curve comprises the step of:

labially expanding the mandibular trough curve adjacent each tooth by an amount determined by calculating, with the computer, horizontal distance from the mandibular trough curve to the tip of such tooth and smoothing the result by a best fit statistical method to produce the second smooth continuous curve.

10. The method of claim 8 further comprising the step of:

representing the mandibular trough curve by a series of successively tangent circle segments;

the smooth continuous curve being produced by radially adjusting circle segments of the mandibular trough curve adjacent each tooth by amounts respectively determined by calculating, with the computer, horizontal distances of the respective tooth tips from the mandibular trough curve;

the custom orthodontic appliance designing step includes the step of defining the appliance by an appliance archform equation in the form of a series of digital values representing circle segment lengths and radii derived from the circle segments of the mandibular trough curve;

the machine readable control signal producing step includes the step of converting the segment lengths and radii to a series of commands to produce the machine readable information, and;

the custom orthodontic appliance fabricating step includes the step of reading the machine readable information, and with the machine, sequentially feeding a wire in accordance with the segment lengths and simultaneously bending the wire to corresponding radii in synchronism with the feeding thereof to conform to the designed appliance configuration.

11. The method of claim 10 wherein:

the anatomical shape digitizing step includes the step of digitizing distances between mesial and distal contact points for each tooth to produce the digitized three dimensional tooth shape data defining mesial-distal widths for each tooth;

the tooth finish position deriving step includes the step of deriving tooth positions to place adjacent mesial and distal contact points of adjacent teeth in mutual contact to form respective mandibular and maxillary tooth placement arches each approximately equal in length to the sum of the mesial-distal widths of the teeth respectively placed thereon; and the series of circle segments representing the mandibular trough curve includes at least two circle segments per tooth spanned by a chord equal to the mesial-distal width of the tooth.

12. The method of claim 6 wherein:

the tooth digitizing step includes the step of digitizing, from each mandibular tooth, positions for determining contact points with adjacent mandibular teeth, and producing thereby digitized data of individual mandibular tooth shape;

processing the digitized tooth shape data of mandibular tooth shape and the mandibular skeletal archform and deriving thereby a mathematical model of a mandibular dental archform; and the finish tooth position deriving step includes the step of deriving, with the computer, mandibular tooth finish positions from the mandibular tooth shape data and the derived mandibular dental archform, to place adjacent mandibular teeth in mutual contact in an arch conforming to the mandibular dental archform.

13. The method of claim 12 wherein the mandibular and maxillary teeth respectively include mandibular and maxillary incisors, cuspids, bicuspids and molars, and wherein:

the tooth shape digitizing step includes the step of digitizing, on each mandibular tooth, locations of tooth intersections with the jaw and locations of tips thereon, and producing thereby digitized data of individual three dimensional mandibular tooth shape, the tips including incisal edges for mandibular incisors and cuspids and buccal cusp tips for teeth distal to the cuspids;

the anatomical shape digitizing step includes the steps of the digitizing the shapes of maxillary teeth of the patient and producing thereby three dimensional tooth shape data of individual maxillary teeth;

the tooth shape digitizing step includes the step of digitizing, on each maxillary tooth, locations of contact points with adjacent maxillary teeth, locations of tips on incisors and cuspids, and locations of central groove/marginal ridge intersections on bicuspids and molars, and producing thereby the digitized data of individual three dimensional maxillary tooth shape; and the finish tooth position deriving step includes the step of deriving, with the computer, maxillary tooth finish positions from the maxillary tooth shape data, the derived mandibular dental archform, and mandibular tooth shape data, the maxillary tooth finish positions being calculated to place adjacent maxillary teeth in mutual contact and to place central groove/marginal ridge intersections of maxillary bicuspids and molars approximately on the smooth arcuate curve.

14. The method of claim 13 wherein:

the maxillary tooth digitizing step includes the step of digitizing positions on at least some of the maxillary incisors and cuspids, and determining, at least partially therefrom and from the tooth finish positions of the mandibular teeth, horizontal distances from the locations of tips on such maxillary incisors and cuspids to points of occlusion with mandibular teeth;

the archform deriving step includes the step of deriving, with the computer, from the determined horizontal distances and the mandibular dental archform, at least one maxillary dental archform for the placement with respect thereto of such maxillary teeth; and the finish tooth position deriving step includes the step of deriving, with the computer, maxillary tooth finish positions in part from the at least one maxillary archform to place the maxillary teeth on a curve related to the at least one maxillary dental archform.

15. The method of claim 14 wherein the maxillary bicuspids include first maxillary bicuspids having buccal cusp tips thereon and the maxillary incisors include lateral incisors having incisal edges thereon, and wherein:

the maxillary tooth finish position deriving step includes the substep of deriving positions of the maxillary cuspids to place tips thereof labially offset from the mandibular skeletal archform and on a transitional arch between the buccal cusp tips of the first maxillary bicuspids and the incisal edges of the lateral incisors.

16. The method of claim 7 further comprising the steps of:

the maxillary tooth finish position deriving step includes the step of deriving tooth finish positions for maxillary incisors from the tooth shape data and the mandibular skeletal archform to place the tips of the maxillary incisors below an occlusal plane of contact between maxillary and mandibular teeth according to predetermined overlap criteria and to place the lingual faces thereof in predetermined horizontal proximity to the mandibular incisors.

17. The method of claim 13 further comprising the steps of:

producing digital inclination data defining inclination angles for each of the teeth;

the dental archform deriving step includes the step of deriving the ideal dental archform based on the mandibular skeletal archform modified based on the digital inclination angle data and the digitized tooth shape data; and the tooth position deriving step including the step of deriving tooth finish positions in part from the established inclination angles to incline teeth at the respective established inclination angles.

18. The method of claim 17 wherein:

the inclination angle establishing step includes the step of setting the inclination angles of the teeth in accordance with predetermined criteria by inputing the digital inclination data; and the mandibular tooth position deriving step includes deriving positions to center the mandibular teeth approximately on but slightly offset from the mandibular skeletal archform an amount that will place the tips of the mandibular teeth on the smooth arcuate curve.

19. The method of claim 1 wherein the teeth have tips thereon and include mandibular cuspids and maxillary cuspids, the mouth of the patient includes a lower jaw having a pivot axis at one end thereof, and the method further comprises the steps of:

establishing, in the computer, distance data representing distances of the individual teeth from the pivot axis of the lower jaw;

establishing, in the computer, an occlusal plane relative to which points of occlusion between upper and lower teeth are defined;

determining, in the computer and from the three dimensional tooth shape data, distances of the tips of mandibular and maxillary teeth respectively above and below the occlusal plane;

calculating, with the computer, a cuspid rise from the distance data and the established and determined distances; and the tooth finish position deriving step including deriving positions of the mandibular and maxillary cuspids to place their tips at distances, respectively above and below the occlusal plane, having a predetermined relationships to the calculated cuspid rise.

20. The method of claim 1 wherein:

the anatomical shape digitizing step includes the step of digitizing distances between mesial and distal contact points for each tooth to define mesial-distal widths for each tooth;

the ideal dental archform deriving step includes the step of deriving mandibular and maxillary tooth placement archforms defined at least in part by series of consecutive mesial-distal widths of respective mandibular and maxillary teeth;

the tooth finish position deriving step includes the step of deriving tooth finish positions spacing mandibular and maxillary teeth along the respective derived mandibular and maxillary archforms to place adjacent mesial and distal contact points of adjacent teeth in mutual contact to form respective mandibular and maxillary tooth placement arches approximately equal in length to the sum of the mesial-distal widths of the teeth placed thereon; and the custom orthodontic appliance designing step includes the step of designing the appliance configuration in part from the mesial-distal widths and tooth placement archforms.

21. The method of claim 1 wherein:

the tooth finish position deriving step includes the step of arranging the teeth to place prominences thereof in the ideal dental archform at a level spaced vertically from the gum;

each tooth has a crown, a root and a long axis extending generally vertically through the center of the crown, intersecting a gingival center point where the crown meets the root: and the tooth finish position deriving step includes the step of initially setting inclination angles of teeth in accordance with predetermined seed values and adjusting the inclination angles to place the gingival center points of the teeth on a smooth continuous gingival center point curve.

22. The method of claim 1 wherein:

the anatomical shape digitizing step includes the step of digitizing, for each tooth, tooth profile data in the form of a series of digitized data points representing the shape of a surface of the tooth at least along a profile thereof extending generally vertically and labial-lingually;

the finish position deriving step includes the step of mathematically relating the tooth profile data to the digitized mathematical archform model;

the connection point establishing step includes the step of locating an appliance connection point on the surface of each of the plurality of teeth along a profile thereof; and the appliance designing step includes the step of designing, from the series of digitized data points representing the shapes of the surfaces of the teeth, the established appliance connection points and the derived tooth finish positions, an appliance such that, when the custom orthodontic appliance is fabricated to conform to the appliance configuration and connected to the teeth at the appliance connection points, and when the teeth have arrived at their respective derived finish positions, the appliance exerts substantially no tooth moving force on the teeth.

23. The method of claim 22 further comprising the steps of:

designing appliance placement jig configurations from the profile data, each having a jig surface that will conform to the surface of a respective tooth for facilitating the location of the connection point thereon and the connection of the appliance thereto;

producing the machine readable information at least in part in accordance with the designed appliance placement jig configurations; and automatically fabricating appliance placement jigs with a machine in response to the machine readable information to conform to the designed appliance placement jig configurations.

24. The method of claim 1 further comprising the steps of:

establishing and inputing into the computer inclination angles for each of the teeth; and the tooth position deriving step including the step of deriving tooth finish positions in part from the established inclination angles to incline teeth at respective inclination angles.

25. The method of claim 1 wherein:

the appliance designing step includes the step of defining the appliance by an appliance archform equation in the form of a series of digital values representing circle segment lengths and radii derived from the digitized mathematical archform model;

the appliance fabricating step includes the step of converting the segment lengths and radii to a series of control signals to produce the machine readable information; and the appliance fabricating step includes the step of, in response to the control signals, shaping an archwire in accordance with the segment lengths and corresponding radii to conform to the designed appliance configuration.

26. The method of claim 25 wherein the appliance fabricating step includes the steps of:

providing a plurality of bracket blanks; and forming an archwire slot in each bracket blank such that each slot will lie in an archwire plane when the bracket is mounted on the connection point of a tooth with the tooth in its derived finish position.

27. The method of claim 25 wherein:

the appliance fabricating step includes the step of forming a bracket for each tooth having a slot therein extending to a depth defined by the intersection of the appliance archform equation with the bracket, when the bracket is mounted on the connection point of a tooth with the tooth in its derived finish position.

28. The method of claim 25 wherein:

the custom orthodontic appliance fabricating step includes the step of forming a bracket having a slot extending to a slot bottom having a curvature of the radius of a circle segment of the appliance archform equation.

29. A method of fabricating an orthodontic appliance for positioning upper and lower teeth of a patient to preferred finish positions in the upper and lower jaws of the patient, the method comprising the steps of:

measuring, in three dimensions, the shapes of individual upper and lower teeth and measuring the shape of the lower jaw of the patient, producing thereby digitized upper and lower tooth data and lower jaw shape data, and inputing the digitized data to a specially programmed computer processor;

deriving, with the computer processor, a lower arch configuration from the digitized lower jaw shape data;

deriving, with the computer processor, a tooth-bearing lower jaw configuration based on assembly of the lower teeth along the lower arch configuration with adjacent teeth in contact with each other and a crown long axis of each tooth intersecting the lower arch configuration at the gum, the teeth being spaced mesio-distally along the arch in accordance with measured dimensions of the teeth in a mesio-distal direction;

with the computer processor, vertically adjusting the tooth bearing lower jaw configuration such that the incisal tips of lower anterior teeth and buccal cusp tips of lower posterior teeth are in substantially the same occlusal plane and are inclined at predetermined angles of inclination;

with the computer processor, reconfiguring the tooth-bearing lower arch configuration to provide a finished tooth bearing lower jaw configuration by labially-lingually repositioning the lower teeth to place the incisal and buccal cusp tips thereof in a smooth arch in the occlusal plane with adjacent teeth in contact with each other;

with the computer processor, deriving a tooth-bearing finished upper tooth configuration in which:

the upper posterior teeth have their central groove/marginal ridge intersections lying horizontally on the finished tooth bearing lower jaw configuration and vertically on an occlusal plane;

the upper teeth anterior to the cuspids have their incisal tips positioned below the occlusal plane to achieve predetermined overlaps and are horizontally labially offset from the finished tooth bearing lower jaw configuration so as to establish a predetermined clearance between the lower anterior teeth lingual faces and the labial faces of the lower anterior teeth;

the cuspids have their incisal tips labially offset from the finished tooth bearing lower jaw configuration and on an archform between the buccal cusp tips of the first maxillary bicuspids and the incisal edges of the maxillary laterals;

with the computer processor, calculating bracket configurations, including bracket slot angle and bracket slot depth, for individual upper and lower tooth brackets, and calculating upper and lower archwire shapes, based upon the calculated finished tooth positions, predetermined upper and lower archwire planes, the tooth shapes, and the positions of the brackets on the teeth;

producing control signals carrying information based on results of the step of calculating bracket configurations and lower and upper archwire shapes; and driving machines with the control signals and thereby fabricating upper and lower archwires to conform to the calculated archwire shapes and fabricating brackets to conform to the calculated bracket configurations.

30. The method of claim 29 wherein the lower jaw has a pivot point at one end thereof and the method further comprises the steps of:

providing criteria describing distances of the individual teeth from the pivot point of the lower jaw;

calculating from the criteria and the tooth shape data a component of cuspid rise; and vertically adjusting the upper and lower cuspids such that their cusp tips are respectively below and above the occlusal plane a distance that has a predetermined relationship to the calculated cuspid rise.

31. The method of claim 30 wherein the tooth-bearing finished upper tooth configuration deriving step includes deriving the configuration in which:

the upper anterior teeth have incisal tips positioned below the occlusal plane so as to achieve predetermined overlaps that have a predetermined relationship to the calculated cuspid rise.

32. The method of claim 29 further comprising the steps of:

positioning the fabricated brackets on the teeth at their respective bracket positions; and locating the upper and lower archwires in slots having the angles and depths of the calculated configurations of the upper and lower brackets, respectively.

33. A method of positioning upper and lower teeth of a patient to preferred finish positions in upper and lower jaws of the patient, at which the teeth occlude in an occlusal plane, and for positioning upper and lower cuspids with cusp tips thereof extending respectively below and above the occlusal plane to provide for cuspid rise occlusion, the method comprising the steps of:

digitizing shapes of individual upper and lower teeth of a patient and producing thereby signals containing digitized upper and lower tooth data, the data including data of distances of the individual teeth from an axis through pivot points which join the upper and lower jaws and data of vertical distances between cusp tips and marginal ridges of maxillary posterior teeth;

calculating from the digitized data contained in the signals, with the aid of a digital computer, based upon the distances, a minimum cuspid rise necessary for opposing pairs of cuspids to clear after all other opposing pairs of teeth clear when the jaws open;

assembling a custom orthodontic appliance configured to move the teeth of the patient, including moving the cuspids to at least the calculated minimum cuspid rise; and orthodontically moving the cuspids of patient, with the assembled appliance, to vertical positions relative to the other teeth of the patient at least to the calculated cuspid rise.

34. The method of claim 33 in which the teeth include incisors having incisal edges thereon and molars and bicuspids having buccal cusp tips and marginal ridges thereon, the method further comprises the steps of:

establishing finish positions of the teeth which place:
the tips of mandibular incisors in a mandibular incisal arch parallel to the occlusal plane,
the tips of maxillary incisors in a maxillary arch spaced labially of the mandibular incisal arch and below the occlusal plane by the amount of an incisal overlap,
the buccal cusp tips of mandibular bicuspids and molars in contact with marginal ridges of the maxillary bicuspids or molars in a buccal cusp arch in the occlusal plane, and
the cusp tips of mandibular and maxillary cuspids are respectively above and below the occlusal plane a distance that has a predetermined relationship to the calculated cuspid rise;

designing with the computer, from the tooth shape data and established finish tooth positions, a custom appliance configuration, and establishing connection points on the teeth for connection of the appliance thereto, such that the custom orthodontic appliance, when made in accordance therewith and connected to the teeth at the connection points, urges the teeth toward the established finish positions;

fabricating the custom orthodontic appliance in accordance with the designed custom appliance configuration;

installing the custom orthodontic appliance at the established connection points on the teeth of the patient; and moving the teeth of the patient to the finish positions with the fabricated custom orthodontic appliance.

35. The method of claim 34 wherein the finish position establishing step further includes:

vertically positioning the maxillary incisors such that their incisal tips are positioned below the occlusal plane so as to achieve predetermined overlaps that have a predetermined relationship to the calculated cuspid rise.

36. A method of making an orthodontic appliance to move teeth of a patient to preferred finish positions in the upper and lower jaws of the patient, the method comprising the steps of:

providing an orthodontic appliance manufacturing system including:
a data input sub-system for digitizing input data of anatomical shapes from the mouth of the patient and generating input signals carrying the digitized input data,
a data processing sub-system for processing the input signals and generating, in response thereto, output signals carrying machine readable information, and
an appliance hardware manufacturing sub-system for fabricating, in response to the output signals, a custom orthodontic appliance for the treatment of the patient by moving the teeth of the patient to the preferred finish positions;

producing, with the data input sub-system, input signals carrying:
digitized input data containing information of relative positions of a plurality of mandibular trough defining points on the lower jaw of the patient;

deriving, with the data processing sub-system:
from the mandibular trough defining point information, a mandibular trough skeletal archform that is a mathematical representation of the shape of a root constraining trough portion of the lower jaw;

generating, with the data processing sub-system, from the derived skeletal archform, output signals carrying machine readable information for operating the appliance hardware manufacturing sub-system to fabricate a custom orthodontic appliance connectable to teeth of the patient, the appliance being of a custom configuration such that forces are exerted thereby on teeth to which it is connected at respective connection points thereon to urge the teeth toward respective finish positions; and fabricating, with the appliance hardware manufacturing sub-system, in response to the output signals and in accordance with the machine readable information, the custom orthodontic appliance of the custom configuration.

37. The method of claim 36 wherein:

the input signal producing step includes the step of producing, with the data input sub-system, input signals further carrying:

digitized input data containing information of relative positions of points on each of a plurality of the patient's teeth, including an incisal tip point, a gingival center point, points defining a surface of the crown of the tooth to which the appliance is to be connected, and a marginal ridge point on each posterior maxillary tooth of the plurality, and digitized input data containing information of relative positions of mesial and distal contact points each tooth of the plurality;

the deriving step further comprises the step of deriving, with the data processing sub-system, from the mandibular trough skeletal archform and the incisal tip and gingival point information, a mandibular tip dental archform that is mathematically related to the mandibular trough skeletal archform and the relative positions of the incisal tip points, mesial and distal contact points, and the respective gingival center points of the mandibular teeth;

the output signal generating step further comprises the step of generating, with the data processing sub-system, from the derived archforms, the information of the relative positions of the incisal tip points, the gingival center points, the surface defining points, the marginal ridge points, and the mesial and distal contact points, the output signals carrying the machine readable information for operating the appliance hardware manufacturing sub-system to fabricate the custom orthodontic appliance, wherein the appliance is connectable to surface defining points of the teeth and is of the custom configuration such that forces are exerted by the appliance on each tooth at the surface defining points of connection to urge the teeth toward respective finish positions at which:

adjacent mesial and distal contact points of adjacent mandibular teeth are in contact, adjacent mesial and distal contact points of adjacent maxillary teeth are in contact, the gingival center points of the mandibular teeth are horizontally aligned with the mandibular trough skeletal archform, the incisal tip points of the mandibular teeth are horizontally aligned on the mandibular tip dental archform and vertically aligned on an occlusal surface spaced with respect the lower jaw, and the marginal ridge points of the maxillary posterior teeth are horizontally aligned, when in occlusion with the mandibular teeth, on the mandibular tip dental archform and vertically aligned on the occlusal surface.

38. The method of claim 37 wherein:

the custom orthodontic appliance includes an archwire having an arcuate shape that is mathematically related to the mandibular trough skeletal archform;

the appliance manufacturing sub-system includes a wire bending apparatus responsive to wire forming control signals carried by the output signal;

the output signal has a form mathematically related to the mandibular trough skeletal archform and includes a series of wire forming control signals for operating the wire bending apparatus to feed a wire and to bend the fed wire into the custom archwire configuration, mathematically related to the mandibular trough skeletal archform, for connection of the archwire to the teeth of a jaw at respective connection points.

39. The method of claim 38 wherein:

the digitized input data contains information sufficient to define the connection points of the appliance and slope of the surface of each tooth at the connection point thereon;

the custom orthodontic appliance includes a plurality of brackets, one for each tooth connection point, each having a base securable to the respective connection point, and each having an archwire slot connectable to the archwire;

the appliance hardware manufacturing sub-system includes a bracket fabricating apparatus responsive to bracket forming control signals carried by the output signal; and the output signal includes a series of bracket forming control signals for operating the bracket fabricating apparatus to fabricate each bracket with the archwire slot positioned with respect to the base to support and orient a point on the archwire with respect to the connection point of the respective tooth to transfer force therebetween to urge the tooth toward its finish position.

40. The method of claim 38 wherein:

the digitized input data contains information describing a contour on the surface of the tooth;

the custom orthodontic appliance includes a bracket placement jig for each bracket, each jig having a surface contoured to conform to the surface of one of the teeth so as to be capable of uniquely positioning the jig with respect to the surface of the tooth and to thereby position the bracket at the connection point of the tooth;

the appliance hardware manufacturing sub-system includes a bracket placement jig fabricating apparatus responsive to jig forming control signals carried by the output signal; and the output signal includes a series of jig forming control signals containing information for operating the bracket placement jig fabricating apparatus to fabricate the bracket placement jig having surfaces for configured to engage the surface of the tooth and the bracket and to relatively position and orient the bracket at the connection point on the surface of the tooth.

41. A method of achieving maxillary expansion in an orthodontic treatment of a patient, comprising the steps of:

digitizing data correlated to shapes of teeth, including maxillary teeth, of the patient;

digitizing data of the initial distance between selected points on the surfaces of contralateral maxillary teeth of the patient;

inputing the digitized data into a especially programmed digital computer;

calculating, with the computer, finish positions of the maxillary teeth of the patient based at least in part on the digitized data of the shapes of the maxillary teeth;

recalculating, with the computer, the distance between selected points based on the calculated finish positions of the maxillary teeth;

comparing, with the computer, the recalculated distance with the initial distance and producing a tangible record of the difference of the comparison;

based on the results of the calculating and recalculating steps, operating manufacturing equipment and thereby fabricating an orthodontic appliance configured for moving the teeth of the patient to the calculated finish positions when installed on the teeth of the patient whose maxilla has been expanded by the amount of the difference between the initial and recalculated distances between the selected points;

providing the fabricated appliance and the tangible record for treatment of the patient; and expanding the maxilla of the patient by the difference based on information in the tangible record and installing the appliance on the teeth of the patient and treating the patient therewith.

42. The method of claim 41 further comprising the steps of:

digitally determining the movement of the selected points due to reorientation of the teeth needed to move the corresponding maxillary teeth to their calculated finish positions; and modifying the digitized initial distances by the amount of movement.

43. The method of claim 41 wherein:

the data digitizing step includes the step of digitizing shapes of the mandibular teeth of the patient;

the maxillary tooth finish position calculating step includes the step of calculating finish positions of the mandibular teeth of the patient based at least in part on the digitized data of the shapes of the mandibular teeth;

calculating the finish positions of the maxillary teeth of the patient based at least in part on the calculated finish positions of the mandibular teeth; and moving the teeth of the patient to the calculated finish positions with the fabricated appliance.

44. The method of claim 41 further comprising the step of:

transmitting the tangible record to an orthodontist for use in the orthodontic treatment of the patient by expansion of the maxilla by the difference.

45. A method of orthodontically positioning teeth in a patient's mouth, comprising the steps of:

sensing anatomical shapes from the mouth of the patient;

digitizing data of the sensed anatomical shapes from the mouth of the patient;

calculating an archform, in a digital computer, at least in part from the digitized data;

with the digital computer, determining the centerline of the calculated archform;

with the digital computer, comparing corresponding contralateral points on the archform on opposite sides of the centerline and, on the basis of the comparison and the calculated archform, calculating a modified archform that is symmetrical about the centerline;

with the digital computer, calculating finish positions of the teeth to symmetrically position corresponding contralateral teeth relative to the modified archform and producing a digitized record based on the calculated finish positions;

fabricating an arcuate orthodontic appliance in response to and in accordance with the digitized record;

securing the fabricated appliance to the teeth of the patient; and orthodontically positioning the teeth in the patient's mouth with the fabricated appliance.

46. The method of claim 45 wherein:

the digitized record producing step includes the step of deriving, from the calculated finish positions and the modified archform, an archwire design having an arcuate shape that is symmetrical about the centerline, and producing the digitized record of the derived archwire design;

the method further comprises the step of deriving a bracket design for a set of orthodontic brackets based on the digitized data and derived archwire design for connecting the teeth to the archwire to move the teeth to the calculated finish positions; and the appliance fabricating step includes the steps of fabricating a symmetrical archwire based on the digitized record in accordance with the derived archwire design and fabricating a set of orthodontic brackets in accordance with the derived bracket design.

47. A method of providing an orthodontic appliance for connection to the teeth of a patient with optimal spacing from the gums of a patient and clearance with teeth of the opposite jaw of the patient, the method comprising the steps of:

digitizing data of shapes of the teeth of the patient and of geometry of parts of an appliance to be connected thereto;

calculating, with a programmed digital computer from the digitized data, finish positions of the teeth of the patient and relationships between points on surfaces of teeth of the opposite jaws when the teeth are occluded and in the calculated finish positions;

calculating, with the computer from the digitized data, appliance connection points on the surfaces of the teeth of one jaw of the patient having a calculated spacing from the gums of a patient and a calculated clearance with teeth of the opposite jaw of the patient;

fabricating an appliance for moving the teeth of the patient to the calculated finish positions when connected to the teeth at the calculated connection points; and connecting the appliance to the teeth of the patient at the calculated connection points.

48. The method of claim 47 further comprising the steps of:

providing, for each connection point, a jig having a surface conforming to one of the digitized shapes and engageable with a surface of a tooth and having a surface engageable with the appliance to guide the placement of the appliance at the calculated connection point on the tooth; and performing the appliance connecting step with the use of the jigs to locate the appliance on the connection point of each respective tooth.

49. A method of forming an orthodontic appliance for achieving cuspid rise in the orthodontic treatment of a patient, the method comprising the steps of:

collecting tooth shape data from teeth of the patient;

processing the collected data with a specially programmed digital computer, thereby identifying occluding pairs of respective upper and lower posterior teeth of the patient, and determining with the computer for each pair from the collected tooth shape data a vertical distance of the highest extent of the lower tooth of the pair above the lowest extent of the upper tooth of the pair when the jaws are in a closed position;

with the computer, performing a calculation for adjusting each determined vertical distance by a factor proportionally related to a distance of each pair from a pivot axis between the upper and lower jaws; and, with the computer, designing an appliance based on the results of the calculation, generating control signals carrying information of the calculated design, and operating manufacturing equipment in response to the generated control signals and thereby forming an orthodontic appliance for the positioning of the cuspids of the patient such that the total cuspid rise is equal to at least the largest adjusted vertical distance of the posterior tooth pairs such that, as the jaws close, contact occurs between pairs of cuspids before contact occurs between pairs of other teeth.

50. The method of claim 49 further comprising the steps of:

calculating from the collected tooth shape data finish positions of the mandibular teeth of the patient at which highest points thereon are at vertical positions on an approximately flat occlusal surface; and calculating finish positions of the upper and lower cuspids of the patient extend respectively below and above the occlusal surface.

51. The method of claim 50 wherein:

the finish positions of the upper and lower cuspids of the patient extend respectively below and above the occlusal surface by amounts approximately equal to two-thirds and one-third, respectively, of the cuspid rise.

52. The method of claim 49 further comprising the step of:

calculating finish positions of maxillary incisors such the lowest points thereon extend below the occlusal surface an amount proportionally related to the cuspid rise.

53. A method of forming an orthodontic appliance for moving teeth of a patient to preferred finish positions, the method comprising the steps of:

sensing the shape of the lower jaw of the patient;

digitizing the sensed shape of the lower jaw of the patient and producing thereby signals containing digitized lower shape data;

deriving with a specially programmed digital computer from the digitized data contained in the signals a skeletal archform mathematically representing the arcuate shape of the patient's cortical bone;

calculating with the computer finish positions of mandibular teeth of the patient to place the mandibular teeth in an ideal dental archform derived from the skeletal archform and having an arcuate shape mathematically related to the arcuate shape of the skeletal archform;

calculating with the computer a design of an orthodontic appliance to move the teeth to the calculated finish positions;

generating control signals containing information of the calculated appliance design; and operating a fabricating machine in response to the control signals to automatically fabricate the appliance in accordance with the calculated design to place the teeth of the patient on the calculated dental archform.

54. The method of claim 53 wherein:

the data digitizing step includes the step of forming a model of the lower jaw of the patient that includes at least a representation of the anatomy supporting the lower teeth in two horizontal dimensions and digitizing boundary points therefrom corresponding to the labial and lingual boundaries of the cortical bone;

the skeletal archform deriving step includes the steps of calculating mandibular trough data points lying approximately intermediate the digitized boundary points and deriving a smooth curve through the data points to define a mandibular trough equation; and the finish position calculating step includes the step establishing the positions of the mandibular teeth with respect to the mandibular trough equation.

55. The method of claim 54 wherein:

the model is a graphical representation of the lower law of the patient in a horizontal plane;

the model forming step includes the step of forming a two dimensional video image of the lower jaw of the patient; and the boundary point digitizing step includes digitizing the boundary points from the video image.

56. The method of claim 54 wherein:

the data digitizing step includes the step of digitizing mesial and distal contact points of each tooth from the model; and the finish position calculating step includes the step calculating the spacing of the teeth on the curve by spacing the mesial and distal contact points in an arch parallel to the curve, 57. The method of claim 54 wherein:

the smooth curve is a cubic spline equation through the data points.

58. The method of claim 54 wherein:

the data digitizing step includes the step providing the model to include a representation of the anatomy of the teeth of the patient in at least two dimensions viewed in a mesial-distal direction and digitizing selected points on the teeth from the tooth anatomy representation; and the mandibular tooth position establishing step includes the step of digitally defining, with a computer, positions of the selected points in relation to the mandibular trough equation.

59. The method of claim 58 wherein:

the model providing step includes the step of providing a three dimensional physical model from a mold of the patient's jaws, and the selected point digitizing step includes the step of scanning the surface of the model with a rotatable and translatable hooked mechanical probe and digitizing the boundary points therefrom.

60. The method of claim 58 wherein:

the model forming and providing steps include the producing of a three dimensional computerized representation of the jaws of the patient, and the boundary and selected point digitizing step includes the step of digitizing the boundary points and selected points from the three-dimensional computerized representation.

61. The method of claim 54 wherein:
determining, with a computer, the centerline of the calculated mandibular trough equation through the center of the cortical bone;
comparing, with the computer, corresponding contralateral points on the equation on opposite sides of the centerline and, on the basis of the comparison, modifying the mandibular trough equation to a form that is symmetrical about the centerline.

62. The method of claim 54 wherein:
the finish position calculating step includes the step defining an ideal mandibular dental archform defined by at least one selected point on each of the mandibular teeth, replacing the mandibular trough equation with a statistical best fit equation with respect thereto for the selected points, and reestablishing the positions of the mandibular teeth by locating the teeth such that the at least one selected points lie on the best fit equation.

63. The method of claim 62 further comprising the steps of:
calculating offset distances from the at least one selected points to the selected point of each respective tooth placed on the best fit equation;
converting the best fit equation to a series of circle segments defined by corresponding radii and arc lengths tangent to adjacent segments and adjoining ends; and
deriving archforms for other teeth by adjusting the radii of the best fit equation.

64. The method of claim 54 further comprising the steps of:
sensing the shapes of the teeth of the patient and digitizing tooth shape data thereof;
selecting points on the surfaces of the teeth from the tooth shape data;
digitally deriving, with a computer, from the mandibular trough equation, a maxillary posterior archform for the maxillary posterior teeth in which at least one of the selected points of each of the maxillary posterior teeth is in contact with a selected point of a corresponding mandibular tooth on the maxillary posterior archform;
digitally deriving, with the computer, from the mandibular trough equation, a maxillary anterior archform for the maxillary incisors in which at least one of the selected points of each of the maxillary incisors is in spaced labial relationship with a selected point on a corresponding mandibular tooth on the maxillary anterior archform; and
digitally defining the finish positions of the maxillary cuspids in an intermediate relation to the two maxillary archforms.

65. The method of claim 64 wherein:
the maxillary cuspids finish positions are derived by averaging the offset from selected points on adjacent teeth.

66. The method of claim 64 wherein:
the data digitizing step includes the step of digitizing mesial and distal contact points of each tooth; and
the maxillary cuspids finish positions are derived to place the mesial and distal contact points thereof in contact with the respective distal and mesial contact points of the adjacent teeth.

67. The method of claim 64 wherein:
the finish positions of the maxillary cuspids are digitally derived from the mandibular trough equation by defining a maxillary cuspid archform to place at least one of the selected points of each in spaced labial relationship with a corresponding mandibular cuspid on the maxillary cuspid archform.

68. The method of claim 53 wherein:
each tooth has a crown, a root and a long axis extending generally vertically through the center of the crown, intersecting a gingival center point where the crown meets the root, and wherein:
the finish position deriving step includes the step of initially setting inclination angles of the teeth in accordance with predetermined values and adjusting the inclination angles to place the gingival center points of the teeth on a smooth continuous gingival center point curve.

69. The method of claim 53 further comprising the steps of:
establishing and inputing into the computer inclination angles for each of the teeth; and
the tooth position deriving step including the step of deriving tooth finish positions in part from the established inclination angles to incline teeth at the established inclination angles.

* * * * *

UNITED STATES PATENT AND TRADEMARK OFFICE
CERTIFICATE OF CORRECTION

PATENT NO. : 5,431,562
DATED : July 11, 1995
INVENTOR(S) : Andreiko et al.

It is certified that error appears in the above-indentified patent and that said Letters Patent is hereby corrected as shown below:

Col. 72, line 47, insert "respective" before "individual".

Col. 88, line 27, "law" should be -- jaw --.

Signed and Sealed this

Fifth Day of December, 1995

Attest:

BRUCE LEHMAN

Attesting Officer

Commissioner of Patents and Trademarks